(12) United States Patent
Beurskens et al.

(10) Patent No.: US 12,173,076 B2
(45) Date of Patent: Dec. 24, 2024

(54) POLYPEPTIDE VARIANTS AND USES THEREOF

(71) Applicant: GENMAB B.V., Utrecht (NL)

(72) Inventors: Frank Beurskens, Utrecht (NL); Marije Overdijk, Utrecht (NL); Annieck M. Diks, Gouda (NL); Rob De Jong, Utrecht (NL); Kristin Strumane, Werkhoven (NL); Janine Schuurman, Diemen (NL); Paul Parren, Odijk (NL)

(73) Assignee: GENMAB B.V., Utrecht (NL)

( * ) Notice: Subject to any disclaimer, the term of this patent is extended or adjusted under 35 U.S.C. 154(b) by 342 days.

(21) Appl. No.: 16/482,747

(22) PCT Filed: Feb. 12, 2018

(86) PCT No.: PCT/EP2018/053464
§ 371 (c)(1),
(2) Date: Aug. 1, 2019

(87) PCT Pub. No.: WO2018/146317
PCT Pub. Date: Aug. 16, 2018

(65) Prior Publication Data
US 2020/0181277 A1  Jun. 11, 2020

(30) Foreign Application Priority Data
Feb. 10, 2017 (DK) .............. PA 2017 00097

(51) Int. Cl.
*C07K 16/28* (2006.01)
*C07K 16/10* (2006.01)

(52) U.S. Cl.
CPC ...... *C07K 16/2878* (2013.01); *C07K 16/1045* (2013.01); *C07K 16/2887* (2013.01); *C07K 16/2893* (2013.01); *C07K 2317/31* (2013.01); *C07K 2317/524* (2013.01); *C07K 2317/526* (2013.01); *C07K 2317/72* (2013.01); *C07K 2317/734* (2013.01); *C07K 2317/75* (2013.01)

(58) Field of Classification Search
None
See application file for complete search history.

(56) References Cited

U.S. PATENT DOCUMENTS

| 5,851,984 | A * | 12/1998 | Matthews | A61P 43/00 424/85.1 |
| 7,335,742 | B2 * | 2/2008 | Presta | A61P 35/00 530/387.1 |
| 10,759,867 | B2 | 9/2020 | Parren et al. | |
| 11,180,572 | B2 | 11/2021 | De Jong et al. | |
| 2014/0242075 | A1 * | 8/2014 | Parren | A61P 35/00 424/136.1 |
| 2015/0175707 | A1 | 6/2015 | De Jong et al. | |
| 2015/0353636 | A1 | 12/2015 | Parren et al. | |
| 2018/0044430 | A1 * | 2/2018 | Chiu | C07K 16/2878 |
| 2019/0276549 | A1 | 9/2019 | De Jong et al. | |
| 2020/0247897 | A1 | 8/2020 | Jensen et al. | |
| 2021/0107988 | A1 | 4/2021 | Oostindie et al. | |
| 2021/0163619 | A1 | 6/2021 | Parren et al. | |
| 2021/0230301 | A1 | 7/2021 | De Jong et al. | |
| 2021/0238296 | A1 | 8/2021 | De Jong et al. | |
| 2023/0107363 | A1 | 4/2023 | De Jong et al. | |

FOREIGN PATENT DOCUMENTS

| WO | 2005/070963 A1 | 8/2005 |
| WO | 2011/122011 A2 | 10/2011 |
| WO | 2013/004842 A2 | 1/2013 |
| WO | 2014/006217 A1 | 1/2014 |
| WO | 2014/108198 A1 | 7/2014 |
| WO | 2016/164480 A1 | 10/2016 |

OTHER PUBLICATIONS

Lloyd et al., Protein Engineering, Design & Selection 22:159-168 (Year: 2009).*
Edwards et al., J Mol Biol. 334(1): 103-118 (Year: 2003).*
Piche-Nicholas et al. MABS 10(1): 81-94 (Year: 2018).*
Idusogie, E.E et al., "Engineered antibodies with increased activity to recruit complement," Journal of Immunology, vol. 166(4): 2571-2575 (2001).
Tammen, A. et al. "Monoclonal antibodies against epidermal growth factor receptor acquire an ability to kill tumor cells through complement activation by mutations that selectively facilitate the hexamerization of IgG on opsonized cells" Journal of Immunology vol. 198(4):1585-1594 (2017).
U.S. Appl. No. 16/921,154, filed Jul. 6, 2020, Paul Parren.
U.S. Appl. No. 14/130,543, filed May 5, 2014, Paul Parren.
U.S. Appl. No. 17/012,102, filed Sep. 4, 2020, Rob N. De Jong.
U.S. Appl. No. 14/413,178, filed Mar. 17, 2015, Rob N. De Jong.
U.S. Appl. No. 14/760,135, filed Jul. 9, 2015, Paul Parren.
U.S. Appl. No. 16/618,722, filed Dec. 2, 2019, Mette Hamborg Jensen.
U.S. Appl. No. 16/345,044, filed Apr. 25, 2019, Rob De Jong.
U.S. Appl. No. 16/963,701, filed Jul. 21, 2020, Simone Oostindie.
U.S. Appl. No. 17/051,205, filed Oct. 28, 2020, Rob De Jong.
U.S. Appl. No. 17/745,667, filed May 16, 2022, Rob De Jong.

* cited by examiner

*Primary Examiner* — Phuong Huynh
(74) *Attorney, Agent, or Firm* — Nelson Mullins Riley & Scarborough LLP; Jane E. Remillard, Esq.; Christopher L. Frank

(57) ABSTRACT

As described herein are polypeptides and antibodies having an Fc region and an antigen binding region where the Fc region has an Fc-Fc-enhancing mutation and a C1q binding-enhancing mutation providing for polypeptides or antibodies with increased CDC activity and/or agonistic activity.

15 Claims, 39 Drawing Sheets
Specification includes a Sequence Listing.

BxPC-3

COLO 205

C1q binding ELISA

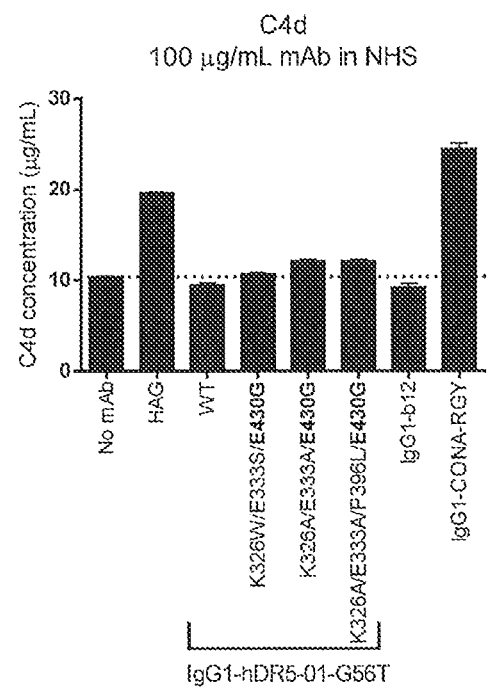

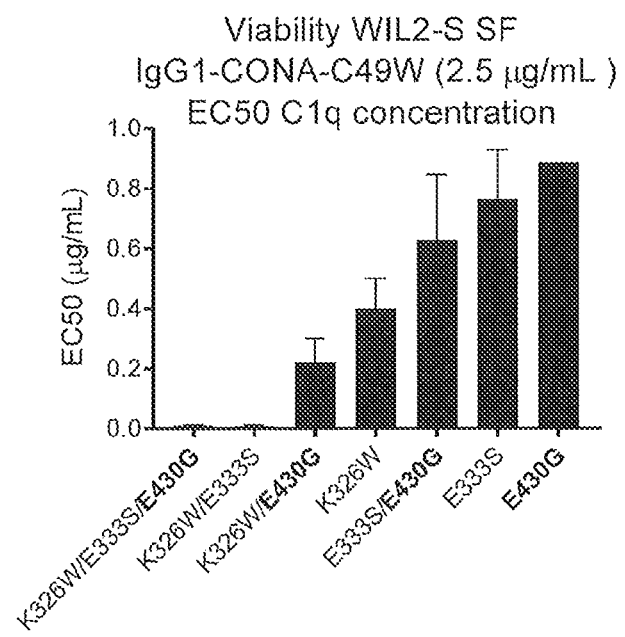

Viability BxPC-3

Viability BxPC-3

Viability WIL2-S SF
t = 24 hours
No C1q

Viability WIL2S-SF
t = 24 hours
No C1q

Viability WIL2-S SF
t = 24 hours
No C1q

POLYPEPTIDE VARIANTS AND USES THEREOF

CROSS-REFERENCE TO RELATED APPLICATIONS

This application is a 35 U.S.C. 371 national stage filing of International Application No. PCT/EP2018/053464, filed Feb. 12, 2018, which claims priority to Danish Patent Application No. PA 2017 00097, filed Feb. 10, 2017. The contents of the aforementioned applications are hereby incorporated by reference.

SEQUENCE LISTING

The instant application contains a Sequence Listing which has been submitted electronically in ASCII format and is hereby incorporated by reference in its entirety. Said ASCII copy, created on Feb. 11, 2020, is named GMI_183US_Sequence_Listing.txt and is 169,925 bytes in size.

FIELD OF THE INVENTION

The present invention relates to Fc region-containing polypeptides comprising a binding region, such as antibodies, that have at least two amino acid substitutions in the Fc region compared to a parent polypeptide or antibody.

BACKGROUND OF THE INVENTION

Fc-mediated effector functions of monoclonal antibodies, such as complement-dependent cytotoxicity (CDC), antibody-dependent cell-mediated cytotoxicity (ADCC) and antibody-dependent cell-mediated phagocytosis (ADCP) contribute to the therapeutic window defined by efficacy and toxicity. CDC is initiated by binding of C1q to the Fc regions of antibodies. C1q is a multimeric protein consisting of six globular binding heads attached to a stalk.

IgG hexamerization upon target binding on the cell surface has been shown to be enhanced by point mutations in the Fc region. The hexamerization is mediated through intermolecular non-covalent Fc-Fc interactions, and Fc-Fc interactions can be enhanced by point mutations in the CH3 domain, including E345R and E430G. WO2013/004842 discloses antibodies or polypeptides comprising variant Fc regions having one or more amino acid modifications resulting in modified effector functions such as complement-dependent cytotoxicity (CDC).

WO2014/108198 discloses polypeptides such as antibodies comprising variant Fc regions having one or more amino acid modifications resulting in increased complement-dependent cytotoxicity (CDC).

WO2016/164480 discloses antigen binding complexes having agonistic activity. Enhanced Fc-Fc interactions between antibodies can be used to amplify the effect of the antibody binding to its target on a cell surface. However only enhancing the Fc-Fc interactions between Fc regions are not always sufficient in creating a strong enough signal to activate a signaling pathway by e.g. binding to a receptor.

Accordingly, it is an object of the present invention to provide a polypeptide or antibody comprising an Fc region of a human IgG and an antigen binding region which polypeptide has increased Fc-Fc interactions and agonistic activity such as increased activation of a target receptor upon binding, when compared to a parent polypeptide, where the parent polypeptide is a human IgG of the same isotype and having the same antigen binding region, but without any mutations in the Fc region i.e. a parent polypeptide or parent antibody.

It is another object of the present invention to provide for a polypeptide that activates signaling, optionally induces enhanced signaling, when the antigen binding region of the polypeptide e.g. antibody is bound to the corresponding antigen compared to a parent polypeptide, where the parent polypeptide does not have any mutations in the Fc region.

It is yet another object of the present invention to provide a polypeptide with enhanced Fc-Fc interaction properties and enhanced effector functions such as CDC.

It is a further object of the present invention to provide for a polypeptide with enhanced Fc-Fc interactions and enhanced C1q binding properties, when compared to a parent polypeptide without any mutations in the Fc region.

SUMMARY OF THE INVENTION

As described herein, the present invention relates to polypeptides or antibodies having an Fc region and an antigen binding region where the Fc region has an Fc-Fc enhancing mutation and a C1q binding mutation providing for polypeptides or antibodies with increased CDC activity and/or agonistic activity.

Without being limited to theory, it is believed that the polypeptides or antibodies of the invention are capable of a stable binding interaction between the Fc regions of two polypeptides or antibody molecules when bound to the target on a cell surface, which leads to an enhanced oligomerization, such as hexamer formation, thereby providing an avid surface. The polypeptides or antibodies of the invention further have an increased Fc effector response compared to their parent polypeptide or parent antibody without any mutations in the Fc region, i.e. a parent polypeptide or antibody of the same isotype.

In one aspect the present invention provides a polypeptide or an antibody comprising an Fc region of a human immunoglobulin and an antigen binding region, wherein the Fc region comprises a) at least one Fc-Fc enhancing substitution at a position selected from the group consisting of: E430, E345 or a S440Y or S440W substitution, and b) at least one C1q binding substitution, wherein the positions correspond to human IgG1, according to EU numbering (Edelman et al., Proc Natl Acad Sci USA. 1969 May; 63(1):78-85; Kabat et al., Sequences of Proteins of Immunological Interest, Fifth Edition. 1991 NIH Publication No. 91-3242).

In one aspect of the invention provides for a polypeptide or antibody comprising an Fc region of an immunoglobulin and an antigen binding region, wherein the Fc region comprises, a) a substitution at a position selected from the group consisting of: E430, E345 or a S440Y or S440W substitution, and b) a substitution at one or more position(s) selected from the group consisting of: G236, S239, S267, H268, S324 K326, I332, E333 and P396, wherein the positions correspond to human IgG1, according to EU numbering.

A substitution at a position corresponding to E430, E345 or a S440Y or S440W substitution is considered an Fc-Fc enhancing substitution according to the present invention.

A substitution at one or more position(s) selected from the group consisting of: G236, S239, S267, H268, S324 K326, I332, E333 and P396, is considered a C1q binding substitution according to the present invention.

That is, the inventors of the present invention in a first aspect of the invention found that introducing a first mutation that enhances Fc-Fc interaction together with a second mutation that enhances C1q binding for provides a polypeptide or antibody with agonistic activity and/or enhanced CDC.

In one aspect the present invention provides for a polypeptide or an antibody comprising an Fc region of a human immunoglobulin and an antigen binding region, wherein the Fc region comprises a) a substitution at a position selected from the group consisting of: E430, E345 or a S440Y or S440W substitution, and b) a substitution at one or more position(s) selected from the group consisting of: G236, S239, S267, H268, S324 K326, I332, E333 and P396, wherein the positions correspond to human IgG1, according to EU numbering.

That is the inventors found that an Fc-Fc enhancing mutation together with one or more C1q binding substitutions(s) at one or more position(s) selected from the group consisting of: G236, S239, S267, H268, S324 K326, I332, E333 and P396 may provide agonistic activity.

The inventors further found that an Fc-Fc enhancing mutation together with one or more C1q binding substitutions(s) at one or more position(s) selected from the group consisting of: G236, S239, S267, H268, S324 K326, I332, E333 and P396 may provide for enhanced Fc mediated effector functions such as enhanced CDC.

The combination of an Fc-Fc enhancing mutation and a C1q binding substitution in a polypeptide or antibody further has the surprising effect of generating a polypeptide or antibody with agonistic properties, when compared to a parent polypeptide or a parent antibody.

In one embodiment of the present invention, the polypeptide or antibody comprises at least one substitution is selected from the group consisting of: E430G, E345K, E430S, E430F, E430T, E345Q, E345R, E345Y, S440W and S440Y.

In one embodiment of the present invention, the polypeptide or antibody comprises at least one substitution selected from the group consisting of: E430G, E430S, E430F and E430T.

In one embodiment of the present invention, the polypeptide or antibody comprises at least one substitution selected from the group consisting of: E345K, E345Q, E345R and E345Y.

In one embodiment of the present invention, the polypeptide or antibody comprises at least a substitution is E430G. In one embodiment of the present invention the polypeptide or antibody comprises at least a substitution is E345K. In one embodiment of the present invention the polypeptide or antibody comprises at least a substitution is S440Y.

In one embodiment of the present invention the polypeptide or antibody comprises a substitution at one or more position (a) selected from the group consisting of: K326, E333 and P396.

In one embodiment of the present invention the polypeptide or antibody comprises a substitution at one or more positions, such as two or three positions selected from the group consisting of: K326A, K326W, E333S, E333A and P396L.

In one embodiment of the present invention the polypeptide or antibody comprises a substitution at one or more positions, such as two or three positions selected from the group consisting of: K326A, K326W, E333S, E333A, E333T and P396L.

In one embodiment of the present invention the polypeptide or antibody comprises the substitutions K326W and E333S.

In a further aspect the present invention relates to a method of increasing agonistic activity of a polypeptide or antibody comprising an Fc region of a human IgG and an antigen binding region, which method comprises a) introducing a substitution at a position selected form the group consisting of: E430, E345 or a S440Y or S440W substitution, and b) introducing a substitutions at one or more position(s) selected from the group consisting of: G236, S239, S267, H268, S324 K326, I332, E333 and P396, wherein the position correspond to human IgG1, according to EU numbering.

In a further aspect the present invention relates to a method of increasing CDC activity of a polypeptide or antibody comprising an Fc region of a human IgG and an antigen binding region, which method comprises a) introducing a substitution at a position selected form the group consisting of: E430, E345 or a S440Y or S440W substitution, and b) introducing a substitutions at one or more position(s) selected from the group consisting of: G236, S239, S267, H268, S324 K326, I332, E333 and P396, wherein the position correspond to human IgG1, according to EU numbering.

In another aspect the present invention relates to a composition comprising at least one polypeptide or antibody as described herein.

In another aspect the present invention relates to a polypeptide, antibody or a composition as described herein for use as a medicament.

In another aspect the present invention relates to a polypeptide, antibody or a composition as described herein for use in the treatment of cancer, autoimmune disease, inflammatory disease or infectious disease.

In another aspect the present invention relates to a method of treating an individual having a disease comprising administering to said individual an effective amount of a polypeptide, an antibody or composition as described herein.

These and other aspects of the invention, particularly various uses and therapeutic applications for the polypeptide or antibody, are described in further detail below.

BRIEF DESCRIPTION OF THE DRAWINGS

FIG. 10 shows solution phase complement activation as measured by quantification of C4d deposition when antibody samples were incubated in NHS for IgG1-hDR5-01-G56T antibody variants containing the 430G Fc-Fc enhancing substitutions in combination with C1q binding substitutions K326W/E333S, K326A/E333A or K326A/E333A/P396L. HAGG (heat aggregated gamma globulin) and IgG1-CONA-RGY were tested as positive controls for solution phase complement activation.

FIGS. 12A-12C show the effect of introducing the K326W, E333S, or K326W/E333S substitutions into IgG-CONA-C49W and IgG1-CONA-C49W-E430G (2.5 µg/mL) on the viability of WIL2-S SF suspension cells in serum-free medium in the presence of a concentration series of purified human C1q, as determined in a 24-hour viability assay. The percentages viable cells were determined in a CellTiter-Glo assay.

(FIG. 20A) Total human IgG in serum samples was determined by ELISA and plotted in a concentration versus time curve. Each data point represents the mean+/−standard deviation of triplicate samples. (FIG. 20B) Clearance until day 21 after administration of the antibody was determined following the formula D*1.000/AUC with D, injected dose and AUC, area under the curve of the concentration-time curve. A representative example of two independent ELISA experiments is shown.

DETAILED DESCRIPTION OF THE INVENTION

Figure 1A:
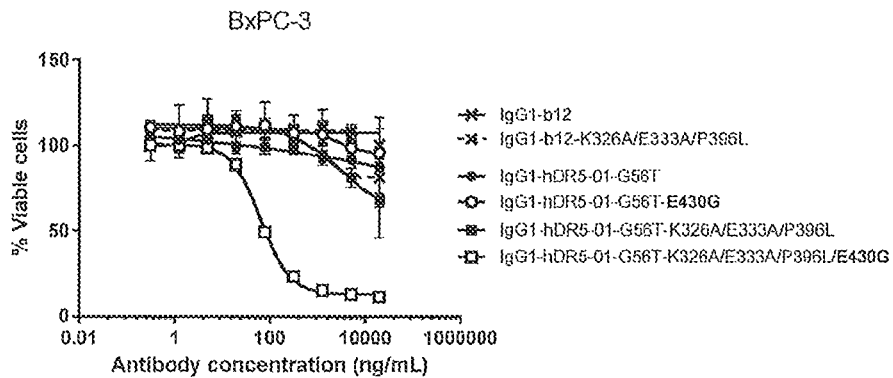
FIGS. 1A-1C show the effect of E430G, K326A/E333A/P396L and K326A/E333A/P396L/E430G on the efficacy of anti-DR5 antibodies IgG1-hDR5-01-G56T (FIG. 1A), IgG1-hDR-05 (FIG. 1B) and the antibody combination (FIG. 1C) on adherent human BxPC-3 pancreatic cancer cells as determined in a 3-days viability assay (CellTiter-Glo). Representative examples of two experiments are shown.

In describing the embodiments of the invention specific terminology will be resorted to for the sake of clarity. However, the invention is not intended to be limited to the specific terms so selected, and it is understood that each specific term includes all technical equivalents which operate in a similar manner to accomplish a similar purpose.

Definitions

The term "parent polypeptide" or "parent antibody", is to be understood as a polypeptide or antibody, which is identical to a polypeptide or antibody according to the invention, but where the parent polypeptide or parent antibody does not have a Fc-Fc enhancing mutation and a C1q binding mutation according to the present invention.

The term "polypeptide comprising an Fc-region of an immunoglobulin and a binding region" refers in the context of the present invention to a polypeptide which comprises an Fc-region of an immunoglobulin and a binding region which is a capable of binding to any molecule, such as a polypeptide, e.g. present on a cell, bacterium, or virion. The Fc-region of an immunoglobulin is defined as the fragment of an antibody which would be typically generated after digestion of an antibody with papain (which is known for someone skilled in the art) which includes the two CH2-CH3 regions of an immunoglobulin and a connecting region, e.g. a hinge region. The constant domain of an antibody heavy chain defines the antibody isotype, e.g. IgG1, IgG2, IgG3, IgG4, IgA1, IgA2, IgM, IgD, or IgE. The Fc-region mediates the effector functions of antibodies with cell surface receptors called Fc receptors and proteins of the complement system. The binding region may be a polypeptide sequence, such as a protein, protein ligand, receptor, an antigen-binding region, or a ligand-binding region capable of binding to a cell, bacterium, or virion. If the binding region is e.g. a receptor, the "polypeptide comprising an Fc-region of an immunoglobulin and a binding region" may have been prepared as a fusion protein of Fc-region of an immunoglobulin and said binding region. If the binding region is an antigen-binding region the "polypeptide comprising an Fc-region of an immunoglobulin and a binding region" may be an antibody, like a chimeric, humanized, or human antibody or a heavy chain only antibody or a ScFv-Fc-fusion. The polypeptide comprising an Fc-region of an immunoglobulin and a binding region may typically comprise a connecting region, e.g. a hinge region, and two CH2-CH3 regions of the heavy chain of an immunoglobulin, thus the "polypeptide comprising an Fc-region of an immunoglobulin and a binding region" may be a "polypeptide comprising at least an Fc-region of an immunoglobulin and a binding region". The term "Fc-region of an immunoglobulin" means in the context of the present invention that a connecting region, e.g. hinge depending on the subtype of antibody, and the CH2 and CH3 region of an immunoglobulin are present, e.g. a human IgG1, IgG2, IgG3, IgG4, IgD, IgA1, IgGA2, IgM, or IgE. The polypeptide is not limited to human origin but can be of any origin, such as e.g. mouse or cynomolgus origin.

The term "wild type Fc-region" means in the context of the present invention an immunoglobulin Fc region with an amino acid sequence as it occurs in nature.

The term "hinge region" as used herein is intended to refer to the hinge region of an immunoglobulin heavy chain. Thus, for example the hinge region of a human IgG1 antibody corresponds to amino acids 216-230 according to the EU numbering.

The term "CH2 region" or "CH2 domain" as used herein is intended to refer to the CH2 region of an immunoglobulin heavy chain. Thus, for example the CH2 region of a human IgG1 antibody corresponds to amino acids 231-340 according to the EU numbering. However, the CH2 region may also be any of the other subtypes as described herein.

The term "CH3 region" or "CH3 domain" as used herein is intended to refer to the CH3 region of an immunoglobulin heavy chain. Thus, for example the CH3 region of a human IgG1 antibody corresponds to amino acids 341-447 according to the EU numbering. However, the CH3 region may also be any of the other subtypes as described herein.

The term "immunoglobulin" refers to a class of structurally related glycoproteins consisting of two pairs of polypeptide chains, one pair of light (L) low molecular weight chains and one pair of heavy (H) chains, all four potentially inter-connected by disulfide bonds. The structure of immunoglobulins has been well characterized. See for instance Fundamental Immunology Ch. 7 (Paul, W., ed., 2nd ed. Raven Press, N.Y. (1989)). Briefly, each heavy chain typically is comprised of a heavy chain variable region (abbreviated herein as VH) and a heavy chain constant region. The heavy chain constant region typically is comprised of three domains, CH1, CH2, and CH3. The heavy chains are inter-connected via disulfide bonds in the so-called "hinge region". Each light chain typically is comprised of a light chain variable region (abbreviated herein as VL) and a light chain constant region. The light chain constant region typically is comprised of one domain, CL. The VH and VL regions may be further subdivided into regions of hypervariability (or hypervariable regions which may be hypervariable in sequence and/or form of structurally defined loops), also termed complementarity determining regions (CDRs), interspersed with regions that are more conserved, termed framework regions (FRs). Each VH and VL is typically composed of three CDRs and four FRs, arranged from amino-terminus to carboxy-terminus in the following order: FR1, CDR1, FR2, CDR2, FR3, CDR3, FR4 (see also Chothia and Lesk J. Mol. Biol. 196, 901 917 (1987)). Unless otherwise stated or contradicted by context, CDR sequences herein are identified according to IMGT rules using DomainGapAlign (Lefranc M P., Nucleic Acids Research 1999; 27:209-212 and Ehrenmann F., Kaas Q. and Lefranc M.-P. Nucleic Acids Res., 38, D301-307 (2010); see also internet http address www.imgt.org/. Unless otherwise stated or contradicted by context, reference to amino acid positions in the Fc region/Fc domain in the present invention is according to the EU-numbering (Edelman et al., Proc Natl Acad Sci USA. 1969 May; 63(1):78-85; Kabat et al., Sequences of proteins of immunological interest. 5th Edition—1991 NIH Publication No. 91-3242).

The term "antibody" (Ab) in the context of the present invention refers to an immunoglobulin molecule, a fragment of an immunoglobulin molecule, or a derivative of either thereof, which has the ability to specifically bind to an antigen. The antibody of the present invention comprises an Fc-domain of an immunoglobulin and an antigen-binding region. An antibody generally contains two CH2-CH3 regions and a connecting region, e.g. a hinge region, e.g. at least an Fc-domain. Thus, the antibody of the present invention may comprise an Fc region and an antigen-binding region. The variable regions of the heavy and light chains of the immunoglobulin molecule contain a binding domain that interacts with an antigen. The constant or "Fc" regions of the antibodies may mediate the binding of the immunoglobulin to host tissues or factors, including various cells of the immune system (such as effector cells) and components of the complement system such as C1q, the first component in the classical pathway of complement activation. An antibody may also be a multispecific antibody, such as a bispecific antibody or similar molecule. The term "bispecific antibody" refers to an antibody having specificities for at least two different, typically non-overlapping, epitopes. Such epitopes may be on the same or different targets. If the epitopes are on different targets, such targets may be on the same cell or different cells or cell types. As indicated above, unless otherwise stated or clearly contradicted by the context, the term antibody herein includes fragments of an antibody which comprise at least a portion of an Fc-region and which retain the ability to specifically bind to the antigen. Such fragments may be provided by any known technique, such as enzymatic cleavage, peptide synthesis and recombinant expression techniques. It has been shown that the antigen-binding function of an antibody may be performed by fragments of a full-length antibody. Examples of binding fragments encompassed within the term "Ab" or "antibody" include, without limitation, monovalent antibodies (described in WO2007059782 by Genmab); heavy-chain antibodies, consisting only of two heavy chains and naturally occurring in e.g. camelids (e.g., Hamers-Casterman (1993) Nature 363:446); ThioMabs (Roche, WO2011069104), strand-exchange engineered domain (SEED or Seed-body) which are asymmetric and bispecific antibody-like molecules (Merck, WO2007110205); Triomab (Pharma/Fresenius Biotech, Lindhofer et al. 1995 J Immunol 155:219; WO2002020039); FcΔAdp (Regeneron, WO2010151792), Azymetric Scaffold (Zymeworks/Merck, WO2012/058768), mAb-Fv (Xencor, WO2011/028952), Xmab (Xencor), Dual variable domain immunoglobulin (Abbott, DVD-Ig, U.S. Pat. No. 7,612,181); Dual domain double head antibodies (Unilever; Sanofi Aventis, WO20100226923), Di-diabody (ImClone/Eli Lilly), Knobs-into-holes antibody formats (Genentech, WO9850431); DuoBody (Genmab, WO 2011/131746); Bispecific IgG1 and IgG2 (Pfizer/Rinat, WO11143545), DuetMab (MedImmune, US2014/0348839), Electrostatic steering antibody formats (Amgen, EP1870459 and WO 2009089004; Chugai, US201000155133; Oncomed, WO2010129304A2); bispecific IgG1 and IgG2 (Rinat neurosciences Corporation, WO11143545), CrossMAbs (Roche, WO2011117329), LUZ-Y (Genentech), Biclonic (Merus, WO2013157953), Dual Targeting domain antibodies (GSK/Domantis), Two-in-one Antibodies or Dual action Fabs recognizing two targets (Genentech, NovImmune, Adimab), Cross-linked Mabs (Karmanos Cancer Center), covalently fused mAbs (AIMM), CovX-body (CovX/Pfizer), FynomAbs (Covagen/Janssen ilag), DutaMab (Dutalys/Roche), iMab (MedImmune), IgG-like Bispecific (ImClone/Eli Lilly, Shen, J., et al. J Immunol Methods, 2007. 318(1-2): p. 65-74), TIG-body, DIG-body and PIG-body (Pharmabcine), Dual-affinity retargeting molecules (Fc-DART or Ig-DART, by Macrogenics, WO/2008/157379, WO/2010/080538), BEAT (Glenmark), Zybodies (Zyngenia), approaches with common light chain (Crucell/Merus, U.S. Pat. No. 7,262,028) or common heavy chains (κλBodies by NovImmune, WO2012023053), as well as fusion proteins comprising a polypeptide sequence fused to an antibody fragment containing an Fc-region like scFv-fusions, like BsAb by ZymoGenetics/BMS, HERCULES by Biogen Idec (U.S. Ser. No. 00/795, 1918), SCORPIONS by Emergent BioSolutions/Trubion and Zymogenetics/BMS, Ts2Ab (MedImmune/AZ (Dimasi, N., et al. J Mol Biol, 2009. 393(3): p. 672-92), scFv fusion by Genetech/Roche, scFv fusion by Novartis, scFv fusion by Immunomedics, scFv fusion by Changzhou Adam Biotech Inc (CN 102250246), TvAb by Roche (WO 2012025525, WO 2012025530), mAb$^2$ by f-Star (WO2008/003116), and dual scFv-fusions. It also should be understood that the term antibody, unless specified otherwise, also includes polyclonal antibodies, monoclonal antibodies (such as human monoclonal antibodies), antibody mixtures (recombinant polyclonals) for instance generated by technologies exploited by Symphogen and Merus (Oligoclonics), multimeric Fc proteins as described in WO2015/158867, fusion proteins as described in WO2014/031646 and antibody-like polypeptides, such as chimeric antibodies and humanized antibodies. An antibody as generated can potentially possess any isotype.

The term "full-length antibody" when used herein, refers to an antibody (e.g., a parent antibody) which contains all heavy and light chain constant and variable domains corresponding to those that are normally found in a wild-type antibody of that isotype.

The term "human antibody", as used herein, is intended to include antibodies having variable and constant regions derived from human germline immunoglobulin sequences. The human antibodies of the invention may include amino acid residues not encoded by human germline immunoglobulin sequences (e.g., mutations, insertions or deletions introduced by random or site-specific mutagenesis in vitro or by somatic mutation in vivo). However, the term "human antibody", as used herein, is not intended to include antibodies in which CDR sequences derived from the germline of another mammalian species, such as a mouse, have been grafted onto human framework sequences.

The term "chimeric antibody", as used herein, refers to an antibody in which both chain types i.e. heavy chain and light chain are chimeric as a result of antibody engineering. A chimeric chain is a chain that contains a foreign variable domain (originating from a non-human species, or synthetic or engineered from any species including human) linked to a constant region of human origin.

The term "humanized antibody, as used herein, refers to an antibody in which both chain types are humanized as a result of antibody engineering. A humanized chain is typically a chain in which the complementarity determining regions (CDR) of the variable domains are foreign (originating from a species other than human, or synthetic) whereas the remainder of the chain is of human origin. Humanization assessment is based on the resulting amino acid sequence, and not on the methodology per se, which allows protocols other than grafting to be used.

The terms "monoclonal antibody", "monoclonal Ab", "monoclonal antibody composition", "mAb", or the like, as used herein refer to a preparation of Ab molecules of single molecular composition. A monoclonal antibody composition displays a single binding specificity and affinity for a particular epitope. Accordingly, the term "human monoclonal antibody" refers to Abs displaying a single binding specificity which have variable and constant regions derived from human germline immunoglobulin sequences. The human mAbs may be generated by a hybridoma which includes a B cell obtained from a transgenic or trans-chromosomal non-human animal, such as a transgenic mouse, having a genome comprising a human heavy chain transgene repertoire and a light chain transgene repertoire, rearranged to produce a functional human antibody and fused to an immortalized cell.

The term "isotype" as used herein, refers to the immunoglobulin class (for instance IgG1, IgG2, IgG3, IgG4, IgD, IgA1, IgA2, IgE, or IgM or any allotypes thereof such as IgG1m(za) and IgG1m(f)) that is encoded by heavy chain constant region genes. Further, each heavy chain isotype can be combined with either a kappa (κ) or lambda (λ) light chain. The term "mixed isotype" used herein refers to Fc region of an immunoglobulin generated by combining structural features of one isotype with the analogous region from another isotype thereby generating a hybrid isotype. A mixed isotype may comprise an Fc region having a sequence comprised of two or more isotypes selected from the following IgG1, IgG2, IgG3, IgG4, IgD, IgA1, IgGA2, IgE, or IgM thereby generating combinations such as e.g. IgG1/IgG3, IgG1/IgG4, IgG2/IgG3, IgG2/IgG4 or IgG1/IgA.

The term "antigen-binding region", "antigen binding region", "binding region" or antigen binding domain, as used herein, refers to a region of an antibody which is capable of binding to the antigen. This binding region is typically defined by the VH and VL domains of the antibody which may be further subdivided into regions of hypervariability (or hypervariable regions which may be hypervariable in sequence and/or form of structurally defined loops), also termed complementarity determining regions (CDRs), interspersed with regions that are more conserved, termed framework regions (FRs). The antigen can be any molecule, such as a polypeptide, e.g. present on a cell, bacterium, or virion.

The term "target", as used herein, refers to a molecule to which the antigen binding region of the antibody binds. The target includes any antigen towards which the raised antibody is directed. The term "antigen" and "target" may in relation to an antibody be used interchangeably and constitute the same meaning and purpose with respect to any aspect or embodiment of the present invention.

The term "epitope" means a protein determinant capable of specific binding to an antibody variable domain. Epitopes usually consist of surface groupings of molecules such as amino acids, sugar side chains or a combination thereof and usually have specific three-dimensional structural characteristics, as well as specific charge characteristics. Conformational and non-conformational epitopes are distinguished in that the binding to the former but not the latter is lost in the presence of denaturing solvents. The epitope may comprise amino acid residues directly involved in the binding (also called immunodominant component of the epitope) and other amino acid residues, which are not directly involved in the binding.

A "antibody" or "antibody variant" or "variant of a parent antibody" of the present invention is an antibody molecule which comprises one or more mutations as compared to a "parent antibody". The different terms may be used interchangeably and constitute the same meaning and purpose with respect to any aspect or embodiment of the present invention. Exemplary parent antibody formats include, without limitation, a wild-type antibody, a full-length antibody or Fc-containing antibody fragment, a bispecific antibody, a human antibody, humanized antibody, chimeric antibody or any combination thereof. Similarly, a "polypeptide" or "a variant of a polypeptide comprising an Fc-region of an immunoglobulin and a binding region" or "a variant of a parent polypeptide comprising an Fc-region of an immunoglobulin and a binding region" of the present invention is a "polypeptide comprising an Fc-region of an immunoglobulin and a binding region", which comprises one or more mutations as compared to a "parent polypeptide comprising an Fc-region of an immunoglobulin and a binding region". The different terms may be used interchangeably and constitute the same meaning and purpose with respect to any aspect or embodiment of the present invention. Amino acid substitutions may exchange a native amino acid for another naturally-occurring amino acid, or for a non-naturally-occurring amino acid derivative. The amino acid substitution may be conservative or non-conservative. In the context of the present invention, conservative substitutions may be defined by substitutions within the classes of amino acids reflected in one or more of the following three tables:

| Amino acid residue classes for conservative substitutions | |
| --- | --- |
| Acidic Residues | Asp (D) and Glu (E) |
| Basic Residues | Lys (K), Arg (R), and His (H) |
| Hydrophilic Uncharged Residues | Ser (S), Thr (T), Asn (N), and Gln (Q) |
| Aliphatic Uncharged Residues | Gly (G), Ala (A), Val (V), Leu (L), and Ile (I) |
| Non-polar Uncharged Residues | Cys (C), Met (M), and Pro (P) |
| Aromatic Residues | Phe (F), Tyr (Y), and Trp (W) |

| Alternative conservative amino acid residue substitution classes | | | |
| --- | --- | --- | --- |
| 1 | A | S | T |
| 2 | D | E | |
| 3 | N | Q | |
| 4 | R | K | |
| 5 | I | L | M |
| 6 | F | Y | W |

| Alternative Physical and Functional Classifications of Amino Acid Residues | |
| --- | --- |
| Alcohol group-containing residues | S and T |
| Aliphatic residues | I, L, V, and M |
| Cycloalkenyl-associated residues | F, H, W, and Y |
| Hydrophobic residues | A, C, F, G, H, I, L, M, R, T, V, W, and Y |
| Negatively charged residues | D and E |
| Polar residues | C, D, E, H, K, N, Q, R, S, and T |
| Positively charged residues | H, K, and R |
| Small residues | A, C, D, G, N, P, S, T, and V |
| Very small residues | A, G, and S |
| Residues involved in turn formation | A, C, D, E, G, H, K, N, Q, R, S, P, and T |
| Flexible residues | Q, T, K, S, G, N, D, E, and R |

In the context of the present invention, a substitution in a variant is indicated as:

Original amino acid—position—substituted amino acid;

The three letter code, or one letter code, are used, including the codes Xaa and X to indicate amino acid residue. Accordingly, the notation "E345R" or "Glu345Arg" means, that the variant comprises a substitution of Glutamic acid with Arginine in the variant amino acid position corresponding to the amino acid in position 345 in the parent antibody.

Where a position as such is not present in an antibody, but the variant comprises an insertion of an amino acid, for example:

Position—substituted amino acid; the notation, e.g., "448E" is used.

Such notation is particular relevant in connection with modification(s) in a series of homologous polypeptides or antibodies.

Similarly when the identity of the substitution amino acid residues(s) is immaterial:

Original amino acid—position; or "E345".

For a modification where the original amino acid(s) and/or substituted amino acid(s) may comprise more than one, but not all amino acid(s), the substitution of Glutamic acid for Arginine, Lysine or Tryptophan in position 345:

"Glu345Arg, Lys,Trp" or "E345R,K,W" or "E345R/K/W" or "E345 to R, K or W" may be used interchangeably in the context of the invention.

Furthermore, the term "a substitution" embraces a substitution into any one of the other nineteen natural amino acids, or into other amino acids, such as non-natural amino acids. For example, a substitution of amino acid E in position 345 includes each of the following substitutions: 345A, 345C, 345D, 345G, 345H, 345F, 345I, 345K, 345L, 345M, 345N, 345P, 345Q, 345R, 345S, 345T, 345V, 345W, and 345Y. This is equivalent to the designation 345X, wherein the X designates any amino acid. These substitutions can also be designated E345A, E345C, etc, or E345A, C, etc, or E345A/C/etc. The same applies to analogy to each and every position mentioned herein, to specifically include herein any one of such substitutions.

As used herein, the term "effector cell" refers to an immune cell which is involved in the effector phase of an immune response, as opposed to the recognition and activation phases of an immune response. Exemplary immune cells include a cell of a myeloid or lymphoid origin, for instance lymphocytes (such as B cells and T cells including cytolytic T cells (CTLs)), killer cells, natural killer cells, macrophages, monocytes, eosinophils, polymorphonuclear cells, such as neutrophils, granulocytes, mast cells, and basophils. Some effector cells express Fc receptors (FcRs) or complement receptors and carry out specific immune functions. In some embodiments, an effector cell such as, e.g., a natural killer cell, is capable of inducing ADCC. For example, monocytes, macrophages, neutrophils, dendritic cells and Kupffer cells which express FcRs, are involved in specific killing of target cells and presenting antigens to other components of the immune system, or binding to cells that present antigens. In some embodiments the ADCC can be further enhanced by antibody driven classical complement activation resulting in the deposition of activated C3 fragments on the target cell. C3 cleavage products are ligands to complement receptors (CRs), such as CR3, expressed on myeloid cells. The recognition of complement fragments by CRs on effector cells may promote enhanced Fc receptor-mediated ADCC. In some embodiments antibody driven classical complement activation leads to C3 fragments on the target cell. These C3 cleavage products may promote direct complement-dependent cellular cytotoxicity (CDCC). In some embodiments, an effector cell may phagocytose a target antigen, target particle or target cell. The expression of a particular FcR or complement receptor on an effector cell may be regulated by humoral factors such as cytokines. For example, expression of FcγRI has been found to be up-regulated by interferon γ (IFN γ) and/or G-CSF. This enhanced expression increases the cytotoxic activity of FcγRI-bearing cells against targets. An effector cell can phagocytose a target antigen or phagocytose or lyse a target cell. In some embodiments antibody driven classical complement activation leads to C3 fragments on the target cell. These C3 cleavage products may promote direct phagocytosis by effector cells or indirectly by enhancing antibody mediated phagocytosis.

The term "Fc effector functions," as used herein, is intended to refer to functions that are a consequence of binding a polypeptide or antibody to its target, such as an antigen, on a cell membrane wherein the Fc effector function is attributable to the Fc region of the polypeptide or antibody. Examples of Fc effector functions include (i) C1q-binding, (ii) complement activation, (iii) complement-dependent cytotoxicity (CDC), (iv) antibody-dependent cell-mediated cytotoxity (ADCC), (v) Fc-gamma receptor-binding, (vi) antibody-dependent cellular phagocytosis (ADCP), (vii) complement-dependent cellular cytotoxicity (CDCC), (viii) complement-enhanced cytotoxicity, (ix) binding to complement receptor of an opsonized antibody mediated by the antibody, (x) opsonisation, and (xi) a combination of any of (i) to (x).

The term "clustering-dependent functions," as used herein, is intended to refer to functions that are a consequence of the formation of antigen complexes after oligomerization of polypeptides or antibodies bound to their antigens, optionally on a cell, on a cell membrane, on a virion, or on another particle. Examples of clustering-dependent effector functions include (i) antibody oligomer formation, (ii) antibody oligomer stability, (iii) antigen oligomer formation, (iv) antigen oligomer stability, (v) induction of apoptosis, (vi) proliferation modulation, such as proliferation reduction, inhibition or stimulation, and (vii) a combination of any of (i) to (vi).

The term "agonistic", as used herein, is understood as stimulation or activation of a receptor on a cell membrane resulting in a biological response such as, intracellular signaling. Such an agonistic effect could result in, induction of apoptosis (programmed cell death) or activation of immune cells, or activation of an intracellular pathway.

Agonistic activity or increased agonistic activity may be determined in a viability assay for antibodies directed to targets expressing an intracellular death domain, as described in Example 2 using the following steps of:

i) Seed a cell line expressing a target corresponding to an antibody e.g. DR5 in polystyrene 96-well flat-bottom plate overnight 37° C., ii) Add a serial dilution of the antibody e.g. an anti-DR5 antibody in a range (0.0003 to 20,000 ng/mL) and incubate for 3 days at 37° C., iii) Determine cell viability by quantifying the presence of ATP e.g. by use of CellTiler-Glo luminescent cell viability assay, iv) Calculate the viable cells using the following formula: % viable cells=[(luminescence antibody sample−luminescence staurosporine sample)/(luminescence no antibody sample−luminescence staurosporine sample)]*100.

Agonistic activity or increased agonistic activity may be determined in a reporter assay for antibodies directed to targets activating intracellular signaling pathway, as described in Example 29, 30, 31 and 32 using the following steps of:

i) Seed Jurkat cells stably transfected with the target e.g. OX40, 4-1BB, CD40 or GITR and a luciferase reporter gene downstream of an NFAT response element expressing, the cells are incubated in a 96-well flat-bottom plate overnight 37° C., ii) Add a serial dilution of the antibody e.g. an anti-OX49, anti-4-1BB, anti-CD40 or anti-GITR antibody in a range e.g. 19.5 to 5,000 ng/mL and incubate for 5 hours, iii) Add a firefly luciferase substrate (5'-fluoroluciferin) to the cells and incubate for 5-10 minutes, iv) Determine the luminescence using an Envision MultiLable Plate reader.

The term "vector," as used herein, is intended to refer to a nucleic acid molecule capable of inducing transcription of a nucleic acid segment ligated into the vector. One type of vector is a "plasmid", which is in the form of a circular double stranded DNA loop. Another type of vector is a viral vector, wherein the nucleic acid segment may be ligated into the viral genome. Certain vectors are capable of autonomous replication in a host cell into which they are introduced (for instance bacterial vectors having a bacterial origin of replication and episomal mammalian vectors). Other vectors (such as non-episomal mammalian vectors) may be integrated into the genome of a host cell upon introduction into the host cell, and thereby are replicated along with the host genome. Moreover, certain vectors are capable of directing the expression of genes to which they are operatively linked. Such vectors are referred to herein as "recombinant expression vectors" (or simply, "expression vectors"). In general, expression vectors of utility in recombinant DNA techniques are often in the form of plasmids. In the present specification, "plasmid" and "vector" may be used interchangeably as the plasmid is the most commonly used form of vector. However, the present invention is intended to include such other forms of expression vectors, such as viral vectors (such as replication defective retroviruses, adenoviruses and adeno-associated viruses), which serve equivalent functions.

The term "recombinant host cell" (or simply "host cell"), as used herein, is intended to refer to a cell into which an expression vector has been introduced. It should be understood that such terms are intended to refer not only to the particular subject cell, but also to the progeny of such a cell. Because certain modifications may occur in succeeding generations due to either mutation or environmental influences, such progeny may not, in fact, be identical to the parent cell, but are still included within the scope of the term "host cell" as used herein. Recombinant host cells include, for example, transfectomas, such as CHO cells, HEK-293 cells, PER.C6, NS0 cells, and lymphocytic cells, and prokaryotic cells such as E. coli and other eukaryotic hosts such as plant cells and fungi.

The term "transfectoma", as used herein, includes recombinant eukaryotic host cells expressing the Ab or a target antigen, such as CHO cells, PER.C6, NS0 cells, HEK-293 cells, plant cells, or fungi, including yeast cells.

The term "preparation" refers to preparations of antibody variants and mixtures of different antibody variants which can have an increased ability to form oligomers when interacting with antigen associated with a cell (e.g., an antigen expressed on the surface of the cell), a cell membrane, a virion or other structure, which may result in enhanced signaling and/or activation by the antigen.

As used herein, the term "affinity" is the strength of binding of one molecule, e.g. an antibody, to another, e.g. a target or antigen, at a single site, such as the monovalent binding of an individual antigen binding site of an antibody to an antigen.

As used herein, the term "avidity" refers to the combined strength of multiple binding sites between two structures, such as between multiple antigen binding sites of antibodies simultaneously interacting with a target or e.g. between antibody and C1q. When more than one binding interactions are present, the two structures will only dissociate when all binding sites dissociate, and thus, the dissociation rate will be slower than for the individual binding sites, and thereby providing a greater effective total binding strength (avidity) compared to the strength of binding of the individual binding sites (affinity).

As used herein, the term "oligomer" refers to a molecule that consists of more than one but a limited number of monomer units (e.g. antibodies) in contrast to a polymer that, at least in principle, consists of an unlimited number of monomers. Exemplary oligomers are dimers, trimers, tetramers, pentamers and hexamers. Greek prefixes are often used to designate the number of monomer units in the oligomer, for example a tetramer being composed of four units and a hexamer of six units.

The term "oligomerization", as used herein, is intended to refer to a process that converts monomers to a finite degree of polymerization. Herein, it is observed, that, polypeptides, antibodies and/or other dimeric proteins comprising target-binding regions according to the invention can form oligomers, such as hexamers, via non-covalent association of Fc-regions after target binding, e.g., at a cell surface.

The term "clustering", as used herein, is intended to refer to oligomerization of antibodies, polypeptides, antigens or other proteins through non-covalent interactions.

The term "Fc-Fc enhancing", as used herein, is intended to refer to increasing the binding strength between, or stabilizing the interaction between, the Fc regions of two Fc-region containing antibodies or polypeptides so that the polypeptides form oligomers upon target binding.

Fc-Fc enhancing substitutions, as used herein refer to substitutions in the following positions corresponding to human IgG1 according to EU numbering E430, E345 or S440 with the proviso that the substitutions in position S440 is S440Y or S440W. Thus, Fc-Fc enhancing substitutions as used herein refer to the following amino acid substitutions E430G, E345K, E430S, E430F, E430T, E345Q, E345R, E345Y, S440W and S440Y. In a preferred embodiment the Fc-Fc enhancing substitution is E430G or E345K.

The term "C1q binding" as used herein, is intended to refer to the direct interaction between C1q and polypeptide or antibody. Direct C1q binding can be evaluated for example by using immobilized antibody on artificial surface (as described in Examples 4, 5 and 6). The multivalent interaction resulting in high avidity binding of C1q to an antibody oligomer can be evaluated when bound to a predetermined antigen on a cellular or virion surface.

C1q binding to a polypeptide or an antibody may be demined in an ELISA assay using the following steps i) coat a 96-well Microlon ELISA plate with the 1 µg/mL of polypeptide or antibody in 100 µl PBS at 4 C overnight, ii) incubate the plate with 100 µL/well of a serial dilution series of C1q, final C1q concentration range 30-0.01 µg/mL in 3 fold dilutions for 1h at 37 C, iii) incubate the plate with 100 µl/well of rabbit anti-human C1q for 1h at RT, iv) incubate the plate with 100 µl/well swine anti-rabbit IgG-HRP for 1h at RT, v) incubate the plate with 100 µL/well of substrate with 1 mg/mL 2,2'-azino-bis (3-ethylbenzothiazoline-6-sulfonic acid) for 15 min at RT, vi) the reaction is stopped by adding 100 µL 2% oxalic acid/well. The absorbance is measured at 405 nm in a BioTek EL808 Microplate reader.

The term C1q binding substitution as used herein, is intended to refer to a substitution in a polypeptide comprising an Fc region of an immunoglobulin and an antigen binding region, that enhances the direct interaction with C1q. Enhanced C1q binding can for example result in a decreased EC50 of the interaction between C1q and the polypeptide comprising an Fc region of an immunoglobulin and an antigen binding region, measured according to the method to determine C1q binding described above.

As used herein, the term "complement activation" refers to the activation of the classical complement pathway, which is initiated by a large macromolecular complex called C1 binding to antibody-antigen complexes on a surface. C1 is a complex, which consists of 6 recognition proteins C1q and a hetero-tetramer of serine proteases, C1r2C1s2. C1 is the first protein complex in the early events of the classical complement cascade that involves a series of cleavage reactions that starts with the cleavage of C4 into C4a and C4b and C2 into C2a and C2b. C4b is deposited and forms together with C2a an enzymatic active convertase called C3 convertase, which cleaves complement component C3 into C3b and C3a, which forms a C5 convertase This C5 convertase splits C5 in C5a and C5b and the last component is deposited on the membrane and that in turn triggers the late events of complement activation in which terminal complement components C5b, C6, C7, C8 and C9 assemble into the membrane attack complex (MAC). The complement cascade results in the creation of pores in the cell membrane which causes lysis of the cell, also known as complement-dependent cytotoxicity (CDC). Complement activation can be evaluated by using C1q efficacy, CDC kinetics CDC assays (as described in WO2013/004842, WO2014/108198) or by the method Cellular deposition of C3b and C4b described in Beurskens et al Apr. 1, 2012 vol. 188 no. 7 3532-3541.

The term "complement-dependent cytotoxicity" ("CDC"), as used herein, is intended to refer to the process of antibody-mediated complement activation leading to lysis of the cell or virion when the antibody bound to its target on a cell or virion as a result of pores in the membrane that are created by MAC assembly.

The term "antibody-dependent cell-mediated cytotoxicity" ("ADCC") as used herein, is intended to refer to a mechanism of killing of antibody-coated target cells or virions by cells expressing Fc receptors that recognize the constant region of the bound antibody. The term "antibody-dependent cellular phagocytosis" ("ADCP") as used herein is intended to refer to a mechanism of elimination of antibody-coated target cells or virions by internalization by phagocytes. The internalized antibody-coated target cells or virions are contained in a vesicle called a phagosome, which then fuses with one or more lysosomes to form a phagolysosome. ADCP may be evaluated by using an in vitro cytotoxicity assay with macrophages as effector cells and video microscopy as described by van Bij et al. in Journal of Hepatology Volume 53, Issue 4, October 2010, Pages 677-685.

The term "complement-dependent cellular cytotoxicity" ("CDCC") as used herein is intended to refer to a mechanism of killing of target cells or virions by cells expressing complement receptors that recognize complement 3 (C3) cleavage products that are covalently bound to the target cells or virions as a result of antibody-mediated complement activation. CDCC may be evaluated in a similar manner as described for ADCC.

The term "plasma half-life" as used herein indicates the time it takes to reduce the concentration of polypeptide in the blood plasma to one half of its initial concentration during elimination (after the distribution phase). For antibodies the distribution phase will typically be 1-3 days during which phase there is about 50% decrease in blood plasma concentration due to redistribution between plasma and tissues. The plasma half-life can be measured by methods well-known in the art.

The term "plasma clearance rate" as used herein is a quantitative measure of the rate at which a polypeptide is removed from the blood upon administration to a living organism. The plasma clearance rate may be calculated as the dose/AUC (mL/day/kg), wherein the AUC value (area under the curve) is determined from a concentration-time curve.

The term "antibody-drug conjugate", as used herein refers to an antibody or Fc-containing polypeptide having specificity for at least one type of malignant cell, a drug, and a linker coupling the drug to e.g. the antibody. The linker is cleavable or non-cleavable in the presence of the malignant cell; wherein the antibody-drug conjugate kills the malignant cell.

The term "antibody-drug conjugate uptake", as used herein refers to the process in which antibody-drug conjugates are bound to a target on a cell followed by uptake/engulfment by the cell membrane and thereby are drawn into the cell. Antibody-drug conjugate uptake may be evaluated as "antibody-mediated internalization and cell killing by anti-TF ADC in an in vitro killing assay" as described in WO 2011/157741.

The term "apoptosis", as used herein refers to the process of programmed cell death (PCD) that may occur in a cell. Biochemical events lead to characteristic cell changes (morphology) and death. These changes include blebbing, cell shrinkage, nuclear fragmentation, chromatin condensation, and chromosomal DNA fragmentation. Binding of an antibody to a certain receptor may induce apoptosis.

The term "programmed cell-death" or "PCD", as used herein refers to the death of a cell in any form mediated by an intracellular program. Different forms of PCD exist, the various types of PCD have in common that they are executed by active cellular processes that can be intercepted by interfering with intracellular signaling. In a particular embodiment, the occurrence of any form of PCD in a cell or tissue may be determined by staining the cell or tissue with conjugated Annexin V, correlating to phosphatidylserine exposure.

The term "Annexin V", as used herein, refers to a protein of the annexin group that binds phosphatidylserine (PS) on the cell surface.

The term "FcRn", as used herein is intended to refer to neonatal Fc receptor which is an Fc receptor. It was first discovered in rodents as a unique receptor capable of transporting IgG from mother's milk across the epithelium of newborn rodent's gut into the newborn's bloodstream. Further studies revealed a similar receptor in humans. In humans, however, it is found in the placenta to help facilitate transport of mother's IgG to the growing fetus and it has also been shown to play a role in monitoring IgG turnover. FcRn binds IgG at acidic pH of 6.0-6.5 but not at neutral or higher pH. Therefore, FcRn can bind IgG from the intestinal lumen (the inside of the gut) at a slightly acidic pH and ensure efficient unidirectional transport to the basolateral side (inside the body) where the pH is neutral to basic (pH 7.0-7.5). This receptor also plays a role in adult salvage of IgG through its occurrence in the pathway of endocytosis in endothelial cells. FcRn receptors in the acidic endosomes bind to IgG internalized through pinocytosis, recycling it to the cell surface, releasing it at the basic pH of blood, thereby preventing it from undergoing lysosomal degradation. This mechanism may provide an explanation for the greater half-life of IgG in the blood compared to other isotypes.

The term "Protein A", as used herein is intended to refer to a 56 kDa MSCRAMM surface protein originally found in the cell wall of the bacterium *Staphylococcus aureus*. It is encoded by the spa gene and its regulation is controlled by DNA topology, cellular osmolarity, and a two-component system called ArlS-ArlR. It has found use in biochemical research because of its ability to bind immunoglobulins. It is composed of five homologous Ig-binding domains that fold into a three-helix bundle. Each domain is able to bind proteins from many of mammalian species, most notably IgGs. It binds the heavy chain Fc region of most immunoglobulins (overlapping the conserved binding site of FcRn receptors) and also interacts with the Fab region of the human VH3 family. Through these interactions in serum, IgG molecules bind the bacteria via their Fc region instead of solely via their Fab regions, by which the bacteria disrupts opsonization, complement activation and phagocytosis.

The term "Protein G", as used herein is intended to refer to an immunoglobulin-binding protein expressed in group C and G Streptococcal bacteria much like Protein A but with differing specificities. It is a 65-kDa (G148 protein G) and a 58 kDa (C40 protein G) cell surface protein that has found application in purifying antibodies through its binding to the Fc region.

Specific Embodiments of the Invention

As described herein, surprisingly, substitutions of amino acids in the Fc region of a polypeptide or antibody provides polypeptides or antibodies with enhanced effector functions e.g. CDC and/or agonistic activity. The inventors found that by introducing a mutation which enhances Fc-Fc interactions such as a substitution at a position selected from the group consisting of: E430, E345 and S440 together with a C1q binding substitution, the Fc effector functions of the polypeptide or antibody may be enhanced. Furthermore, the inventors also found that the combination of a Fc-Fc enhancing mutation and a C1q binding substitution may result in polypeptides, such as antibodies, with agonistic properties or enhanced agonistic properties.

In one aspect the present invention provides a polypeptide or an antibody comprising an Fc region of a human immunoglobulin and an antigen binding region, wherein the Fc region comprises a) at least one Fc-Fc enhancing substitution at a position selected from the group consisting of: E430, E345 and S440, with the proviso that the mutation in S440 is S440Y or S440W, and b) at least one C1q binding substitution, wherein the positions correspond to human IgG1, according to EU numbering (Edelman et al., Proc Natl Acad Sci USA. 1969 May; 63(1):78-85; Kabat et al., Sequences of Proteins of Immunological Interest, Fifth Edition. 1991 NIH Publication No. 91-3242)

In one aspect of the invention provides for a polypeptide or antibody comprising an Fc region of an immunoglobulin and an antigen binding region, wherein the Fc region comprises, a) a substitution at a position selected from the group consisting of: E430, E345 or a S440Y or S440W substitution, and b) a substitution at one or more position(s) selected from the group consisting of: G236, S239, S267, H268, S324 K326, I332, E333 and P396, wherein the positions correspond to human IgG1, according to EU numbering.

A substitution at a position corresponding to E430, E345 or a S440Y or S440W substitution is considered an Fc-Fc enhancing substitution according to the present invention.

A substitution at one or more position(s) selected from the group consisting of: G236, S239, S267, H268, S324 K326, I332, E333 and P396, is considered a C1q binding substitution according to the present invention.

A mutation in one of the following positions E430, E345 or S440 with the proviso that the mutation in S440 is S440Y or S440W introduces the effect of enhanced Fc-Fc interactions and oligomerization in the polypeptide or antibody. The enhanced oligomerization occurs when the antigen binding region of the polypeptide or antibody is bound to the corresponding target antigen. The enhanced oligomerization generates oligomers such as e.g. hexamers. The generation of oligomeric structures, such as hexamers has the effect of increasing Fc effector functions e.g. CDC by increasing C1q binding avidity of the polypeptide. The combination of a Fc-Fc enhancing mutation with a C1q binding substitution such as one or more substitution(s) at a position selected from the group of: G236, S239, S267, H268, S324 K326, I332, E333 and P396, generates a polypeptide or antibody with enhanced effector functions. The combination of an Fc-Fc enhancing substitution and a C1q binding substitution further has the effect of generating a polypeptide or antibody with agonistic activity. In one embodiment the polypeptide or antibody may have increased agonistic activity when compared to a parent polypeptide or a parent antibody.

Polypeptides or antibodies according to the present invention are of particular interest when activating an intracellular signaling pathway through binding to a cell surface receptor.

In one embodiment according to the invention an increased or enhanced Fc effector function or activity of a polypeptide or antibody having a Fc-Fc enhancing substitution and a C1q binding substitution is to be understood as when the polypeptide or antibody is compared to a parent polypeptide or parent antibody, that is the parent polypeptide or parent antibody is without the substitutions according the invention but otherwise identical.

The present invention allows for novel polypeptide or antibody-based therapeutics with increased properties such as CDC an agonistic activity. That is the polypeptides or antibodies according to the invention have increased properties depending on the Fc region such as CDC and they have also increased properties depending on the antigen binding region such as agonistic activity.

In one aspect the present invention provides a polypeptide or an antibody comprising an Fc region of a human immunoglobulin and an antigen binding region, wherein the Fc region comprises a) a substitution at a position selected from the group consisting of: E430, E345 or a S440Y or S440W substitution, and b) a substitution at one or more a position(s) selected from the group of: G236, S239, S267, H268, S324 K326, I332, E333 and P396, wherein the positions correspond to human IgG1, according to EU numbering. In one embodiment of the invention the polypeptide or antibody comprises at least one substitution at a position selected from the group consisting of: E430, E345 or a S440Y or S440W substitution. In one embodiment of the invention the polypeptide or antibody comprises a substitution(s) at one or more position(s) selected from the group of: G236, S239, S267, H268, S324 K326, I332, E333 and P396.

In one embodiment of the invention the polypeptide or antibody comprises a substitution at two or three position(s) selected from the group consisting of: G236, S239, S267, H268, S324 K326, I332, E333 and P396.

In one embodiment of the invention the polypeptide or antibody comprises C1q binding substitutions selected form one of the groups consisting of;
  i) Two C1q binding substitutions at positions K326, E333
  ii) three C1q binding substitutions at positions f: K326, E333 and P396, and
  iii) three C1q binding substitutions at positions S267, H268 and S324.

In one embodiment of the invention one or more C1q binding substitution(s) are at a position selected from the group consisting of G236, S239, S267, H268, S324 K326, I332, E333 and P396, with the proviso that the substitution in position G236 is not G236F, G236R, G236Y.

In one embodiment of the invention one or more C1q binding substitution(s) are at a position selected from the group consisting of G236, S239, S267, H268, S324 K326, I332, E333 and P396, with the proviso that the substitution in position S267 is not S267H, 52671, S267K, S267G.

In one embodiment of the invention one or more C1q binding substitution(s) are at a position selected from the group consisting of G236, S239, S267, H268, S324 K326, I332, E333 and P396, with the proviso that the substitution in position H268 is not H268K, H268D, H268E.

In one embodiment of the invention at least one Fc-Fc enhancing substitution is selected from the group consisting of: E430G, E345K, E430S, E430F, E430T, E345Q, E345R, E345Y, S440W and S440Y.

In one embodiment of the invention at least one Fc-Fc enhancing substitution is selected from the group consisting of: E430G, E430S, E430F and E430T.

In one embodiment of the invention at least one Fc-Fc enhancing substitution is selected from the group consisting of: E345K, E345Q, E345R and E345Y.

In one embodiment of the invention the polypeptide or antibody has at least an E430G substitution. In one embodiment of the invention the polypeptide or antibody has at least an E345K substitution. In one embodiment of the invention the polypeptide or antibody has at least an E345R substitution. In one embodiment of the invention the polypeptide or antibody has at least a S440Y substitution.

In one embodiment of the invention the polypeptide or antibody comprises at least one substitution is selected from the group consisting of: E430G, E430S, E430F and E430T and a substitution at one or more position(s) selected from the group of: G236, S239, S267, H268, S324 K326, I332, E333 and P396.

In one embodiment of the invention the polypeptide or antibody comprises at least one a substitution is selected from the group consisting of: E430G, E430S, E430F and E430T and a substitution at one or more a position(s) selected from the group of: K326, E333 and P396.

In one embodiment of the invention the Fc region comprises an E430G substitution and a substitution at one or more position(s) selected from the group of: G236, S239, S267, H268, S324 K326, I332, E333 and P396.

In one embodiment of the invention the polypeptide or antibody comprises at least a substitution is selected from the group consisting of: E345K, E345Q, E345R and E345Y, and a substitution at one or more position(s) selected from the group of: G236, S239, S267, H268, S324 K326, I332, E333 and P396.

In one embodiment of the invention the polypeptide or antibody comprises at least a substitution is selected from the group consisting of: E345K, E345Q, E345R and E345Y, and a substitution at one or more position(s) selected from the group of: K326, E333 and P396.

In one embodiment of the invention the Fc region comprises a E345K substitution and a substitution at one or more positions selected from the group of: G236, S239, S267, H268, S324, K326, I332, E333 and P396.

In one embodiment of the invention the Fc region comprises a E345R substitution and a substitution at one or more position(s) selected from the group of: G236, S239, S267, H268, S324, K326, I332, E333 and P396.

In one embodiment of the invention the Fc region comprises at least a substitution is selected from the group consisting of: S440Y or S440W and a substitution at one or more position(s) selected from the group of: G236, S239, S267, H268, S324, K326, I332, E333 and P396.

In one embodiment of the invention the Fc region comprises at least a substitution selected from the group consisting of: S440Y or S440W and a substitution at one or more position(s) selected from the group of: K326, E333 and P396.

In one embodiment of the invention the Fc region comprises a S440Y substitution and a substitution at one or more position(s) selected from the group of: G236, S239, S267, H268, S324, K326, I332, E333 and P396.

Hereby are embodiments provided that allow for enhanced C1q binding and/or agonistic properties of polypeptides or antibodies upon cell surface antigen binding. In one embodiment the polypeptides or antibodies comprise enhanced agonistic properties. In one embodiment the polypeptides or antibodies comprise an Fc region comprising a first heavy chain and a second heavy chain, wherein one of the above mentioned substitutions may be present in the first and/or the second heavy chain.

In one embodiment of the invention the polypeptide or antibody comprises substitutions at one or more position(s) selected from the group consisting of: K326, E333 and P396. In one embodiment of the invention the polypeptide or antibody comprises a substitution, such as two or three substitutions at one or more position(s) selected from the group consisting of: K326, E333 and P396. In one embodiment of the invention the polypeptide or antibody comprises substitutions at positions K326 and E333. In one embodiment of the invention the polypeptide or antibody comprises substitutions at positions K326 and P396. In one embodiment of the invention the polypeptide or antibody comprises substitutions at positions P396 and E333. In one embodiment of the invention the polypeptide or antibody comprises substitutions at positions K326, E333 and P396.

In one embodiment of the invention the polypeptide or antibody comprises a substitution at position E430 and substitutions at one or more position(s) selected from the group consisting of: K326, E333 and P396. In one embodiment of the invention the polypeptide or antibody comprises a substitution at position E430 and a substitution at one or more positions, such as two or three position(s) selected from the group consisting of: K326, E333 and P396. In one embodiment of the invention the polypeptide or antibody comprises a substitution at position E430 and substitutions at the positions K326 and E333. In one embodiment of the invention the polypeptide or antibody comprises a substitution at position E430 and substitutions at the positions K326 and P396. In one embodiment of the invention the polypeptide or antibody comprises a substitution at position E430 and substitutions at the positions E333 and P396. In one embodiment of the invention the polypeptide or antibody comprises a substitution at position E430 and substitutions at the positions K326, E333 and P396.

In one embodiment of the invention the polypeptide or antibody comprises a substitution at position E345 and substitutions at one or more position(s) selected from the group consisting of: K326, E333 and P396. In one embodiment of the invention the polypeptide or antibody comprises a substitution at position E345 and a substitution at one or more positions, such as two or three position(s) selected from the group consisting of: K326, E333 and P396. In one embodiment of the invention the polypeptide or antibody comprises a substitution at position E345 and substitutions at the positions K326 and E333. In one embodiment of the invention the polypeptide or antibody comprises a substitution at position E345 and substitutions at the positions K326 and P396. In one embodiment of the invention the polypeptide or antibody comprises a substitution at position E345 and substitutions at the positions E333 and P396. In one embodiment of the invention the polypeptide or antibody comprises a substitution at position E345 and substitutions at the positions K326, E333 and P396.

In one embodiment of the invention the polypeptide or antibody comprises a substitution at S440Y or S440W and a substitution at one or more position(s) selected from the group consisting of: K326, E333 and P396. In one embodiment of the invention the polypeptide or antibody comprises a substitution S440Y or S440W and a substitution at one or more positions, such as two or three position(s) selected from the group consisting of: K326, E333 and P396. In one embodiment of the invention the polypeptide or antibody comprises a substitution at S440Y or S440W and substitutions at the positions K326 and E333. In one embodiment of the invention the polypeptide or antibody comprises a substitution at S440Y or S440W and substitutions at the positions K326 and P396. In one embodiment of the invention the polypeptide or antibody comprises a substitution at S440Y or S440W substitutions at the positions E333 and P396. In one embodiment of the invention the polypeptide or antibody comprises a substitution at S440Y or S440W substitutions at the positions K326, E333 and P396.

In one embodiment of the invention the polypeptide or antibody comprises a substitution at position K326 selected form the group consisting of: K326W, K326A, K326D, K326N, K326G, K326F, K326E, K326F, K326Y, K326H, and K326M.

In one embodiment of the invention the polypeptide or antibody comprises a substitution at position E333 selected form the group consisting of: E333S, E333A, E333T and E333G.

In one embodiment of the invention the polypeptide or antibody comprises a substitution at position E396 selected form the group consisting of: E396L, E396I, E396V, E396Q, E396N, and E396A.

In one embodiment of the invention the polypeptide or antibody comprises one or more, such as two or three substitutions selected from the group consisting of: K326W, E333S, and P396L. In one embodiment of the invention the polypeptide or antibody comprises one or more, such as two or three substitutions selected from the group consisting of: K326W, E333A and P396L. In one embodiment of the invention the polypeptide or antibody comprises one or more, such as two or three substitutions selected from the group consisting of: K326W, E333T and P396L. In one embodiment of the invention the polypeptide or antibody comprises one or more, such as two or three substitutions selected from the group consisting of: K326A, E333S, and P396L. In one embodiment of the invention the polypeptide or antibody comprises one or more, such as two or three substitutions selected from the group consisting of: K326A, E333A and P396L. In one embodiment of the invention the polypeptide or antibody comprises a K326A substitution. In one embodiment of the invention the polypeptide or antibody comprises a K326W substitution. In one embodiment of the invention the polypeptide or antibody comprises an E333S substitution. In one embodiment of the invention the polypeptide or antibody comprises an E333A substitution. In one embodiment of the invention the polypeptide or antibody comprises an E333T substitution. In one embodiment of the invention the polypeptide or antibody comprises a P396L substitution. In one embodiment of the invention the polypeptide or antibody comprises the substitutions K326W and E333S. In one embodiment of the invention the polypeptide or antibody comprises the substitutions K326W and E333T. In one embodiment of the invention the polypeptide or antibody comprises the substitutions K326W and E333A. In one embodiment of the invention the polypeptide or antibody comprises the substitutions K326W and P396L. In one embodiment of the invention the polypeptide or antibody comprises the substitutions K326A and E333A. In one embodiment of the invention the polypeptide or antibody comprises the substitutions K326A and E333S. In one embodiment of the invention the polypeptide or antibody comprises the substitutions K326A and E333T. In one embodiment of the invention the polypeptide or antibody comprises the substitutions K326A and P396L. In one embodiment of the invention the polypeptide or antibody comprises the substitutions E333A and P396L. In one embodiment of the invention the polypeptide or antibody comprises the substitutions E333S and P396L. In one embodiment of the invention the polypeptide or antibody comprises the substitutions K326A, E333A and P396L. In one embodiment of the invention the polypeptide or antibody comprises the substitutions K326S, E333A and P396L. In one embodiment of the invention the polypeptide or antibody comprises the substitutions K326W, E333A and P396L. In one embodiment of the invention the polypeptide or antibody comprises the substitutions K326W, E333S and P396L. In one embodiment of the invention the polypeptide or antibody comprises the substitutions K326W, E333T and P396L.

In one embodiment of the invention the polypeptide or antibody comprises one or more C1q binding substitutions at a position selected from the group consisting of: S267, H268 and S324. In one embodiment of the invention the polypeptide or antibody comprises one or more substitutions, such as two or three substitutions at a position selected from the group consisting of: S267, H268 and S324. In one embodiment of the invention the polypeptide or antibody comprises substitutions at the positions S267 and H268. In one embodiment of the invention the polypeptide or antibody comprises substitutions at the positions S267 and S324. In one embodiment of the invention the polypeptide or antibody comprises substitutions at the positions H268 and S324. In one embodiment of the invention the polypeptide or antibody comprises substitutions at the positions S267, H268 and S324.

In one embodiment of the invention the polypeptide or antibody comprises a substitution at position E430 and a substitutions at one or more position(s) selected from the group consisting of: S267, H268 and S324. In one embodiment of the invention the polypeptide or antibody comprises a substitution at position E430 and a substitution at one or more position(s) selected from the group consisting of: S267, H268 and S324. In one embodiment of the invention the polypeptide or antibody comprises a substitution at position E430 and substitutions at the positions S267 and H268. In one embodiment of the invention the polypeptide or antibody comprises a substitution at position E430 and substitutions at the positions S267 and S324. In one embodiment of the invention the polypeptide or antibody comprises a substitution at position E430 and substitutions at the positions H268 and S324. In one embodiment of the invention the polypeptide or antibody comprises a substitution at position E430 and substitutions at the positions S267, H268 and S324.

In one embodiment of the invention the polypeptide or antibody comprises a substitution at position E345 and a substitutions at one or more position(s) selected from the group consisting of: S267, H268 and S324. In one embodiment of the invention the polypeptide or antibody comprises a substitution at position E345 and a substitution at one or more position(s) selected from the group consisting of:

S267, H268 and S324. In one embodiment of the invention the polypeptide or antibody comprises a substitution at position E345 and substitutions at the positions S267 and H268. In one embodiment of the invention the polypeptide or antibody comprises a substitution at position E345 and substitutions at the positions S267 and S324. In one embodiment of the invention the polypeptide or antibody comprises a substitution at position E345 and substitutions at the positions H268 and S324. In one embodiment of the invention the polypeptide or antibody comprises a substitution at position E E345 and substitutions at the positions S267, H268 and S324.

In one embodiment of the invention the polypeptide or antibody comprises a substitution S440Y or S440W and a substitution at one or more position selected from the group consisting of: S267, H268 and S324. In one embodiment of the invention the polypeptide or antibody comprises a substitution S440Y or S440W and a substitution at one or more positions, such a two or three position(s) selected from the group consisting of: S267, H268 and S324. In one embodiment of the invention the polypeptide or antibody comprises a substitution S440Y or S440W and substitutions at the positions S267 and H268. In one embodiment of the invention the polypeptide or antibody comprises a substitution S440Y or S440W and substitutions at the positions S267 and S324. In one embodiment of the invention the polypeptide or antibody comprises a substitution S440Y or S440W and substitutions at the positions H268 and S324. In one embodiment of the invention the polypeptide or antibody comprises a substitution S440Y or S440W and substitutions at the positions S267, H268 and S324.

In one embodiment of the invention one or more substitutions selected from the group consisting of: S267E, H268F and S324T. In one embodiment of the invention the polypeptide or antibody comprises one or more, such as two or three substitutions selected from the group consisting of: S267E, H268F and S324T. In one embodiment of the invention the polypeptide or antibody comprises a S267E substitution. In one embodiment of the invention the polypeptide or antibody comprises a H268F substitution. In one embodiment of the invention the polypeptide or antibody comprises a S324T substitution. In one embodiment of the invention the polypeptide or antibody comprises the substitutions of S267E and H268F. In one embodiment of the invention the polypeptide or antibody comprises the substitutions S267E and S324T. In one embodiment of the invention the polypeptide or antibody comprises the substitutions H268F and S324T. In one embodiment of the invention the polypeptide or antibody comprises the substitutions S267E, H268F and S324T.

In one embodiment of the invention the polypeptide or antibody comprises, a) at least one substitution at a position selected form the group consisting of: E430, E345 or a S440Y or S440W substitution and, b) at least a substitution selected from one of the following groups consisting of:
  i. K326A,
  ii. E333A,
  iii. E333T
  iv. P396L,
  v. E333S,
  vi. K326W, E333S
  vii. K326W, E333T
  viii. K326A, E333A,
  ix. K326A, K333A, P396L
  x. S267E, H268F,
  xi. S267E, S324T,
  xii. H268F, S324T,
  xiii. S267E, H268F, S324T, and
  xiv. S324, I332.

In one embodiment of the invention the polypeptide or antibody comprises, a substitution at position E430 and at least a substitution selected from one of the following groups consisting of:
  i. K326A,
  ii. E333A,
  iii. E333T
  iv. P396L,
  v. E333S,
  vi. K326W, E333S
  vii. K326W, E333T
  viii. K326A, E333A,
  ix. K326A, K333A, P396L
  x. S267E, H268F,
  xi. S267E, S324T,
  xii. H268F, S324T
  xiii. S267E, H268F, S324T, and
  xiv. S324, I332.

Hereby embodiments are provided wherein one substitution is at position E430. In one embodiment the substitution at position E430 is selected from is the group consisting of: E430G, E430S, E430F, E430T.

In one embodiment of the invention the polypeptide or antibody comprises, an E430G substitution and a substitution selected from one of the following groups consisting of:
  i. K326A,
  ii. E333A,
  iii. E333T
  iv. P396L,
  v. E333S,
  vi. K326W, E333S
  vii. K326W, E333T
  viii. K326A, E333A,
  ix. K326A, K333A, P396L
  x. S267E, H268F,
  xi. S267E, S324T,
  xii. H268F, S324T,
  xiii. S267E, H268F, S324T, and
  xiv. S324, I332.

In one embodiment of the invention the polypeptide or antibody comprises, an E430G, K326W and E333S substitution. In one embodiment of the invention the polypeptide or antibody comprises, an E430G, K326A and E333A substitution. In one embodiment of the invention the polypeptide or antibody comprises, an E430G, K333A and P396L substitution. In one embodiment of the invention the polypeptide or antibody comprises, an E430G, K326A, E333A and P396L substitution In one embodiment of the invention the polypeptide or antibody comprises, an E430S, K326W and E333S substitution. In one embodiment of the invention the polypeptide or antibody comprises, an E430S, K326A and E333A substitution. In one embodiment of the invention the polypeptide or antibody comprises, an E430S, K333A and P396L substitution. In one embodiment of the invention the polypeptide or antibody comprises, an E430S, K326A, E333A and P396L substitution.

In one embodiment of the invention the polypeptide or antibody comprises, an E430F, K326W and E333S substitution. In one embodiment of the invention the polypeptide or antibody comprises, an E430F, K326A and E333A substitution. In one embodiment of the invention polypeptide or antibody comprises, an E430F, K333A and P396L substitution. In one embodiment of the invention the polypeptide or antibody comprises, an E430F, K326A, E333A and P396L substitution.

In one embodiment of the invention the polypeptide or antibody comprises, an E430T, K326W and E333S substitution. In one embodiment of the invention the polypeptide or antibody comprises, an E430T, K326A and E333A substitution. In one embodiment of the invention the polypeptide or antibody comprises, an E430T, K333A and P396L substitution. In one embodiment of the invention the polypeptide or antibody comprises, an E430T, K326A, E333A and P396L substitution.

In one embodiment of the invention polypeptide or antibody comprises, a substitution at position E345 and at least a substitution selected from one of the following groups consisting of:
i. K326A,
ii. E333A,
iii. E333T
iv. P396L,
v. E333S,
vi. K326W, E333S
vii. K326W, E333T
viii. K326A, E333A,
ix. K326A, K333A, P396L
x. S267E, H268F,
xi. S267E, 5324T,
xii. H268F, 5324T,
xiii. S267E, H268F, 5324T, and
xiv. S324, I332.

Hereby embodiments are provided wherein one substitution is at position E345. In one embodiment the substitution at position E345 is selected from the group consisting of: E345K, E345Q, E345R, E345Y.

In one embodiment of the invention the polypeptide or antibody comprises, a E345K substitution and at least a substitution selected from one of the following groups consisting of:
i. K326A,
ii. E333A,
iii. E333T
iv. P396L,
v. E333S,
vi. K326W, E333S
vii. K326W, E333T
viii. K326A, E333A,
ix. K326A, K333A, P396L
x. S267E, H268F,
xi. S267E, 5324T,
xii. H268F, 5324T,
xiii. S267E, H268F, 5324T, and
xiv. S324, I332.

In one embodiment of the invention the polypeptide or antibody comprises, an E345K, K326W and E333S substitution. In one embodiment of the invention the polypeptide or antibody comprises, an E345K, K326A and E333A substitution. In one embodiment of the invention the polypeptide or antibody comprises, an E345R, K333A and P396L substitution. In one embodiment of the invention the polypeptide or antibody comprises, an E345K, K326A, E333A and P396L substitution.

In one embodiment of the invention the polypeptide or antibody comprises, a E345R substitution and at least a substitution selected from one of the following groups consisting of:
i. K326A,
ii. E333A,
iii. E333T
iv. P396L,
v. E333S,
vi. K326W, E333S
vii. K326W, E333T
viii. K326A, E333A,
ix. K326A, K333A, P396L
x. S267E, H268F,
xi. S267E, 5324T,
xii. H268F, 5324T,
xiii. S267E, H268F, 5324T, and
xiv. S324, I332.

In one embodiment of the invention the polypeptide or antibody comprises, an E345R, K326W and E333S substitution. In one embodiment of the invention the polypeptide or antibody comprises, an E345R, K326A and E333A substitution. In one embodiment of the invention the polypeptide or antibody comprises, a E345R, K333A and P396L substitution. In one embodiment of the invention the polypeptide or antibody comprises, an E345R, K326A, E333A and P396L substitution.

In one embodiment of the invention the polypeptide or antibody comprises, an E345Q, K326W and E333S substitution. In one embodiment of the invention the polypeptide or antibody comprises, an E345Q, K326A and E333A substitution. In one embodiment of the invention the polypeptide or antibody comprises, an E345Q, K333A and P396L substitution. In one embodiment of the invention the polypeptide or antibody comprises, an E345Q, K326A, E333A and P396L substitution.

In one embodiment of the invention the polypeptide or antibody comprises, an E345Y, K326W and E333S substitution. In one embodiment of the invention the polypeptide or antibody comprises, an E345Y, K326A and E333A substitution. In one embodiment of the invention the polypeptide or antibody comprises, an E345Y, K333A and P396L substitution. In one embodiment of the invention the polypeptide or antibody comprises, an E345Y, K326A, E333A and P396L substitution.

In one embodiment of the invention the polypeptide or antibody comprises, a S440Y or S440W substitution and at least a substitution selected from one of the following groups consisting of:
i. K326A,
ii. E333A,
iii. E333T
iv. P396L,
v. E333S,
vi. K326W, E333S
vii. K326W, E333T
viii. K326A, E333A,
ix. K326A, K333A, P396L
x. S267E, H268F,
xi. S267E, 5324T,
xii. H268F, 5324T,
xiii. S267E, H268F, 5324T, and
xiv. S324, I332.

In one embodiment of the invention the polypeptide or antibody comprises, a S440Y substitution and at least a substitution selected from one of the following groups consisting of:
i. K326A,
ii. E333A,
iii. E333T
iv. P396L,
v. E333S,
vi. K326W, E333S vii. K326W, E333T
viii. K326A, E333A,
ix. K326A, K333A, P396L
x. S267E, H268F,
xi. S267E, S324T,
xii. H268F, S324T,
xiii. S267E, H268F, S324T, and
xiv. S324, I332.

In one embodiment of the invention the polypeptide or antibody comprises, a S440Y, K326W and E333S substitution. In one embodiment of the invention the polypeptide or antibody comprises, a S440Y, K326A and E333A substitution. In one embodiment of the invention the polypeptide or antibody comprises, a S440Y, K333A and P396L substitution. In one embodiment of the invention the polypeptide or antibody comprises, a S440Y, K326A, E333A and P396L substitution.

In one embodiment of the invention the polypeptide or antibody comprises, a S440W, K326W and E333S substitution. In one embodiment of the invention the polypeptide or antibody comprises, a S440W, K326A and E333A substitution. In one embodiment of the invention the polypeptide or antibody comprises, a S440W, K333A and P396L substitution. In one embodiment of the invention the polypeptide or antibody comprises, a S440W, K326A, E333A and P396L substitution.

In one embodiment of the invention the polypeptide or antibody further comprises one or more substitutions selected form the group consisting of: G236A, I332E, S239D and I332E.

In one embodiment of the invention the polypeptide or antibody further comprises at least two substitutions selected from the group consisting of:
i. G236A, I332E, and
ii. S239D, I332E.

In one embodiment of the invention the polypeptide or antibody comprises, a) at least one substitution at a position selected form the group consisting of: E430, E345 or a S440Y or S440W substitution and, b) substitutions selected from one of the following groups consisting of:
i. H268F, S324T, G236A, I332E,
ii. H268F, S324T, S239D, I332E
iii. S267E, H268F, S324T, G236A, I332E, and
iv. S267E, H268F, S324T, S239D, I332E.

In one embodiment of the invention the polypeptide or antibody comprises, a substitution at position E430 and the substitutions selected from one of the following groups consisting of:
i. H268F, S324T, G236A, I332E,
ii. H268F, S324T, S239D, I332E
iii. S267E, H268F, S324T, G236A, I332E, and
iv. S267E, H268F, S324T, S239D, I332E.

In one embodiment of the invention the polypeptide or antibody comprises, an E430G substitution and the substitutions selected from one of the following groups consisting of:
i. H268F, S324T, G236A, I332E,
ii. H268F, S324T, S239D, I332E
iii. S267E, H268F, S324T, G236A, I332E, and
iv. S267E, H268F, S324T, S239D, I332E.

In one embodiment of the invention the polypeptide or antibody comprises, a substitution at position E345 and the substitutions selected from one of the following groups consisting of:
i. H268F, S324T, G236A, I332E,
ii. H268F, S324T, S239D, I332E
iii. S267E, H268F, S324T, G236A, I332E, and
iv. S267E, H268F, S324T, S239D, I332E.

In one embodiment of the invention the polypeptide or antibody comprises, an E345K substitution and the substitutions selected from one of the following groups consisting of:
i. H268F, S324T, G236A, I332E,
ii. H268F, S324T, S239D, I332E
iii. S267E, H268F, S324T, G236A, I332E, and
iv. S267E, H268F, S324T, S239D, I332E.

In one embodiment of the invention the polypeptide or antibody comprises, an E345R substitution and the substitutions selected from one of the following groups consisting of:
i. H268F, S324T, G236A, I332E,
ii. H268F, S324T, S239D, I332E
iii. S267E, H268F, S324T, G236A, I332E, and
iv. S267E, H268F, S324T, S239D, I332E.

In one embodiment of the invention the polypeptide or antibody comprises, a S440Y or S440W substitution and the substitutions selected from one of the following groups consisting of:
i. H268F, S324T, G236A, I332E,
ii. H268F, S324T, S239D, I332E
iii. S267E, H268F, S324T, G236A, I332E, and
iv. S267E, H268F, S324T, S239D, I332E.

In one embodiment of the invention the polypeptide or antibody comprises, a S440Y substitution and the substitutions selected from one of the following groups consisting of:
i. H268F, S324T, G236A, I332E,
ii. H268F, S324T, S239D, I332E,
iii. S267E, H268F, S324T, G236A, I332E, and
iv. S267E, H268F, S324T, S239D, I332E.

In one embodiment of the invention the polypeptide or antibody comprises one or more further substitutions. That is, in one embodiment of the invention the polypeptide or antibody according to any aspect or embodiment described herein comprising one or more further substitutions in the Fc region.

In one embodiment of the invention the polypeptide or antibody comprises a further substitution corresponding to position K439 or where the Fc region does not comprise a substitution in position S440 the further substitution may be at position S440.

In one embodiment of the invention the polypeptide or antibody comprises a further substitution in the polypeptide or antibody corresponding to position K439 or S440, with the proviso that the substitution in S440 is not S440Y or S440W.

Polypeptides or antibodies comprising an Fc-Fc enhancing substitution and a C1q binding substitution according to the present invention and a further substitution at position S440 such as S440K do not form oligomers with polypeptides or antibodies comprising a substitution at position S440 such as S440K. Polypeptides or antibodies comprising an Fc-Fc enhancing substitution and a C1q binding substitution according to the present invention and a further substitution at position K439 such as K439E do not form oligomers with polypeptides or antibodies comprising a mutation at position K439 such as K439E. In one embodiment of the invention the further substitution is selected from S440K or K439E.

In one embodiment of the present invention the Fc region comprises a further substitution which is a hexamerization-inhibiting substitution corresponding to K439E or S440K in human IgG1 EU numbering. That is in one embodiment of the present invention the Fc region comprises an Fc-Fc enhancing substitution such as E430G and a hexamerization-inhibiting substitution K439E. In one embodiment of the present invention the Fc region comprises an Fc-Fc enhancing substitution such as E345K and a hexamerization-inhibiting substitution K439E. In another embodiment of the present invention the Fc region comprises an Fc-Fc enhancing substitution such as E430G and a hexamerization-inhibiting substitution S440K. In one embodiment of the present invention the Fc region comprises a Fc-Fc enhancing substitution such as E345K and hexamerization-inhibiting substitution a S440K. Hereby are embodiments provided that allow for exclusive hexamerization between combinations of antibodies comprising a K439E substitution and antibodies comprising a S440K substitution. That is, the inhibiting substitutions K439E and S440K may be viewed as complementary substitutions. Combinations of antibodies with two different complementary hexamerization-inhibiting substitutions may be of particular interest in compositions having at least two antibodies with different specificities.

In one embodiment of the invention the polypeptide or antibody comprises a) a substitution at a position selected from the group consisting of: E430, E345 and S440, with the proviso that the substitution in S440 is not S440Y or S440W and b) a substitution at one or more position(s) selected from the group of: G236, S239, S267, H268, S324 K326, I332, E333 and P396 and c) a K439E substitution.

In one embodiment of the invention the polypeptide or antibody comprises a) a substitution at a position selected from the group consisting of: E430 and E345 and b) a substitution at one or more position(s) selected from the group of: G236, S239, S267, H268, S324 K326, I332, E333 and P396 and c) a S440K substitution.

In one embodiment of the invention the polypeptide or antibody comprises, an E430G, K326W, E333S and K439E substitution. In one embodiment of the invention the polypeptide or antibody comprises, an E430G, K326A, E333A and K439E substitution. In one embodiment of the invention the polypeptide or antibody comprises, an E430G, K333A, P396L and K439E substitution. In one embodiment of the invention the polypeptide or antibody comprises, an E430G, K326A, E333A, P396L and K439E substitution.

In one embodiment of the invention the polypeptide or antibody comprises, an E345K, K326W, E333S and K439E substitution. In one embodiment of the invention the polypeptide or antibody comprises, an E345K, K326A, E333A and K439E substitution. In one embodiment of the invention the polypeptide or antibody comprises, an E345K, K333A, P396L and K439E substitution. In one embodiment of the invention the polypeptide or antibody comprises, an E345K, K326A, E333A, P396L and K439E substitution.

In one embodiment of the invention the polypeptide or antibody comprises, an E345R, K326W, E333S and K439E substitution. In one embodiment of the invention the polypeptide or antibody comprises, an E345R, K326A, E333A and K439E substitution. In one embodiment of the invention the polypeptide or antibody comprises, an E345R, K333A, P396L and K439E substitution. In one embodiment of the invention the polypeptide or antibody comprises, an E345R, K326A, E333A, P396L and K439E substitution.

In one embodiment of the invention the polypeptide or antibody comprises, a S440Y, K326W, E333S and K439E substitution. In one embodiment of the invention the polypeptide or antibody comprises, a S440Y, K326A, E333A and K439E substitution. In one embodiment of the invention the polypeptide or antibody comprises, a S440Y, K333A, P396L and K439E substitution. In one embodiment of the invention the polypeptide or antibody comprises, a S440Y, K326A, E333A, P396L and K439E substitution.

In one embodiment of the invention the polypeptide or antibody comprises a) a substitution at a position selected from the group consisting of: E430 and E345, and b) a substitution at one or more position(s) selected from the group of: G236, S239, S267, H268, S324 K326, I332, E333 and P396 and c) a S440K substitution.

In one embodiment of the invention the polypeptide or antibody comprises, an E430G, K326W, E333S and S440K substitution. In one embodiment of the invention the polypeptide or antibody comprises, an E430G, K326A, E333A and S440S substitution. In one embodiment of the invention the polypeptide or antibody comprises, an E430G, K333A, P396L and S440S substitution. In one embodiment of the invention the polypeptide or antibody comprises, an E430G, K326A, E333A, P396L and S440K substitution.

In one embodiment of the invention the polypeptide or antibody comprises, an E345K, K326W, E333S and S440K substitution. In one embodiment of the invention the polypeptide or antibody comprises, an E345K, K326A, E333A and S440K substitution. In one embodiment of the invention the polypeptide or antibody comprises, an E345K, K333A, P396L and S440K substitution. In one embodiment of the invention the polypeptide or antibody comprises, an E345K, K326A, E333A, P396L and S440K substitution.

In one embodiment of the invention the polypeptide or antibody comprises, an E345R, K326W, E333S and S440K substitution. In one embodiment of the invention the polypeptide or antibody comprises, an E345R, K326A, E333A and S440S substitution. In one embodiment of the invention the polypeptide or antibody comprises, an E345R, K333A, P396L and S440K substitution. In one embodiment of the invention the polypeptide or antibody comprises, an E345R, K326A, E333A, P396L and S440K substitution.

The polypeptide or antibody according to the invention has a least a Fc-Fc enhancing substitution and one or more C1q binding substitutions, but as described above may also have additional substitutions to introduce additional functions into the polypeptide or antibody. In one embodiment the polypeptide or antibody comprises at most ten substitutions, such as nine substitutions, such as eight substitutions, such as seven substitutions, such as six substitutions, such as five substitutions, such as four substitutions, such as three substitutions or such as two substitutions.

Hereby embodiments are provided that allow for polypeptides or antibodies of the invention to have additional substitutions which introduces additional features into the polypeptide or antibody. Further, the additional substitutions also allow for a variation in the Fc region at positions which are not involved in Fc-Fc interaction, as well as in positions not involved in Fc effector functions. Further, additional substitutions may also be due to allelic variations.

In one embodiment of the invention the polypeptide or antibody has an Fc effector function increased by at least 20% compared to a parent polypeptide or parent antibody which is identical to the antibody except that it does not comprise a Fc-Fc enhancing substitution and a C1q binding substitution in the Fc region.

In one embodiment of the invention the polypeptide or antibody has an Fc effector function increased by at least 40%, at least 50% or at least 60% compared to a parent polypeptide or parent antibody which is identical to the antibody except that it does not comprise an Fc-Fc enhancing substitution and a C1q binding substitution in the Fc region.

In one embodiment of the invention the polypeptide or antibody comprises an increased Fc effector function.

In one embodiment of the invention the Fc effector function is selected from the following group; complement-dependent cytotoxicity (CDC), complement-dependent cell-mediated cytotoxicity, complement activation, antibody-dependent cell-mediated cytotoxicity (ADCC), antibody-dependent cell-mediated phagocytosis, C1q binding and FcγR binding. In one embodiment the Fc effector function is FcγRIIIa signaling. That is the second mutation according to the invention is able to decrease at least one Fc effector function.

In one embodiment of the invention the polypeptide or antibody comprises agonistic activity. That is, the polypeptide or antibody comprises agonistic activity when compared to a parent polypeptide or parent antibody.

In one embodiment of the invention the polypeptide or antibody comprises enhanced agonistic activity. That is, the polypeptide or antibody comprises enhanced agonistic activity when compared to a parent polypeptide or parent antibody. In one embodiment of the invention the polypeptide or antibody comprises enhanced agonistic activity, when compared to a polypeptide or antibody comprising the same Fc-Fc enhancing mutation but no C1q binding mutation.

Agonistic activity of receptors of the TNFR-SF requires exogenous crosslinking to achieve agonistic activity. This can be measured in surrogate assays using e.g. HEK293 cells containing NF-kB-driven secreted reporter gene (e.g. pMetLuc-Reportor gene expressing luciferase, Clontech) which are stably transfected with the TNFR-SF receptor of interest. Crosslinking of the receptor leads to promotor activation and secretion of e.g. luciferase protein in the medium. At desired time points assay luciferase activity can be measured, by transferring media sample and adding substrate. Luciferase activity can be measured in a luminometer, which is a measure for agonistic activity. An example for OX40 see Zhang et al. J Biol Chem. 2016 Dec. 30; 291(53):27134-27146

In one embodiment of the invention the polypeptide or antibody comprises increased agonistic activity. That is, the polypeptide or antibody comprises increased agonistic activity when compared to a parent polypeptide or parent antibody.

In one embodiment of the invention the polypeptide is an antibody, monospecific antibody, bispecific antibody or multispecific antibody. In one embodiment the polypeptide is a monospecific polypeptide, a bispecific polypeptide or a multispecific polypeptide.

The polypeptide of the invention is not limited to antibodies which have a natural, e.g. a human Fc domain but it may also be an antibody having other mutations than those of the present invention, such as e.g. mutations that affect glycosylation or enables the antibody to be a bispecific antibody. By the term "natural antibody" is meant any antibody which does not comprise any genetically introduced mutations. An antibody which comprises naturally occurring modifications, e.g. different allotypes, is thus to be understood as a "natural antibody" in the sense of the present invention, and can thereby be understood as a parent antibody. Such antibodies may serve as a template for the at least two substitutions according to the present invention, and thereby providing the antibodies of the invention. An example of a parent antibody comprising other substitutions than those of the present invention is the bispecific antibody as described in WO2011/131746 (Genmab), utilizing reducing conditions to promote half-molecule exchange of two antibodies comprising IgG4-like CH3 regions, thus forming bispecific antibodies without concomitant formation of aggregates. Other examples of parent antibodies include but are not limited to bispecific antibodies such as heterodimeric bispecifics: Triomabs (Fresenius); bispecific IgG1 and IgG2 (Rinat neurosciences Corporation); FcΔAdp (Regeneron); Knobs-into-holes (Genentech); Electrostatic steering (Amgen, Chugai, Oncomed); SEEDbodies (Merck); Azymetric scaffold (Zymeworks); mAb-Fv (Xencor); and LUZ-Y (Genentech). Other exemplary parent antibody formats include, without limitation, a wild type antibody, a full-length antibody or Fc-containing antibody fragment, a human antibody, humanized antibody, chimeric antibody or any combination thereof.

In one embodiment the polypeptide or antibody comprises an Fc region comprising an R435H substitution.

In one embodiment the present invention provides a polypeptide or an antibody comprising an Fc region of a human immunoglobulin and an antigen-binding region, wherein the Fc region comprises a) a substitution at a position selected from the group consisting of: E430, E345 or a S440Y or S440W substitution, and b) a substitution at one or more position(s) selected from the group of: G236, S239, S267, H268, S324 K326, I332, E333 and P396, and c) a R435H substitution, wherein the positions correspond to human IgG1, according to EU numbering.

The polypeptide or antibody may be any human antibody of any isotype, e.g. IgG1, IgG2, IgG3, IgG4, IgE, IgD, IgM, or IgA, optionally a human full-length antibody, such as a human full-length IgG1 antibody.

In one embodiment of the invention the polypeptide or antibody is a human IgG1 antibody, e.g. the IgG1m(za) or IgG1m(f) allotype.

In one embodiment of the invention the polypeptide or antibody has an Fc region that is a human IgG1, IgG2, IgG3, IgG4, IgE, IgD, IgM, IgA isotype or a mixed isotype. That is the Fc region of a polypeptide or antibody according to the invention has at least a first and a second mutation introduced into the Fc region corresponding to a human IgG1, IgG2, IgG3, IgG4, IgE, IgD, IgM, IgA isotype or a mixed isotype. In one embodiment of the invention the Fc region is a mixed isotype selected form the following group: IgG1/IgG2, IgG1/IgG3, IgG1/IgG4, IgG2/IgG3, IgG2/IgG4 and IgG3/IgG4. In a mixed isotype the Fc region is comprised of amino acid sequence form more than one isotype.

In one embodiment of the invention the Fc region is a human IgG1, IgG2, IgG3, IgG4 isotype or a mixed isotype.

In one embodiment of the invention the Fc region is a human IgG.

In a preferred embodiment of the invention the polypeptide or antibody has an Fc region that is a human IgG1 isotype.

In one embodiment of the invention the polypeptide or antibody has an Fc region that is an IgG1m(f), IgG1m(a), IgG1m(z), IgG1m(x) allotype or mixed allotype.

In one embodiment of the invention the polypeptide or antibody comprises an Fc region as set forth in SEQ ID NO: 73, 74, 75, 76, 89, 168, 169 or 170, wherein the Fc region comprises a substitution in a position selected from the group corresponding to E430, E345 and S440, with the proviso that the substitution in S440 is S440Y or S440W, and a substitution at one or more positions selected from the group consisting of G236, S239, S267, H268, S324, K326, I332, E333 and P396, wherein the positions correspond to human IgG1, according to EU numbering.

In one embodiment of the invention the polypeptide or antibody comprises an Fc region as set forth in SEQ ID NO:77, 78 or 90 wherein the Fc region comprises a substitution at one or more position(s) selected from the group consisting of G236, S239, S267, H268, S324, K326, I332, E333 and P396, wherein the positions correspond to human IgG1, according to EU numbering.

In one embodiment of the invention the polypeptide or antibody comprises an Fc region as set forth in SEQ ID NO: 80, 82, 83, 84, 87 or 88.

In one embodiment of the invention the polypeptide is a human antibody, humanized antibody or chimeric antibody.

Multispecific Antibodies

The polypeptide or antibody of the invention is not limited to antibodies which have a natural, e.g. a human Fc domain but it may also be an antibody having other mutations than those of the present invention, such as e.g. mutations that affect glycosylation or enables the antibody to be a multispecific antibody or a bispecific antibody. By the term "natural antibody" is meant any antibody which does not comprise any genetically introduced mutations. An antibody which comprises naturally occurring modifications, e.g. different allotypes, is thus to be understood as a "natural antibody" in the sense of the present invention, and can thereby be understood as a parent antibody. Such antibodies may serve as a template for the at least two substitutions according to the present invention, and thereby providing the antibodies of the invention. An example of a parent antibody comprising other substitutions than those of the present invention is the bispecific antibody as described in WO2011/131746 (Genmab), utilizing reducing conditions to promote half-molecule exchange of two antibodies comprising IgG4-like CH3 regions, thus forming bispecific antibodies without concomitant formation of aggregates. Other examples of parent antibodies include but are not limited to bispecific antibodies such as heterodimeric bispecifics: Triomabs (Fresenius); bispecific IgG1 and IgG2 (Rinat neurosciences Corporation); FcΔAdp (Regeneron); Knobs-into-holes (Genentech); Electrostatic steering (Amgen, Chugai, Oncomed); SEEDbodies (Merck); Azymetric scaffold (Zymeworks); mAb-Fv (Xencor); and LUZ-Y (Genentech). Other exemplary parent antibody formats include, without limitation, a wild type antibody, a full-length antibody or Fc-containing antibody fragment, a human antibody, humanized antibody, chimeric antibody or any combination thereof.

It is to be understood that any embodiment of the present invention described herein may be used in a multispecific antibody aspect described below.

Thus in one embodiment the variant of the present invention is an antibody selected from a monospecific antibody, bispecific antibody or multispecific antibody.

In a particular embodiment, the bispecific antibody has the format described in WO 2011/131746.

The bispecific antibody of the present invention is not limited to a particular format and it may be any of those described herein.

In another aspect, the invention relates to a polypeptide or antibody which is a bispecific polypeptide or antibody comprising a first heavy chain of an immunoglobulin and a first antigen-binding region, and a second polypeptide or antibody comprising a second heavy chain of an immunoglobulin and a second antigen-binding region, wherein the first and second antigen-binding regions bind different epitopes on the same or on different antigens, and wherein the first and/or second heavy chain comprise a) a substitution in a position selected from the group corresponding to E430, E345 and S440, with the proviso that the substitution in S440 is S440Y or S440W, b) one or more substitution(s) at a position selected form the group consisting of: G236, S267, H268, S324, K326, I332, E333 and P396, and c) wherein the first heavy chain comprises a further substitution in a position selected from the group consisting of: K409, T366, L368, K370, D399, F405, and Y407; and the second heavy chain comprises a further substitution in a position selected from the group consisting of: F405, T366, L368, K370, D399, Y407 and K409, and wherein the further mutation in the first polypeptide is different from the further mutation in the second polypeptide.

In one aspect the present invention provides a polypeptide or antibody comprising a f Fc region of a human IgG comprising a first heavy chain and a first antigen binding region, a second heavy chain and a second antigen binding region, wherein said first and second heavy chain comprises a) a substitution at a position selected from the group consisting of: E430, E345 and S440, with the proviso that the substitution in S440 is S440Y or S440W and b) a substitution at one or more position(s) selected form the group consisting of: G236, S267, H268, S324, K326, I332, E333 and P396 and c) a further substitution in position F405 or K409; wherein the further substitution is different from the first heavy chain and the second heavy chain so that if the first heavy chain has substitution in position F405 then second heavy chain has a substitution in K409 and vice versa.

Hereby embodiments are provided wherein the first heavy chain and the second heavy chain are not identical due to the (c) further mutation is not located in the same position in the first and second heavy chain.

It is to be understood that any embodiment of the present invention described herein may be used in a multispecific antibody aspect described below.

Thus in one embodiment the variant of the present invention is an antibody selected from a monospecific antibody, bispecific antibody or multispecific antibody.

In a particular embodiment, the bispecific antibody has the format described in WO 2011/131746.

In one particular embodiment of the present invention, the first heavy chain comprises a further substitution corresponding to K409, such as K409R; and the second heavy chain comprises a further substitution corresponding to F405, such as F405L.

In one embodiment of the present invention the first and/or second heavy chain comprise, a) a substitution corresponding to position E430, b) a substitution at one or more position(s) selected form the group consisting of: G236, S267, H268, S324, K326, I332, E333 and P396, and c) wherein the first heavy chain comprises a further substitution corresponding to K409R; and the second heavy chain comprises a further substitution corresponding to F405L.

In one embodiment of the present invention the first and/or second heavy chain comprise, a) a substitution corresponding to position E345, b) a substitution at one or more position(s) selected form the group consisting of: G236, S267, H268, S324, K326, I332, E333 and P396, and c) wherein the first heavy chain comprises a further substitution corresponding to K409R; and the second heavy chain comprises a further substitution corresponding to F405L.

In one embodiment of the present invention the first and/or second Fc heavy chain comprise,
a) a substitution corresponding to S440Y or S440W,
b) a substitution at one or more position(s) selected form the group consisting of: G236, S267, H268, S324, K326, I332, E333 and P396, and
c) wherein the first heavy chain comprises a further substitution corresponding to K409R; and the second heavy chain comprises a further substitution corresponding to F405L.

In one embodiment of the present invention the first and/or second Fc heavy chain comprise,
a) a substitution corresponding to E430G,
b) two substitutions corresponding to K326W, E333S, and
c) wherein the first heavy chain comprises a further substitution corresponding to K409R, and the second heavy chain comprises a further substitution corresponding to F405L.

In one embodiment of the present invention the first and/or second Fc heavy chain comprise,
a) a substitution corresponding to E430G,
b) two substitutions corresponding to K326W, E333T, and
c) wherein the first heavy chain comprises a further substitution corresponding to K409R, and the second heavy chain comprises a further substitution corresponding to F405L.

In one embodiment of the present invention the first and/or second Fc region comprise,
a) a substitution corresponding to E430G,
b) two substitutions corresponding to K326A, E333A, and
c) wherein the first heavy chain comprises a further substitution corresponding to K409R, and the second heavy chain comprises a further substitution corresponding to F405L.

In one embodiment of the present invention the first and/or second heavy chain comprise,
a) a substitution corresponding to E430G,
b) two substitutions corresponding to K333A, P396L, and
c) wherein the first heavy chain comprises a further substitution corresponding to K409R, and the second heavy chain comprises a further substitution corresponding to F405L.

In one embodiment of the present invention the first and/or second heavy chain comprise,
a) a substitution corresponding to E430G,
b) three substitutions corresponding to K326A, E333A, P396L, and
c) wherein the first heavy chain comprises a further substitution corresponding to K409R, and the second heavy chain comprises a further substitution corresponding to F405L.

In one embodiment of the present invention the first and/or second heavy chain comprise,
a) a substitution corresponding to E430G,
b) three substitutions corresponding to K326A, E333T, P396L, and
c) wherein the first heavy chain comprises a further substitution corresponding to K409R, and the second heavy chain comprises a further substitution corresponding to F405L.

In one embodiment of the present invention the first and/or second heavy chain comprise,
a) a substitution corresponding to E345K,
b) two substitutions corresponding to K326W, E333S, and
c) wherein the first heavy chain comprises a further substitution corresponding to K409R; and the second heavy chain comprises a further substitution corresponding to F405L.

In one embodiment of the present invention the first and/or second heavy chain comprise,
a) a substitution corresponding to E345K,
b) two substitutions corresponding to K326W, E333T, and
c) wherein the first heavy chain comprises a further substitution corresponding to K409R; and the second heavy chain comprises a further substitution corresponding to F405L.

In one embodiment of the present invention the first and/or second heavy chain comprise,
a) a substitution corresponding to E345K,
b) two substitutions corresponding to K326A, E333A, and
c) wherein the first heavy chain comprises a further substitution corresponding to K409R; and the second heavy chain comprises a further substitution corresponding to F405L.

In one embodiment of the present invention the first and/or second heavy chain comprise,
a) a substitution corresponding to E345K,
b) two substitutions corresponding to K333A, P396L, and
c) wherein the first heavy chain comprises a further substitution corresponding to K409R; and the second heavy chain comprises a further substitution corresponding to F405L.

In one embodiment of the present invention the first and/or second heavy chain comprise,
a) a substitution corresponding to E345K,
b) three substitutions corresponding to K326A, E333A, P396L, and
c) wherein the first heavy chain comprises a further substitution corresponding to K409R; and the second heavy chain comprises a further substitution corresponding to F405L.

In one embodiment of the present invention the first and/or second heavy chain comprise,
a) a substitution corresponding to E345K,
b) three substitutions corresponding to K326A, E333T, P396L, and
c) wherein the first heavy chain comprises a further substitution corresponding to K409R; and the second heavy chain comprises a further substitution corresponding to F405L.

In one embodiment of the present invention the first and/or second heavy chain comprise,
a) a substitution corresponding to E345R,
b) two substitutions corresponding to K326W, E333S, and
c) wherein the first heavy chain comprises a further substitution corresponding to K409R; and the second heavy chain comprises a further substitution corresponding to F405L.

In one embodiment of the present invention the first and/or second heavy chain comprise,
a) a substitution corresponding to E345R,
b) two substitutions corresponding to K326W, E333T, and
c) wherein the first heavy chain comprises a further substitution corresponding to K409R; and the second heavy chain comprises a further substitution corresponding to F405L.

In one embodiment of the present invention the first and/or second heavy chain comprise,
a) a substitution corresponding to E345R,
b) two substitutions corresponding to K326A, E333A, and
c) wherein the first heavy chain comprises a further substitution corresponding to K409R, and the second heavy chain comprises a further substitution corresponding to F405L.

In one embodiment of the present invention the first and/or second heavy chain comprise,
a) a substitution corresponding to E345R,
b) two substitutions corresponding to K333A, P396L, and
c) wherein the first heavy chain comprises a further substitution corresponding to K409R, and the second heavy chain comprises a further substitution corresponding to F405L.

In one embodiment of the present invention the first and/or second heavy chain comprise,
a) a substitution corresponding to E345R,
b) three substitutions corresponding to K326A, E333A, P396L, and
c) wherein the first heavy chain comprises a further substitution corresponding to K409R, and the second heavy chain comprises a further substitution corresponding to F405L.

In one embodiment of the present invention the first and/or second heavy chain comprise,
a) a substitution corresponding to S440Y,
b) two substitutions corresponding to K326W, E333S, and
c) wherein the first heavy chain comprises a further substitution corresponding to K409R, and the second heavy chain comprises a further substitution corresponding to F405L.

In one embodiment of the present invention the first and/or second heavy chain comprise,
a) a substitution corresponding to S440Y,
b) two substitutions corresponding to K326W, E333T, and
c) wherein the first heavy chain comprises a further substitution corresponding to K409R, and the second heavy chain comprises a further substitution corresponding to F405L.

In one embodiment of the present invention the first and/or second heavy chain comprise,
a) a substitution corresponding to S440Y,
b) two substitutions corresponding to K326A, E333A, and
c) wherein the first heavy chain comprises a further substitution corresponding to K409R, and the second heavy chain comprises a further substitution corresponding to F405L.

In one embodiment of the present invention the first and/or second heavy chain comprise,
a) a substitution corresponding to S440Y,
b) two substitutions corresponding to K333A, P396L, and
c) wherein the first heavy chain comprises a further substitution corresponding to K409R; and the second heavy chain comprises a further substitution corresponding to F405L.

In one embodiment of the present invention the first and/or second heavy chain comprise,
a) a substitution corresponding to S440Y,
b) three substitutions corresponding to K326A, E333A, P396L, and
c) wherein the first heavy chain comprises a further substitution corresponding to K409R; and the second heavy chain comprises a further substitution corresponding to F405L.

Targets and Method of Use

The polypeptide or antibody according to the present invention may bind a target which activate a signal transduction pathway. In one embodiment the target is a target which activate, inhibit, modulates and or regulates a signal transduction pathway. Examples of targets that may be particularly suitable as targets according to the present invention are cell surface receptors and ligands.

Cell surface receptors include, for example, receptors that belong to receptor families such as the hematopoietic factor receptor family, cytokine receptor family, tyrosine kinase receptor family, serine/threonine kinase receptor family, TNF receptor family, G protein-coupled receptor family, GPI-anchored receptor family, tyrosine phosphatase receptor family, adhesion factor family, and hormone receptor family. Various references that relate to receptors belonging to these receptor families and their characteristics are available and include, for example, Cooke B A., King R J B., van der Molen H J. ed. New Comprehensive Biochemistry Vol. 18B "Hormones and their Actions Part π" pp. 1-46 (1988) Elsevier Science Publishers BV., New York, USA; Patthy L. (1990) Cell, 61: 13-14; Ullrich A., et al. (1990) Cell, 61: 203-212; Massagul J. (1992) Cell, 69: 1067-1070; Miyajima A., et al. (1992) Annu. Rev. Immunol., 10: 295-331; Taga T. and Kishimoto T. (1992) FASEB J., 7: 3387-3396; Fantl W I., et al. (1993) Annu. Rev. Biochem., 62: 453-481; Smith C A., et al. (1994) Cell, 76: 959-962; Flower D R. (1999) Biochim. Biophys. Acta, 1422: 207-234; and M. Miyasaka ed., Cell Technology, supplementary volume, Handbook series, "Handbook for Adhesion Factors" (1994) (Shujunsha, Tokyo, Japan).

In one embodiment of the invention the polypeptide or antibody comprises an antigen binding region wherein the antigen binding region binds to a member of the tumor necrosis factor receptor super family (TNFR-SF) or G-protein Coupled Receptor (GPCR) superfamily.

In one embodiment of the invention the polypeptide or antibody binds to a cell surface receptor include, for example, hormone receptors and cytokine receptors. Exemplary cytokine receptors include, for example, hematopoietic factor receptor, lymphokine receptor, growth factor receptor, differentiation control factor receptor and the like. Examples of cytokine receptors are erythropoietin (EPO) receptor, thrombopoietin (TPO) receptor, granulocyte colony stimulating factor (G-CSF) receptor, macrophage colony stimulating factor (M-CSF) receptor, granular macrophage colony stimulating factor (GM-CSF) receptor, tumor necrosis factor (TNF) receptor, interleukin-1 (IL-1) receptor, interleukin-2 (IL-2) receptor, interleukin-3 (IL-3) receptor, interleukin-4 (IL-4) receptor, interleukin-5 (IL-5) receptor, interleukin-6 (IL-6) receptor, interleukin-7 (IL-7) receptor, interleukin-9 (IL-9) receptor, interleukin-10 (IL-10) receptor, interleukin-11 (IL-11) receptor, interleukin-12 (IL-12) receptor, interleukin-13 (IL-13) receptor, interleukin-15 (IL-15) receptor, interferon-alpha (IFN-alpha) receptor, interferon-beta (IFN-beta) receptor, interferon-gamma (IFN-gamma) receptor, growth hormone (GH) receptor, insulin receptor, blood stem cell proliferation factor (SCF) receptor, vascular epidermal growth factor (VEGF) receptor, epidermal cell growth factor (EGF) receptor, nerve growth factor (NGF) receptor, fibroblast growth factor (FGF) receptor, platelet-derived growth factor (PDGF) receptor, transforming growth factor-beta (TGF-beta) receptor, leukocyte migration inhibitory factor (LIF) receptor, ciliary neurotrophic factor (CNTF) receptor, oncostatin M (OSM) receptor, and Notch family receptor.

The tumor necrosis factor receptor superfamily (TNFRSF) is a group of receptors characterized by the ability to bind ligands of the tumor necrosis factor superfamily (TNFSF) via an extracellular cysteine-rich domain. The TNF receptors form trimeric complexes in the plasma membrane. The TNFRSF include the following list of 29 proteins; TNFR1 (Uniprot P19438), FAS (Uniprot P25445), DR3 (Uniprot Q93038), DR4 (Uniprot O00220), DR5 (Uniprot O14763), DR6 (Uniprot O75509), NGFR (Uniprot P08138), EDAR (Uniprot Q9UNE0), DcR1 (Uniprot O14798), DcR2(Uniprot Q9UBN6), DcR3 (Uniprot O95407), OPG (Uniprot O00300), TROY (Uniprot Q9NS68), XEDAR (Uniprot Q9HAV5), LTbR (Uniprot P36941), HVEM (Uniprot Q92956), TWEAKR (Uniprot Q9NP84), CD120b (Uniprot P20333), OX40 (Uniprot P43489), CD40 (Uniprot P25942), CD27 (Uniprot P26842), CD30 (Uniprot P28908), 4-1BB (Uniprot Q07011), RANK (Uniprot Q9Y6Q6), TACI (Uniprot O14836), BLySR (Uniprot Q96RJ3), BCMA (Uniprot Q02223), GITR (Uniprot Q9Y5U5), RELT (Uniprot Q969Z4).

Some TNFRSF are involved in apoptosis and contains an intracellular death domain such as FAS, DR4, DR5, TNFR1, DR6, DR3, EDAR and NGFR. Other TNFRSF are involved in other signal transduction pathways, such as proliferation, survival, and differentiation such as DcR1, DcR2, DcR3, OPG, TROY, XEDAR, LTbR, HVEM, TWEAKR, CD120b, OX40, CD40, CD27, CD30, 4-1BB, RANK, TACI, BLySR, BCMA, GITR, RELT. TNF receptors are expressed in a wide variety of tissues in mammals, especially in leukocytes.

In one embodiment of the invention the antigen binding region binds to a member of the TNFR-SF selected form the group consisting of: FAS, DR4, DR5, TNFR1, DR6, DR3, EDAR, NGFR, OX40, CD40, CD30, CD27, 4-1BB, RANK, TACI, BLySR, BCMA, RELT and GITR.

In one embodiment of the invention the antigen binding region binds to a member of the TNFR-SF. In one embodiment of the invention the antigen binding region binds to a member of the TNFR-SF which does not comprise an intracellular death domain. In one embodiment of the invention the TNFR-SF is selected from the group of: OX40, CD40, CD30, CD27, 4-1BB, RANK, TACI, BLySR, BCMA, RELT and GITR. In one embodiment of the invention the TNFR-SF is selected form the group of: FAS, DR4, DR4, TNFR1, DR6, DR3, EDAR, and NGFR.

In one embodiment of the invention the antibody comprises an antigen binding region binding to OX40, wherein the IgG1 Fc region comprises,
 a. an E430G substitution, and
 b. a K326W and E333S substitution.

In one embodiment of the invention the antibody comprises an antigen binding region binding to CD40, wherein the IgG1 Fc region comprises,
 a. an E430G substitution, and
 b. a K326W and E333S substitution.

In one embodiment of the invention the antibody comprises an antigen binding region binding to CD137, wherein the IgG1 Fc region comprises,
 a. an E430G substitution, and
 b. a K326W and E333S substitution.

In one embodiment of the invention the antibody comprises an antigen binding region binding to GITR, wherein the IgG Fc region comprises,
 a. an E430G substitution, and
 b. a K326W and E333S substitution.

In one embodiment of the invention the antibody comprises an antigen binding region binding to GITR, wherein the IgG1 Fc region comprises,
 a. an E430G substitution, and
 b. a K326W and E333S substitution.

In one embodiment of the invention the antibody comprises an antigen binding region binding to GITR, wherein the IgG2 Fc region comprises,
 a. an E430G substitution, and
 b. a K326W and E333S substitution.

The polypeptide or antibody according to the invention may bind any target, examples of such targets or antigens according to the invention may be, directed against are: TNFR1, FAS, DR3, DR4, DR5, DR6, NGFR, EDAR, DcR1, DcR2, DcR3, OPG, TROY, XEDAR, LTbR, HVEM, TWEAKR, CD120b, OX40, CD40, CD27, CD30, 4-1BB, RANK, TACI, BLySR, BCMA, GITR, RELT.

In one embodiment of the invention the antibody comprises an antigen binding region binding to FAS, wherein the IgG1 Fc region comprises,
 a. an E430G substitution, and
 b. a K326W and E333S substitution.

In one embodiment of the invention the antibody comprises an antigen binding region binding to DR5, wherein the IgG1 Fc region comprises,
 a. an E430G substitution, and
 b. a K326A and E333A substitution.

In one embodiment of the invention the antibody comprises an antigen binding region binding to DR5, wherein the IgG1 Fc region comprises,
 a. an E430G substitution, and
 b. a K326A and E333T substitution.

In one embodiment of the invention the antibody comprises an antigen binding region binding to DR5, wherein the IgG1 Fc region comprises,
 a. an E430G substitution, and
 b. a K326A substitution.

In one embodiment of the invention the antibody comprises an antigen binding region binding to DR5, wherein the IgG1 Fc region comprises,
 a. an E430G substitution, and
 b. an E333A substitution.

In one embodiment of the invention the antibody comprises an antigen binding region binding to DR5, wherein the IgG1 Fc region comprises,
 a. an E430G substitution, and
 b. a K326W and E333S substitution.

In one embodiment of the invention the antibody comprises an antigen binding region binding to CD20, wherein the IgG1 Fc region comprises,
 a. an E430G substitution, and
 b. a K326W and E333S substitution.

In one embodiment of the invention the antigen binding region binds to a member of the tumor necrosis factor superfamily (TNF-SF):

In one embodiment of the invention the antigen binding region binds to a member of the TNF-SF selected form the group consisting of: Lymphotoxin beta (TNF-C), OX40L, CD154, FasL, CD70, CD153, RANKL, APRIL and GAFF.

In one embodiment of the invention the polypeptide or antibody binds to a cell surface receptor include, for example, hormone receptors and cytokine receptors. Exemplary cytokine receptors include, for example, hematopoietic factor receptor, lymphokine receptor, growth factor receptor, differentiation control factor receptor and the like. Examples of cytokine receptors are erythropoietin (EPO)

receptor, thrombopoietin (TPO) receptor, granulocyte colony stimulating factor (G-CSF) receptor, macrophage colony stimulating factor (M-CSF) receptor, granular macrophage colony stimulating factor (GM-CSF) receptor, tumor necrosis factor (TNF) receptor, interleukin-1 (IL-1) receptor, interleukin-2 (IL-2) receptor, interleukin-3 (IL-3) receptor, interleukin-4 (IL-4) receptor, interleukin-5 (IL-5) receptor, interleukin-6 (IL-6) receptor, interleukin-7 (IL-7) receptor, interleukin-9 (IL-9) receptor, interleukin-10 (IL-10) receptor, interleukin-11 (IL-11) receptor, interleukin-12 (IL-12) receptor, interleukin-13 (IL-13) receptor, interleukin-15 (IL-15) receptor, interferon-alpha (IFN-alpha) receptor, interferon-beta (IFN-beta) receptor, interferon-gamma (IFN-gamma) receptor, growth hormone (GH) receptor, insulin receptor, blood stem cell proliferation factor (SCF) receptor, vascular epidermal growth factor (VEGF) receptor, epidermal cell growth factor (EGF) receptor, nerve growth factor (NGF) receptor, fibroblast growth factor (FGF) receptor, platelet-derived growth factor (PDGF) receptor, transforming growth factor-beta (TGF-beta) receptor, leukocyte migration inhibitory factor (LIF) receptor, ciliary neurotrophic factor (CNTF) receptor, oncostatin M (OSM) receptor, and Notch family receptor.

In one embodiment of the invention the antigen binding region binds to a cell surface receptor selected form the group consisting of: CTLA-4, PD1, TIM-3, LAG-3, ICOS, CD28 and PDL-1.

The polypeptide or antibody according to the invention may bind any target, examples of such targets or antigens according are described above.

Methods of Increasing Agonistic Activity of a Polypeptide or Antibody

It is to be understood that the embodiments described below with reference to a polypeptide or antibody refers to a polypeptide or antibody comprising an Fc region of an immunoglobulin and an antigen-binding region, a polypeptide or antibody may also be a multispecific polypeptide or antibody having a first Fc region of an immunoglobulin and a first antigen-binding region, and a second polypeptide or antibody having a second Fc region of an immunoglobulin and a second antigen-binding region.

In one aspect the present invention relates to a method of increasing agonistic activity of a polypeptide or antibody by introducing an Fc-Fc enhancing substitution and a C1q binding substitution.

In one aspect the present invention relates to a method of increasing agonistic activity of a polypeptide or antibody comprising an Fc region of a human immunoglobulin and an antigen binding region, which method comprises a) introducing at least one substitution at a position selected from the group consisting of: E430, E345 or a S440Y or S440W substitution, and b) introducing one or more substitutions at a position selected from the group consisting of: G236, S239, S267, H268, S324 K326, I332, E333 and P396, wherein the position correspond to human IgG1, according to EU numbering.

Introducing a) at least one substitution according to the invention which is in one of the following positions E430, E345 or S440 introduces the effect of enhanced Fc-Fc interactions of the polypeptide or antibody. Introducing b) one or more substitution according to the invention which is in one of the following positions G236, S239, S267, H268, S324 K326, I332, E333 and P396 introduces the effect of increased agonistic activity in the polypeptide or antibody.

In another aspect the present invention relates to a method of increasing agonistic activity of a polypeptide or antibody comprising an Fc region of a human immunoglobulin and an antigen binding region, wherein the Fc region comprises a) at least one substitution at a position selected from the group consisting of: E430, E345 or a S440Y or S440W substitution, and which method comprises b) introducing one or more substitutions at a position selected from the group consisting of: G236, S239, S267, H268, S324 K326, I332, E333 and P396, wherein the position correspond to human IgG1, according to EU numbering.

In one embodiment of the present invention relates to a method of increasing agonistic activity of a polypeptide or antibody comprising an Fc region of a human immunoglobulin and an antigen binding region, wherein the Fc region comprises a) at least one substitution at a position selected from the group consisting of: E430, E345 or a S440Y or S440W substitution, and which method comprises b) introducing at least two substitutions at a position selected from the group consisting of: G236, S239, S267, H268, S324 K326, I332, E333 and P396, wherein the position correspond to human IgG1, according to EU numbering.

Increasing agonistic activity of a polypeptide or antibody according to the present invention is to be understood as increasing the agonistic activity of the polypeptide or antibody compared to a parent polypeptide or antibody, alternatively increasing the agonistic activity of the polypeptide or antibody may also refer to when the polypeptide or antibody is compared to a polypeptide or antibody comprising an Fc-Fc enhancing mutation but not a C1q binding mutation. Thus, it is to be understood that the polypeptide or antibody may be compared to a parent polypeptide or parent antibody having the identical antigen binding region and an Fc region without an Fc-Fc enhancing substitution and without a C1q binding substitution, alternatively the the polypeptide or antibody may be compared to a polypeptide or antibody having the identical antigen binding region and an Fc region with an Fc-Fc enhancing substitution, but without a C1q binding substitution.

In one embodiment of the invention one or more substitution(s) at a position selected from the group of G236, S239, S267, H268, S324 K326, I332, E333 and P396, with the proviso that the substitution in position G236 is not G236F, G236R, G236Y.

In one embodiment of the invention one or more substitution(s) at a position selected from the group of G236, S239, S267, H268, S324 K326, I332, E333 and P396, with the proviso that the substitution in position S267 is not S267H, 52671, S267K, S267G.

In one embodiment of the invention one or more substitution(s) at a position selected from the group of G236, S239, S267, H268, S324 K326, I332, E333 and P396, with the proviso that the substitution in position H268 is not H268K, H268D, H268E.

In one embodiment of the invention at least one substitution is selected from the group consisting of: E430G, E345K, E430S, E430F, E430T, E345Q, E345R, E345Y, S440W and S440Y. Hereby embodiments are provided in which the substitution enhances Fc-Fc interactions.

In one embodiment of the invention at least one substitution is selected from the group consisting of: E430G, E430S, E430F, E430T.

In one embodiment of the invention at least one substitution is selected from the group consisting of: E345K, E345Q, E345R, E345Y.

In one embodiment of the invention the polypeptide or antibody has at least an E430G substitution. In one embodiment of the invention the polypeptide or antibody has at least an E345K substitution. In one embodiment of the invention the polypeptide or antibody has at least an E345R substitution. In one embodiment of the invention the polypeptide or antibody has at least a S440Y substitution.

In one embodiment, the present invention relates to a method of increasing agonistic activity of a polypeptide or antibody wherein the Fc region comprises at least one substitution selected from the group consisting of: E430G, E430S, E430F and E430T, which method comprises introducing one or more substitution(s) at a position selected from the group of: G236, S239, S267, H268, S324 K326, I332, E333 and P396.

In one embodiment, the present invention relates to a method of increasing agonistic activity of a polypeptide or antibody wherein the Fc region comprises at least one substitution selected from the group consisting of: E430G, E430S, E430F and E430T, which method comprises introducing one or more substitution(s) selected from the group of: K326A, K326W, E333A, E333S, E333T, and P396L.

In one embodiment, the present invention relates to a method of increasing agonistic activity of a polypeptide or antibody wherein the Fc region comprises an E430G substitution, which method comprises introducing one or more substitution(s) at a position selected from the group of: G236, S239, S267, H268, S324, K326, I332, E333 and P396.

In one embodiment, the present invention relates to a method of increasing agonistic activity of a polypeptide or antibody wherein the Fc region comprises an E430G substitution, which method comprises introducing one or more substitution(s) selected from the group of: K326A, K326W, E333A, E333S, E333T, and P396L.

In one embodiment, the present invention relates to a method of increasing agonistic activity of a polypeptide or antibody wherein the Fc region comprises an E430G substitution, which method comprises introducing the substitution(s) from one of the groups consisting of:
  i) K326W and E333S,
  ii) K326W and E333T,
  iii) K326A and E333A,
  iv) K326A, E333A and P396L,
  v) K326W,
  vi) E333S, and
  vii) E333T.

In one embodiment, the present invention relates to a method of increasing agonistic activity of a polypeptide or antibody wherein the Fc region comprises at least one substitution selected from the group consisting of: E345K, E345Q, E345R and E345Y, which method comprises introducing one or more substitution(s) at a position selected from the group of: G236, S239, S267, H268, S324 K326, I332, E333 and P396.

In one embodiment, the present invention relates to a method of increasing agonistic activity of a polypeptide or antibody wherein the Fc region comprises at least one substitution selected from the group consisting of: E345K, E345Q, E345R and E345Y, which method comprises introducing one or more substitution(s) selected from the group of: K326A, K326W, E333A, E333S, E333T, and P396L.

In one embodiment, the present invention relates to a method of increasing agonistic activity of a polypeptide or antibody wherein the Fc region comprises an E345K substitution, which method comprises introducing one or more substitution(s) at a position selected from the group of: G236, S239, S267, H268, S324 K326, I332, E333 and P396.

In one embodiment, the present invention relates to a method of increasing agonistic activity of a polypeptide or antibody wherein the Fc region comprises an E345K substitution, which method comprises introducing one or more substitution(s) selected from the group of: K326A, K326W, E333A, E333S, E333T, and P396L.

In one embodiment, the present invention relates to a method of increasing agonistic activity of a polypeptide or antibody wherein the Fc region comprises an E345K substitution, which method comprises introducing the substitution(s) from one of the groups consisting of:
  i) K326W and E333S,
  ii) K326W and E333T,
  iii) K326A and E333A,
  iv) K326A, E333A and P396L,
  v) K326W,
  vi) E333S, and
  vii) E333T.

In one embodiment, the present invention relates to a method of increasing agonistic activity of a polypeptide or antibody wherein the Fc region comprises an E345R substitution, which method comprises introducing one or more substitution(s) at a position selected from the group of: G236, S239, S267, H268, S324 K326, I332, E333 and P396.

In one embodiment, the present invention relates to a method of increasing agonistic activity of a polypeptide or antibody wherein the Fc region comprises an E345R substitution, which method comprises introducing one or more substitution(s) selected from the group of: K326A, K326W, E333A, E333S, E333T, and P396L.

In one embodiment, the present invention relates to a method of increasing agonistic activity of a polypeptide or antibody wherein the Fc region comprises an E345R substitution, which method comprises introducing the substitution(s) from one of the groups consisting of:
  i) K326W and E333S,
  ii) K326W and E333T,
  iii) K326A and E333A,
  iv) K326A, E333A and P396L,
  v) K326W,
  vi) E333S, and
  vii) E333T.

In one embodiment, the present invention relates to a method of increasing agonistic activity of a polypeptide or antibody wherein the Fc region comprises at least one substitution selected from the group consisting of: S440Y and S440W, which method comprises introducing one or more substitution(s) at a position selected from the group of: G236, S239, S267, H268, S324 K326, I332, E333 and P396.

In one embodiment, the present invention relates to a method of increasing agonistic activity of a polypeptide or antibody wherein the Fc region comprises at least one substitution selected from the group consisting of: S440W and S440W, which method comprises introducing one or more substitution(s) selected from the group of: K326A, K326W, E333A, E333S, E333T, and P396L.

In one embodiment, the present invention relates to a method of increasing agonistic activity of a polypeptide or antibody wherein the Fc region comprises a S440Y substitution, which method comprises one or more substitution(s) at a position selected from the group of: G236, S239, S267, H268, S324 K326, I332, E333 and P396.

In one embodiment, the present invention relates to a method of increasing agonistic activity of a polypeptide or antibody wherein the Fc region comprises an S440Y substitution, which method comprises introducing one or more substitution(s) selected from the group of: K326A, K326W, E333A, E333S, E333T, and P396L.

In one embodiment, the present invention relates to a method of increasing agonistic activity of a polypeptide or antibody wherein the Fc region comprises an S440Y substitution, which method comprises introducing the substitution(s) from one of the groups consisting of:
  i) K326W and E333S,
  ii) K326W and E333T,
  iii) K326A and E333A,
  iv) K326A, E333A and P396L,
  v) K326W,
  vi) E333S, and
  vii) E333T.

Hereby are embodiments provided that allow for increased agonistic properties of polypeptides or antibodies upon cell surface antigen binding. In one embodiment the polypeptides or antibodies comprise increased agonistic properties. In one embodiment the polypeptides or antibodies comprise an Fc region comprising a first heavy chain and a second heavy chain, wherein one of the above mentioned substitutions may be present in the first and/or the second heavy chain.

In one embodiment of the invention one or more substitutions at a position selected from the group consisting of: K326, E333 and P396. In one embodiment of the invention one or more substitutions, such as two or three substitutions at a position selected from the group consisting of: K326, E333 and P396. In one embodiment of the invention the polypeptide or antibody comprises substitutions at the positions K326 and E333. In one embodiment of the invention the polypeptide or antibody comprises substitutions at the positions K326 and P396. In one embodiment of the invention the polypeptide or antibody comprises substitutions at the positions P396 and E333. In one embodiment of the invention the polypeptide or antibody comprises substitutions at the positions K326, E333 and P396.

In one embodiment of the invention the polypeptide or antibody comprises one or more, such as two or three substitutions selected from the group consisting of: K326A, K326W, E333S, E333A and P396L. In one embodiment of the invention the polypeptide or antibody comprises a K326A substitution. In one embodiment of the invention the polypeptide or antibody comprises a K326W substitution. In one embodiment of the invention the polypeptide or antibody comprises a E333S substitution. In one embodiment of the invention the polypeptide or antibody comprises a E333A substitution. In one embodiment of the invention the polypeptide or antibody comprises a P396L substitution. In one embodiment of the invention the polypeptide or antibody comprises the substitutions of K326W and E333S. In one embodiment of the invention the polypeptide or antibody comprises the substitutions of K326W and E333A. In one embodiment of the invention the polypeptide or antibody comprises the substitutions of K326W and P396L. In one embodiment of the invention the polypeptide or antibody comprises the substitutions of K326A and E333A. In one embodiment of the invention the polypeptide or antibody comprises the substitutions of K326A and E333S. In one embodiment of the invention the polypeptide or antibody comprises the substitutions of K326A and P396L. In one embodiment of the invention the polypeptide or antibody comprises the substitutions of E333A and P396L. In one embodiment of the invention the polypeptide or antibody comprises the substitutions of E333S and P396L. In one embodiment of the invention the polypeptide or antibody comprises the substitutions of K326A, E333A and P396L. In one embodiment of the invention the polypeptide or antibody comprises the substitutions of K326S, E333A and P396L. In one embodiment of the invention the polypeptide or antibody comprises the substitutions of K326W, E333A and P396L. In one embodiment of the invention the polypeptide or antibody comprises the substitutions of K326W, E333S and P396L.

In one embodiment of the invention one or more substitutions at a position selected from the group consisting of: S267, H268 and S324. In one embodiment of the invention one or more substitutions, such as two or three substitutions at a position selected from the group consisting of: S267, H268 and S324. In one embodiment of the invention the polypeptide or antibody comprises substitutions at the positions S267 and H268. In one embodiment of the invention the polypeptide or antibody comprises substitutions at the positions S267 and S324. In one embodiment of the invention the polypeptide or antibody comprises substitutions at the positions H268 and S324. In one embodiment of the invention the polypeptide or antibody comprises substitutions at the positions S267, H268 and S324.

In one embodiment of the invention one or more substitutions at a position selected from the group consisting of: S267E, H268F and 5324T. In one embodiment of the invention the polypeptide or antibody comprises one or more, such as two or three substitutions selected from the group consisting of: S267E, H268F and 5324T. In one embodiment of the invention the polypeptide or antibody comprises a S267E substitution. In one embodiment of the invention the polypeptide or antibody comprises a H268F substitution. In one embodiment of the invention the polypeptide or antibody comprises a 5324T substitution. In one embodiment of the invention the polypeptide or antibody comprises the substitutions of S267E and H268F. In one embodiment of the invention the polypeptide or antibody comprises the substitutions of S267E and 5324T. In one embodiment of the invention the polypeptide or antibody comprises the substitutions of H268F and 5324T. In one embodiment of the invention the polypeptide or antibody comprises the substitutions of: S267E, H268F and 5324T.

In one embodiment, the present invention relates to a method wherein the Fc region comprises one or more further substitutions.

In one embodiment, the present invention relates to a method wherein the Fc region comprises a further substitution in the following positions in human IgG1 according to EU numbering: S440 or K439. In one embodiment of the invention the Fc region comprises a further substitution corresponding to one of the following position S440 or K439, with the proviso that the further substitution is not in position S440 if the Fc-Fc enhancing substitution is in S440. Polypeptides or antibodies comprising a Fc-FC enhancing substitution and a C1q binding substitution according to the present invention and a further substitution at position S440 such as S440K do not form oligomers with polypeptides or antibodies comprising a mutation at position S440 such as S440K. Polypeptides or antibodies comprising a Fc-Fc enhancing substitution and a C1q binding substitution according to the present invention and a further substitution at position K439 such as K439E do not form oligomers with polypeptides or antibodies comprising a mutation at position K439 such as K439E. Hereby a method is provided that allows for the formation of oligomers between polypeptides or antibodies wherein a first polypeptide or antibody comprises a K439E substitution and the second polypeptide or antibody comprises a S440K substitution. In this way oligomers such as e.g. hexamers can be forced to be formed in certain patterns of first and second polypeptides. This may be of interest in methods where the polypeptides bind different targets or epitopes and oligomers should be formed in combinations of these different targets or epitopes.

In one embodiment, the present invention relates to a method wherein the further substitution is selected from S440K or K439E.

In one embodiment, the present invention relates to a method of increasing agonistic activity wherein the agonistic activity is increased by at least 20% compared to a parent polypeptide or parent antibody which is identical to the polypeptide or antibody or alternatively a polypeptide or antibody with an identical Fc-Fc enhancing substitution, but without a C1q binding substitution. In another embodiment of the invention the polypeptide or antibody has an increased agonistic activity of at least 30%, at least 40%, at least 50% at least 60%, at least 70% at least 80%, at least 90%, at least 95% compared to a parent polypeptide or parent antibody or alternatively a polypeptide or antibody with an identical Fc-Fc enhancing substitution, but without a C1q binding substitution.

Methods of Increasing CDC Activity

In one aspect the present invention relates to a method of increasing CDC activity of a polypeptide or antibody by introducing an Fc-Fc enhancing substitution and a C1q binding substitution.

In one aspect the present invention relates to a method of increasing CDC activity of a polypeptide or antibody comprising an Fc region of a human immunoglobulin and an antigen binding region, which method comprises a) introducing at least one substitution at a position selected from the group consisting of: E430, E345 or a S440Y or S440W substitution, and b) introducing one or more substitutions at a position selected from the group consisting of: G236, S239, S267, H268, S324 K326, I332, E333 and P396, wherein the position correspond to human IgG1, according to EU numbering.

Introducing a) at least one substitution according to the invention which is in one of the following positions E430, E345 or S440 introduces the effect of enhanced Fc-Fc interactions of the polypeptide or antibody. Introducing b) one or more substitution according to the invention which is in one of the following positions G236, S239, S267, H268, S324 K326, I332, E333 and P396 introduces the effect of increased CDC activity in the polypeptide or antibody.

In another aspect the present invention relates to a method of increasing CDC activity of a polypeptide or antibody comprising an Fc region of a human immunoglobulin and an antigen binding region, wherein the Fc region comprises a) at least one substitution at a position selected from the group consisting of: E430, E345 or a S440Y or S440W substitution, and which method comprises b) introducing one or more substitutions at a position selected from the group consisting of: G236, S239, S267, H268, S324 K326, I332, E333 and P396, wherein the position correspond to human IgG1, according to EU numbering.

In one embodiment of the present invention relates to a method of increasing CDC activity of a polypeptide or antibody comprising an Fc region of a human immunoglobulin and an antigen binding region, wherein the Fc region comprises a) at least one substitution at a position selected from the group consisting of: E430, E345 or a S440Y or S440W substitution, and which method comprises b) introducing at least two substitutions at a position selected from the group consisting of: G236, S239, S267, H268, S324 K326, I332, E333 and P396, wherein the position correspond to human IgG1, according to EU numbering.

Increasing agonistic activity of a polypeptide or antibody according to the present invention is to be understood as increasing the CDC activity of the polypeptide or antibody compared to a parent polypeptide or antibody, alternatively increasing the agonistic activity of the polypeptide or antibody may also refer to when the polypeptide or antibody is compared to a polypeptide or antibody comprising an Fc-Fc enhancing mutation but not a C1q binding mutation. Thus, it is to be understood that the polypeptide or antibody may be compared to a parent polypeptide or parent antibody having the identical antigen binding region and an Fc region without an Fc-Fc enhancing substitution and without a C1q binding substitution, alternatively the polypeptide or antibody may be compared to a polypeptide or antibody having the identical antigen binding region and an Fc region with an Fc-Fc enhancing substitution, but without a C1q binding substitution.

In one embodiment of the invention one or more substitution(s) at a position selected from the group of G236, S239, S267, H268, S324 K326, I332, E333 and P396, with the proviso that the substitution in position G236 is not G236F, G236R, G236Y.

In one embodiment of the invention one or more substitution(s) at a position selected from the group of G236, S239, S267, H268, S324 K326, I332, E333 and P396, with the proviso that the substitution in position S267 is not S267H, S2671, S267K, S267G.

In one embodiment of the invention one or more substitution(s) at a position selected from the group of G236, S239, S267, H268, S324 K326, I332, E333 and P396, with the proviso that the substitution in position H268 is not H268K, H268D, H268E.

In one embodiment of the invention at least one substitution is selected from the group consisting of: E430G, E345K, E430S, E430F, E430T, E345Q, E345R, E345Y, S440W and S440Y. Hereby embodiments are provided in which the substitution enhances Fc-Fc interactions.

In one embodiment of the invention at least one substitution is selected from the group consisting of: E430G, E430S, E430F, E430T.

In one embodiment of the invention at least one substitution is selected from the group consisting of: E345K, E345Q, E345R, E345Y.

In one embodiment of the invention the polypeptide or antibody has at least an E430G substitution. In one embodiment of the invention the polypeptide or antibody has at least an E345K substitution. In one embodiment of the invention the polypeptide or antibody has at least an E345R substitution. In one embodiment of the invention the polypeptide or antibody has at least a S440Y substitution.

In one embodiment, the present invention relates to a method of increasing CDC activity of a polypeptide or antibody wherein the Fc region comprises at least one substitution selected from the group consisting of: E430G, E430S, E430F and E430T, which method comprises introducing one or more substitution(s) at a position selected from the group of: G236, S239, S267, H268, S324 K326, I332, E333 and P396.

In one embodiment, the present invention relates to a method of increasing CDC activity of a polypeptide or antibody wherein the Fc region comprises at least one substitution selected from the group consisting of: E430G, E430S, E430F and E430T, which method comprises introducing one or more substitution(s) selected from the group of: K326A, K326W, E333A, E333S, E333T, and P396L.

In one embodiment, the present invention relates to a method of increasing CDC activity of a polypeptide or antibody wherein the Fc region comprises an E430G substitution, which method comprises introducing one or more substitution(s) at a position selected from the group of: G236, S239, S267, H268, S324, K326, I332, E333 and P396.

In one embodiment, the present invention relates to a method of increasing CDC activity of a polypeptide or antibody wherein the Fc region comprises an E430G substitution, which method comprises introducing one or more substitution(s) selected from the group of: K326A, K326W, E333A, E333S, E333T, and P396L.

In one embodiment, the present invention relates to a method of increasing CDC activity of a polypeptide or antibody wherein the Fc region comprises an E430G substitution, which method comprises introducing the substitution(s) from one of the groups consisting of:
  i) K326W and E333S,
  ii) K326W and E333T,
  iii) K326A and E333A,
  iv) K326A, E333A and P396L,
  v) K326W,
  vi) E333S, and
  vii) E333T.

In one embodiment, the present invention relates to a method of increasing CDC activity of a polypeptide or antibody wherein the Fc region comprises at least one substitution selected from the group consisting of: E345K, E345Q, E345R and E345Y, which method comprises introducing one or more substitution(s) at a position selected from the group of: G236, S239, S267, H268, S324 K326, I332, E333 and P396.

In one embodiment, the present invention relates to a method of increasing CDC activity of a polypeptide or antibody wherein the Fc region comprises at least one substitution selected from the group consisting of: E345K, E345Q, E345R and E345Y, which method comprises introducing one or more substitution(s) selected from the group of: K326A, K326W, E333A, E333S, E333T, and P396L.

In one embodiment, the present invention relates to a method of increasing CDC activity of a polypeptide or antibody wherein the Fc region comprises an E345K substitution, which method comprises introducing one or more substitution(s) at a position selected from the group of: G236, S239, S267, H268, S324 K326, I332, E333 and P396.

In one embodiment, the present invention relates to a method of increasing CDC activity of a polypeptide or antibody wherein the Fc region comprises an E345K substitution, which method comprises introducing one or more substitution(s) selected from the group of: K326A, K326W, E333A, E333S, E333T, and P396L.

In one embodiment, the present invention relates to a method of increasing CDC activity of a polypeptide or antibody wherein the Fc region comprises an E345K substitution, which method comprises introducing the substitution(s) from one of the groups consisting of:
  i) K326W and E333S,
  ii) K326W and E333T,
  iii) K326A and E333A,
  iv) K326A, E333A and P396L,
  v) K326W,
  vi) E333S, and
  vii) E333T.

In one embodiment, the present invention relates to a method of increasing CDC activity of a polypeptide or antibody wherein the Fc region comprises an E345R substitution, which method comprises introducing one or more substitution(s) at a position selected from the group of: G236, S239, S267, H268, S324 K326, I332, E333 and P396.

In one embodiment, the present invention relates to a method of increasing CDC activity of a polypeptide or antibody wherein the Fc region comprises an E345R substitution, which method comprises introducing one or more substitution(s) selected from the group of: K326A, K326W, E333A, E333S, E333T, and P396L.

In one embodiment, the present invention relates to a method of increasing CDC activity of a polypeptide or antibody wherein the Fc region comprises an E345R substitution, which method comprises introducing the substitution(s) from one of the groups consisting of:
  i) K326W and E333S,
  ii) K326W and E333T,
  iii) K326A and E333A,
  iv) K326A, E333A and P396L,
  v) K326W,
  vi) E333S, and
  vii) E333T.

In one embodiment, the present invention relates to a method of increasing CDC activity of a polypeptide or antibody wherein the Fc region comprises at least one substitution selected from the group consisting of: S440Y and S440W, which method comprises introducing one or more substitution(s) at a position selected from the group of: G236, S239, S267, H268, S324 K326, I332, E333 and P396.

In one embodiment, the present invention relates to a method of increasing CDC activity of a polypeptide or antibody wherein the Fc region comprises at least one substitution selected from the group consisting of: S440W and S440W, which method comprises introducing one or more substitution(s) selected from the group of: K326A, K326W, E333A, E333S, E333T, and P396L.

In one embodiment, the present invention relates to a method of increasing CDC activity of a polypeptide or antibody wherein the Fc region comprises a S440Y substitution, which method comprises one or more substitution(s) at a position selected from the group of: G236, S239, S267, H268, S324 K326, I332, E333 and P396.

In one embodiment, the present invention relates to a method of increasing CDC activity of a polypeptide or antibody wherein the Fc region comprises an S440Y substitution, which method comprises introducing one or more substitution(s) selected from the group of: K326A, K326W, E333A, E333S, E333T, and P396L.

In one embodiment, the present invention relates to a method of increasing CDC activity of a polypeptide or antibody wherein the Fc region comprises an S440Y substitution, which method comprises introducing the substitution(s) from one of the groups consisting of:
  i) K326W and E333S,
  ii) K326W and E333T,
  iii) K326A and E333A,
  iv) K326A, E333A and P396L,
  v) K326W,
  vi) E333S, and
  vii) E333T.

Hereby are embodiments provided that allow for increased CDC activity of polypeptides or antibodies upon cell surface antigen binding. In one embodiment the polypeptides or antibodies comprise increased CDC activity. In one embodiment the polypeptides or antibodies comprise an Fc region comprising a first heavy chain and a second heavy chain, wherein one of the above mentioned substitutions may be present in the first and/or the second heavy chain.

In one embodiment of the invention one or more substitutions at a position selected from the group consisting of: K326, E333 and P396. In one embodiment of the invention one or more substitutions, such as two or three substitutions at a position selected from the group consisting of: K326, E333 and P396. In one embodiment of the invention the polypeptide or antibody comprises substitutions at the positions K326 and E333. In one embodiment of the invention the polypeptide or antibody comprises substitutions at the positions K326 and P396. In one embodiment of the invention the polypeptide or antibody comprises substitutions at the positions P396 and E333. In one embodiment of the invention the polypeptide or antibody comprises substitutions at the positions K326, E333 and P396.

In one embodiment of the invention the polypeptide or antibody comprises one or more, such as two or three substitutions selected from the group consisting of: K326A, K326W, E333S, E333A and P396L. In one embodiment of the invention the polypeptide or antibody comprises a K326A substitution. In one embodiment of the invention the polypeptide or antibody comprises a K326W substitution. In one embodiment of the invention the polypeptide or antibody comprises an E333S substitution. In one embodiment of the invention the polypeptide or antibody comprises an E333A substitution. In one embodiment of the invention the polypeptide or antibody comprises a P396L substitution. In one embodiment of the invention the polypeptide or antibody comprises the substitutions of K326W and E333S. In one embodiment of the invention the polypeptide or antibody comprises the substitutions of K326W and E333A. In one embodiment of the invention the polypeptide or antibody comprises the substitutions of K326W and P396L. In one embodiment of the invention the polypeptide or antibody comprises the substitutions of K326A and E333A. In one embodiment of the invention the polypeptide or antibody comprises the substitutions of K326A and E333S. In one embodiment of the invention the polypeptide or antibody comprises the substitutions of K326A and P396L. In one embodiment of the invention the polypeptide or antibody comprises the substitutions of E333A and P396L. In one embodiment of the invention the polypeptide or antibody comprises the substitutions of E333S and P396L. In one embodiment of the invention the polypeptide or antibody comprises the substitutions of K326A, E333A and P396L. In one embodiment of the invention the polypeptide or antibody comprises the substitutions of K326S, E333A and P396L. In one embodiment of the invention the polypeptide or antibody comprises the substitutions of K326W, E333A and P396L. In one embodiment of the invention the polypeptide or antibody comprises the substitutions of K326W, E333S and P396L.

In one embodiment of the invention one or more substitutions at a position selected from the group consisting of: S267, H268 and S324. In one embodiment of the invention one or more substitutions, such as two or three substitutions at a position selected from the group consisting of: S267, H268 and S324. In one embodiment of the invention the polypeptide or antibody comprises substitutions at the positions S267 and H268. In one embodiment of the invention the polypeptide or antibody comprises substitutions at the positions S267 and S324. In one embodiment of the invention the polypeptide or antibody comprises substitutions at the positions H268 and S324. In one embodiment of the invention the polypeptide or antibody comprises substitutions at the positions S267, H268 and S324.

In one embodiment of the invention one or more substitutions at a position selected from the group consisting of: S267E, H268F and 5324T. In one embodiment of the invention the polypeptide or antibody comprises one or more, such as two or three substitutions selected from the group consisting of: S267E, H268F and 5324T. In one embodiment of the invention the polypeptide or antibody comprises a S267E substitution. In one embodiment of the invention the polypeptide or antibody comprises a H268F substitution. In one embodiment of the invention the polypeptide or antibody comprises a 5324T substitution. In one embodiment of the invention the polypeptide or antibody comprises the substitutions of S267E and H268F. In one embodiment of the invention the polypeptide or antibody comprises the substitutions of S267E and 5324T. In one embodiment of the invention the polypeptide or antibody comprises the substitutions of H268F and 5324T. In one embodiment of the invention the polypeptide or antibody comprises the substitutions of: S267E, H268F and 5324T.

Compositions

It is to be understood that the embodiments described below with reference to a polypeptide or antibody refers to a polypeptide or antibody comprising an Fc region of an immunoglobulin and an antigen-binding region, a polypeptide or antibody may also be a multispecific polypeptide or antibody having a first Fc region of an immunoglobulin and a first antigen-binding region, and a second polypeptide or antibody having a second Fc region of an immunoglobulin and a second antigen-binding region.

The invention also relates to compositions comprising polypeptides or antibodies described herein and variations hereof. Specific aspects and embodiments will be described below. Furthermore, such polypeptide or antibody may be obtained according to any method described herein.

In one aspect the present invention relates to a composition comprising at least one polypeptide or antibody described herein.

In one embodiment of the present invention the composition comprises one or more polypeptides or antibodies according to any aspect or embodiment described herein.

In one embodiment of the present invention the composition comprises a first polypeptide or antibody and a second polypeptide or antibody as described in any aspect or embodiment herein.

In one aspect of the invention, the composition comprises a first and a second polypeptide or antibody, wherein the first and the second polypeptide or antibody comprises an Fc region comprising,
 (i) at least one substitution, which is an Fc-Fc enhancing mutation; and
 (ii) one or more substitutions, which are C1q binding substitutions; and
 (iii) a further mutation, which prevents oligomerization between Fc regions having the identical further mutation, wherein the first and the second polypeptide or antibody does not comprise the same further mutation.

In one embodiment of the present invention, the composition comprises a first polypeptide or antibody and a second polypeptide or antibody wherein the first and second polypeptide or antibody comprises a i) at least one or more substitutions selected from the group consisting of: E430, E345 or a S440Y or S440W substitution, and ii) one or more substitutions at a position selected form the group consisting of: G236, S239, S267, H268, S324, K326, I332, E333, and P396 and iii) a further mutation wherein the first and the second polypeptide or antibody does not comprise the same further mutation. Thus, the composition comprises a first polypeptide or antibody comprising a first Fc region and a second polypeptide or antibody comprising a second Fc region.

In one embodiment of the invention, the composition comprises a first polypeptide or antibody comprising a first antigen-binding region and a first Fc region, a second polypeptide or antibody comprising second antigen-binding region and a second Fc region, wherein the first and second Fc region comprises:
- (i) least one or more substitutions selected from the group consisting of: E430, E345 or a S440Y or S440W substitution; and;
- (ii) one or more substitutions at a position selected form the group consisting of: G236, S239, S267, H268, S324, K326, I332, E333, and P396; and
- (iii) a further substitution at position K439 or S440, with the proviso that if the further substitution is at S440 then the substitution according to (i) is not at S440, with the proviso that the first and second Fc region does not comprise a further substitution according to (iii) in the same amino acid position,
- (iv) wherein the substitutions corresponds to the amino acid positions in human IgG1, according to EU numbering.

In one embodiment of the invention, the composition comprises a first polypeptide or antibody comprising a first antigen-binding region and a first Fc region, a second polypeptide or antibody comprising second antigen-binding region and a second Fc region, wherein the first and second Fc region comprises (i) a first mutation, (ii) a second mutation, (iii) a further mutation, wherein the mutations corresponds to the following amino acid positions in human IgG1, according to EU numbering:
- (i) least one or more substitutions selected from the group consisting of: E430, E345 or a S440Y or S440W substitution; and;
- (ii) one or more substitutions at a position selected form the group consisting of: G236, S239, S267, H268, S324, K326, I332, E333, and P396; and
- (iii) a further substitution at position K439 in the first Fc region and a further substitution at position S440 in the second Fc region, or vice versa, with the proviso that if the further substitution is at position S440 then the first substitution is not at S440;
- (iv) wherein the substitutions corresponds to the amino acid positions in human IgG1, according to EU numbering.

In one embodiment of the invention, the composition comprises a first polypeptide or antibody comprising a first antigen-binding region and a first Fc region, a second polypeptide or antibody comprising second antigen-binding region and a second Fc region, wherein the first and second Fc region comprises:
- (i) least one or more substitutions selected from the group consisting of: E430, E345 or a S440Y or S440W substitution; and
- (ii) one or more substitutions at a position selected form the group consisting of: G236, S239, S267, H268, S324, K326, I332, E333, and P396; and
- (iii) a further K439E substitution in the first Fc region and a further S440K substitution in the second Fc region, and
- (iv) wherein the substitutions corresponds to the amino acid positions in human IgG1, according to EU numbering.

In one embodiment of the invention, the composition comprises a first polypeptide or antibody comprising a first antigen-binding region and a first Fc region, a second polypeptide or antibody comprising second antigen-binding region and a second Fc region, wherein the first and second Fc region comprises:
- (i) least one or more substitutions selected from the group consisting of: E430, E345 or a S440Y or S440W substitution; and
- (ii) one or more substitutions at a position selected form the group consisting of: G236, S239, S267, H268, S324, K326, I332, E333, and P396; and
- (iii) a further S440K substitution in the first Fc region and a further K439E substitution in the second Fc region;
- (iv) wherein the substitutions corresponds to the amino acid positions in human IgG1, according to EU numbering.

Hereby embodiments are provided wherein either both the first and the second polypeptide or antibody has increased agonistic activity and/or CDC activity, or only the first or the second polypeptide has a increased agonistic activity and/or CDC activity.

In one embodiment of the invention, the composition comprises a first polypeptide or antibody comprising a first antigen-binding region and a first Fc region, a second polypeptide or antibody comprising second antigen-binding region and a second Fc region, wherein the first and second Fc region comprises:
- (i) a substitution in the amino acid position corresponding to E430, and
- (i) (ii) one or more substitutions at a position selected form the group consisting of: G236, S239, S267, H268, S324, K326, I332, E333, and P396; and
- (ii) (iii) a further K439E substitution in the first Fc region and a further S440K substitution in the second Fc region, or vice versa.

In one embodiment of the invention, the composition comprises a first polypeptide or antibody comprising a first antigen-binding region and a first Fc region, a second polypeptide or antibody comprising second antigen-binding region and a second Fc region, wherein the first and second Fc region comprises:
- i) a substitution in the amino acid position corresponding to E345, and
- ii) one or more substitutions at a position selected form the group consisting of: G236, S239, S267, H268, S324, K326, I332, E333, and P396; and
- iii) a further K439E substitution in the first Fc region and a further S440K substitution in the second Fc region, or vice versa.

In one embodiment of the invention, the composition comprises a first polypeptide or antibody comprising a first antigen-binding region and a first Fc region, a second polypeptide or antibody comprising second antigen-binding region and a second Fc region, wherein the first and second Fc region comprises:
- i) a E430G, and
- ii) one or more substitutions selected form the group consisting of: K326W, K326A, E333S, E333A, P396L, S267E, H268F, 5324T, G263A, S324E, I332E and S239D; and
- iii) a further K439E substitution in the first Fc region and a further S440K substitution in the second Fc region, or vice versa.

In one embodiment of the invention, the composition comprises a first polypeptide or antibody comprising a first antigen-binding region and a first Fc region, a second polypeptide or antibody comprising second antigen-binding region and a second Fc region, wherein the first and second Fc region comprises:

i) a E430G, and
ii) one or more substitutions selected form the group consisting of: K326W, K326A, E333S, E333A and P396L; and
iii) a further K439E substitution in the first Fc region and a further S440K substitution in the second Fc region, or vice versa.

In one embodiment of the invention, the composition comprises a first polypeptide or antibody comprising a first antigen-binding region and a first Fc region, a second polypeptide or antibody comprising second antigen-binding region and a second Fc region, wherein the first and second Fc region comprises:
i) a E430G, and
ii) at least two substitutions selected form the group consisting of: K326W, K326A, E333S, E333A and P396L; and
iii) a further K439E substitution in the first Fc region and a further S440K substitution in the second Fc region, or vice versa.

In one embodiment of the invention, the composition comprises a first polypeptide or antibody comprising a first antigen-binding region and a first Fc region, a second polypeptide or antibody comprising second antigen-binding region and a second Fc region, wherein the first and second Fc region comprises:
i) a E430G substitution, and
ii) a K326W and E333S substitution; and
iii) a further K439E substitution in the first Fc region and a further S440K substitution in the second Fc region, or vice versa.
(ii).

In one embodiment of the invention, the composition comprises a first polypeptide or antibody comprising a first antigen-binding region and a first Fc region, a second polypeptide or antibody comprising second antigen-binding region and a second Fc region, wherein the first and second Fc region comprises:
i) a E345K, and
ii) one or more substitutions selected form the group consisting of: K326W, K326A, E333S, E333A, P396L, S267E, H268F, 5324T, G263A, S324E, I332E and S239D; and
iii) a further K439E substitution in the first Fc region and a further S440K substitution in the second Fc region, or vice versa.

In one embodiment of the invention, the composition comprises a first polypeptide or antibody comprising a first antigen-binding region and a first Fc region, a second polypeptide or antibody comprising second antigen-binding region and a second Fc region, wherein the first and second Fc region comprises:
i) a E345K, and
ii) one or more substitutions selected form the group consisting of: K326W, K326A, E333S, E333A and P396L; and
iii) a further K439E substitution in the first Fc region and a further S440K substitution in the second Fc region, or vice versa.

In one embodiment of the invention, the composition comprises a first polypeptide or antibody comprising a first antigen-binding region and a first Fc region, a second polypeptide or antibody comprising second antigen-binding region and a second Fc region, wherein the first and second Fc region comprises:

i) a E345K, and
ii) at least two substitutions selected form the group consisting of: K326W, K326A, E333S, E333A and P396L; and
iii) a further K439E substitution in the first Fc region and a further S440K substitution in the second Fc region, or vice versa.

In one embodiment of the invention, the composition comprises a first polypeptide or antibody comprising a first antigen-binding region and a first Fc region, a second polypeptide or antibody comprising second antigen-binding region and a second Fc region, wherein the first and second Fc region comprises:
i) a E345K substitution, and
ii) a K326W and E333S substitution; and
iii) a further K439E substitution in the first Fc region and a further S440K substitution in the second Fc region, or vice versa.

In one embodiment of the invention, the composition comprises a first polypeptide or antibody comprising a first antigen-binding region and a first Fc region, a second polypeptide or antibody comprising second antigen-binding region and a second Fc region, wherein the first and second Fc region comprises:
i) a E345R, and
ii) one or more substitutions selected form the group consisting of: K326W, K326A, E333S, E333A, P396L, S267E, H268F, 5324T, G263A, S324E, I332E and S239D; and
iii) a further K439E substitution in the first Fc region and a further S440K substitution in the second Fc region, or vice versa.

In one embodiment of the invention, the composition comprises a first polypeptide or antibody comprising a first antigen-binding region and a first Fc region, a second polypeptide or antibody comprising second antigen-binding region and a second Fc region, wherein the first and second Fc region comprises:
i) a E345R, and
ii) one or more substitutions selected form the group consisting of: K326W, K326A, E333S, E333A and P396L; and
iii) a further K439E substitution in the first Fc region and a further S440K substitution in the second Fc region, or vice versa.

In one embodiment of the invention, the composition comprises a first polypeptide or antibody comprising a first antigen-binding region and a first Fc region, a second polypeptide or antibody comprising second antigen-binding region and a second Fc region, wherein the first and second Fc region comprises:
i) a E345R, and
ii) at least two substitutions selected form the group consisting of: K326W, K326A, E333S, E333A and P396L; and
iii) a further K439E substitution in the first Fc region and a further S440K substitution in the second Fc region, or vice versa.

In one embodiment of the invention, the composition comprises a first polypeptide or antibody comprising a first antigen-binding region and a first Fc region, a second polypeptide or antibody comprising second antigen-binding region and a second Fc region, wherein the first and second Fc region comprises:

i) a E345R substitution, and
ii) a K326W and E333S substitution; and
iii) a further K439E substitution in the first Fc region and a further S440K substitution in the second Fc region, or vice versa.

In another embodiment of the invention, the composition comprises a first and a second polypeptide or antibody, wherein the first and the second polypeptide or antibody comprises an Fc region comprising,
(i) at least one substitution, which is an Fc-Fc enhancing mutation;
(ii) a further mutation, which prevents oligomerization between Fc regions having the identical further mutation, wherein the first and the second polypeptide or antibody does not comprise the same further mutation,
(iii) and either the first or the second Fc region comprises one or more substitutions, which are C1q binding substitutions. Thus, in some embodiments only first or the second polypeptide or antibody comprises a second mutation that decreases Fc effector functions.

In one embodiment of the invention, the composition comprises a first polypeptide or antibody comprising a first antigen-binding region and a first Fc region, a second polypeptide or antibody comprising a second antigen-binding region and a second Fc region, wherein the first and second Fc region comprises
(i) least one or more substitutions selected from the group consisting of: E430, E345 or a S440Y or S440W substitution,
(iii) a further K439E or S440K mutation, wherein the first and second Fc region does not comprise the same further substitution, and wherein if at least one substitution is S440Y or S440W then the further mutation is not S440K;
(ii) and either the first or the second Fc region comprises one or more substitutions at a position selected form the group consisting of: G236, S239, S267, H268, S324, K326, I332, E333, and P396.

In one embodiment of the invention, the composition comprises a first polypeptide or antibody comprising a first antigen-binding region and a first Fc-region, a second polypeptide or antibody comprising second antigen-binding region and a second Fc-region, wherein the first Fc-region comprises (i) least one or more substitutions selected from the group consisting of: E430, E345 or a S440Y or S440W substitution, and ii) one or more substitutions at a position selected form the group consisting of: G236, S239, S267, H268, S324, K326, I332, E333, and P396, and a iii) further K439E mutation; and the second Fc-region comprises i) least one or more substitutions selected from the group consisting of: E430, E345 or a S440Y or S440W substitution, and a further S440K mutation. Hereby embodiments are provided where only the first polypeptide or antibody has increased agonistic activity and/or increased CDC activity.

In one embodiment of the invention, the composition comprises a first polypeptide or antibody comprising a first antigen-binding region and a first Fc-region, a second polypeptide or antibody comprising second antigen-binding region and a second Fc-region, wherein the first Fc-region comprises (i) least one or more substitutions selected from the group consisting of: E430, E345, and ii) one or more substitutions at a position selected form the group consisting of: G236, S239, S267, H268, S324, K326, I332, E333, and P396, and a iii) further S440K mutation; and the second Fc-region comprises i) least one or more substitutions selected from the group consisting of: E430, E345 or a S440Y or S440W substitution, and a further K439E muta-tion. Hereby embodiments are provided where only the first polypeptide or antibody has increased agonistic activity and/or increased CDC activity.

In one embodiment of the invention, the composition comprises a first polypeptide or antibody comprising a first antigen-binding region and a first Fc-region, a second polypeptide or antibody comprising second antigen-binding region and a second Fc-region, wherein the first Fc-region comprises (i) a E430G substitution and ii) one or more substitutions selected form the group consisting of: K326W, K326A, E333S, E333A and P396L and iii) a further K439E substitution; and the second Fc-region comprises i) a E430G substitution, and a further S440K substitution.

In one embodiment of the invention, the composition comprises a first polypeptide or antibody comprising a first antigen-binding region and a first Fc-region, a second polypeptide or antibody comprising second antigen-binding region and a second Fc-region, wherein the first Fc-region comprises (i) a E430G substitution and ii) one or more substitutions selected form the group consisting of: K326W, K326A, E333S, E333A and P396L and iii) a further S440K substitution; and the second Fc-region comprises i) a E430G substitution, and a further K439E substitution.

In one embodiment of the invention, the composition comprises a first polypeptide or antibody comprising a first antigen-binding region and a first Fc-region, a second polypeptide or antibody comprising second antigen-binding region and a second Fc-region, wherein the first Fc-region comprises (i) a E430G substitution and ii) a K326W and E333S substitution, and iii) a further S440K substitution; and the second Fc-region comprises i) a E430G substitution, and a further K439E substitution. In one embodiment of the invention, the composition comprises a first polypeptide or antibody comprising a first antigen-binding region and a first Fc-region, a second polypeptide or antibody comprising second antigen-binding region and a second Fc-region, wherein the first Fc-region comprises (i) a E430G substitution and ii) a K326W and E333S substitution, and iii) a further K439E substitution; and the second Fc-region comprises i) a E430G substitution, and a further S440K substitution.

In one embodiment of the present invention the composition comprises a polypeptide or antibody capable of binding to a member of the Tumor Necrosis Factor Receptor Superfamily (TNFR-SF) or G-protein Coupled Receptor (GPCR) superfamily In one embodiment of the present invention the composition comprises a polypeptide or antibody capable of binding to a member of the TNFR-SF selected from the group consisting of: TNFR1, FAS, DR3, DR4, DR5, DR6, NGFR, EDAR DcR1, DcR2, DcR3, OPG, TROY, XEDAR, LTbR, HVEM, TWEAKR, CD120b, OX40, CD40, CD27, CD30, 4-1BB, RANK, TACI, BLySR, BCMA, GITR and RELT.

In one embodiment of the present invention the composition comprises a polypeptide or antibody capable of binding to a member of the TNFR-SF with an intracellular death domain selected from the following group consisting of: TNFR1, FAS, DR3, DR4, DR5, DR6, NGFR and EDAR.

In one embodiment of the present invention the composition comprises a polypeptide or antibody capable of binding to a member of the TNFR-SF without an intracellular death domain selected form the following group consisting of: DcR1, DcR2, DcR3, OPG, TROY, XEDAR, LTbR, HVEM, TWEAKR, CD120b, OX40, CD40, CD27, CD30, 4-1BB, RANK, TACI, BLySR, BCMA, GITR, RELT.

In one embodiment of the present invention the composition comprises a polypeptide or antibody capable of binding to a member of the TNFR-SF belonging to the group of immune activators consisting of: OX40, CD40, CD27, CD30, 4-1BB, RANK, TACI, BLySR, BCMA, GITR and RELT.

In one embodiment of the present invention the composition comprises a polypeptide or antibody wherein a first polypeptide and a second polypeptide bind different epitopes on one or more members of the TNFR-SF without an intracellular death domain, selected from the following group consisting of: OX40, CD40, CD27, CD30, 4-1BB, RANK, TACI, BLySR, BCMA, GITR and RELT.

In one embodiment of the present invention the composition comprises a polypeptide or antibody wherein a first polypeptide binding to one member of the TNFR-SF without an intracellular death domain selected form the following group consisting of: OX40, CD40, CD27, CD30, 4-1BB, RANK, TACI, BLySR, BCMA, GITR and RELT does not block binding of said second antibody binding to one member of the TNFR-SF without an intracellular death domain selected from the following group consisting of: OX40, CD40, CD27, CD30, 4-1BB, RANK, TACI, BLySR, BCMA, GITR and RELT.

In one embodiment of the present invention the composition comprising a first polypeptide or antibody and a second polypeptide or antibody are present in the composition at a 1:49 to 49:1 molar ratio, such as a 1:1 molar ratio, a 1:2 molar ratio, a 1:3 molar ratio, a 1:4 molar ratio, a 1:5 molar ratio, a 1:6 molar ratio, a 1:7 molar ratio, a 1:8 molar ratio, a 1:9 molar ratio, a 1:10 molar ratio, a 1:15 molar ratio, a 1:20 molar ratio, a 1:25 molar ratio, a 1:30 molar ratio, a 1:35 molar ratio, a 1:40 molar ratio, a 1:45 molar ratio, a 1:50 molar ratio, a 50:1 molar ratio, a 45:1 molar ratio, a 40:1 molar ratio, a 35:1 molar ratio, a 30:1 molar ratio, a 25:1 molar ratio, a 20:1 molar ratio, a 15:1 molar ratio, a 10:1 molar ratio, a 9:1 molar ratio, a 8:1 molar ratio, a 7:1 molar ratio, a 6:1 molar ratio, a 5:1 molar ratio, a 4:1 molar ratio, a 3:1 molar ratio, a 2:1 molar ratio.

In one embodiment of the present invention the composition comprising a first polypeptide and a second polypeptide and/or any additional polypeptide are present in the composition at an equimolar ratio.

In one embodiment of the present invention the composition according to any aspect or embodiment is a pharmaceutical composition.

Therapeutic Applications

The polypeptides, antibodies, bispecific antibodies or compositions according to any aspect or embodiment of the present invention may be used as a medicament, i.e. for therapeutic applications.

In one aspect the present invention provides a polypeptide, antibody or a composition according to any aspect or embodiment disclosed herein for use as a medicament.

In another aspect the present invention provides a polypeptide, antibody or a composition according to any aspect or embodiment disclosed herein for use in the treatment of cancer, autoimmune disease, inflammatory disease or infectious disease.

In another aspect the present invention relates to a method of treating an individual having a disease comprising administering to the individual an effective amount of a polypeptide, antibody or composition according to any aspect or embodiment disclosed herein.

In one embodiment of the invention the disease is selected from the group of: cancer, autoimmune disease, inflammatory disease and infectious disease.

In one embodiment of the invention the method according to any aspect or embodiment disclosed herein relates to further administering an additional therapeutic agent.

In one embodiment of the invention the additional therapeutic agent is one or more anti-cancer agent(s) selected from the group consisting of chemotherapeutics (including but not limited to paclitaxel, temozolomide, cisplatin, carboplatin, oxaliplatin, irinotecan, doxorubicin, gemcitabine, 5-fluorouracil, pemetrexed), kinase inhibitors (including but not limited to sorafenib, sunitinib or everolimus), apoptosis-modulating agents (including but not limited to recombinant human TRAIL or birinapant), RAS inhibitors, proteasome inhibitors (including but not limited to bortezomib), histon deacetylase inhibitors (including but not limited to vorinostat), nutraceuticals, cytokines (including but not limited to IFN-γ), antibodies or antibody mimetics (including but not limited to anti-EGFR, anti-IGF-1R, anti-VEGF, anti-CD20, anti-CD38, anti-HER2, anti-PD-1, anti-PD-L1, anti-CTLA4, anti-CD40, anti-CD137, anti-GITR antibodies and antibody mimetics), antibody-drug conjugates.

Kit-of-Parts

It is to be understood that the embodiments described below with reference to a polypeptide or antibody refers to a polypeptide or antibody comprising an Fc region of an immunoglobulin and an antigen-binding region, a polypeptide or antibody may also be a multispecific polypeptide or antibody having a first Fc region of an immunoglobulin and a first antigen-binding region, and a second polypeptide or antibody having a second Fc region of an immunoglobulin and a second antigen-binding region.

The invention also relates to kit-of-parts for simultaneous, separate or sequential use in therapy comprising polypeptides or antibodies described herein. Furthermore, such variants may be obtained according to any method described herein.

In one aspect the present invention relates to a kit of parts comprising a polypeptide, antibody or composition according to any aspect or embodiment described herein, wherein said polypeptide, antibody or composition is in one or more containers such as vials.

In one embodiment of the present invention the kit of parts comprises a polypeptide, antibody or a composition according to any aspect or embodiment described herein, for simultaneous, separate or sequential use in therapy.

In another aspect, the present invention relates to use of a polypeptide, an antibody, a composition or kit-of-parts according to any of the embodiments herein described for use in a diagnostic method.

In another aspect, the present invention relates to a diagnostic method comprising administering a polypeptide, antibody, a composition or a kit-of-parts according to any embodiments herein described to at least a part of the body of a human or other mammal.

In another aspect, the present invention relates to use of a polypeptide, an antibody, a composition or kit-of-parts according to any of the embodiments herein described in imaging at least a part of the body of a human or other mammal.

In another aspect, the present invention relates to a method for imaging of at least a part of the body of a human or other mammal, comprising administering a variant, a composition or a kit-of-parts according to any embodiments herein described.

Further Uses

It is to be understood that the embodiments described below with reference to a polypeptide or antibody refers to a polypeptide or antibody comprising an Fc region of an immunoglobulin and an antigen-binding region, a polypeptide or antibody may also be a multispecific polypeptide or antibody having a first Fc region of an immunoglobulin and a first antigen-binding region, and a second polypeptide or antibody having a second Fc region of an immunoglobulin and a second antigen-binding region.

In a further aspect, the invention relates to a polypeptide, antibody of the invention as described above for use as a medicament, in particular for use as a medicament for the treatment of diseases or disorders. Examples of such diseases and disorders include, without limitation, cancer, autoimmune diseases, inflammatory diseases, infectious diseases, bacterial, viral or fungal infections.

In another aspect, the present invention relates to the polypeptide, antibody, bispecific antibodies, compositions and kit-of-parts described herein, for treatment of a disease, such as cancer.

In another aspect, the present invention relates to a method for treatment of a human disease, comprising administration of a variant, a composition or a kit-of-parts described herein.

In another aspect, the present invention relates to a method for treatment of cancer in a human comprising administration of a variant, a composition or a kit-of-parts.

"Treatment" refers to the administration of an effective amount of a therapeutically active compound of the present invention with the purpose of easing, ameliorating, arresting or eradicating (curing) symptoms or disease states.

An "effective amount" or "therapeutically effective amount" refers to an amount effective, at dosages and for periods of time necessary, to achieve a desired therapeutic result. A therapeutically effective amount of an antibody may vary according to factors such as the disease state, age, sex, and weight of the individual, and the ability of the antibody to elicit a desired response in the individual. A therapeutically effective amount is also one in which any toxic or detrimental effects of the antibody or antibody portion are outweighed by the therapeutically beneficial effects.

Dosages

It is to be understood that the embodiments described below with reference to a polypeptide or antibody refers to a polypeptide or antibody comprising an Fc region of an immunoglobulin and an antigen-binding region, a polypeptide or antibody may also be a multispecific polypeptide or antibody having a first Fc region of an immunoglobulin and a first antigen-binding region, and a second polypeptide or antibody having a second Fc region of an immunoglobulin and a second antigen-binding region.

Efficient dosages and the dosage regimens for the antibody depend on the disease or condition to be treated and may be determined by the persons skilled in the art. An exemplary, non-limiting range for a therapeutically effective amount of an antibody of the present invention is about 0.1 to 100 mg/kg, such as about 0.1 to 50 mg/kg, for example about 0.1 to 20 mg/kg, such as about 0.1 to 10 mg/kg, for instance about 0.5, about such as 0.3, about 1, about 3, about 5, or about 8 mg/kg.

Polypeptides or antibodies of the present invention may also be administered in combination therapy, i.e., combined with other therapeutic agents relevant for the disease or condition to be treated. Accordingly, in one embodiment, the antibody-containing medicament is for combination with one or more further therapeutic agents, such as a cytotoxic, chemotherapeutic or anti-angiogenic agents. Such combined administration may be simultaneous, separate or sequential.

In a further embodiment, the present invention provides a method for treating or preventing disease, such as cancer, which method comprises administration to a subject in need thereof of a therapeutically effective amount of a variant or pharmaceutical composition of the present invention, in combination with radiotherapy and/or surgery.

Method of Preparation

It is to be understood that the embodiments described below with reference to a polypeptide or antibody refers to a polypeptide or antibody comprising an Fc region of an immunoglobulin and an antigen-binding region, a polypeptide or antibody may also be a multispecific polypeptide or antibody having a first Fc region of an immunoglobulin and a first antigen-binding region, and a second polypeptide or antibody having a second Fc region of an immunoglobulin and a second antigen-binding region.

The invention also provides isolated nucleic acids and vectors encoding a variant according to any one of the aspects described above, as well as vectors and expression systems encoding the variants. Suitable nucleic acid constructs, vectors and expression systems for antibodies and variants thereof are known in the art, and described in the Examples. In embodiments where the variant comprises not only a heavy chain (or Fc-containing fragment thereof) but also a light chain, the nucleotide sequences encoding the heavy and light chain portions may be present on the same or different nucleic acids or vectors.

The invention also provides a method for producing, in a host cell, a polypeptide or antibody according to any one of the aspects described above, wherein said polypeptide or antibody comprises at least the Fc region of a heavy chain, said method comprising the following steps:
 a) providing a nucleotide construct encoding said Fc region of said variant,
 b) expressing said nucleotide construct in a host cell, and
 c) recovering said antibody variant from a cell culture of said host cell.

In some embodiments, the antibody is a heavy-chain antibody. In most embodiments, however, the antibody will also contain a light chain and thus said host cell further expresses a light-chain-encoding construct, either on the same or a different vector.

Host cells suitable for the recombinant expression of antibodies are well-known in the art, and include CHO, HEK-293, Expi293, PER-C6, NS/0 and Sp2/0 cells. In one embodiment, said host cell is a cell which is capable of Asn-linked glycosylation of proteins, e.g. a eukaryotic cell, such as a mammalian cell, e.g. a human cell. In a further embodiment, said host cell is a non-human cell which is genetically engineered to produce glycoproteins having human-like or human glycosylation. Examples of such cells are genetically-modified *Pichia pastoris* (Hamilton et al., Science 301 (2003) 1244-1246; Potgieter et al., J. Biotechnology 139 (2009) 318-325) and genetically-modified *Lemna minor* (Cox et al., Nature Biotechnology 12 (2006) 1591-1597).

In one embodiment, said host cell is a host cell which is not capable of efficiently removing C-terminal lysine K447 residues from antibody heavy chains. For example, Table 2 in Liu et al. (2008) J Pharm Sci 97: 2426 (incorporated herein by reference) lists a number of such antibody production systems, e.g. Sp2/0, NS/0 or transgenic mammary gland (goat), wherein only partial removal of C-terminal lysines is obtained. In one embodiment, the host cell is a host cell with altered glycosylation machinery. Such cells have been described in the art and can be used as host cells in which to express variants of the invention to thereby produce an antibody with altered glycosylation. See, for example, Shields, R. L. et al. (2002) J. Biol. Chem. 277: 26733-26740; Umana et al. (1999) Nat. Biotech. 17:176-1, as well as EP1176195; WO03/035835; and WO99/54342. Additional methods for generating engineered glycoforms are known in the art, and include but are not limited to those described in Davies et al., 2001, Biotechnol Bioeng 74:288-294; Shields et al, 2002, J Biol Chem 277:26733-26740; Shinkawa et al., 2003, J Biol Chem 278:3466-3473), U.S. Pat. No. 6,602,684, WO00/61739A1; WO01/292246A1; WO02/311140A1; WO 02/30954A1; Potelligent™ technology (Biowa, Inc. Princeton, N.J.); GlycoMAb™ glycosylation engineering technology (GLYCART biotechnology AG, Zurich, Switzerland); US 20030115614; Okazaki et al., 2004, JMB, 336: 1239-49.

The invention also relates to an antibody obtained or obtainable by the method of the invention described above.

In a further aspect, the invention relates to a host cell capable of producing a polypeptide or antibody of the invention. In one embodiment, the host cell has been transformed or transfected with a nucleotide construct of the invention.

The present invention is further illustrated by the following examples which should not be construed as further limiting.

TABLE 1

| SEQ ID NO: | Name | Sequence | Clone |
|---|---|---|---|
| SEQ ID NO: 1 | VH hDR5-01-G56T CDR1 | GFNIKDTF | hDR5-01-G56T |
| SEQ ID NO: 2 | VH hDR5-01-G56T CDR2 | IDPANTNT | |
| SEQ ID NO: 3 | VH hDR5-01-G56T CDR3 | VRGLYTYYFDY | |
| SEQ ID NO: 4 | VH hDR5-01-G56T | EVQLQQSGAEVVKPGASVKLSCKASGFNIKDTFIHWVKQAPG QGLEWIGRIDPANTNTKYDPKFQGKATITTDTSSNTAYMELSS LRSEDTAVYYCVRGLYTYYFDYWGQGTLVTVSS | |
| SEQ ID NO: 5 | HC hDR5-01-G56T | EVQLQQSGAEVVKPGASVKLSCKASGFNIKDTFIHWVKQAPG QGLEWIGRIDPANTNTKYDPKFQGKATITTDTSSNTAYMELSS LRSEDTAVYYCVRGLYTYYFDYWGQGTLVTVSSASTKGPSVFPL APSSKSTSGGTAALGCLVKDYFPEPVTVSWNSGALTSGVHTFP AVLQSSGLYSLSSVVTVPSSSLGTQTYICNVNHKPSNTKVDKRV EPKSCDKTHTCPPCPAPELLGGPSVFLFPPKPKDTLMISRTPEVT CVVVDVSHEDPEVKFNWYVDGVEVHNAKTKPREEQYNSTYR VVSVLTVLHQDWLNGKEYKCKVSNKALPAPIEKTISKAKGQPR EPQVYTLPPSREEMTKNQVSLTCLVKGFYPSDIAVEWESNGQP ENNYKTTPPVLDSDGSFFLYSKLTVDKSRWQQGNVFSCSVMH EALHNHYTQKSLSLSPGK | |
| SEQ ID NO: 6 | VL hDR5-01 CDR1 | QSISNN | |
| | VL hDR5-01 CDR2 | FAS | |
| SEQ ID NO: 7 | VL hDR5-01 CDR3 | QQGNSWPYT | |
| SEQ ID NO: 8 | VL hDR5-01 | EIVMTQSPATLSVSPGERATLSCRASQSISNNLHWYQQKPGQ APRLLIKFASQSITGIPARFSGSGSGTEFTLTISSLQSEDFAVYYC QQGNSWPYTFGQGTKLEIK | |
| SEQ ID NO: 9 | LC hDR5-01 | EIVMTQSPATLSVSPGERATLSCRASQSISNNLHWYQQKPGQ APRLLIKFASQSITGIPARFSGSGSGTEFTLTISSLQSEDFAVYYC QQGNSWPYTFGQGTKLEIKRTVAAPSVFIFPPSDEQLKSGTAS VVCLLNNFYPREAKVQWKVDNALQSGNSQESVTEQDSKDSTY SLSSTLTLSKADYEKHKVYACEVTHQGLSSPVTKSFNRGEC | |
| SEQ ID NO: 10 | VH hDR5-05 CDR1 | GFNIKDTH | hDR5-05 |
| SEQ ID NO: 11 | VH hDR5-05 CDR2 | IDPANGNT | |
| SEQ ID NO: 12 | VH hDR5-05 CDR3 | ARWGTNVYFAY | |
| SEQ ID NO: 13 | VH hDR5-05 | QVQLVQSGAEVKKPGASVKVSCKASGFNIKDTHMHWVRQAP GQRLEWIGRIDPANGNTEYDQKFQGRVTITVDTSASTAYMEL SSLRSEDTAVYYCARWGTNVYFAYWGQGTLVTVSS | |
| SEQ ID NO: 14 | HC hDR5-05 | QVQLVQSGAEVKKPGASVKVSCKASGFNIKDTHMHWVRQAP GQRLEWIGRIDPANGNTEYDQKFQGRVTITVDTSASTAYMEL SSLRSEDTAVYYCARWGTNVYFAYWGQGTLVTVSSASTKGPS VFPLAPSSKSTSGGTAALGCLVKDYFPEPVTVSWNSGALTSGV HTFPAVLQSSGLYSLSSVVTVPSSSLGTQTYICNVNHKPSNTKV | |

TABLE 1-continued

| SEQ ID NO: | Name | Sequence | Clone |
|---|---|---|---|
| | | DKRVEPKSCDKTHTCPPCPAPELLGGPSVFLFPPKPKDTLMISR<br>TPEVTCVVVDVSHEDPEVKFNWYVDGVEVHNAKTKPREEQY<br>NSTYRVVSVLTVLHQDWLNGKEYKCKVSNKALPAPIEKTISKAK<br>GQPREPQVYTLPPSREEMTKNQVSLTCLVKGFYPSDIAVEWES<br>NGQPENNYKTTPPVLDSDGSFFLYSKLTVDKSRWQQGNVFSC<br>SVMHEALHNHYTQKSLSLSPGK | |
| SEQ ID NO: 15 | VL hDR5-05 CDR1 | SSVSY | |
| | VL hDR5-05 CDR2 | RTS | |
| SEQ ID NO: 16 | VL hDR5-05 CDR3 | QQYHSYPPT | |
| SEQ ID NO: 17 | VL hDR5-05 | DIQLTQSPSSLSASVGDRVTITCSASSSVSYMYWYQQKPGKAP<br>KPWIYRTSNLASGVPSRFSGSGSGTDFTLTISSLQPEDFATYYC<br>QQYHSYPPTFGGGTKVEIK | |
| SEQ ID NO: 18 | LC hDR5-05 | DIQLTQSPSSLSASVGDRVTITCSASSSVSYMYWYQQKPGKAP<br>KPWIYRTSNLASGVPSRFSGSGSGTDFTLTISSLQPEDFATYYC<br>QQYHSYPPTFGGGTKVEIKRTVAAPSVFIFPPSDEQLKSGTASV<br>VCLLNNFYPREAKVQWKVDNALQSGNSQESVTEQDSKDSTYS<br>LSSTLTLSKADYEKHKVYACEVTHQGLSSPVTKSFNRGEC | |
| SEQ ID NO: 19 | VH CONA-C49W-CDR1 | GGSISSGDYF | IgG1-CONA-C49W |
| SEQ ID NO: 20 | VH CONA-C49W-CDR2 | IHNSGTT | |
| SEQ ID NO: 21 | VH CONA-C49W-CDR3 | ARDRGGDYYYGMDV | |
| SEQ ID NO: 22 | VH CONA-C49W-C49W | QVQLQESGPGLVKPSQTLSLTCTVSGGSISSGDYFWSWIRQLP<br>GKGLEWIGHIHNSGTTYYNPSLKSRVTISVDTSKKQFSLRLSSVT<br>AADTAVYYCARDRGGDYYYGMDVWGQGTTVTVSS | |
| SEQ ID NO: 23 | HC CONA-C49W | QVQLQESGPGLVKPSQTLSLTCTVSGGSISSGDYFWSWIRQLP<br>GKGLEWIGHIHNSGTTYYNPSLKSRVTISVDTSKKQFSLRLSSVT<br>AADTAVYYCARDRGGDYYYGMDVWGQGTTVTVSSASTKGPS<br>VFPLAPSSKSTSGGTAALGCLVKDYFPEPVTVSWNSGALTSGV<br>HTFPAVLQSSGLYSLSSVVTVPSSSLGTQTYICNVNHKPSNTKV<br>DKRVEPKSCDKTHTCPPCPAPELLGGPSVFLFPPKPKDTLMISR<br>TPEVTCVVVDVSHEDPEVKFNWYVDGVEVHNAKTKPREEQY<br>NSTYRVVSVLTVLHQDWLNGKEYKCKVSNKALPAPIEKTISKAK<br>GQPREPQVYTLPPSREEMTKNQVSLTCLVKGFYPSDIAVEWES<br>NGQPENNYKTTPPVLDSDGSFFLYSKLTVDKSRWQQGNVFSC<br>SVMHEALHNHYTQKSLSLSPGK | |
| SEQ ID NO: 24 | VL CONA-C49W-CDR1 | QGISRSY | |
| | VL CONA-C49W-CDR2 | GAS | |
| SEQ ID NO: 25 | VL CONA-C49W-CDR3 | QQFGSSPWT | |
| SEQ ID NO: 26 | VL CONA-C49W | EIVLTQSPGTLSLSPGERATLSCRASQGISRSYLAWYQQKPGQA<br>PSLLIYGASSRATGIPDRFSGSGSGTDFTLTISRLEPEDFAVYYCQ<br>QFGSSPWTFGQGTKVEIK | |
| SEQ ID NO: 27 | LC CONA-C49W | EIVLTQSPGTLSLSPGERATLSCRASQGISRSYLAWYQQKPGQA<br>PSLLIYGASSRATGIPDRFSGSGSGTDFTLTISRLEPEDFAVYYCQ<br>QFGSSPWTFGQGTKVEIK<br>EIVLTQSPGTLSLSPGERATLSCRASQGISRSYLAWYQQKPGQA<br>PSLLIYGASSRATGIPDRFSGSGSGTDFTLTISRLEPEDFAVYYCQ<br>QFGSSPWTFGQGTKVEIKRTVAAPSVFIFPPSDEQLKSGTASVV<br>CLLNNFYPREAKVQWKVDNALQSGNSQESVTEQDSKDSTYSL<br>SSTLTLSKADYEKHKVYACEVTHQGLSSPVTKSFNRGEC | |
| SEQ ID NO: 28 | VH 7D8 CDR1 | GFTFHDYA | 7D8 |
| SEQ ID NO: 29 | VH 7D8 CDR2 | ISWNSGTI | |

TABLE 1-continued

| SEQ ID NO: | Name | Sequence | Clone |
|---|---|---|---|
| SEQ ID NO: 30 | VH 7D8 CDR3 | AKDIQYGNYYYGMDV | |
| SEQ ID NO: 31 | VH 7D8 | EVQLVESGGGLVQPDRSLRLSCAASGFTFHDYAMHW VRQAPGKGLEWVSTISWNSGTIGYADSVKGRFTISRD NAKNSLYLQMNSLRAEDTALYYCAKDIQYGNYYYGMD VWGQGTTVTVSS | |
| SEQ ID NO: 32 | HC 7D8 | EVQLVESGGGLVQPDRSLRLSCAASGFTFHDYAMHW VRQAPGKGLEWVSTISWNSGTIGYADSVKGRFTISRD NAKNSLYLQMNSLRAEDTALYYCAKDIQYGNYYYGMD VWGQGTTVTVSSASTKGPSVFPLAPSSKSTSGGTAAL GCLVKDYFPEPVTVSWNSGALTSGVHTFPAVLQSSGL YSLSSVVTVPSSSLGTQTYICNVNHKPSNTKVDKRVEP KSCDKTHTCPPCPAPELLGGPSVFLFPPKPKDTLMISRT PEVTCVVVDVSHEDPEVKFNWYVDGVEVHNAKTKPRE EQYNSTYRVVSVLTVLHQDWLNGKEYKCKVSNKALPA PIEKTISKAKGQPREPQVYTLPPSREEMTKNQVSLTCLV KGFYPSDIAVEWESNGQPENNYKTTPPVLDSDGSFFLY SKLTVDKSRWQQGNVFSCSVMHEALHNHYTQKSLSL SPGK | |
| SEQ ID NO: 33 | VL 7D8 CDR1 | QSVSSY | |
| | VL 7D8 CDR2 | DAS | |
| SEQ ID NO: 34 | VL 7D8 CDR3 | QQRSNWPIT | |
| SEQ ID NO: 35 | VL 7D8 | EIVLTQSPATLSLSPGERATLSCRASQSVSSYLAWYQQ KPGQAPRLLIYDASNRATGIPARFSGSGSGTDFTLTISS LEPEDFAVYYCQQRSNWPITFGQGTRLEIK | |
| SEQ ID NO: 36 | LC 7D8 | EIVLTQSPATLSLSPGERATLSCRASQSVSSYLAWYQQKPGQAP RLLIYDASNRATGIPARFSGSGSGTDFTLTISSLEPEDFAVYYCQ QRSNWPITFGQGTRLEIKRTVAAPSVFIFPPSDEQLKSGTASVV CLLNNFYPREAKVQWKVDNALQSGNSQESVTEQDSKDSTYSL SSTLTLSKADYEKHKVYACEVTHQGLSSPVTKSFNRGEC | |
| SEQ ID NO: 37 | VH 11B8 CDR1 | GFTFSYHA | 11B8 |
| SEQ ID NO: 38 | VH 11B8 CDR2 | IGTGGVT | |
| SEQ ID NO: 39 | VH 11B8 CDR3 | ARDYYGAGSFYDGLYGMDV | |
| SEQ ID NO: 40 | VH 11B8 | EVQLVQSGGGLVHPGGSLRLSCTGSGFTFSYHAMHW VRQAPGKGLEWVSIIGTGGVTYYADSVKGRFTISRDN VKNSLYLQMNSLRAEDMAVYYCARDYYGAGSFYDGLY GMDVWGQGTTVTVSS | |
| SEQ ID NO: 41 | HC 11B8 | EVQLVQSGGGLVHPGGSLRLSCTGSGFTFSYHAMHW VRQAPGKGLEWVSIIGTGGVTYYADSVKGRFTISRDN VKNSLYLQMNSLRAEDMAVYYCARDYYGAGSFYDGLY GMDVWGQGTTVTVSSASTKGPSVFPLAPSSKSTSGG TAALGCLVKDYFPEPVTVSWNSGALTSGVHTFPAVLQS SGLYSLSSVVTVPSSSLGTQTYICNVNHKPSNTKVDKR VEPKSCDKTHTCPPCPAPELLGGPSVFLFPPKPKDTLMI SRTPEVTCVVVDVSHEDPEVKFNWYVDGVEVHNAKTK PREEQYNSTYRVVSVLTVLHQDWLNGKEYKCKVSNKA LPAPIEKTISKAKGQPREPQVYTLPPSREEMTKNQVSLT CLVKGFYPSDIAVEWESNGQPENNYKTTPPVLDSDGS FFLYSKLTVDKSRWQQGNVFSCSVMHEALHNHYTQK SLSLSPGK | |
| SEQ ID NO: 42 | VL 11B8 CDR1 | QSVSSY | |
| | VL 11B8 CDR2 | DAS | |
| SEQ ID NO: 43 | VL 11B8 CDR3 | QQRSDWPLT | |

TABLE 1-continued

| SEQ ID NO: | Name | Sequence | Clone |
|---|---|---|---|
| SEQ ID NO: 44 | VL 11B8 | EIVLTQSPATLSLSPGERATLSCRASQSVSSYLAWYQQ KPGQAPRLLIYDASNRATGIPARFSGSGSGTDFTLTISS LEPEDFAVYYCQQRSDWPLTFGGGTKVEIK | |
| SEQ ID NO: 45 | LC 11B8 | EIVLTQSPATLSLSPGERATLSCRASQSVSSYLAWYQQKPGQAP RLLIYDASNRATGIPARFSGSGSGTDFTLTISSLEPEDFAVYYCQ QRSDWPLTFGGGTKVEIKRTVAAPSVFIFPPSDEQLKSGTASVV CLLNNFYPREAKVQWKVDNALQSGNSQESVTEQDSKDSTYSL SSTLTLSKADYEKHKVYACEVTHQGLSSPVTKSFNRGEC | |
| SEQ ID NO: 46 | VH ALEM CDR1 | GFTFTDFY | alemtuzumab |
| SEQ ID NO: 47 | VH ALEM CDR2 | IRDKAKGYTT | |
| SEQ ID NO: 48 | VH ALEM CDR3 | AREGHTAAPFDY | |
| SEQ ID NO: 49 | VH ALEM | QVQLQESGPGLVRPSQTLSLTCTVSGFTFTDFYMNWV RQPPGRGLEWIGFIRDKAKGYTTEYNPSVKGRVTMLV DTSKNQFSLRLSSVTAADTAVYYCAREGHTAAPFDYW GQGSLVTVSS | |
| SEQ ID NO: 50 | HC ALEM | QVQLQESGPGLVRPSQTLSLTCTVSGFTFTDFYMNWV RQPPGRGLEWIGFIRDKAKGYTTEYNPSVKGRVTMLV DTSKNQFSLRLSSVTAADTAVYYCAREGHTAAPFDYW GQGSLVTVSSASTKGPSVFPLAPSSKSTSGGTAALGCL VKDYFPEPVTVSWNSGALTSGVHTFPAVLQSSGLYSLS SVVTVPSSSLGTQTYICNVNHKPSNTKVDKRVEPKSC DKTHTCPPCPAPELLGGPSVFLFPPKPKDTLMISRTPEV TCVVVDVSHEDPEVKFNWYVDGVEVHNAKTKPREEQ YNSTYRVVSVLTVLHQDWLNGKEYKCKVSNKALPAPIE KTISKAKGQPREPQVYTLPPSREEMTKNQVSLTCLVKG FYPSDIAVEWESNGQPENNYKTTPPVLDSDGSFFLYSK LTVDKSRWQQGNVFSCSVMHEALHNHYTQKSLSLSP GK | |
| SEQ ID NO: 51 | VL ALEM CDR1 | QNIDKY | |
| | VL ALEM CDR2 | NTN | |
| SEQ ID NO: 52 | VL ALEM CDR3 | LQHISRPRT | |
| SEQ ID NO: 53 | VL ALEM | DIQMTQSPSSLSASVGDRVTITCKASQNIDKYLNWYQQKPGK APKLLIYNTNNLQTGVPSRFSGSGSGTDFTFTISSLQPEDIATYY CLQHISRPRTFGQGTKVEIK | |
| SEQ ID NO: 54 | LC ALEM | DIQMTQSPSSLSASVGDRVTITCKASQNIDKYLNWYQQKPGK APKLLIYNTNNLQTGVPSRFSGSGSGTDFTFTISSLQPEDIATYY CLQHISRPRTFGQGTKVEIKRTVAAPSVFIFPPSDEQLKSGTASV VCLLNNFYPREAKVQWKVDNALQSGNSQESVTEQDSKDSTYS LSSTLTLSKADYEKHKVYACEVTHQGLSSPVTKSFNRGEC | |
| SEQ ID NO: 55 | VH 2F8 CDR1 | GFTFSTYG | 2F8 |
| SEQ ID NO: 56 | VH 2F8 CDR2 | IWDDGSYK | |
| SEQ ID NO: 57 | VH 2F8 CDR3 | ARDGITMVRGVMKDYFDY | |
| SEQ ID NO: 58 | VH 2F8 | QVQLVESGGGVVQPGRSLRLSCAASGFTFSTYGMHW VRQAPGKGLEWVAVIWDDGSYKYYGDSVKGRFTISR DNSKNTLYLQMNSLRAEDTAVYYCARDGITMVRGVMK DYFDYWGQGTLVTVSS | |
| SEQ ID NO: 59 | HC 2F8 | QVQLVESGGGVVQPGRSLRLSCAASGFTFSTYGMHW VRQAPGKGLEWVAVIWDDGSYKYYGDSVKGRFTISR DNSKNTLYLQMNSLRAEDTAVYYCARDGITMVRGVMK DYFDYWGQGTLVTVSSASTKGPSVFPLAPSSKSTSGG TAALGCLVKDYFPEPVTVSWNSGALTSGVHTFPAVLQS SGLYSLSSVVTVPSSSLGTQTYICNVNHKPSNTKVDKR VEPKSCDKTHTCPPCPAPELLGGPSVFLFPPKPKDTLMI | |

TABLE 1-continued

| SEQ ID NO: | Name | Sequence | Clone |
|---|---|---|---|
| | | SRTPEVTCVVVDVSHEDPEVKFNWYVDGVEVHNAKTK<br>PREEQYNSTYRVVSVLTVLHQDWLNGKEYKCKVSNKA<br>LPAPIEKTISKAKGQPREPQVYTLPPSREEMTKNQVSLT<br>CLVKGFYPSDIAVEWESNGQPENNYKTTPPVLDSDGS<br>FFLYSKLTVDKSRWQQGNVFSCSVMHEALHNHYTQK<br>SLSLSPGK | |
| SEQ ID NO: 60 | VL 2F8 CDR1 | QDISSA | |
| | VL 2F8 CDR2 | DAS | |
| SEQ ID NO: 61 | VL 2F8 CDR3 | QQFNSYPLT | |
| SEQ ID NO: 62 | VL 2F8 | AIQLTQSPSSLSASVGDRVTITCRASQDISSALVWYQQKPGKAP<br>KLLIYDASSLESGVPSRFSGSESGTDFTLTISSLQPEDFATYYCQQ<br>FNSYPLTFGGGTKVEIK | |
| SEQ ID NO: 63 | LC 2F8 | AIQLTQSPSSLSASVGDRVTITCRASQDISSALVWYQQKPGKAP<br>KLLIYDASSLESGVPSRFSGSESGTDFTLTISSLQPEDFATYYCQQ<br>FNSYPLTFGGGTKVEIKRTVAAPSVFIFPPSDEQLKSGTASVVCL<br>LNNFYPREAKVQWKVDNALQSGNSQESVTEQDSKDSTYSLSS<br>TLTLSKADYEKHKVYACEVTHQGLSSPVTKSFNRGEC | |
| SEQ ID NO: 64 | VH b12 CDR1 | GYRFSNFV | b12 |
| SEQ ID NO: 65 | VH b12 CDR2 | INPYNGNK | |
| SEQ ID NO: 66 | VH b12 CDR3 | ARVGPYSWDDSPQDNYYMDV | |
| SEQ ID NO: 67 | VH b12 | QVQLVQSGAEVKKPGASVKVSCQASGYRFSNFVIHW<br>VRQAPGQRFEWMGWINPYNGNKEFSAKFQDRVTFTA<br>DTSANTAYMELRSLRSADTAVYYCARVGPYSWDDSPQ<br>DNYYMDVWGKGTTVIVSS | |
| SEQ ID NO: 68 | HC b12 | QVQLVQSGAEVKKPGASVKVSCQASGYRFSNFVIHW<br>VRQAPGQRFEWMGWINPYNGNKEFSAKFQDRVTFTA<br>DTSANTAYMELRSLRSADTAVYYCARVGPYSWDDSPQ<br>DNYYMDVWGKGTTVIVSSASTKGPSVFPLAPSSKSTS<br>GGTAALGCLVKDYFPEPVTVSWNSGALTSGVHTFPAV<br>LQSSGLYSLSSVVTVPSSSLGTQTYICNVNHKPSNTKV<br>DKRVEPKSCDKTHTCPPCPAPELLGGPSVFLFPPKPKD<br>TLMISRTPEVTCVVVDVSHEDPEVKFNWYVDGVEVHN<br>AKTKPREEQYNSTYRVVSVLTVLHQDWLNGKEYKCKV<br>SNKALPAPIEKTISKAKGQPREPQVYTLPPSREEMTKN<br>QVSLTCLVKGFYPSDIAVEWESNGQPENNYKTTPPVLD<br>SDGSFFLYSKLTVDKSRWQQGNVFSCSVMHEALHNH<br>YTQKSLSLSPGK | |
| SEQ ID NO: 69 | VL b12 CDR1 | HSIRSRR | |
| | VL b12 CDR2 | GVS | |
| SEQ ID NO: 70 | VL b12 CDR3 | QVYGASSYT | |
| SEQ ID NO: 71 | VL b12 | EIVLTQSPGTLSLSPGERATFSCRSSHSIRSRRVAWYQHKPGQA<br>PRLVIHGVSNRASGISDRFSGSGSGTDFTLTITRVEPEDFALYYC<br>QVYGASSYTFGQGTKLERK | |
| SEQ ID NO: 72 | LC b12 | EIVLTQSPGTLSLSPGERATFSCRSSHSIRSRRVAWYQHKPGQA<br>PRLVIHGVSNRASGISDRFSGSGSGTDFTLTITRVEPEDFALYYC<br>QVYGASSYTFGQGTKLERKRTVAAPSVFIFPPSDEQLKSGTASV<br>VCLLNNFYPREAKVQWKVDNALQSGNSQESVTEQDSKDSTYS<br>LSSTLTLSKADYEKHKVYACEVTHQGLSSPVTKSFNRGEC | |

TABLE 1-continued

| SEQ ID NO: | Name | Sequence | Clone |
|---|---|---|---|
| SEQ ID NO: 73 | Fc IgG1m(f) | ASTKGPSVFPLAPSSKSTSGGTAALGCLVKDYFPEPVTVSWNS GALTSGVHTFPAVLQSSGLYSLSSVVTVPSSSLGTQTYICNVNH KPSNTKVDKRVEPKSCDKTHTCPPCPAPELLGGPSVFLFPPKPK DTLMISRTPEVTCVVVDVSHEDPEVKFNWYVDGVEVHNAKTK PREEQYNSTYRVVSVLTVLHQDWLNGKEYKCKVSNKALPAPIE KTISKAKGQPREPQVYTLPPSREEMTKNQVSLTCLVKGFYPSDI AVEWESNGQPENNYKTTPPVLDSDGSFFLYSKLTVDKSRWQQ GNVFSCSVMHEALHNHYTQKSLSLSPGK | |
| SEQ ID NO: 74 | Fc IgG1m(z) | ASTKGPSVFPLAPSSKSTSGGTAALGCLVKDYFPEPVT VSWNSGALTSGVHTFPAVLQSSGLYSLSSVVTVPSSS LGTQTYICNVNHKPSNTKVDKKVEPKSCDKTHTCPPC PAPELLGGPSVFLFPPKPKDTLMISRTPEVTCVVVDVSH EDPEVKFNWYVDGVEVHNAKTKPREEQYNSTYRVVSV LTVLHQDWLNGKEYKCKVSNKALPAPIEKTISKAKGQP REPQVYTLPPSREEMTKNQVSLTCLVKGFYPSDIAVEW ESNGQPENNYKTTPPVLDSDGSFFLYSKLTVDKSRWQ QGNVFSCSVMHEALHNHYTQKSLSLSPGK | |
| SEQ ID NO: 75 | Fc IgG1m(a) | ASTKGPSVFPLAPSSKSTSGGTAALGCLVKDYFPEPVT VSWNSGALTSGVHTFPAVLQSSGLYSLSSVVTVPSSS LGTQTYICNVNHKPSNTKVDKPVEPKSCDKTHTCPPCP APELLGGPSVFLFPPKPKDTLMISRTPEVTCVVVDVSHE DPEVKFNWYVDGVEVHNAKTKPREEQYNSTYRVVSVL TVLHQDWLNGKEYKCKVSNKALPAPIEKTISKAKGQP REPQVYTLPPSRDELTKNQVSLTCLVKGFYPSDIAVEW ESNGQPENNYKTTPPVLDSDGSFFLYSKLTVDKSRWQ QGNVFSCSVMHEALHNHYTQKSLSLSPGK | |
| SEQ ID NO: 76 | Fc IgG1m(x) | ASTKGPSVFPLAPSSKSTSGGTAALGCLVKDYFPEPVT VSWNSGALTSGVHTFPAVLQSSGLYSLSSVVTVPSSS LGTQTYICNVNHKPSNTKVDKPVEPKSCDKTHTCPPCP APELLGGPSVFLFPPKPKDTLMISRTPEVTCVVVDVSHE DPEVKFNWYVDGVEVHNAKTKPREEQYNSTYRVVSVL TVLHQDWLNGKEYKCKVSNKALPAPIEKTISKAKGQP REPQVYTLPPSREEMTKNQVSLTCLVKGFYPSDIAVEW ESNGQPENNYKTTPPVLDSDGSFFLYSKLTVDKSRWQ QGNVFSCSVMHEGLHNHYTQKSLSLSPGK | |
| SEQ ID NO: 77 | Fc IgG1m(f)-E430G | ASTKGPSVFPLAPSSKSTSGGTAALGCLVKDYFPEPVT VSWNSGALTSGVHTFPAVLQSSGLYSLSSVVTVPSSS LGTQTYICNVNHKPSNTKVDKRVEPKSCDKTHTCPPCP APELLGGPSVFLFPPKPKDTLMISRTPEVTCVVVDVSHE DPEVKFNWYVDGVEVHNAKTKPREEQYNSTYRVVSVL TVLHQDWLNGKEYKCKVSNKALPAPIEKTISKAKGQP REPQVYTLPPSREEMTKNQVSLTCLVKGFYPSDIAVEW ESNGQPENNYKTTPPVLDSDGSFFLYSKLTVDKSRWQ QGNVFSCSVMHGALHNHYTQKSLSLSPGK | |
| SEQ ID NO: 78 | Fc IgG1m(f)-E345K | ASTKGPSVFPLAPSSKSTSGGTAALGCLVKDYFPEPVT VSWNSGALTSGVHTFPAVLQSSGLYSLSSVVTVPSSS LGTQTYICNVNHKPSNTKVDKRVEPKSCDKTHTCPPCP APELLGGPSVFLFPPKPKDTLMISRTPEVTCVVVDVSHE DPEVKFNWYVDGVEVHNAKTKPREEQYNSTYRVVSVL TVLHQDWLNGKEYKCKVSNKALPAPIEKTISKAKGQP RKPQVYTLPPSREEMTKNQVSLTCLVKGFYPSDIAVEW ESNGQPENNYKTTPPVLDSDGSFFLYSKLTVDKSRWQ QGNVFSCSVMHEALHNHYTQKSLSLSPGK | |
| SEQ ID NO: 79 | Fc IgG1m(f)-K326A/E333A/P396L | ASTKGPSVFPLAPSSKSTSGGTAALGCLVKDYFPEPVTVSWNS GALTSGVHTFPAVLQSSGLYSLSSVVTVPSSSLGTQTYICNVNH KPSNTKVDKRVEPKSCDKTHTCPPCPAPELLGGPSVFLFPPKPK DTLMISRTPEVTCVVVDVSHEDPEVKFNWYVDGVEVHNAKTK PREEQYNSTYRVVSVLTVLHQDWLNGKEYKCKVSNAALPAPIA KTISKAKGQPREPQVYTLPPSREEMTKNQVSLTCLVKGFYPSDI AVEWESNGQPENNYKTTPLLDSDGSFFLYSKLTVDKSRWQQ GNVFSCSVMHEALHNHYTQKSLSLSPGK | |
| SEQ ID NO: 80 | Fc IgG1m(f)-K326A/E333A/P396L/E430G | ASTKGPSVFPLAPSSKSTSGGTAALGCLVKDYFPEPVTVSWNS GALTSGVHTFPAVLQSSGLYSLSSVVTVPSSSLGTQTYICNVNH KPSNTKVDKRVEPKSCDKTHTCPPCPAPELLGGPSVFLFPPKPK DTLMISRTPEVTCVVVDVSHEDPEVKFNWYVDGVEVHNAKTK PREEQYNSTYRVVSVLTVLHQDWLNGKEYKCKVSNAALPAPIA KTISKAKGQPREPQVYTLPPSREEMTKNQVSLTCLVKGFYPSDI AVEWESNGQPENNYKTTPLVLDSDGSFFLYSKLTVDKSRWQQ GNVFSCSVMHGALHNHYTQKSLSLSPGK | |

TABLE 1-continued

| SEQ ID NO: | Name | Sequence | Clone |
|---|---|---|---|
| SEQ ID NO: 81 | Fc IgG1m(f)-K326A/E333A | ASTKGPSVFPLAPSSKSTSGGTAALGCLVKDYFPEPVTVSWNS GALTSGVHTFPAVLQSSGLYSLSSVVTVPSSSLGTQTYICNVNH KPSNTKVDKRVEPKSCDKTHTCPPCPAPELLGGPSVFLFPPKPK DTLMISRTPEVTCVVVDVSHEDPEVKFNWYVDGVEVHNAKTK PREEQYNSTYRVVSVLTVLHQDWLNGKEYKCKVSNAALPAPIA KTISKAKGQPREPQVYTLPPSREEMTKNQVSLTCLVKGFYPSDI AVEWESNGQPENNYKTTPPVLDSDGSFFLYSKLTVDKSRWQQ GNVFSCSVMHEALHNHYTQKSLSLSPGK | |
| SEQ ID NO: 82 | Fc IgG1m(f)-K326A/E333A/E430G | ASTKGPSVFPLAPSSKSTSGGTAALGCLVKDYFPEPVTVSWNS GALTSGVHTFPAVLQSSGLYSLSSVVTVPSSSLGTQTYICNVNH KPSNTKVDKRVEPKSCDKTHTCPPCPAPELLGGPSVFLFPPKPK DTLMISRTPEVTCVVVDVSHEDPEVKFNWYVDGVEVHNAKTK PREEQYNSTYRVVSVLTVLHQDWLNGKEYKCKVSNAALPAPIA KTISKAKGQPREPQVYTLPPSREEMTKNQVSLTCLVKGFYPSDI AVEWESNGQPENNYKTTPPVLDSDGSFFLYSKLTVDKSRWQQ GNVFSCSVMHGALHNHYTQKSLSLSPGK | |
| SEQ ID NO: 83 | Fc IgG1m(f)-K326A/P396L/E430G | ASTKGPSVFPLAPSSKSTSGGTAALGCLVKDYFPEPVTVSWNS GALTSGVHTFPAVLQSSGLYSLSSVVTVPSSSLGTQTYICNVNH KPSNTKVDKRVEPKSCDKTHTCPPCPAPELLGGPSVFLFPPKPK DTLMISRTPEVTCVVVDVSHEDPEVKFNWYVDGVEVHNAKTK PREEQYNSTYRVVSVLTVLHQDWLNGKEYKCKVSNAALPAPIE KTISKAKGQPREPQVYTLPPSREEMTKNQVSLTCLVKGFYPSDI AVEWESNGQPENNYKTTPLVLDSDGSFFLYSKLTVDKSRWQQ GNVFSCSVMHGALHNHYTQKSLSLSPGK | |
| SEQ ID NO: 84 | Fc IgG1m(f)-E333A/P396L/E430G | ASTKGPSVFPLAPSSKSTSGGTAALGCLVKDYFPEPVTVSWNS GALTSGVHTFPAVLQSSGLYSLSSVVTVPSSSLGTQTYICNVNH KPSNTKVDKRVEPKSCDKTHTCPPCPAPELLGGPSVFLFPPKPK DTLMISRTPEVTCVVVDVSHEDPEVKFNWYVDGVEVHNAKTK PREEQYNSTYRVVSVLTVLHQDWLNGKEYKCKVSNKALPAPIA KTISKAKGQPREPQVYTLPPSREEMTKNQVSLTCLVKGFYPSDI AVEWESNGQPENNYKTTPLVLDSDGSFFLYSKLTVDKSRWQQ GNVFSCSVMHGALHNHYTQKSLSLSPGK | |
| SEQ ID NO: 85 | Fc IgG1m(f)-I253D/K322A | ASTKGPSVFPLAPSSKSTSGGTAALGCLVKDYFPEPVTVSWNS GALTSGVHTFPAVLQSSGLYSLSSVVTVPSSSLGTQTYICNVNH KPSNTKVDKRVEPKSCDKTHTCPPCPAPELLGGPSVFLFPPKPK DTLMDSRTPEVTCVVVDVSHEDPEVKFNWYVDGVEVHNAKT KPREEQYNSTYRVVSVLTVLHQDWLNGKEYKCAVSNKALPAPI EKTISKAKGQPREPQVYTLPPSREEMTKNQVSLTCLVKGFYPSD IAVEWESNGQPENNYKTTPPVLDSDGSFFLYSKLTVDKSRWQ QGNVFSCSVMHEALHNHYTQKSLSLSPGK | |
| SEQ ID NO: 86 | Fc IgG1m(f)-K326W/E333S | ASTKGPSVFPLAPSSKSTSGGTAALGCLVKDYFPEPVTVSWNS GALTSGVHTFPAVLQSSGLYSLSSVVTVPSSSLGTQTYICNVNH KPSNTKVDKRVEPKSCDKTHTCPPCPAPELLGGPSVFLFPPKPK DTLMISRTPEVTCVVVDVSHEDPEVKFNWYVDGVEVHNAKTK PREEQYNSTYRVVSVLTVLHQDWLNGKEYKCKVSNWALPAPI SKTISKAKGQPREPQVYTLPPSREEMTKNQVSLTCLVKGFYPSD IAVEWESNGQPENNYKTTPPVLDSDGSFFLYSKLTVDKSRWQ QGNVFSCSVMHEALHNHYTQKSLSLSPGK | |
| SEQ ID NO: 87 | Fc IgG1m(f)-K326W/E333S/E430G | ASTKGPSVFPLAPSSKSTSGGTAALGCLVKDYFPEPVTVSWNS GALTSGVHTFPAVLQSSGLYSLSSVVTVPSSSLGTQTYICNVNH KPSNTKVDKRVEPKSCDKTHTCPPCPAPELLGGPSVFLFPPKPK DTLMISRTPEVTCVVVDVSHEDPEVKFNWYVDGVEVHNAKTK PREEQYNSTYRVVSVLTVLHQDWLNGKEYKCKVSNWALPAPI SKTISKAKGQPREPQVYTLPPSREEMTKNQVSLTCLVKGFYPSD IAVEWESNGQPENNYKTTPPVLDSDGSFFLYSKLTVDKSRWQ QGNVFSCSVMHGALHNHYTQKSLSLSPGK | |
| SEQ ID NO: 88 | Fc IgG1m(f)-S267E/H268F/S324T/E430G | ASTKGPSVFPLAPSSKSTSGGTAALGCLVKDYFPEPVTVSWNS GALTSGVHTFPAVLQSSGLYSLSSVVTVPSSSLGTQTYICNVNH KPSNTKVDKRVEPKSCDKTHTCPPCPAPELLGGPSVFLFPPKPK DTLMISRTPEVTCVVVDVEFEDPEVKFNWYVDGVEVHNAKTK PREEQYNSTYRVVSVLTVLHQDWLNGKEYKCKVTNKALPAPIE KTISKAKGQPREPQVYTLPPSREEMTKNQVSLTCLVKGFYPSDI AVEWESNGQPENNYKTTPPVLDSDGSFFLYSKLTVDKSRWQQ GNVFSCSVMHGALHNHYTQKSLSLSPGK | |

TABLE 1-continued

| SEQ ID NO: | Name | Sequence | Clone |
|---|---|---|---|
| SEQ ID NO: 89 | Fc IgG113F [Fc IgG1(f)m-K274Q/N276K/Y300F/A339T/N384S/K392N/V397M/V422I] | ASTKGPSVFPLAPSSKSTSGGTAALGCLVKDYFPEPVTVSWNS GALTSGVHTFPAVLQSSGLYSLSSVVTVPSSSLGTQTYICNVNH KPSNTKVDKRVEPKSCDKTHTCPPCPAPELLGGPSVFLFPPKPK DTLMISRTPEVTCVVVDVSHEDPEVQFKWYVDGVEVHNAKTK PREEQYNSTFRVVSVLTVLHQDWLNGKEYKCKVSNKALPAPIE KTISKTKGQPREPQVYTLPPSREEMTKNQVSLTCLVKGFYPSDI AVEWESSGQPENNYNTTPPMLDSDGSFFLYSKLTVDKSRWQ QGNIFSCSVMHEALHNHYTQKSLSLSPGK | |
| SEQ ID NO: 90 | Fc IgG113F-E430G | ASTKGPSVFPLAPSSKSTSGGTAALGCLVKDYFPEPVTVSWNS GALTSGVHTFPAVLQSSGLYSLSSVVTVPSSSLGTQTYICNVNH KPSNTKVDKRVEPKSCDKTHTCPPCPAPELLGGPSVFLFPPKPK DTLMISRTPEVTCVVVDVSHEDPEVQFKWYVDGVEVHNAKTK PREEQYNSTFRVVSVLTVLHQDWLNGKEYKCKVSNKALPAPIE KTISKTKGQPREPQVYTLPPSREEMTKNQVSLTCLVKGFYPSDI AVEWESSGQPENNYNTTPPMLDSDGSFFLYSKLTVDKSRWQ QGNIFSCSVMHGALHNHYTQKSLSLSPGK | |
| SEQ ID NO: 91 | VH BMS-663513 CDR1 | GGSFSGYY | BMS-663513 |
| SEQ ID NO: 92 | VH BMS-663513 CDR2 | INHGGYV | |
| SEQ ID NO: 93 | VH BMS-663513 CDR3 | ARDYGPGNYDWYFDL | |
| SEQ ID NO: 94 | VH BMS-663513 | QVQLQQWGAGLLKPSETLSLTCAVYGGSFSGYYWSWIRQSPE KGLEWIGEINHGGYVTYNPSLESRVTISVDTSKNQFSLKLSSVTA ADTAVYYCARDYGPGNYDWYFDLWGRGTLVTVSS | |
| SEQ ID NO: 95 | VL BMS-663513 CDR1 | QSVSSY | |
| | VL BMS-663513 CDR2 | DAS | |
| SEQ ID NO: 96 | VL BMS-663513 CDR3 | QQRSNWPPALT | |
| SEQ ID NO: 97 | VL BMS-663513 | EIVLTQSPATLSLSPGERATLSCRASQSVSSYLAWYQQKPGQAP RLLIYDASNRATGIPARFSGSGSGTDFTLTISSLEPEDFAVYYCQ QRSNWPPALTFGGGTKVEIK | |
| SEQ ID NO: 98 | VH CD134-SF2 CDR1 | GYTFKDYT | CD134-SF2 |
| SEQ ID NO: 99 | VH CD134-SF2 CDR2 | IYPNNGGS | |
| SEQ ID NO: 100 | VH CD134-SF2 CDR3 | ARMGYHGPHLDFDV | |
| SEQ ID NO: 101 | VH CD134-SF2 | QVQLVQSGAEVKKPGSSVKVSCKASGYTFKDYTMHWVRQAP GQGLEWIGGIYPNNGGSTYNQNFKDRVTLTADKSTSTAYMEL SSLRSEDTAVYYCARMGYHGPHLDFDVWGQGTTVTVSS | |
| SEQ ID NO: 102 | VL CD134-SF2 CDR1 | QDVGAA | |
| | VL CD134-SF2 CDR2 | WAS | |
| SEQ ID NO: 103 | VL CD134-SF2 CDR3 | QQYINYPLT | |
| SEQ ID NO: 104 | VL CD134-SF2 | DIQMTQSPSSLSASVGDRVTITCKASQDVGAAVAWYQQKPG KAPKLLIYWASTRHTGVPSRFSGSGSGTDFTLTISSLQPEDFATY YCQQYINYPLTFGGGTKVEIK | |
| SEQ ID NO: 105 | VH CD137-MOR7480 CDR1 | GYSFSTYW | CD137-MOR7480 |
| SEQ ID NO: 106 | VH CD137-MOR7480 CDR2 | IYPGDSYT | |

TABLE 1-continued

| SEQ ID NO: | Name | Sequence | Clone |
|---|---|---|---|
| SEQ ID NO: 107 | VH CD137-MOR7480 CDR3 | ARGYGIFDY | |
| SEQ ID NO: 108 | VH CD137-MOR7480 | EVQLVQSGAEVKKPGESLRISCKGSGYSFSTYWISWVRQMPG KGLEWMGKIYPDSYTNYSPSFQGQVTISADKSISTAYLQWSS LKASDTAMYYCARGYGIFDYWGQGTLVTVSS | |
| SEQ ID NO: 109 | VL CD137-MOR7480 CDR1 | NIGDQY | |
| | VL CD137-MOR7480 CDR2 | QDK | |
| SEQ ID NO: 110 | VL CD137-MOR7480 CDR3 | ATYTGFGSLAV | |
| SEQ ID NO: 111 | VL CD137-MOR7480 | SYELTQPPSVSVSPGQTASITCSGDNIGDQYAHWYQQKPGQS PVLVIYQDKNRPSGIPERFSGSNSGNTATLTISGTQAMDEADY YCATYTGFGSLAVFGGGTKLTVL | |
| SEQ ID NO: 112 | VH CD40-CP870893 CDR1 | GYTFTGYY | CD40-CP870893 |
| SEQ ID NO: 113 | VH CD40-CP870893 CDR2 | INPDSGGT | |
| SEQ ID NO: 114 | VH CD40-CP870893 CDR3 | ARDQPLGYCTNGVCSYFDY | |
| SEQ ID NO: 115 | VH CD40-CP870893 | QVQLVQSGAEVKKPGASVKVSCKASGYTFTGYYMHWVRQAP GQGLEWMGWINPDSGGTNYAQKFQGRVTMTRDTSISTAYM ELNRLRSDDTAVYYCARDQPLGYCTNGVCSYFDYWGQGTLVT VSS | |
| SEQ ID NO: 116 | VL CD40-CP870893 CDR1 | QGIYSW | |
| | VL CD40-CP870893 CDR2 | TAS | |
| SEQ ID NO: 117 | VL CD40-CP870893 CDR3 | QQANIFPLT | |
| SEQ ID NO: 118 | VL CD40-CP870893 | DIQMTQSPSSVSASVGDRVTITCRASQGIYSWLAWYQQKPGK APNLLIYTASTLQSGVPSRFSGSGSGTDFTLTISSLQPEDFATYYC QQANIFPLTFGGGTKVEIK | |
| SEQ ID NO: 119 | VH CD40-SGN40 CDR1 | GYSFTGYY | CD40-SGN40 |
| SEQ ID NO: 120 | VH CD40-SGN40 CDR2 | VIPNAGGT | |
| SEQ ID NO: 121 | VH CD40-SGN40 CDR3 | AREGIYW | |
| SEQ ID NO: 122 | VH CD40-SGN40 | EVQLVESGGGLVQPGGSLRLSCAASGYSFTGYYIHWVRQAPG KGLEWVARVIPNAGGTSYNQKFKGRFTLSVDNSKNTAYLQM NSLRAEDTAVYYCAREGIYWGQGTLVTVSS | |
| SEQ ID NO: 123 | VL CD40-SGN40 CDR1 | QSLVHSNGNTF | |
| | VL CD40-SGN40 CDR2 | TVS | |
| SEQ ID NO: 124 | VL CD40-SGN40 CDR3 | SQTTHVPWT | |
| SEQ ID NO: 125 | VL CD40-SGN40 | DIQMTQSPSSLSASVGDRVTITCRSSQSLVHSNGNTFLHWYQ QKPGKAPKLLIYTVSNRFSGVPSRFSGSGSGTDFTLTISSLQPED FATYFCSQTTHVPWTFGQGTKVEIK | |
| SEQ ID NO: 126 | VH CD95-APO1 CDR1 | GFTFNTNA | CD95-APO1 |

TABLE 1-continued

| SEQ ID NO: | Name | Sequence | Clone |
|---|---|---|---|
| SEQ ID NO: 127 | VH CD95-APO1 CDR2 | IRSKSNNYAT | |
| SEQ ID NO: 128 | VH CD95-APO1 CDR3 | VTDGYY | |
| SEQ ID NO: 129 | VH CD95-APO1 | EVQLVETGGGLVQPKGSLKLSCAASGFTFNTNAMNWVRQAP GKGLEWVARIRSKSNNYATYYAESVKDRFTISRDDSQSMLYLQ MNNLKAEDTAMYYCVTDGYYWGQGTTLTVSS | |
| SEQ ID NO: 130 | VL CD95-APO1 CDR1 | ESVEYYGTSL | |
| | VL CD95-APO1 CDR2 | VAS | |
| SEQ ID NO: 131 | VL CD95-APO1 CDR3 | QQSTKVPWT | |
| SEQ ID NO: 132 | VL CD95-APO1 | DIVLTQSPASLAVSLGQRATISCRASESVEYYGTSLMQWYQQK PGQPPKLLIYVASNVESGVPARFSGSGSGTDFSLNIHPVEEDDI AMYFCQQSTKVPWTFGGGTKLEIK | |
| SEQ ID NO: 133 | VH CD95-HFE7A CDR1 | GYTFTSYW | CD95-HFE7A |
| SEQ ID NO: 134 | VH CD95-HFE7A CDR2 | IDPSDSYT | |
| SEQ ID NO: 135 | VH CD95-HFE7A CDR3 | ARNRDYSNNWYFDV | |
| SEQ ID NO: 136 | VH CD95-HFE7A | QVQLQQPGAELVKPGASVKLSCKASGYTFTSYWMQWVKQR PGQGLEWIGEIDPSDSYTNYNQKFKGKATLTVDTSSSTAYMQL SSLTSEDSAVYYCARNRDYSNNWYFDVWGTGTTVTVSS | |
| SEQ ID NO: 137 | VL CD95-HFE7A CDR1 | QSVDYDGDSY | |
| | VL CD95-HFE7A CDR2 | AAS | |
| SEQ ID NO: 138 | VL CD95-HFE7A CDR3 | QQSNEDPRT | |
| SEQ ID NO: 139 | VL CD95-HFE7A | DIVLTQSPASLAVSLGQRATISCKASQSVDYDGDSYMNWYQQ KPGQPPKLLIYAASNLESGIPARFSGSGSGTDFTLNIHPVEEEDA ATYYCQQSNEDPRTFGGGTKLEIK | |
| SEQ ID NO: 140 | VH DR4-chCTB007 CDR1 | GFNIKDTY | DR4-chCTB007 |
| SEQ ID NO: 141 | VH DR4-chCTB007 CDR2 | IDPANGNT | |
| SEQ ID NO: 142 | VH DR4-chCTB007 CDR3 | AYYYVSNAWFTY | |
| SEQ ID NO: 143 | VH DR4-chCTB007 | EVQLQQSGAELVKPGASVKLSCTASGFNIKDTYMHWVKQRPE QGLEWIGRIDPANGNTKYDPKFQGKATITADTSSNTAYLQLSS LTSEDTAVYYCAYYYVSNAWFTYWGQGTLVTVSA | |
| SEQ ID NO: 144 | VL DR4-chCTB007 CDR1 | ENIYSN | |
| | VL DR4-chCTB007 CDR2 | AAT | |
| SEQ ID NO: 145 | VL DR4-chCTB007 CDR3 | QHFWGTWT | |
| SEQ ID NO: 146 | VL DR4-chCTB007 | DIQMTQSPASLSVSVGETVTITCRASENIYSNLEWYQQKQGKS PQLLVYAATNLADGVPSRFSGSGSGTQYSLKINSLQSEDFGSYY CQHFWGTWTFGGGTKLEIK | |
| SEQ ID NO: 147 | VH FAS-E09 CDR1 | GASISANSYY | FAS-E09 |

TABLE 1-continued

| SEQ ID NO: | Name | Sequence | Clone |
|---|---|---|---|
| SEQ ID NO: 148 | VH FAS-E09 CDR2 | IAYRGNSNSGST | |
| SEQ ID NO: 149 | VH FAS-E09 CDR3 | ARRQLLDDGTGYQWAAFDV | |
| SEQ ID NO: 150 | VH FAS-E09 | QLQLQESGPGLVKPSETLSLTCTVSGASISANSYYGVWVRQSP GKGLEWVGSIAYRGNSNSGSTYYNPSLKSRATVSVDTSKNQVS LRLTSVTAADTALYYCARRQLLDDGTGYQWAAFDVWGQGT MVTVSS | |
| SEQ ID NO: 151 | VL FAS-E09 CDR1 | SFNIGRYP | |
| | VL FAS-E09 CDR2 | YNN | |
| SEQ ID NO: 152 | VL FAS-E09 CDR3 | STWDDTLKGWV | |
| SEQ ID NO: 153 | VL FAS-E09 | QSVLTQPPSVSEAPRQTVTISCSGNSFNIGRYPVNWYQQLPGK APKLLIYYNNLRFSGVSDRFSGSKSGTSASLAIRDLLSEDEADYY CSTWDDTLKGWVFGGGTKVTVL | |
| SEQ ID NO: 154 | VH GITR-36E5 CDR1 | GFTFSSYA | GITR-36E5 |
| SEQ ID NO: 155 | VH GITR-36E5 CDR2 | ISSGGTT | |
| SEQ ID NO: 156 | VH GITR-36E5 CDR3 | ARVGGYYDSMDY | |
| SEQ ID NO: 157 | VH GITR-36E5 | EVNLVESGGGLVKPGGSLKVSCAASGFTFSSYAMSWVRQTPE KRLEWVASISSGGTTYYPDSVKGRFTISRDNARNILYLQMSSLR SEDTAMYYCARVGGYYDSMDYWGQGISVTDSS | |
| SEQ ID NO: 158 | VL GITR-36E5 CDR1 | ESVDNYGVSF | |
| | VL GITR-36E5 CDR2 | AAS | |
| SEQ ID NO: 159 | VL GITR-36E5 CDR3 | QQTKEVTWT | |
| SEQ ID NO: 160 | VL GITR-36E5 | DIVLTQSPASLAVSLGQRATISCRASESVDNYGVSFMNWFQQ KPGQPPKLLIYAASNQGSGVPARFSGSGSGTDFSLNIHPMEED DTAMYFCQQTKEVTWTFGGGTKLEIK | |
| SEQ ID NO: 161 | VH GITR-INCAGN01876 CDR1 | GYTFTDYA | GITR-INCAGN01876 |
| SEQ ID NO: 162 | VH GITR-INCAGN01876 CDR2 | IRTYSGDV | |
| SEQ ID NO: 163 | VH GITR-INCAGN01876 CDR3 | AKSGTVRGFAY | |
| SEQ ID NO: 164 | VH GITR-INCAGN01876 | QVQLLQSGTELVRPGVSVKISCKGSGYTFTDYAMYWVKQSHA KSLEWIGVIRTYSGDVTYNQKFKDKATMTVDKSSSIAYMELAR LSSEDSAIYYCAKSGTVRGFAYWGQGTLVTVSS | |
| SEQ ID NO: 165 | VL GITR-INCAGN01876 CDR1 | QSLLNSGNQKNY | |
| | VL GITR-INCAGN01876 CDR2 | WAS | |
| SEQ ID NO: 166 | VL GITR-INCAGN01876 CDR3 | QNDYSYPYT | |

TABLE 1-continued

| SEQ ID NO: | Name | Sequence | Clone |
|---|---|---|---|
| SEQ ID NO: 167 | VL GITR-INCAGNO1876 | DIVMTQSPSSLTVTAGEKVIMSCKSSQSLLNSGNQKNYLTWY QQKPGQPPKLLIYWASTRESGVPDRFTGSGSGTDFTLTISSVQ AEDLAVYHCQNDYSYPYTFGGGTKLEIK | |
| SEQ ID NO: 168 | Fc IgG2 | ASTKGPSVFPLAPCSRSTSESTAALGCLVKDYFPEPVTVSWNSG ALTSGVHTFPAVLQSSGLYSLSSVVTVPSSNFGTQTYTCNVDHK PSNTKVDKTVERKCCVECPPCPAPPVAGPSVFLFPPKPKDTLMI SRTPEVTCVVVDVSHEDPEVQFNWYVDGVEVHNAKTKPREE QFNSTFRVVSVLTVVHQDWLNGKEYKCKVSNKGLPAPIEKTIS KTKGQPREPQVYTLPPSREEMTKNQVSLTCLVKGFYPSDIAVE WESNGQPENNYKTTPPMLDSDGSFFLYSKLTVDKSRWQQGN VFSCSVMHEALHNHYTQKSLSLSPGK | Human IgG2 |
| SEQ ID NO: 169 | Fc IgG3 | ASTKGPSVFPLAPCSRSTSGGTAALGCLVKDYFPEPVTVSWNS GALTSGVHTFPAVLQSSGLYSLSSVVTVPSSSLGTQTYTCNVNH KPSNTKVDKRVELKTPLGDTTHTCPRCPEPKSCDTPPPCPRCPE PKSCDTPPPCPRCPEPKSCDTPPPCPRCPAPELLGGPSVFLFPP KPKDTLMISRTPEVTCVVVDVSHEDPEVQFKWYVDGVEVHNA KTKPREEQYNSTFRVVSVLTVLHQDWLNGKEYKCKVSNKALPA PIEKTISKTKGQPREPQVYTLPPSREEMTKNQVSLTCLVKGFYPS DIAVEWESSGQPENNYNTTPPMLDSDGSFFLYSKLTVDKSRW QQGNIFSCSVMHEALHNRFTQKSLSLSPGK | Human IgG3 |
| SEQ ID NO: 170 | Fc IgG4 | ASTKGPSVFPLAPCSRSTSESTAALGCLVKDYFPEPVTVSWNSG ALTSGVHTFPAVLQSSGLYSLSSVVTVPSSSLGTKTYTCNVDHK PSNTKVDKRVESKYGPPCPSCPAPEFLGGPSVFLFPPKPKDTLM ISRTPEVTCVVVDVSQEDPEVQFNWYVDGVEVHNAKTKPREE QFNSTYRVVSVLTVLHQDWLNGKEYKCKVSNKGLPSSIEKTISK AKGQPREPQVYTLPPSQEEMTKNQVSLTCLVKGFYPSDIAVE WESNGQPENNYKTTPPVLDSDGSFFLYSRLTVDKSRWQEGNV FSCSVMHEALHNHYTQKSLSLSLGK | Human IgG4 |
| SEQ ID NO: 171 | FcRnECDHisBAF | AESHLSLLYHLTAVSSPAPGTPAFWVSGWLGPQQYLSYNSLRG EAEPCGAWVWENQVSWYWEKETTDLRIKEKLFLEAFKALGGK GPYTLQGLLGCELGPDNTSVPTAKFALNGEEFMNFDLKQGTW GGDWPEALAISQRWQQQDKAANKELTFLLFSCPHRLREHLER GRGNLEWKEPPSMRLKARPSSPGFSVLTCSAFSFYPPELQLRFL RNGLAAGTGQGDFGPNSDGSFHASSSLTVKSGDEHHYCCIVQ HAGLAQPLRVELESPAKSSPGSSSHHHHHHPGGGLNDIFEAQ KIEWHE | Human FcRn |
| SEQ ID NO: 172 | B2M | IQRTPKIQVYSRHPAENGKSNFLNCYVSGFHPSDIEVDLLKNGE RIEKVEHSDLSFSKDWSFYLLYYTEFTPTEKDEYACRVNHVTLSQ PKIVKWDRDM | B2M |

EXAMPLES

Example 1: Antibody Generation, Production and Purification

Expression Constructs for Antibodies

For antibody expression, variable heavy (VH) chain and variable light (VL) chain sequences were prepared by gene synthesis (GeneArt Gene Synthesis; ThermoFisher Scientific, Germany) and cloned in pcDNA3.3 expression vectors (ThermoFisher Scientific, US) containing IgG1 heavy chain (HC) and light chain (LC) constant regions. Desired mutations were introduced either by gene synthesis or site directed mutagenesis. Antibodies mentioned in this application have VH and VL sequences derived from previously described DR5 antibodies hDR5-01, hDR5-05 (WO2014/009358) and conatumumab (U.S. Pat. No. 7,521,048 B2 and WO2010/138725), DR4 antibody chCTB007 (US 2009/0136503), FAS antibodies E09 (Chodorge Cell Death Differ. 2012 July; 19(7): 1187-1195), APO1 (WO 2014/076292) and HFE7A (U.S. Pat. No. 6,972,323), OX40 antibody SF2 (US2014/0377284), CD40 antibodies SGN 40 (U.S. Pat. No. 6,838,261) and CP870893 (U.S. Pat. No. 7,338,660), 4-1BB antibodies MOR7480 (WO 2012/032433) and BMS-663513 (U.S. Pat. No. 8,475,790), CD20 antibodies HuMab-7D8 and 1168 (WO2004/035607), CD52 antibody alemtuzumab (Crowe et al., Clin Exp Immunol. 1992; 87(1):105-10), and EGFR antibody 2F8 (WO2002/100348). In some of the examples the human IgG1 antibody b12, a gp120-specific antibody was used as a negative control (Barbas et al., J Mol Biol. 1993 Apr. 5; 230(3):812-23).

Transient Expression

Antibodies were expressed as IgG1,κ. Plasmid DNA mixtures encoding both heavy and light chains of antibodies were transiently transfected in Expi293 cells (Life/Thermo Scientific, USA) using Expifectamine (Invitrogen, US) essentially as described by the manufacturer.

Purification and Analysis of Proteins

Antibodies were purified by protein A affinity chromatography. Culture supernatants were filtered over a 0.20 μM dead-end filter and loaded on 5 mL MabSelect SuRe columns (GE Healthcare), washed and eluted with 0.02 M sodium citrate-NaOH, pH 3. The eluates were loaded on a HiPrep Desalting column (GE Healthcare) immediately after purification and the antibodies were buffer exchanged into 12.6 mM NaH$_2$PO$_4$, 140 mM NaCl, pH 7.4 buffer (B. Braun or Thermo Fisher). After buffer exchange, samples were sterile filtered over 0.2 μm dead-end filters. Purified proteins were analyzed by a number of bioanalytical assays including capillary electrophoresis on sodium dodecyl sulfate-polyacrylamide gels (CE-SDS) and high-performance size exclusion chromatography (HP-SEC). Concentration was measured by absorbance at 280 nm. Purified antibodies were stored at 2-8° C.

Generation of Bispecific Antibodies

Bispecific IgG1 antibodies were generated by Fab-arm-exchange under controlled reducing conditions. The basis for this method is the use of complimentary CH3 domains, which promote the formation of heterodimers under specific assay conditions as described in WO2011/131746. The F405L and K409R (EU numbering) mutations were introduced in anti-DR5 IgG1 antibodies to create antibody pairs with complementary CH3 domains. The F405L mutation was introduced in IgG1-b12-K326A/E333A/P396L/E430G and IgG1-CONA-C49W-K326W/E333S/E430G; the K409R mutation was introduced in IgG1-b12-K326W/E333S/E430G and IgG1-hDR5-01-G56T-K326A/E333A/P396L/E430G. To generate bispecific antibodies, two parental complementary antibodies, each antibody at a final concentration of 0.5 mg/mL, were incubated with 75 mM 2-mercaptoethylamine-HCl (2-MEA) in a total volume of 100 μL PBS at 31° C. for 5 hours. The reduction reaction was stopped by removing the reducing agent 2-MEA using spin columns (Microcon centrifugal filters, 30 k, Millipore) according to the manufacturer's protocol. The antibodies were buffer exchanged into 12.6 mM $NaH_2PO_4$, 140 mM NaCl, pH 7.4 buffer (B. Braun or Thermo). In this way the bispecific antibodies IgG1-hDR5-01-G56T-K326A/E333A/P396L/K409R/E430G×IgG1-b12-K326A/E333A/P396L/F405L/E430G referred to as BsAb (hDR5-01-G56T-K409R×b12-F405L)-K326A/E333A/P396L/E430G and IgG1-CONA-C49W-F405L-K326W/E333S/E430G×IgG1-b12-K409R-K326W/E333S/E430G, referred to as BsAb (IgG1-CONA-C49W-F405L×IgG1-b12-K409R)-K326W/E333S/E430G, were generated.

Example 2: Effect of Combining E430G and K326A/E333A/P396L on the Efficacy of Agonistic Anti-DR5 Antibodies A viability assay was performed to evaluate the effect of the combination of Fc-Fc-enhancing substitution E430G (WO2013/004842; WO2014/108198; WO2014/006217; de Jong et al., 2016) and K326A/E333A/P396L (WO2016/116635) on the agonistic activity of anti-DR5 antibodies IgG1-hDR5-01-G56T and IgG1-hDR-05 on DR5-positive BxPC-3 cells (ATCC, CRL-1687). Cells were harvested by trypsinization and passed through a cell strainer. Cells were pelleted by centrifugation for 5 minutes at 1,200 rpm and resuspended in culture medium (RPMI 1640 with 25 mM Hepes and L-Glutamine (Lonza Cat nr BE12-115F)+10% heat inactivated Donor Bovine Serum with Iron (DBSI; Life Technologies Cat nr 10371-029)+50 U/mL Penicillin/Streptomycin (Pen/Strep; Lonza; Cat nr DE17-603E) at a concentration of $0.5 \times 10^5$ cells/mL. 100 μL of the single cell suspensions (5,000 cells per well) were seeded in polystyrene 96-well flat-bottom plates (Greiner Bio-One, Cat nr 655182) and allowed to adhere overnight at 37° C. Next, 50 μL of a serial dilution antibody preparation series (range 0.0003 to 20,000 ng/mL final concentrations in 4-fold dilutions) was added and incubated for 3 days at 37° C. As a negative and positive control, cells were incubated without antibody or with 5 μM staurosporine (Sigma Aldrich, Cat nr S6942), respectively. The viability of the cell cultures was determined in a CellTiter-Glo luminescent cell viability assay (Promega, Cat nr G7571) that quantifies the ATP present, which is an indicator of metabolically active cells. From the kit, 20 μL luciferin solution reagent was added per well and mixed by shaking the plate for 2 minutes at 500 rpm. Next, plates were incubated for 1.5 hours at 37° C. 100 μL supernatant was transferred to a white OptiPlate-96 (Perkin Elmer, Cat nr 6005299) and luminescence was measured on an EnVision Multilabel Reader (PerkinElmer). Data were analyzed and plotted using non-linear regression (sigmoidal dose-response with variable slope) using Graph-Pad Prism software. FIG. 1 shows the percentage viable cells, as calculated using the following formula: % viable cells=[(luminescence antibody sample−luminescence staurosporine sample)/(luminescence no antibody sample−luminescence staurosporine sample)]*100.

Figure 1B:
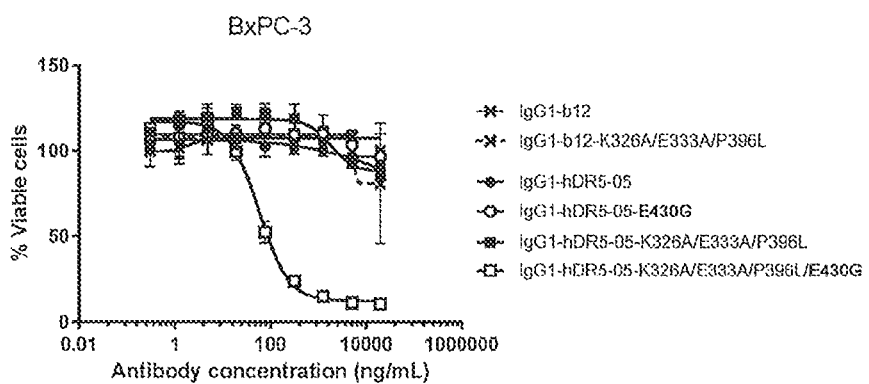
Figure 1C:
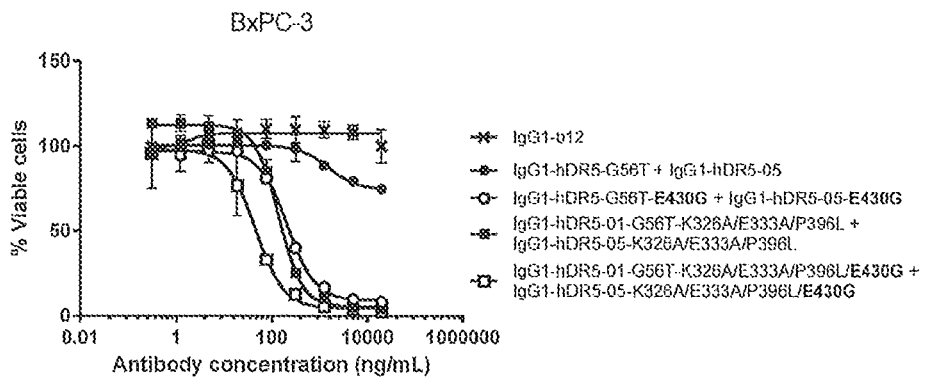

FIG. 1 shows that combining the Fc-Fc-enhancing substitution E430G and the three substitutions K326A/E333A/P396L resulted in induction of killing efficacy for the anti-DR5 antibodies IgG1-hDR5-01-G56T (FIG. 1A) and IgG1-hDR5-05 (FIG. 1B) when tested as single agent in an in vitro viability assay on adherent human BxPC-3 pancreas cancer cells. In contrast, these antibodies did not show efficient killing on these pre-adhered BxPC-3 cells when only E430G or K326A/E333A/P396L was present. Also for the combination of non-crossblocking antibodies IgG1-hDR5-01-G56T+IgG1-hDR5-05, introduction of the combined substitutions K326A/E333A/P396L/E430G resulted in the most efficacious killing of pre-adhered BxPC-3 cells (FIG. 1C).

These data show that the K326A/E333A/P396L/E430G substitutions induced strong agonistic activity for anti-DR5 antibodies on adherent BxPC-3 cells.

Example 3: Efficacy of Monovalent Anti-DR5 Antibody Containing K326A/E333A/P396L/E430G A viability assay was performed on human BxPC-3 pancreatic and COLO 205 colon cancer cells to study the efficacy of monovalent anti-DR5 antibody containing K326A/E333A/P396L/E430G. The monovalent DR5 antibody was generated by controlled Fab-arm exchange between IgG1-hDR5-01-G56T-K326A/E333A/P396L/K409R/E430G and IgG1-b12-K326A/E333A/P396L/F405L/E430G as described in Example 1. The generated bispecific antibody, referred to as BsAb (hDR5-01-G56T-K409R×b12-F405L)-K326A/E333A/P396L/E430G, contains one arm specific for DR5 and one non-specific arm against HIV glycoprotein gp120, resulting in monovalent DR5 binding on DR5-positive human cancer cells. BxPC-3 cells were harvested as described in Example 2. COLO 205 cells (ATCC, CCL-222) were harvested by pooling the culture supernatant containing non-adherent cells and trypsinized adherent COLO 205 cells. Cells were pelleted by centrifugation for 5 minutes at 1,200 rpm and resuspended in culture medium (RPMI 1640 with 25 mM Hepes and L-Glutamine+10% heat inactivated DBSI+50 U/mL Pen/Strep at a concentration of $0.5 \times 10^5$ cells/mL. 100 μL of the single cell suspensions (5,000 cells per well) were seeded in polystyrene 96-well flat-bottom plates and allowed to adhere overnight at 37° C. Next, 50 μL of a serial dilution antibody preparation series (range 0.0024 to 10,000 ng/mL final concentrations in 4-fold dilutions) was added and incubated for 3 days at 37° C. As a negative and positive control, cells were incubated without antibody or with 5 μM staurosporine, respectively. The viability of the cultured cells was determined in a CellTiter-Glo luminescent cell viability assay as described in Example 2.

Figure 2A:
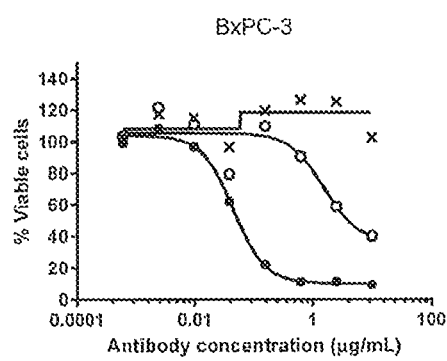
FIGS. 2A and 2B show the efficacy of a monovalent anti-DR5 antibody with K326A/E333A/P396L/E430G on adherent human BxPC-3 pancreatic (FIG. 2A) and COLO 205 colon (FIG. 2B) cancer cells as determined in a 3-days viability assay (CellTiter-Glo). As a monovalent anti-DR5 antibody, a bispecific antibody with one DR5-specific arm derived from IgG1-hDR5-01-G56T and one non-specific arm against HIV protein gp120 derived from IgG1-b12 was generated by controlled Fab-arm exchange. Representative examples of three experiments are shown.
Figure 2B:
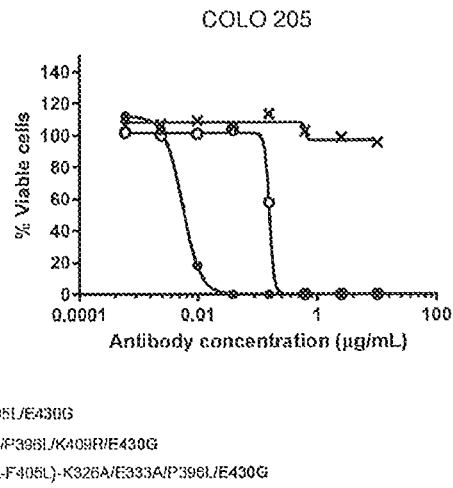

FIG. 2 shows that in the presence of the K326A/E333A/P396L/E430G mutations, the monovalent variant of IgG1- hDR5-01-G56T could still induce killing of human BxPC-3 pancreatic and COLO 205 colon cancer cells.

Example 4: Effect of Combining E430G and K326A/E333A, K326A/P396L or E333A/P396L on C1q Binding and the Efficacy of Agonistic Anti-DR5 Antibodies A viability assay was performed to study the effect of the combination of Fc-Fc-enhancing substitution E430G with two of the three substitution in K326A/E333A/P396L on the agonistic activity of anti-DR5 antibody IgG1-hDR5-01-G56T on DR5-positive BxPC-3 and COLO 205 cells. As a reference, the combination of E430G with all three substitutions K326A/E333A/P396L as described in Example 2 was included in the experiment. The viability assay was performed as described in Example 3. The viability of the cultured cells was determined in a CellTiter-Glo luminescent cell viability assay as described in Example 2.

Figure 3A:
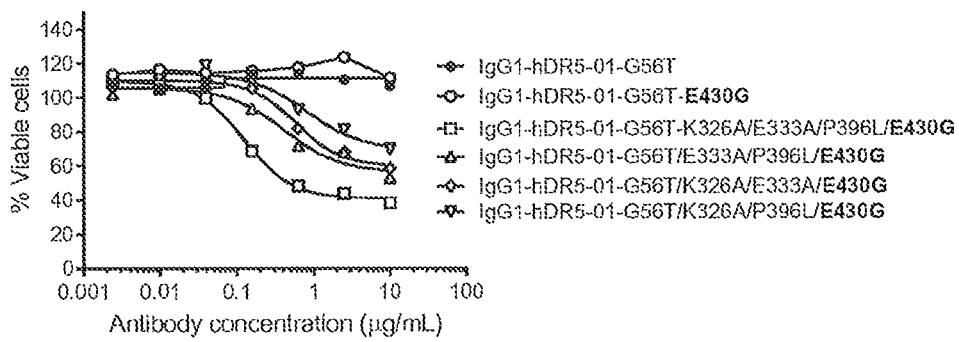
FIGS. 3A-3C show the effect of E430G combined with K326A/E333A/P396L or two of these substitutions E333A/P396L, K326A/E333A or K326A/P396L, on the efficacy of anti-DR5 antibody IgG1-hDR5-01-G56T on adherent human BxPC-3 pancreatic (FIG. 3A) and COLO 205 colon cancer (FIG. 3B) cancer cells as determined in a 3-days viability assay (CellTiter-Glo), and on C1q binding as determined in an ELISA assay (FIG. 3C). Representative examples of three experiments are shown.
Figure 3B:
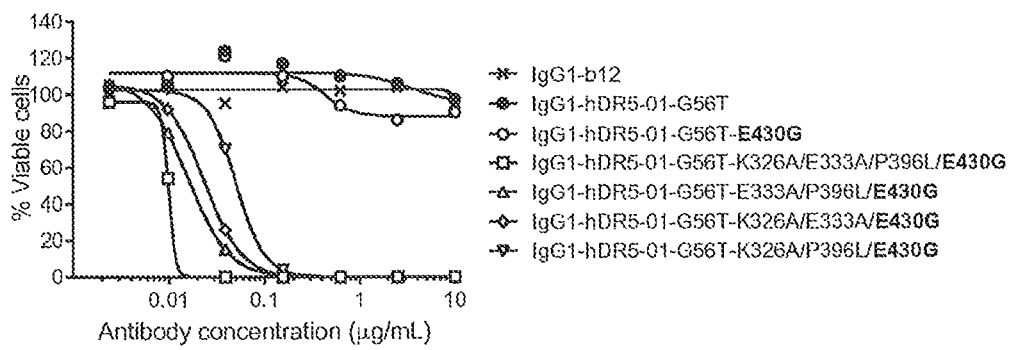

FIG. 3 shows that combining the Fc-Fc-enhancing substitution E430G and two substitutions from K326A/E333A/P396L (E333A/P396L, K326A/E333A or K326A/P396L) resulted in induction of killing efficacy for the anti-DR5 antibody IgG1-hDR5-01-G56T when tested as single agent in an in vitro viability assay on adherent human BxPC-3 pancreas (FIG. 3A) and COLO 205 colon (FIG. 3B) cancer cells. In contrast, no killing on these pre-adhered cancer cells was observed when only E430G was present. Most efficient killing was observed when E430G was combined with all three mutations K326A/E333A/P396L.

A binding ELISA was performed to evaluate the effect of different substitutions on C1q binding. Purified antibody samples of IgG-hDR5-01-G56T variants containing the E430G substitution in combination with the K326A/E333A, K326A/P396L, E333A/P396L or K326A/E333A/P396L substitutions were tested and compared to WT IgG-hDR5-01-G56T and IgG-hDR5-01-G56T-E430G. IgG-2F8-I253D/K322A was used as a negative control for C1q binding. Coating of in 96-well Microlon ELISA plates (Greiner Cat #655092) was performed by overnight incubation at 4° C. with 1 µg/mL antibody samples in 100 µL PBS. Plates were washed and blocked for 1 hour at RT with 200 µL/well 0.5×PBS supplemented with 0.025% Tween 20 and 0.1% gelatin while shaking. With washings in between incubations, plates were sequentially incubated with 100 µL per well of a serial dilution series of purified C1q (Quidel Cat #A400; final C1q concentration range 30-0.010 µg/mL in 3-fold dilutions) for 1 h at 37° C., 100 µL per well rabbit anti-human C1q (DAKO, product #A0136, 1/4.000) for 1 h at RT, and with 100 µL/well swine anti-rabbit IgG-HRP (DAKO, P0399, 1:10.000) as detecting antibody for 1 h at RT, and finally 100 µL/well substrate with 1 mg/mL 2,2'-azino-bis (3-ethylbenzothiazoline-6-sulfonic acid) (ABTS; Roche Cat #11112 597001) for circa 15 min at RT. The reaction was stopped by the addition of 100 µL 2% oxalic acid. Absorbance was measured at 405 nm in a BioTek EL808 Microplate Reader (BioSPX). Log transformed data were analyzed by fitting sigmoidal dose-response curves with variable slope using GraphPad Prism software.

Figure 3C:
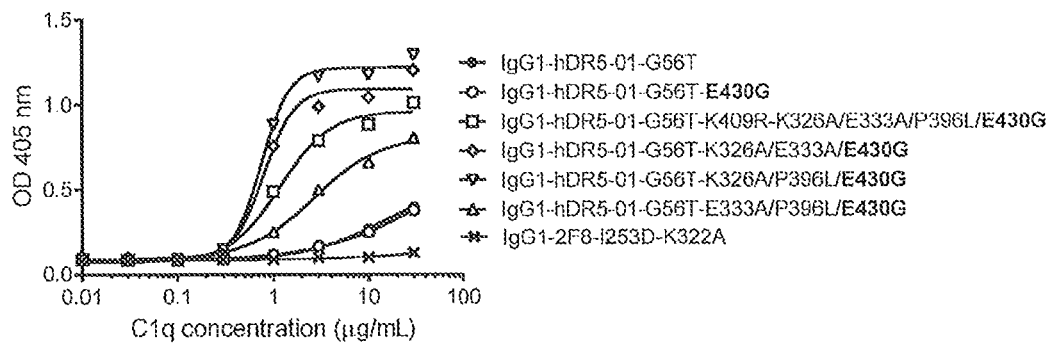

FIG. 3C shows that introduction of the E430G Fc-Fc-enhancing substitution did not affect the apparent C1q binding affinity to 1 µg/mL coated IgG1-hDR5-01-G56T antibody, whereas the antibody variants containing the combination of the E430G substitution and the K326A/E333A, K326A/P396L, E333A/P396L or K326A/E333A/P396L substitutions showed enhanced C1q binding compared to IgG1-hDR5-01-G56T and IgG1-hDR5-01-G56T-E430G (Table 2).

TABLE 2

EC50 values of C1q binding to IgG1-hDR5-01-G56T antibody variants (ELISA)

| IgG1-hDR5-01-G56T antibody variant (1 µg/mL) | C1q binding EC50 (µg/mL) | SD | n | Antibody variant versus WT[1] | Antibody variant versus E430G[1] |
|---|---|---|---|---|---|
| WT | 18.8 | 9.9 | 6 | Not applicable | Not significant |
| E430G | 20.7 | 12.6 | 6 | Not significant | Not applicable |
| K326A/E333A/P396L/E430G | 1.3 | 0.2 | 3 | p < 0.05 | p < 0.05 |
| K326A/E333A/E430G | 0.8 | 0.1 | 3 | p < 0.05 | p < 0.05 |
| K326A/P396L/E430G | 0.6 | 0.1 | 3 | p < 0.05 | p < 0.05 |
| E333A/P396L/E430G | 1.9 | 0.8 | 3 | p < 0.05 | p < 0.05 |

[1]One-way ANOVA p value = 0.0022; Bonferroni post hoc test Ab vs. WT: p < 0.05 as indicated.

Together, these data showed that combining the E430G Fc-Fc-enhancing substitution with the K326A/E333A, K326A/P396L, E333A/P396L or K326A/E333A/P396L substitution resulted in increased C1q binding and increased agonistic activity of the anti-DR5 antibody IgG1-hDR5-01-G56T-E430G with only the E430G Fc-Fc-enhancing mutation.

Example 5: Effect of Combining E430G and K326W/E333S on C1q Binding and the Efficacy of Agonistic Anti-DR5 Antibodies A binding ELISA was performed to evaluate the effect of K326A/E333A and K326W/E333S on C1q binding to an antibody containing the E430G Fc-Fc-enhancing mutation. Purified antibody samples of IgG1-CONA-C49W variants containing the E430G substitution in combination with the K326A/E333A or K326W/E333S mutations were tested and compared to WT IgG1-CONA-C49W and IgG1-CONA-C49W-E430G. Also IgG1-CONA-C49W-K326W/E333S without the E430G substitution was tested. IgG1-2F8-I253D/K322A was used as a negative control for C1q binding. The C1q binding ELISA was performed on ELISA plates coated with 1 µg/mL antibody as described in Example 4.

Figure 4A:
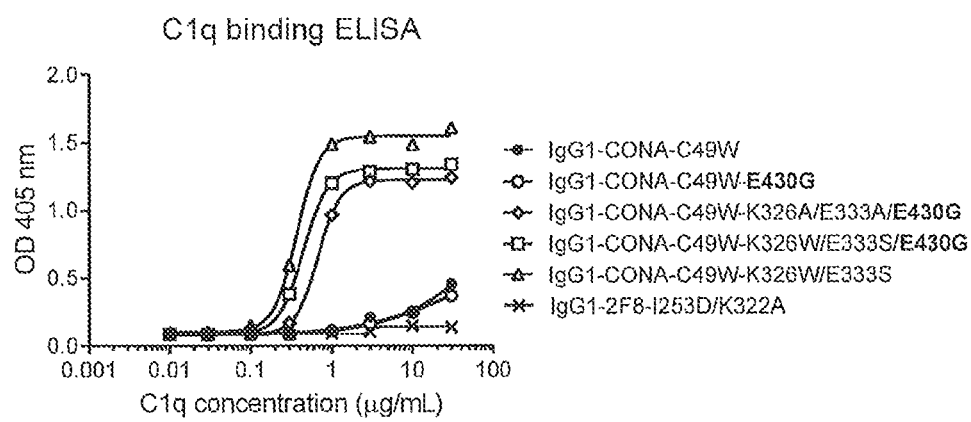
FIGS. 4A-4C show the effect of E430G combined with K326A/E333A or K326W/E333S on C1q binding to anti-DR5 antibody IgG1-CONA-C49W as determined in an ELISA assay (FIG. 4A) and on the efficacy of anti-DR5 antibody IgG1-hDR5-01-G56T on adherent human BxPC-3 pancreatic (FIG. 4B) and COLO 205 colon cancer (FIG. 4C) cancer cells as determined in a 3-days viability assay (Cell-Titer-Glo). Representative examples of three experiments are shown.

Strong enhancement of C1q binding by introduction of the K326W/E333S substitution was confirmed when compared to the WT antibody (FIG. 4A). In contrast, introduction of the E430G Fc-Fc-enhancing mutation did not affect the apparent C1q binding affinity to 1 µg/mL coated IgG1-CONA-C49W antibody. The antibody variants containing the combination of the E430G substitution and the K326A/E333A or K326W/E333S substitution showed strongly enhanced C1q binding compared to IgG1-hDR5-01-G56T and IgG1-hDR5-01-G56T-E430G (Table 3).

TABLE 3

EC50 values C1q binding to IgG1-CONA-C49W antibody variants (ELISA)

| IgG1-CONA-C49W antibody variant (1 µg/mL) | C1q binding EC50 (µg/mL) | SD | n | Antibody variant versus WT[1] | Antibody variant versus E430G[1] |
|---|---|---|---|---|---|
| WT | 15.2 | 12.2 | 3 | Not applicable | Not significant |
| E430G | 15.4 | 6.1 | 3 | Not significant | Not applicable |
| K326W/E333S | 0.3 | 0.1 | 3 | p < 0.05 | p < 0.05 |
| K326A/E333A/E430G | 0.8 | 0.3 | 3 | p < 0.05 | p < 0.05 |
| K326W/E333S/E430G | 0.5 | 0.1 | 3 | p < 0.05 | p < 0.05 |

[1]One-way ANOVA p value = 0.0013; Bonferroni post hoc test Ab vs. WT: p < 0.05 as indicated.

Figure 4B:
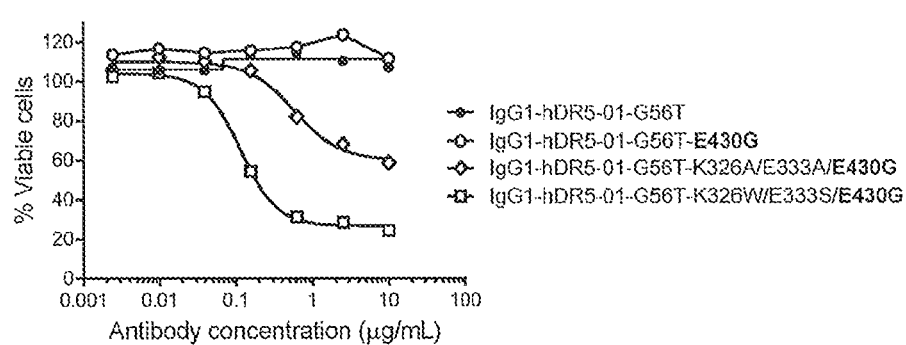
Figure 4C:
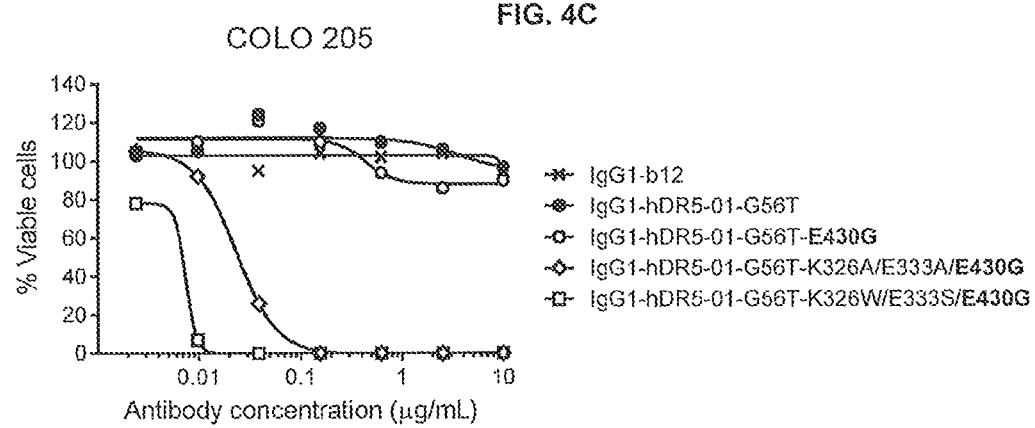

A viability assay was performed to study the effect of the combination of Fc-Fc-enhancing mutation E430G with C1q binding substitutions K326A/E333A or K326W/E333S on the agonistic activity of anti-DR5 antibody IgG1-hDR5-01-G56T on DR5-positive BxPC-3 and COLO 205 cells. The viability assay was performed as described in Example 3. The viability of the cultured cells was determined in a CellTiter-Glo luminescent cell viability assay as described in Example 2. FIG. 4B/C shows that combining the Fc-Fc-enhancing substitution E430G and the two mutations K326W/E333S resulted in induction of strong killing efficacy for the anti-DR5 antibody IgG1-hDR5-01-G56T when tested as single agent in an in vitro viability assay on adherent human BxPC-3 pancreas (FIG. 4B) and COLO 205 colon (FIG. 4C) cancer cells. In contrast, the WT antibody and IgG1-hDR5-01-G56T-E430G did not show efficacy. Killing efficacy of IgG1-hDR5-01-G56T-K326W/E333S/E430G was better than for IgG1-hDR5-01-G56T-K326A/E333A/E430G on both BxPC-3 and COLO 205 cancer cells.

Together, these data showed that combining the E430G Fc-Fc-enhancing substitution with the K326A/E333A or K326W/E333S substitutions resulted in increased C1q binding and increased agonistic activity of anti-DR5 antibody IgG1-CONA-C49W-E430G with only the E430G hexamerization-enhancing mutation.

Example 6: Effect of Combining E430G with Other Fc Variants on C1q Binding and the Efficacy of Agonistic Anti-DR5 Antibodies A C1q binding ELISA was performed to study the effect C1q binding substitutions S267E/H268F/S324T or the IgG1/IgG3 chimeric isotype IgG1 variant 113F on the binding of C1q to an antibody containing the E430G Fc-Fc enhancing substitution (Tammen et al., J Immunol. 2017). Purified antibody samples of IgG1-hDR5-01-G56T variants with and without these substitutions were tested and compared to WT IgG1-hDR5-01-G56T and IgG1-hDR5-01-G56T-E430G. IgG1-2F8-I253D/K322A was used as a negative control for C1q binding. The C1q binding ELISA was performed on ELISA plates coated with 1 µg/mL antibody as described in Example 4.

Figure 5A:
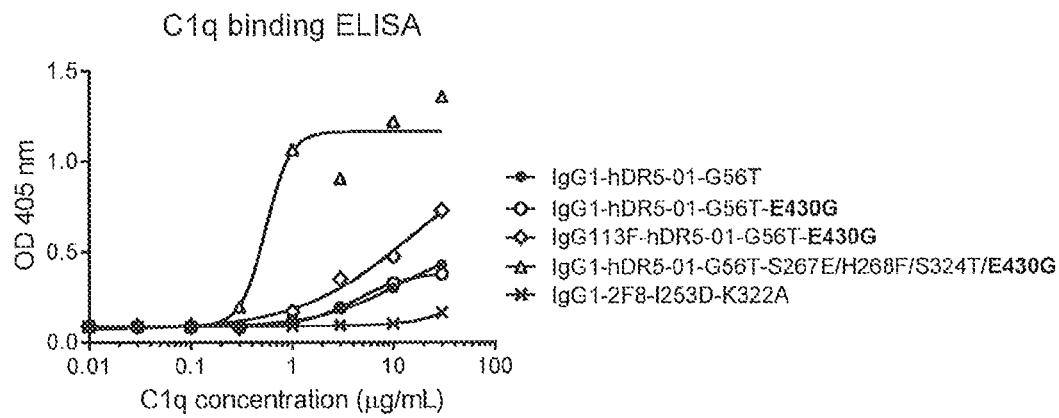
FIGS. 5A-5C show the effect of E430G combined with C1q binding substitutions S267E/H268F/S324T or the IgG1/IgG3 chimeric isotype IgG1 variant 113F on C1q binding to anti-DR5 antibody IgG1-hDR5-01-G56T as determined in an ELISA assay (FIG. 5A) and on the efficacy of anti-DR5 antibody IgG1-hDR5-01-G56T on adherent human BxPC-3 pancreatic (FIG. 5B) and COLO 205 colon (FIG. 5C) cancer cells as determined in a 3-days viability assay (CellTiter-Glo). Representative examples of three experiments are shown.

FIG. 5A shows that introduction of the E430G Fc-Fc enhancing substitution did not affect the apparent C1q binding affinity to 1 µg/mL coated IgG1-hDR5-01-G56T antibody. In contrast, the antibody variant containing the combination of the E430G substitution and the S267E/H268F/S324T substitutions showed strongly enhanced C1q binding compared to IgG1-hDR5-01-G56T and IgG1-hDR5-01-G56T-E430G, whereas the introduction of the E430G substitution in the IgG113F-hDR5-01-G56T format variant resulted in a slightly enhanced C1q binding compared to IgG1-hDR5-01-G56T and IgG1-hDR5-01-G56T-E430G (Table 4).

TABLE 4

EC50 values C1q binding to IgG1-hDR5-01-G56T antibody variants (ELISA)

| IgG1-hDR5-01-G56T antibody variant (1 µg/mL) | C1q binding EC50 (µg/mL) | SD | n | Antibody variant versus WT[1] | Antibody variant versus E430G[1] |
|---|---|---|---|---|---|
| WT | 15.2 | 12.2 | 3 | Not applicable | Not significant |
| E430G | 15.4 | 6.1 | 3 | Not significant | Not applicable |
| S267E/H268F/S324T/E430G | 0.5 | 0.1 | 3 | p < 0.05 | p < 0.05 |
| IgG113F-E430G | 11.4 | 3.9 | 3 | Not significant | Not significant |

[1]One-way ANOVA p value = 0.0013; Bonferroni post hoc test Ab vs. WT: p < 0.05 as indicated.

A viability assay was performed to study the effect of the combination of Fc-Fc enhancing substitution E430G with C1q binding substitutions S267E/H268F/S324T (Moore et al., MAbs 2010) or the IgG1/IgG3 chimeric isotype variant 113F (Natsume et al., Cancer Res. 2008) on the agonistic activity of anti-DR5 antibody IgG1-hDR5-01-G56T on DR5-positive BxPC-3 and COLO 205 cells. The viability assay was performed as described in Example 3. The viability of the cultured cells was determined in a CellTiter-Glo luminescent cell viability assay as described in Example 2.

Figure 5B:
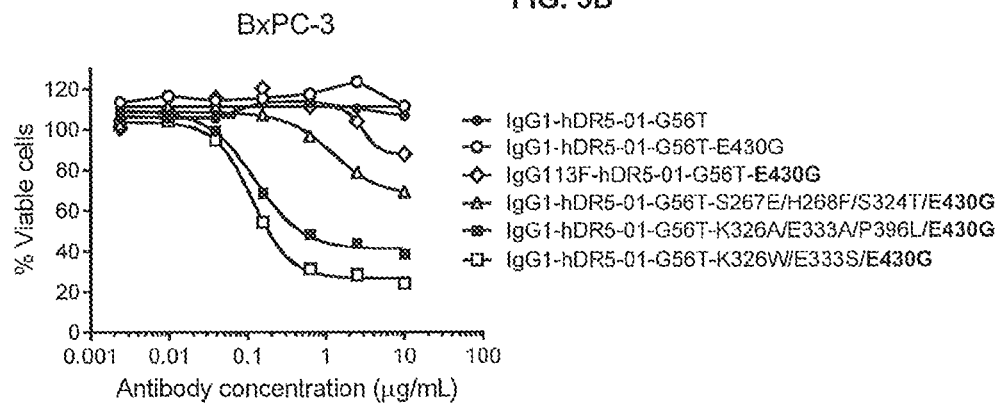
Figure 5C:
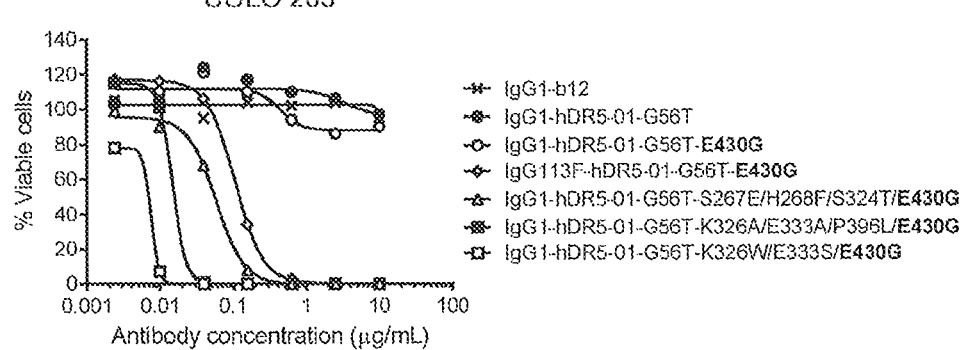

FIG. 5B/C shows that combining the Fc-Fc enhancing substitution E430G with the C1q binding substitutions S267E/H268F/S324T resulted in induction of killing efficacy for the anti-DR5 antibody IgG1-hDR5-01-G56T when tested as single agent in an in vitro viability assay on adherent human BxPC-3 pancreas (FIG. 5B) and COLO 205 colon (FIG. 5C) cancer cells. When E430G was incorporated in the IgG1/IgG3 chimeric isotype IgG1 variant 113F of IgG1-hDR5-01-G56T, induction of killing efficacy was observed on COLO 205 (FIG. 5C) and slightly on BxPC-3 where agonistic activity was only observed at the highest antibody concentration tested (FIG. 5B). However, the efficacy of these variants IgG1-hDR5-01-G56T-S267E/H268F/S324T/E430G and IgG113F-hDR5-01-G56T-E430G was significant lower than for IgG1-hDR5-01-G56T-K326W/E333S/E430G and IgG1-hDR5-01-G56T-K326A/E333A/P396L/E430G on both cell lines. As in the previous examples, the WT antibody and IgG1-hDR5-01-G56T-E430G did not show efficacy.

Together, these data showed that combining the E430G Fc-Fc enhancing substitution with the S267E/H268F/S324T substitutions resulted in strongly increased C1q binding and agonistic activity of anti-DR5 antibody IgG1-hDR5-01-G56T-E430G with only the E430G Fc-Fc enhancing substitution. Introduction of the E430G substitution in the IgG113F-hDR5-01-G56T format variant resulted in slightly enhanced C1q binding and agonistic activity of the antibody.

Example 7: Summary of the Effect of Combining E430G with Other Fc Mutations and Variants on the Efficacy of Agonistic Anti-DR5 Antibodies In the previous examples, viability assays were described in which the effect on the agonistic activity of anti-DR5 antibody IgG1-hDR5-01-G56T was tested when the Fc-Fc enhancing substitution E430G was combined with other Fc region substitution or variants that were described to affect either DR5 agonism or C1q binding. In this example, a summary is presented of all viability assays on adherent human pancreatic BxPC-3 cancer cells by representation and ranking of the percentage viable cells after incubation for three days with 10 μg/mL of the indicated antibodies relative to WT IgG1-hDR5-01-G56T, which was shown to have no effect in Examples 2, 4, 5 and 6. Details of the viability assays on adherent BxPC-3 cells and the CellTiter-Glo luminescent assay are described in Example 2.

Figure 6:
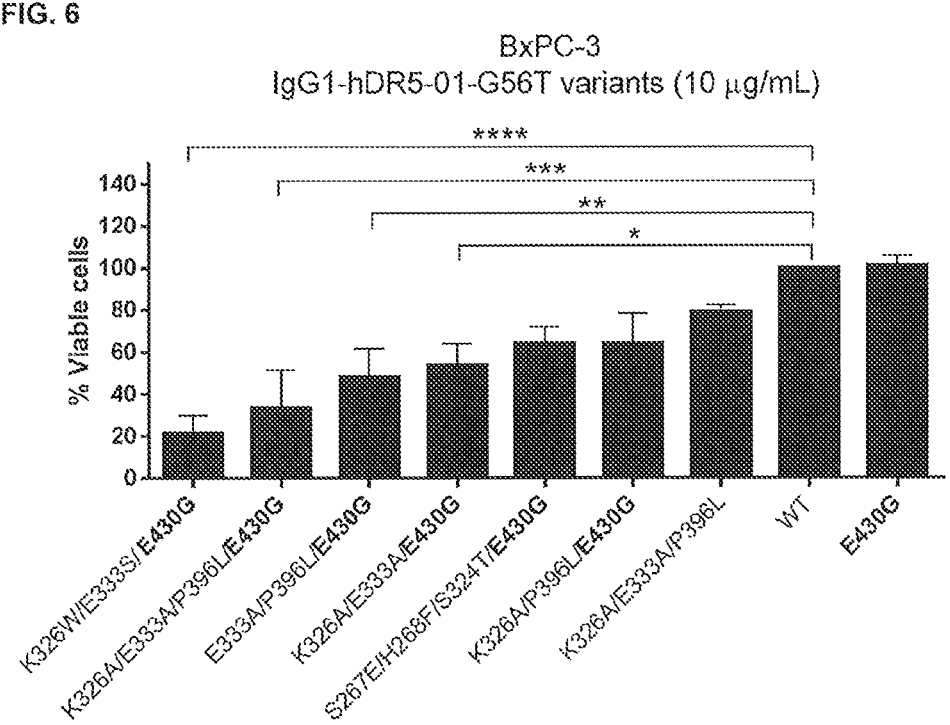
FIG. 6 shows a summary of 3-days viability assays (CellTiter-Glo) on adherent human BxPC-3 pancreatic cancer cells with 10 µg/mL IgG1-hDR5-01-G56T variants containing the indicated mutations. The effect is represented by and ranked by the percentage viable cells relative to WT IgG1-hDR5-01-G56T, which was set at 100%. Significant effects on cell viability compared to WT are indicated as *P<0.05, P<0.01, *P<0.001, ****P<0.0001 (One-way ANOVA with Dunnett's multiple comparisons test).

FIG. 6 shows that the combination of the Fc-Fc enhancing substitution E430G with the C1q binding double substitution K326W/E333S showed the most significant effect when compared to the WT IgG1-hDR5-01-G56T antibody after a three-days incubation period of adherent human BxPC-3 pancreatic cancer cells with 10 μg/mL antibody in full culture medium containing heat inactivated fetal calf serum. Also the combinations of E430G with K326A/E333A/P396L, E333A/P396L and K326A/E333A resulted in significantly lower percentages of viable cells than WT antibody. Other Fc variants that has been shown to enhance C1q binding, such as S267E/H268F/S324T and IgG1/IgG3 chimeric IgG-113F, did not show significant induction of killing efficacy when combined with E430G in IgG1-hDR5-01-G56T in the experimental setup here with 10 μg/mL antibody on adherent BxPC-3 cells, in which also IgG1-hDR5-01-G56T-E430G did not result in the induction of killing efficacy when tested as a single agent.

Example 8: Effect of C1q on the In Vitro Activity of Agonistic Anti-DR5 Antibodies with a Fc-Fc Enhancing Substitution in Combination with C1q Binding Substitutions The previous examples suggested that enhanced C1q binding contributes to better agonistic activity of the tested anti-DR5 antibodies containing the E430G Fc-Fc-enhancing mutation. To test the effect of C1q, a viability assay was performed with IgG1-CONA-K326A/E333A/P396L/E430G and IgG1-hDR5-01-G56T-K326W/E333S/E430G on WIL2-S SF cells in serum-free medium in the presence or absence of purified human C1q. WIL2-S SF cells were derived from WIL2-S (ATCC, CRL-8885) B lymphoblasts and adapted to grow under serum-free conditions in culture medium formulated by HyQ-ADCF-Mab (Perbio, Cat #SH30349) containing 50 U/mL Pen/Strep and 1 mM sodium pyruvate. WIL2-S SF suspension cells were passed through a cell strainer, pelleted by centrifugation for 5 minutes at 300×g, and resuspended in the serum-free culture medium at a concentration of $0.5 \times 10^6$ cells/mL. 100 μL of the single cell suspensions (50,000 cells per well) were seeded in polystyrene 96-well flat-bottom plates (Greiner Bio-One, Cat nr 655182). 25 μL of a serial dilution antibody preparation series (range 0.0003 to 20,000 ng/mL final concentrations in 4-fold dilutions) and 25 μL purified C1q (Quidel, Cat #A400; 2.5 μg/mL final concentration) were added and incubated for 1 day at 37° C. As a negative and positive control, cells were incubated in medium without antibody or with 5 μM staurosporine (Sigma Aldrich, Cat nr S6942), respectively. Cell viability was determined by TO-PRO-3 staining. TO-PRO-3 is a cell-impermeant carbocyanine monomer stain that binds double stranded DNA. As such, TO-PRO-3 can be used as a dead cell indicator. All samples were transferred to polystyrene 96-well U-bottom plates (Greiner Bio-One, Cat nr 650261) and centrifuged for 3 minutes at 300×g before removing 70 μL of the supernatant. 10 μL TO-PRO-3 mixture (Invitrogen, Cat #T3605) 20 μL TO-PRO-3+1980 μL PBS) was added before resuspending the cells by pipetting. The amount of TO-PRO-3-positive cells was determined by flow cytometry on a BD LSRFortessa X-20 cell analyzer (BD Biosciences).

Figure 7A:
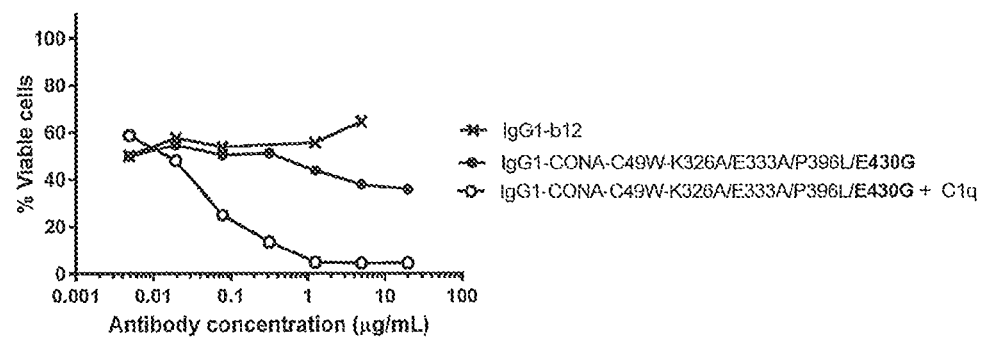
FIGS. 7A and 7B show the agonistic effect of anti-DR5 antibody IgG1-CONA-C49W-K326A/E333A/P396L/E430G (FIG. 7A) and IgG1-hDR5-01-G56T-K326W/E333S/E430G (FIG. 7B) on WIL2-S SF suspension cells in serum-free medium in the presence or absence of 2.5 µg/mL purified human C1q as determined in a 24-hours viability assay. The percentage viable cells is represented by the percentage TO-PRO-3-negative cells.
Figure 7B:
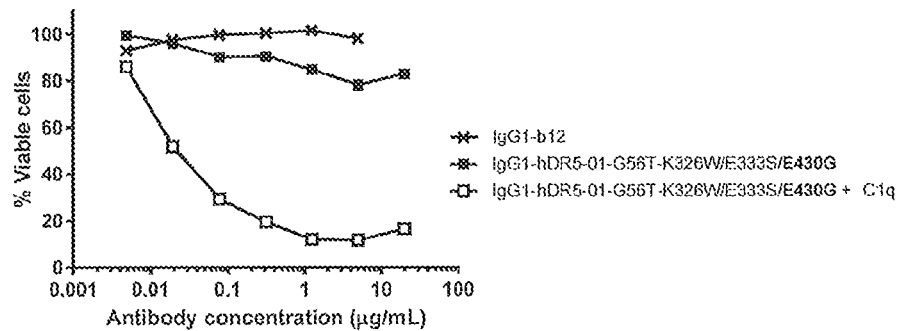

FIG. 7 shows that adding purified C1q to serum-free medium greatly enhanced the potency of both IgG1-CONA-K326A/E333A/P396L/E430G (FIG. 7A) and IgG1-hDR5-01-G56T-K326W/E333S/E430G (FIG. 7B) on WIL2-S SF cells. These data indicate that C1q binding contributes to better agonistic activity of agonistic anti-DR5 antibodies containing the E430G Fc-Fc enhancing substitution in combination with the K326A/E333A/P396L or C1q binding K326W/E333S substitutions.

Example 9: Effect of C1q on the In Vitro Agonistic Activity of Agonistic Anti-DR5 Antibodies with a Fc-Fc Enhancing Substitution in Combination with C1q Binding Substitutions In Example 8 the effect of C1q on the efficacy of agonistic anti-DR5 antibodies was tested in a viability assay on WIL2-S SF cells in serum-free medium with an antibody concentration series and a fixed C1q concentration. In this example, the effect of a concentration series of C1q was tested on the efficacy of agonistic IgG1-hDR5-01-G56T antibody variants with a Fc-Fc enhancing substitution (E430G) in combination with C1q binding substitutions (K326A/E333A/P396L, K326W/E333S or K326A/E333A) in a viability assay on WIL2-S SF cells in serum-free medium. The viability was performed, essentially as described in Example 8, with a fixed antibody concentration of 2.5 μg/mL and a concentration series of purified C1q ranging from 0.0002 to 2.5 μg/mL final concentrations in 4-fold dilutions.

Figure 8A:
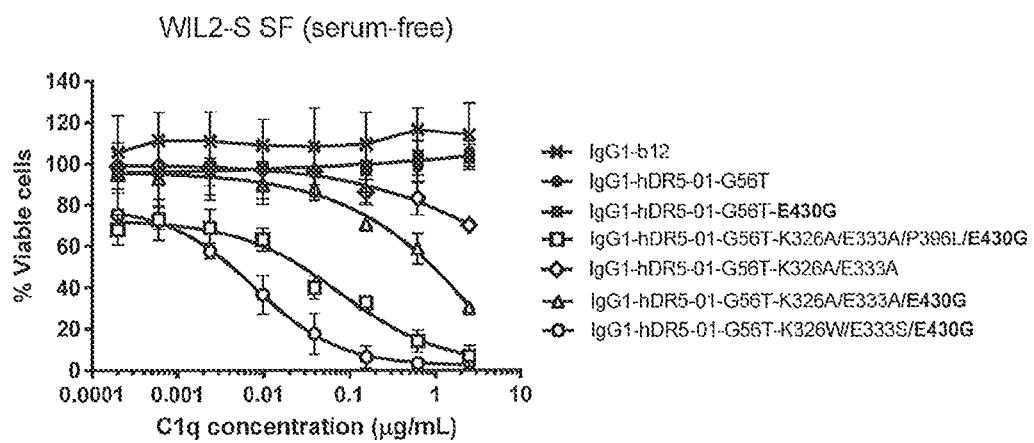
FIGS. 8A and 8B show the agonistic effect of 2.5 µg/mL anti-DR5 antibody variants of IgG1-hDR5-01-G56T with the E430G a Fc-Fc enhancing substitution in combination with C1q binding substitutions (FIG. 8A) and the antibody combination IgG1-hDR5-01-G56T-E430G+IgG1-hDR5-05-E430G (FIG. 8B) on WIL2-S SF suspension cells in serum-free medium in the presence or absence of a concentrations series of purified human C1q as determined in a 24-hours viability assay. The percentages viable cells are represented by the percentage TO-PRO-3-negative cells. Data of four different experiments are represented with error bars indicating the standard deviation.
Figure 8B:
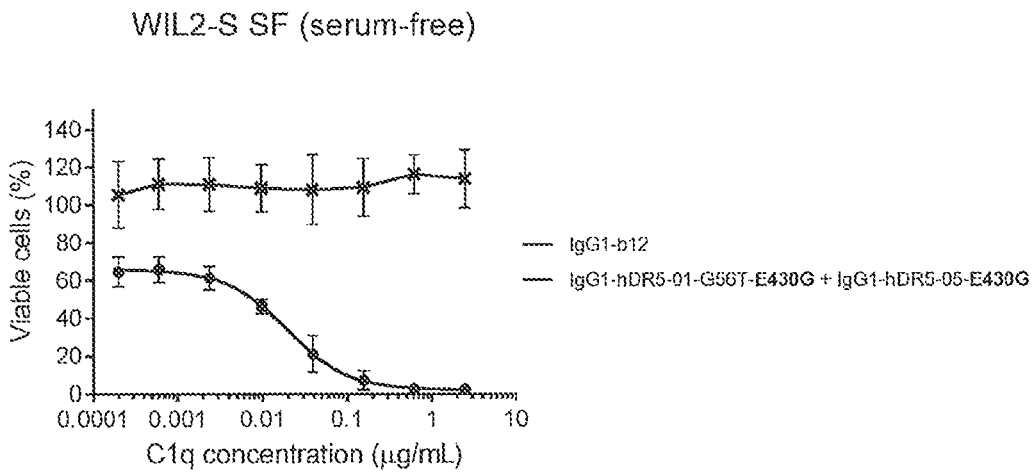

FIG. 8 shows that adding purified C1q to serum-free medium enhanced the potency of anti-DR5 antibodies containing the E430G Fc-Fc enhancing substitution. All tested IgG1-hDR5-01-G56T-E430G antibody variants containing C1q binding-enhancing substitutions (K326A/E333S/P396L, K326W/E333S or K326A/E333A) showed efficacy on WIL2-S SF cells in a C1q dose-dependent manner (FIG. 8A). IgG1-hDR5-01-G56T-K326W/E333S/E430G showed highest efficacy of all tested antibodies and reached maximal kill at a C1q concentration range starting from 0.16 μg/mL. These data indicate that C1q binding contributes to better activity of agonistic anti-DR5 antibodies containing the E430G Fc-Fc-enhancing substitution in combination with the K326A/E333A/P396L, K326W/E333S or K326A/E333A C1q binding substitutions. Also the dual epitope targeting antibody combination IgG1-hDR5-01-G56T-E430G+IgG1-hDR5-05-E430G showed a C1q dose-dependent increase in efficacy to kill WIL2S-SF cells in serum-free medium, reaching maximal kill around 0.16 μg/mL C1q (FIG. 8B).

Example 10: Effect of C1q Neutralization on the In Vitro Agonistic Activity of Agonistic Anti-DR5 Antibodies with a Fc-Fc Enhancing Substitution in Combination with C1q Binding Substitutions The requirement of C1q for the efficacy of agonistic anti-DR5 IgG1-hDR5-01-G56T-K326W/E333S/E430G containing the E430G Fc-Fc enhancing substitution in combination with the K326W/E333S substitution for C1q binding was tested by using an anti-C1q neutralizing antibody directed against the C1q globular head region, in a viability assay on WIL2-S SF cells in serum-free medium containing purified C1q. Similarly, the effect of neutralizing C1q was also tested in the same settings for the dual epitope targeting antibody combination IgG1-hDR5-01-G56T-E430G+IgG1-hDR5-05-E430G. The viability assay was performed, essentially as described in Example 8. Briefly, WIL2-S SF cells were resuspended in serum-free culture medium at a concentration of $0.67 \times 10^6$ cells/mL. 75 µL of the single cell suspensions (50,000 cells per well) were seeded in serum-free culture medium in polystyrene 96-well flat-bottom plates. Next, 25 µL anti-DR5 antibody sample (2.5 µg/mL final concentration), 25 µL purified C1q (0.01 µg/mL final concentration) and 25 µL anti-C1q antibody sample (Sanquin, CLB/C1q-85 CAT #MW1828; 10 µg/mL final concentration) were added and incubated for 1 day at 37° C. Cell viability was determined by TO-PRO-3 staining as described in Example 8.

Figure 9A:
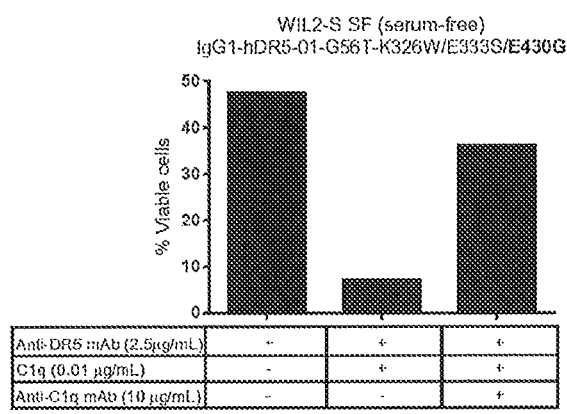
FIGS. 9A and 9B show the efficacy of 2.5 µg/mL agonistic anti-DR5 IgG1-hDR5-01-G56T-K326W/E333S/E430G (FIG. 9A) and the antibody combination IgG1-hDR5-01-G56T-E430G+IgG1-hDR5-05-E430G (FIG. 9B) on WIL2-S SF suspension cells in serum-free medium with or without purified human C1q and anti-C1q neutralizing antibody as determined in a 24-hours viability assay. The percentages viable cells are represented by the percentage TO-PRO-3-negative cells.
Figure 9B:
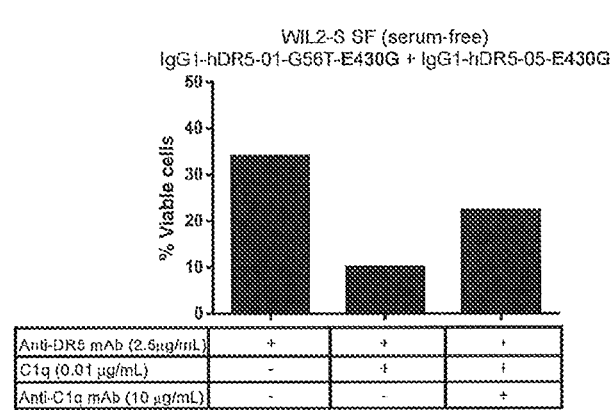

The effect of adding purified C1q to serum-free medium to enhance the potency of anti-DR5 antibody IgG1-hDR5-01-G56T-K326W/E333S/E430G as described in Example 9 was confirmed in this experiment (FIG. 9A). Moreover, this potency was diminished when binding of the supplemented C1q to the anti-DR5 antibody was neutralized by the presence of an excess of anti-C1q antibody (FIG. 9A). These data illustrate that C1q binding is required for optimal activity of agonistic anti-DR5 antibodies containing the E430G Fc-Fc enhancing substitution in combination with K326W/E333S C1q binding substitution. C1q-dependent efficacy for killing WIL2S-SF cells was also confirmed for the dual epitope targeting antibody combination IgG1-hDR5-01-G56T-E430G+IgG1-hDR5-05-E430G showing enhanced efficacy upon adding C1q to the serum-free medium, and neutralization of this effect by the presence of an excess of anti-C1q antibody (FIG. 9B).

Example 11: Solution Phase Complement Activation Assay for Antibodies with a Fc-Fc Enhancing Substitution in Combination with C1q Binding Substitutions Target binding-independent complement activation by antibody variants was determined by quantification of C4d, a marker for classical complement pathway activation, after antibodies were incubated in normal human serum (NHS). A three-steps ELISA procedure was performed using the MicroVue C4d Enzyme Immuno Assay (Quidel, Cat #A0008) containing (1) a microassay plate coated with a mouse monoclonal antibody that binds specifically to C4d-containing activation fragments of human C4, (2) an HRP-conjugated goat anti-human C4d antibody, and (3) a chromogenic substrate. Internal controls and standards were supplemented with the kit and used as described by the manufacturer's instructions. As a positive control, heat aggregated gamma globulin was prepared as follows. 1 mL aliquots in 1.5 ml vials of IVIG solution (60 mg/mL; Sanquin, Cat #04H04H443A) were heated for 20 min at 63° C. Vials were pooled and diluted to 20 mg/mL with PBS and filtered through 0.22 µm pore surfactant-free cellulose acetate (SFCA) membrane syringe filter (Corning, Cat #431219). Aliquots of ~0.2 mL were stored at 4° C. For the antibody samples, 50 µL samples of 100 µg/mL antibody preparation in 90% normal human serum (NHS, Sanquin M0008AC) were incubated in polypropylene 96-well U-bottom plates (Greiner Bio-One; Cat #650261) for 1 hour at 37° C. Next, 5 µL of these samples were diluted 90× with Specimen Diluent and 100 µL of the diluted samples were incubated per well for 30 minutes at room temperature while shaking in the Coated Strips that were prewashed three times with 250 µL Wash Solution. Next, wells were washed five times with 250 µL Wash Solution before incubating 50 µL C4d Conjugate per well for 30 minutes at RT while shaking. Wells were washed five times with 250 µL Wash Solution before incubating 100 µL Substrate per well for 30 minutes at RT while shaking. The reactions were stopped by adding 50 µL Stop Solution per well and the color intensity was measured spectrophotometrically at 405 nm on a BioTek EL808 Microplate Reader (BioSPX).

Positive control samples showed clearly enhanced C4d levels compared to negative control samples (FIG. 10). In contrast, no clear enhancement of C4d levels were observed for all tested IgG1-hDR5-01-G56T antibody variants containing the E430G Fc-Fc enhancing substitution in combination with C1q binding substitutions K326W/E333S, K326A/E333A or K326A/E333A/P396L when incubated in NHS in absence of target cells (FIG. 10), whereas C4d was produced when the positive controls HAGG, representing random immune complexes, and IgG1-CONA-RGY, representing fluid phase IgG1 hexamers, were incubated in NHS. These data indicate that IgG1-hDR5-01-G56T antibody variants containing the E430G Fc-Fc enhancing substitutions in combination with C1q binding substitutions K326W/E333S, K326A/E333A or K326A/E333A/P396L do not show target-independent hexamerization and complement activation in solution phase.

Figure 11A:
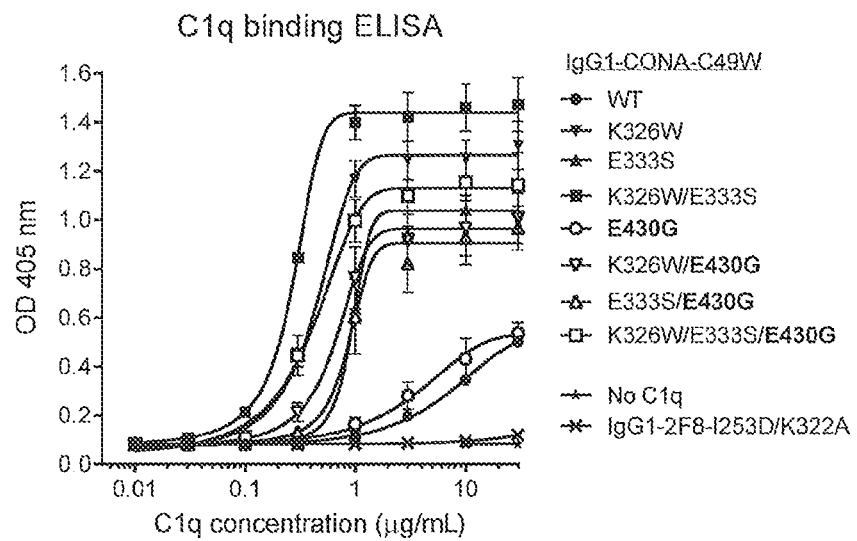
FIGS. 11A-11G show the effect of introducing the K326W, E333S, or K326W/E333S substitutions in IgG-CONA-C49W and IgG1-CONA-C49W-E430G on C1q binding as determined in an ELISA assay (FIGS. 11A and 11B), C1q binding to the antibodies bound to DR5-positive WIL2-S SF cells as determined by flow cytometry (FIGS. 11C and 11D), and on the reduction of cell viability of WIL2-S SF suspension cells as determined in a 3-day viability assay (CellTiter-Glo) (FIGS. 11E-11G). Standard deviations were calculated from two independent experiments.
Figure 11B:
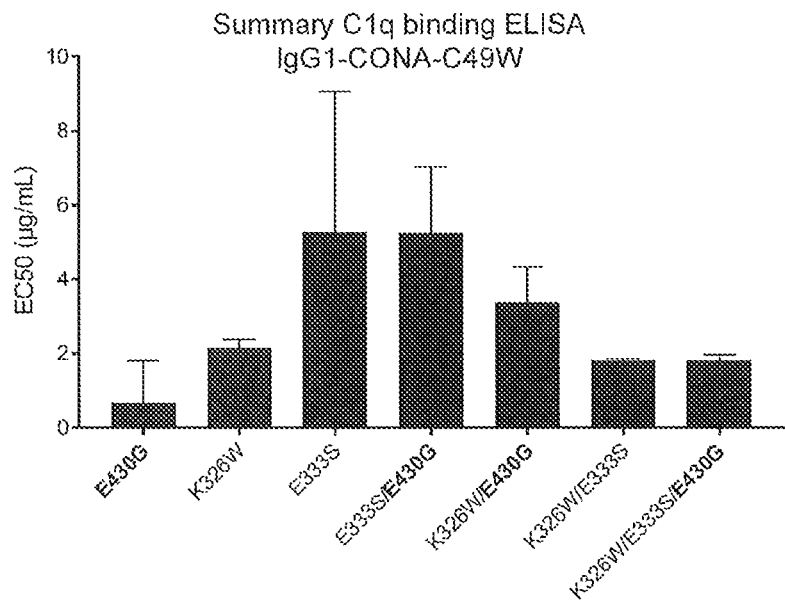
Figure 11C:
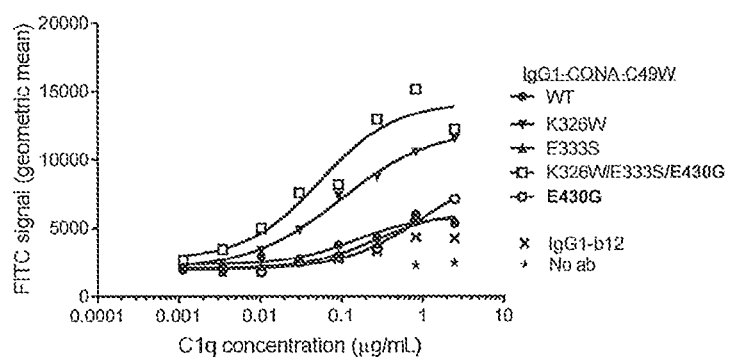
Figure 11D:
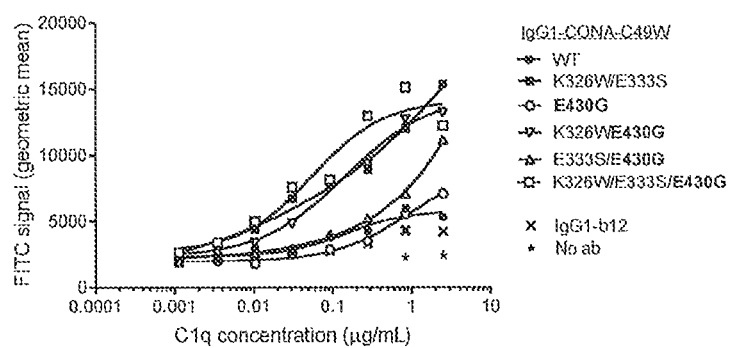

Example 12: Effect of Combining E430G and K326W, E333S or K326W/E333S on the C1q Binding and Efficacy of Agonistic Anti-DR5 Antibodies A C1q binding ELISA was performed to evaluate the effect of introducing the K326W, E333S, or K326W/E333S substitutions on C1q binding to IgG-CONA-C49W variants with or without the E430G substitution. IgG-2F8-I253D/K322A was used as a negative control for C1q binding. The ELISA experiment was performed in 96-well plates coated with 1 µg/mL antibody that were tested for binding of different concentrations purified C1q (range 0.010-30 µg/mL in 3-fold dilutions) as described in Example 4. Absorbance was measured at 405 nm and log-transformed data were analyzed by fitting sigmoidal dose-response curves with variable slope using GraphPad Prism software. FIG. 11A,B shows that introduction of the K326W, E333S, or K326W/E333S substitutions all resulted in increased C1q binding to randomly immobilized antibody for both anti-DR5 antibody IgG1-CONA-C49W and its variant IgG1-CONA-C49W-E430G with the E430G Fc-Fc interaction enhancing and hexamerization-enhancing mutation. IgG1-CONA-C49W-K326W/E333S/E430G showed the highest apparent C1q binding affinity of all tested antibody variants. Binding of purified antibody variants of to WIL2-S SF suspension cells was analyzed by flow cytometry. Cells were harvested, counted, washed in PBS and resuspended at $3.33 \times 10^6$ cells/mL in culture medium. 30 µL cells ($1 \times 10^5$ cells per well) were pipetted in 96-well plates. 50 µL samples of antibody titration series (range 0.001-2.5 µg/mL final antibody concentrations in 3-fold dilutions) were added and incubated for 15 minutes at 37° C. Subsequently, 20 µL purified C1q (2.5 µg/mL final concentration) was added and incubated for 45 minutes at 4° C. Next, 100 µL FACS buffer (PBS+0.1% (w/v) bovine serum albumin (BSA)+0.02% (w/v) sodium azide) was added before washing the cells twice with 150 µL FACS buffer. The washed cells were incubated for 30 minutes at 4° C. with 50 μL FITC-labelled rabbit anti-human C1q antibody (20 μg/mL final concentration; DAKO Cat. No. F0254). 100 μL FACS buffer was added and cells were washed twice with FACS buffer. Cells were resuspended in 30 μL FACS buffer and fluorescence was measured by flow cytometry using an iQue Screener (IntelliCyt). Binding curves with a log transformed C1q concentration axis were analyzed using non-linear regression analysis (sigmoidal dose-response with variable slope) using GraphPad Prism software. FIG. 11C,D shows that introduction of only the E333S or E430G substitution in anti-DR5 antibody IgG1-CONA-C49W had no effect on C1q binding to the antibody bound to DR5-positive WIL2-S SF cells (FIG. 11C). Introduction of the K326W mutation in anti-DR5 antibody IgG1-CONA-C49W or IgG1-CONA-C49W-E430G resulted in increased C1q binding to anti-DR5 antibody-opsonized WIL2-S SF cells, consistent with the increased C1q binding observed for cells opsonized with IgG1-CONA-C49W-K326W/E333S/E430G (FIG. 11C, D). Introduction of the E333S in anti-DR5 antibody IgG1-CONA-C49W-E430G resulted in modest increase in C1q binding to antibody-opsonized WIL2-S SF cells (FIG. 11D). These flow cytometry data indicate that cell-bound IgG1-CONA-C49W-K326W/E333S/E430G showed the most avid C1q binding.

Figure 11E:
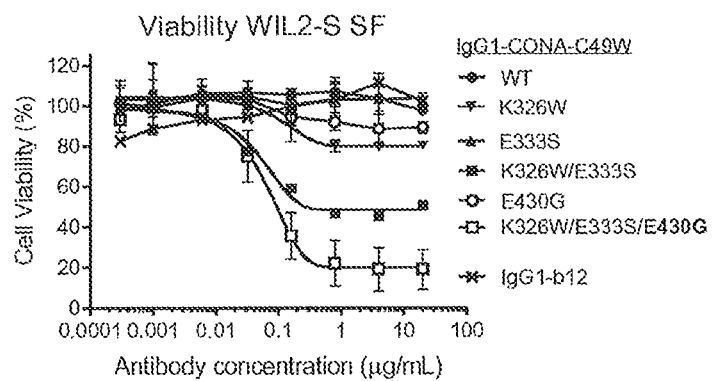
Figure 11F:
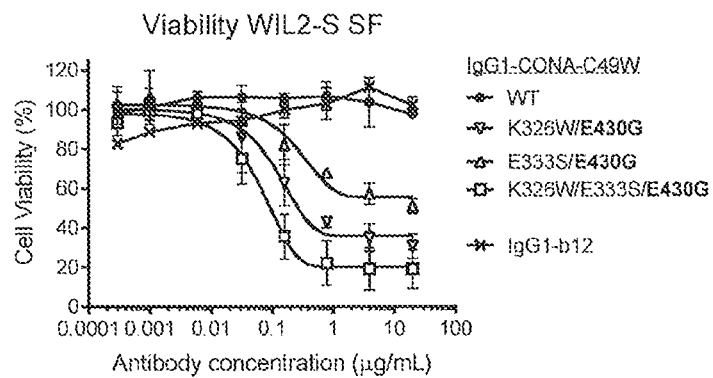
Figure 11G:
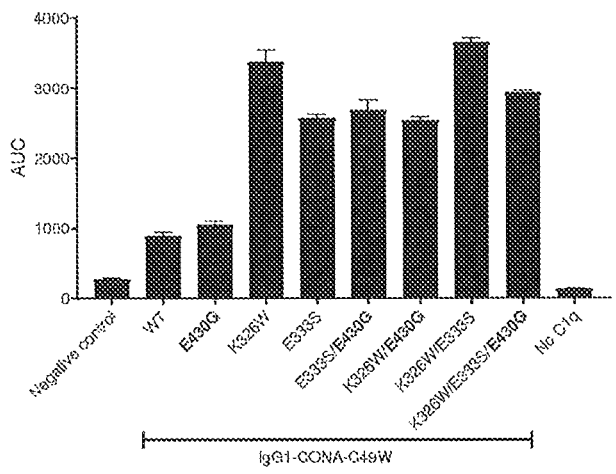

A viability assay was performed to evaluate the effect of introducing the K326W, E333S, or K326W/E333S in anti-DR5 IgG1-CONA-C49W variants with or without the E430G substitution on the DR5 agonist activity on WIL2-S SF cells. A 1-day viability assay was performed, essentially as described in Example 8. Briefly, 100 μL cells in serum-free medium (50.000 cells/well) were pipetted in 96-well plates. 25 μL purified C1q (final concentration 2.5 μg/mL) and 25 μL antibody samples of a concentration dilution series (range 0.0003-20 μg/mL final concentrations in 5-folds dilutions) were added and incubated at 37° C. for 1 day. Cell viability was determined using the CellTiterGlo assay as described in Example 2. Luminescence was measured on an EnVision Multilabel Reader (PerkinElmer). Log-transformed C1q concentration data were analyzed and plotted using non-linear regression (sigmoidal dose-response with variable slope) using GraphPad Prism software. FIG. 11E-G shows that introducing only the K326W, E333S or E430G mutation in anti-DR5 antibody IgG1-CONA-C49W did not result in the induction of DR5 agonist activity in WIL2-S SF cells, whereas the K326W/E333S double mutation in IgG1-CONA-C49W resulted in the induction of DR5 agonist activity and partial killing of WIL2-S SF cells (FIG. 11E). Combining mutation K326W, E333S mutation, or double mutation K362W/E333S with the Fc-Fc-enhancing mutation E430G in the anti-DR5 antibody IgG1-CONA-C49W resulted in the induction of DR5 agonist activity, with K362W/E333S/E430G resulting in the highest maximal kill in WIL2-S SF cells (FIG. 11F).

Figure 12A:
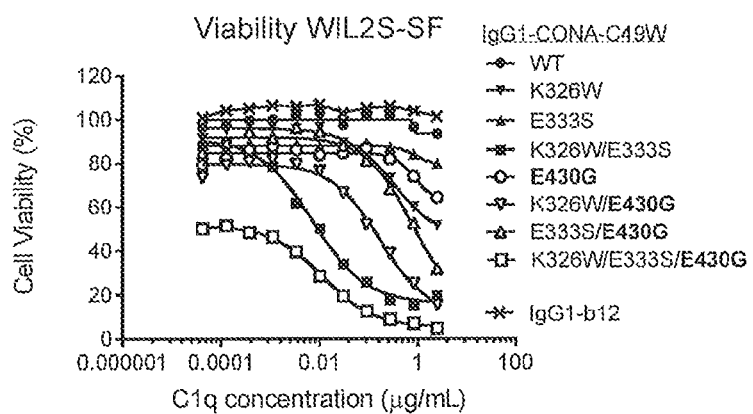
Figure 12B:
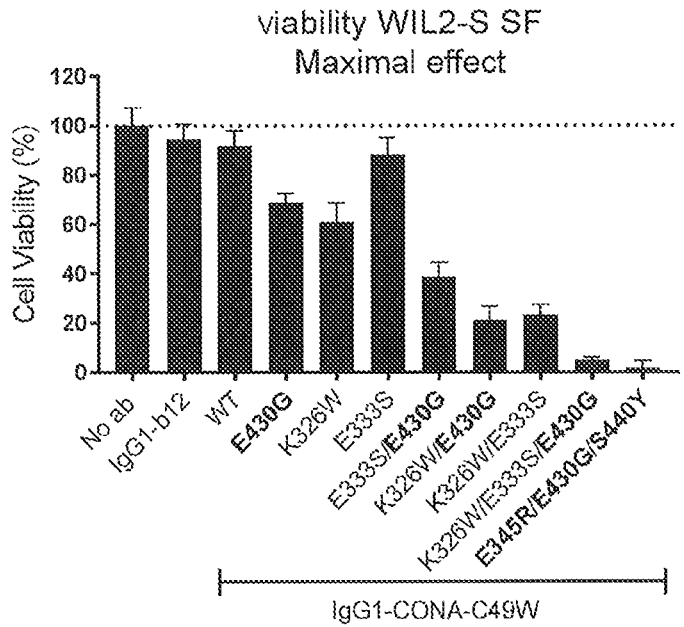

Example 13: Effect of Combining E430G and K326W, E333S or K326W/E333S on the C1q-Dependent Efficacy of Agonistic Anti-DR5 Antibodies The effect of introducing the K326W, E333S, or K326W/E333S substitutions in anti-DR5 IgG-CONA-C49W antibody variants, with or without mutation E430G, on the C1q-dependent agonistic activity was tested. A 1-day viability assay was performed in vitro using WIL2-S SF cells in serum-free medium with a C1q concentration dilution series, essentially as described in Example 8. Briefly, 100 μL cells in serum-free medium (50.000 cells/well) were pipetted in 96-well plates. 25 μL antibody samples (2.5 μg/mL final concentration) and 25 μL of a concentration dilution series of purified C1q (range 42 pg/mL-2.5 μg/mL final concentrations in 3-folds dilutions) were added and incubated at 37° C. for 1 day. Cell viability was determined using the CellTiter-Glo assay as described in Example 2. Luminescence was measured on an EnVision Multilabel Reader (PerkinElmer). C1q concentration log-transformed data were analyzed and plotted using non-linear regression (sigmoidal dose-response with variable slope) using GraphPad Prism software. FIG. 12 shows that introducing the Fc-Fc-enhancing substitution E430G or the C1q binding-enhancing substitutions K326W or E333S as a single mutation in anti-DR5 antibody IgG1-CONA-C49W resulted in the induction of C1q dose-dependent killing of WIL2-S SF cells, and compared to this, introduction of the K326W/E333S double mutation resulted in more efficient induction of C1q dose-dependent killing of WIL2-S SF cells. Combining the E430G Fc-Fc-enhancing substitution and the tested C1q binding substitutions resulted in more efficient killing, with IgG-CONA-C49W-K326W/E333S/E430G inducing the most efficient C1q dose-dependent killing of WIL2-S SF cells (FIG. 12).

Figure 13:
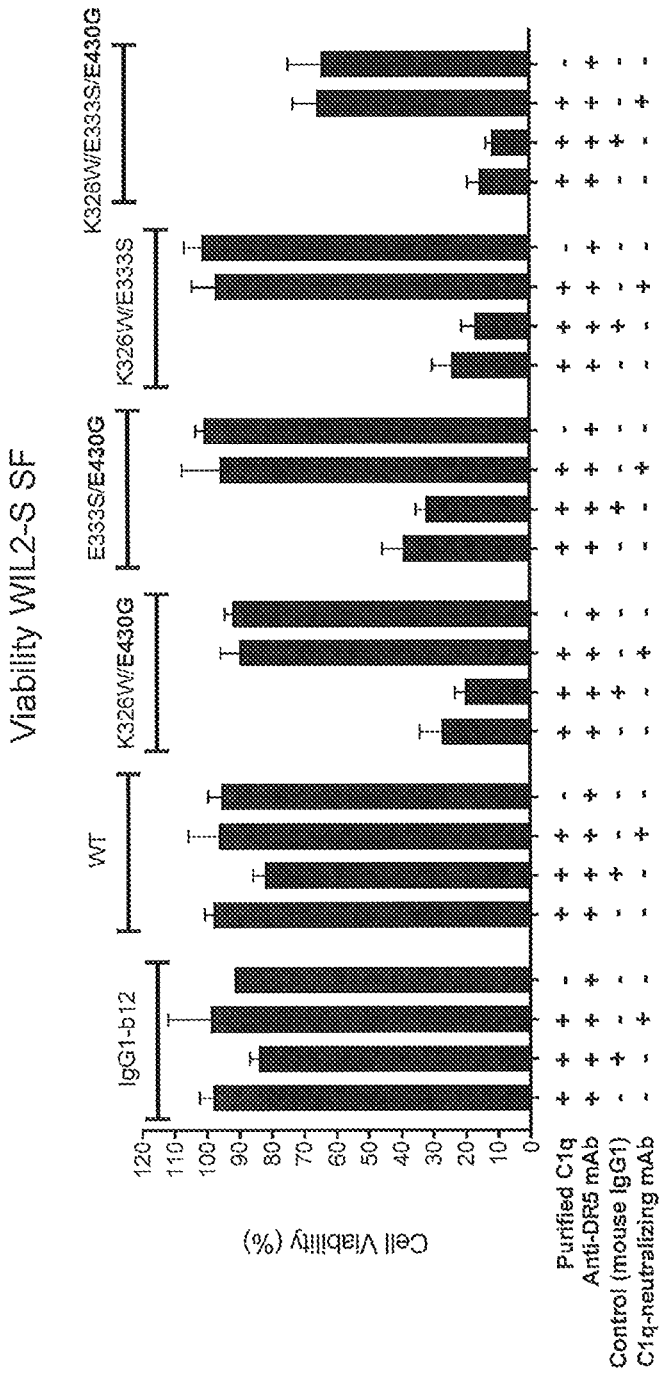
FIG. 13 shows the effect of adding an anti-C1q antibody on the efficacy of anti-DR5 IgG1-CONA-C49W antibody variants with C1q binding-enhancing and/or Fc-Fc interaction-enhancing mutations in a 24-hours viability assay on WIL2-5 SF suspension cells in serum-free medium supplemented with purified human C1q. The percentages viable cells were determined in a CellTiter-Glo assay.

Example 14: Effect of C1q Neutralization on the In Vitro Agonistic Activity of Anti-DR5 Antibodies with an E430G Mutation in Combination with K326W, E333S or K326W/E333S Mutations To test the contribution of C1q to the efficacy of agonist anti-DR5 antibodies containing the E430G Fc-Fc-enhancing mutation, a C1q-neutralizing antibody was added in a viability assay with WIL2-S SF cells opsonized with IgG1-CONA-C49W variants in serum-free medium containing purified human C1q. The experiment was performed essentially as described in Example 8. Briefly, 75 μL cell suspensions were seeded in serum-free medium in polystyrene 96-well flat-bottom plates (50,000 cells per well). 25 μL IgG1-CONA-C49W antibody variants (2.5 μg/mL final concentration), 25 μL purified C1q (at final C1q concentrations approximating the EC90 concentration for each different antibody according to Table 5) and 25 μL (10 μg/mL final concentration) C1q-neutralizing antibody (CLB-C1q-85; Sanquin, Article No. MW1828) or isotype control antibody (Purified mouse IgG1, κ Clone MOPC-21; BD Biosciences Cat. No. 555746) were added to WIL2-S SF cells and incubated at 37° C. for 1 day. Cell viability was determined using the CellTiter-Glo assay as described in Example 2. Luminescence was measured on an EnVision Multilabel Reader (PerkinElmer). Data were analyzed and plotted using GraphPad Prism software. FIG. 13 shows that in the presence of the C1q-neutralizing antibody, the DR5 agonist activity of the IgG1-CONA-C49W variants with the K326W/E430G, E333S/E430G or K326W/E333S substitutions was completely inhibited. For IgG1-CONA-C49W-K326W/E333S/E430G, C1q neutralization resulted in partial inhibition of DR5 agonist activity.

TABLE 5

C1q EC90 values for 2.5 µg/mL of the indicated antibodies in a viability assay on WIL2-S SF cells in serum-free medium supplemented with purified C1q concentrations series as described in Example 13 (data not shown).

| Antibody | C1q EC90 (µg/mL) | C1q concentration in FIG. 13 (µg/mL) |
|---|---|---|
| IgG1-b12 | >2.5 | 2.5 |
| IgG1-CONA-C49W | >2.5 | 2.5 |
| IgG1-CONA-C49W-K326W/E430G | 1.0 | 1.0 |
| IgG1-CONA-C49W-E333S/E430G | >2.5 | 2.5 |
| IgG1-CONA-C49W-K326W/E333S | 0.3 | 0.3 |
| IgG1-CONA-C49W-K326W/E333S/E430G | 0.1 | 0.1 |

Figure 14:
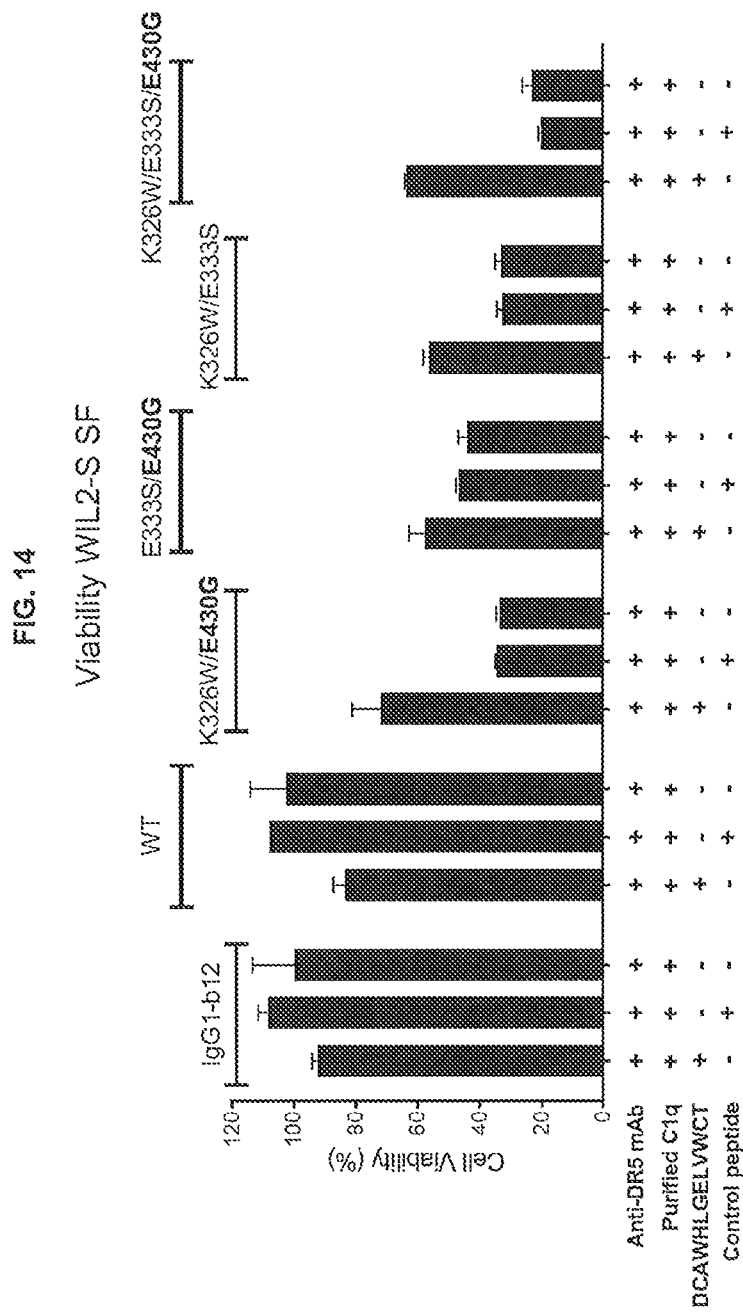
FIG. 14 shows the effect of adding a peptide that inhibits Fc-Fc interactions between anti-DR5 IgG1-CONA-C49W antibody variants opsonized to WIL2-S SF suspension cells, incubated in serum-free medium supplemented with purified human C1q, in a 24-hour viability assay. The percentages viable cells were determined in a CellTiter-Glo assay. Scrambled peptide WCDLEGVTWHACL was used as a non-specific control peptide.

Example 15: Effect of Fc-Fc Interaction Inhibition on the In Vitro Agonistic Activity of Anti-DR5 Antibodies with an E430G Mutation in Combination with K326W, E333S or K326W/E333S To test the involvement of Fc-Fc-mediated antibody hexamerization in the induction of cell death by IgG1-CONA antibody variants, we made use of the 13-residue peptide DCAWHLGELVWCT (DeLano et al., Science 2000 Feb. 18; 287(5456):1279-83) that binds the Fc in a region containing the core amino acids in the hydrophobic knob area involved in Fc-Fc interactions (Diebolder et al., Science. 2014 Mar. 14; 343(6176):1260-3). The viability of WIL2-S SF cells was determined in the presence or absence of the DCAWHLGELVWCT peptide, essentially as described in Example 14. Briefly, 75 µL WIL2-S SF cell suspensions were seeded in serum-free medium in polystyrene 96-well flat-bottom plates (50,000 cells per well). 25 µL of antibody (2.5 µg/mL final concentration) was added and incubated for 10 minutes at room temperature. Next, 25 µL of Fc-Fc-inhibiting peptide DCAWHLGELVWCT or scrambled control peptide WCDLEGVTWHACL (80 µg/mL) was added and incubated for 10 minutes at room temperature. Then, 25 µL purified C1q (at final C1q concentrations approximating the EC90 for each different antibody, as listed in Example 14, Table 1) was added and the reaction mixtures were incubated at 37° C. for 1 day. Cell viability was determined using the CellTiter-Glo assay as described in Example 2. Luminescence was measured on an EnVision Multilabel Reader (PerkinElmer). Data were analyzed and plotted using GraphPad Prism software. FIG. 14 shows that in presence of the Fc-Fc-inhibiting peptide DCAWHLGELVWCT, the DR5 agonist activity of the IgG1-CONA-C49W variants with the K326W/E430G, E333S/E430G, K326W/E333S, or K326W/E333S/E430G substitutions was partially inhibited. The Fc-Fc-inhibiting peptide inhibited the agonistic activity of IgG1-CONA-C49W-K326W/E333S/E430G with the Fc-Fc-enhancing mutation E430G more strongly than of IgG1-CONA-C49W-K326W/E333S without mutation E430G.

Figure 15A:
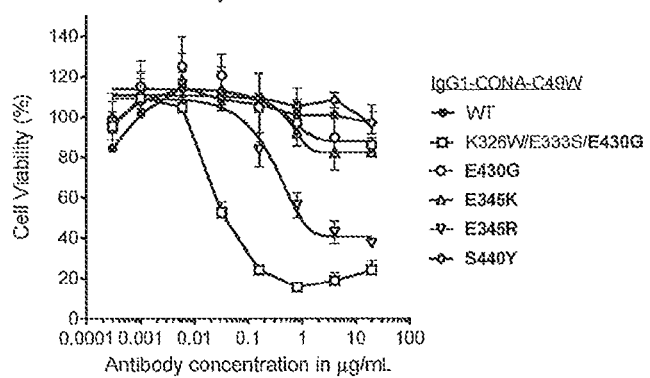
FIGS. 15A and 15B show the effect of combining the C1q binding substitutions K326W/E333S with of the Fc-Fc-enhancing mutations E345K, E345R, or S440Y on the agonist activity of anti-DR5 antibody IgG1-CONA-C49W on adherent human BxPC-3 pancreatic cancer cells as determined in a 3-days viability assay (CellTiter-Glo).
Figure 15B:
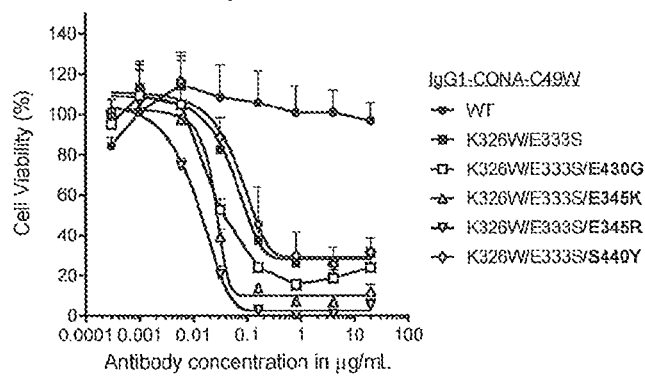

Example 16: Effect of Combining K326W/E333S with Fc-Fc-Enhancing Mutation E345K, E345R, or S440Y on the Agonist Activity of an Anti-DR5 Antibody A viability assay was performed to study the effect of combining the C1q binding substitutions K326W/E333S with f the Fc-Fc-enhancing mutations E345K, E345R, or S440Y on the agonist activity of anti-DR5 antibody IgG1-CONA-C49W opsonized to BxPC-3 cells. The viability assay was performed essentially as described in Example 2. Briefly, 100 µL BxPC-3 single cell suspensions were seeded in full culture medium (RPMI containing 10% DBSI) in polystyrene 96-well flat-bottom plates (5,000 cells per well) and allowed to adhere overnight at 37° C. Next, 50 µL of a serial dilution antibody preparation series (range 0.0003 to 20 µg/mL final concentrations in 5-fold dilutions) was added and incubated for 3 days at 37° C. Cell viability was determined using the CellTiter-Glo assay. Luminescence was measured on an EnVision Multilabel Reader (PerkinElmer). Data with log-transformed concentration axes were analyzed and plotted using non-linear regression (sigmoidal dose-response with variable slope) using GraphPad Prism software. FIG. 15A shows that killing of BxPC-3 cells by IgG1-CONA-C49W was strongly inducted by introduction of the E345R mutation, slightly induced by the E430G or E345K mutation, whereas S440Y did not have an effect. FIG. 15B shows that killing of BxPC-3 cells by IgG1-CONA-C49W-K326W/E333S variants was increased by introduction of the E430G, E345K or E345R mutation, whereas it was not further enhanced by introduction of the S440Y mutation. Together, these data indicate that the C1q binding-enhancing K326W/E333S mutation can enhance the efficacy of anti-DR5 agonist IgG1 antibodies with different Fc-Fc-enhancing mutations, such as E430G, E345K or E345R.

Figure 16A:
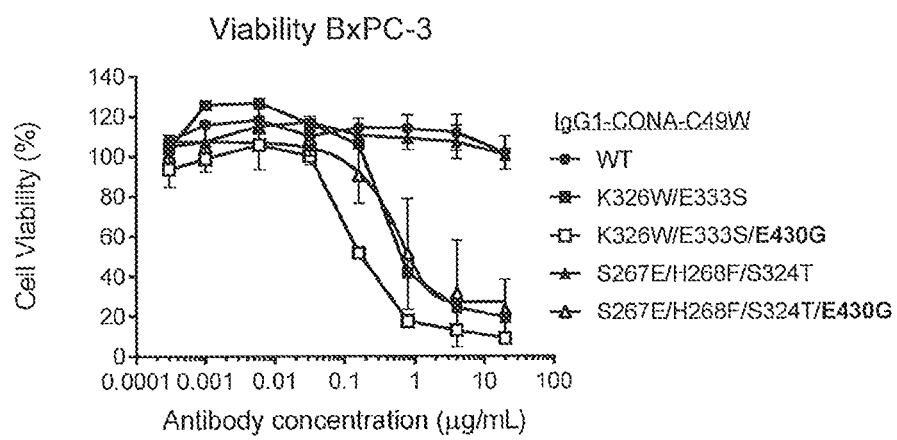
FIGS. 16A and 16B show the effect of mutation E430G, combined with C1q binding-enhancing mutations 5267E/H268F/S324T or the IgG1/IgG3 chimeric isotype IgG1 variant 113F, introduced into anti-DR5 antibody IgG1-CONA-C49W, on the viability of adherent human BxPC-3 pancreatic cancer cells as determined in a 3-day viability assay (CellTiter-Glo).
Figure 16B:
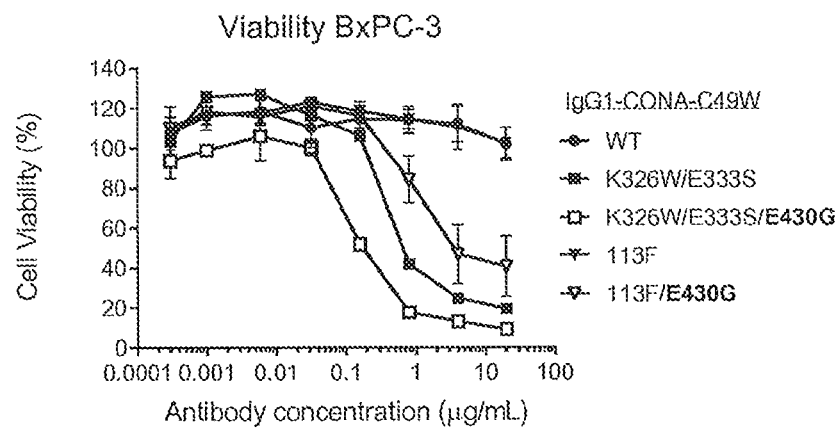

Example 17: Effect of Combining E430G with Other Fc Modifications on the Efficacy of Agonistic Anti-DR5 Antibodies A viability assay was performed to study the effect of combining Fc-Fc enhancing substitution E430G with C1q binding substitutions S267E/H268F/S324T or the IgG1/IgG3 chimeric isotype variant 113F on the agonistic activity of anti-DR5 antibody IgG1-CONA-C49W opsonized to DR5-positive BxPC-3 cells. The viability assay was performed essentially as described in Example 3. Briefly, 100 µL BxPC-3 single cell suspensions were seeded in culture medium (RPMI containing 10% heat-inactivated DBSI) in polystyrene 96-well flat-bottom plates (5,000 cells per well) and allowed to adhere overnight at 37° C. 25 µL purified C1q (2.5 µg/mL final concentration) and 25 µL antibody samples of a concentration dilution series (range 0.0003-20 µg/mL final concentrations in 5-folds dilutions) were added and incubated at 37° C. for 3 days. The viability of the cultured cells was determined in a CellTiter-Glo assay as described in Example 2. Luminescence was measured on an EnVision Multilabel Reader (PerkinElmer). Data with log-transformed concentration axes were analyzed using non-linear regression (sigmoidal dose-response with variable slope) and plotted using GraphPad Prism software. FIG. 16 shows that combining the E430G Fc-Fc enhancing substitution with the C1q binding-enhancing formats S267E/H268F/S324T (FIG. 16A) or IgG113F (FIG. 16B) resulted in the induction of agonist activity of anti-DR5 antibody IgG1-CONA-C49W on adherent human BXPC-3 pancreatic cancer cells. Combining the E430G substitution with the K326W/E333S C1q binding-enhancing mutations resulted in stronger DR5 agonistic activity by IgG1-CONA-C49W-K326W/E333S/E430G compared to IgG1-CONA-C49W-S267E/H268F/S324T/E430G and IgG113F-CONA-C49W-E430G.

Figure 17:
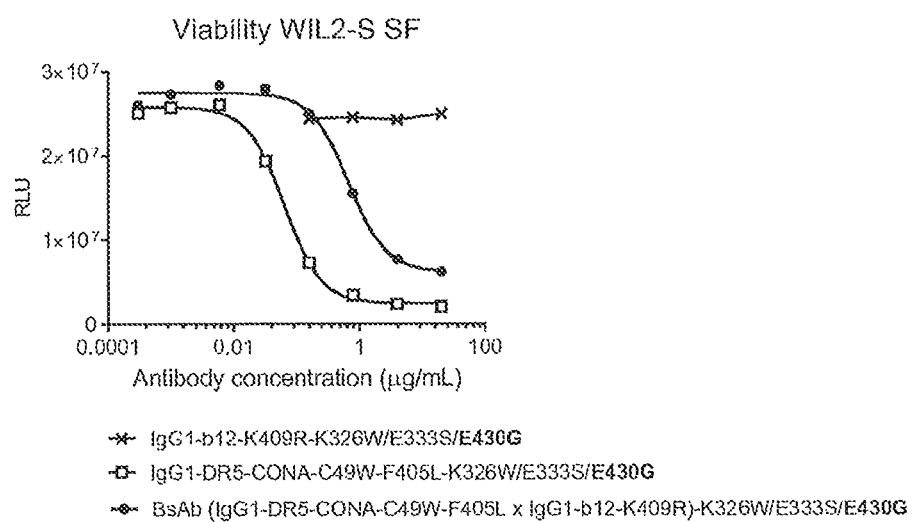
FIG. 17 shows the effect of a functionally monovalent anti-DR5 antibody with K326W/E333S/E430G mutations on the viability of WIL2-S SF suspension cells as determined in a 1-day viability assay (CellTiter-Glo). The functionally monovalent anti-DR5 antibody was generated as a bispecific antibody, by controlled Fab-arm exchange of IgG1-CONA-C49W-F405L-K326W/E333S/E430G (DR5-specific arm) and IgG1-b12-K409R-K326W/E333S/E430G (non-specific arm, directed against HIV protein gp120). RLU: relative luminescence units.

Example 18: Efficacy of Monovalent Anti-DR5 Antibody Containing the K326W/E333S/E430G Substitutions A viability assay was performed to study the effect on the agonist activity of monovalent anti-DR5 antibody containing the K326W/E333S/E430G substitutions opsonized to BxPC-3 pancreatic cancer cells. The monovalent DR5 antibody was generated by controlled Fab-arm exchange between IgG1-CONA-C49W-F405L-K326W/E333S/E430G and IgG1-b12-K409R-K326W/E333S/E430G as described in Example 1. The generated bispecific antibody, referred to as BsAb (IgG1-CONA-C49W-F405L×IgG1-b12-K409R)-K326W/E333S/E430G, contains one arm specific for DR5 and one non-specific arm against HIV glycoprotein gp120, resulting in monovalent DR5 binding on DR5-positive human cells. A 1-day viability assay was performed on WIL2-S SF cells, essentially as described in Example 8. Briefly, 100 µL WIL2-S SF cells in serum-free medium were pipetted in 96-well plates (50.000 cells/well). 25 µL purified C1q (2.5 µg/mL final concentration) and 25 µL antibody samples of a concentration dilution series (range 0.0003-20 µg/mL final concentrations in 5-folds dilutions) were added to the cells and incubated at 37° C. for 1 day. Cell viability was determined using the CellTiter-Glo assay as described in Example 2. Luminescence was measured on an EnVision Multilabel Reader (PerkinElmer). Data with log-transformed concentration axes were analyzed using non-linear regression (sigmoidal dose-response with variable slope) and plotted using GraphPad Prism software. FIG. 17 shows that that in the presence of the K326W/E333S/E430G mutations, the monovalent variant of IgG1-CONA-C49W could still induce killing of WIL2-S SF cells.

Figure 18A:
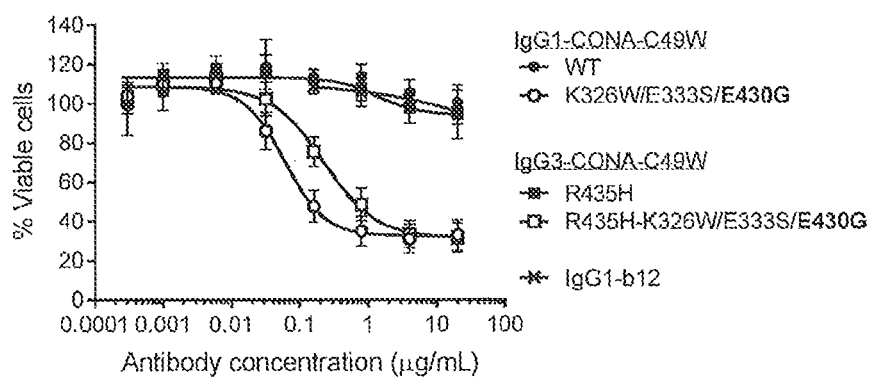
FIGS. 18A-18D show the effect of introducing the K326W/E333S/E430G substitutions on the agonist activity of IgG1 and IgG3 isotype variants of an anti-DR5 antibody (IgG1-CONA-C49W and IgG3-CONA-C49W-R345H) as determined in a 1-day viability assay on WIL2-S SF cells (FIG. 18A) and 3-days viability assays on BxPC-3 (FIG. 18B), HPAF-II (FIG. 18C) and HT-29 cells (FIG. 18D). Viability was determined using the CellTiter-Glo kit.
Figure 18B:
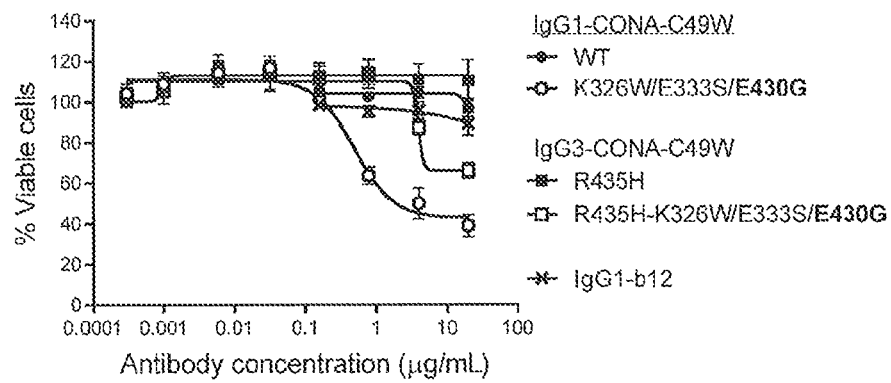
Figure 18C:
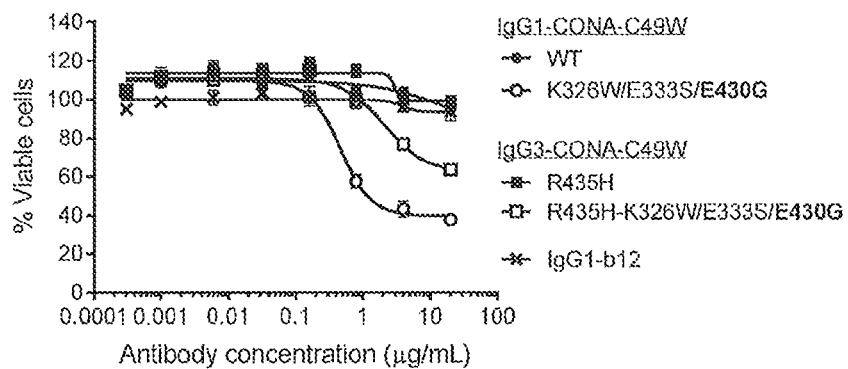
Figure 18D:
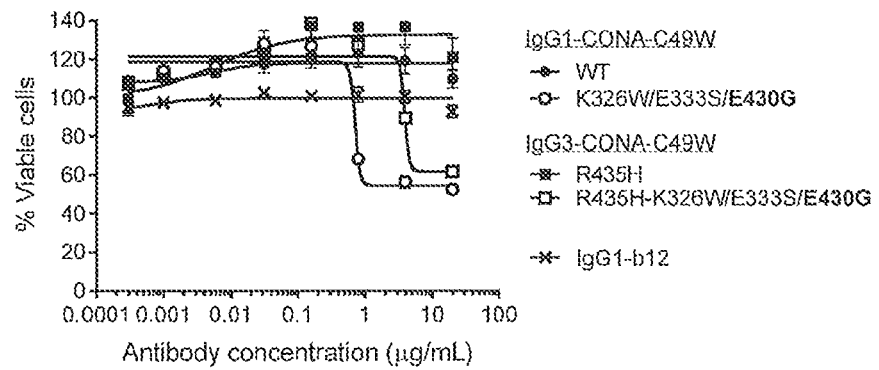

Example 19: Effect of Combining E430G and K326W/E333S on the Agonist Activity of Different Isotype Variants of an Anti-DR5 Antibody To test if the introduction of the K326W/E333S/E430G substitutions can induce agonist activity of anti-DR5 antibodies in a non-IgG1 antibody backbone, IgG3 isotypic variants of IgG1-CONA-C49W with constant domains of human IgG3 were generated by methods known in the art, yielding IgG3-CONA-C49W. The IgG3 backbone also contained the R345H mutation for enhanced FcRn binding (Stapleton et al., 2011 Nat Commun). The K326W/E333S/E430G substitutions were introduced in both the IgG1 and IgG3 isotype variants and agonist activity of the different antibodies was tested in in vitro viability assays using different cell lines: human WIL2-S SF B lymphoblast cells, BxPC-3 and HPAF-II (ATCC, CRL-1997) pancreatic cancer cells and HT-29 (ATCC, HTB-38) colon cancer cells. The viability assays using WIL2-S SF suspension cells were performed, essentially as described in Example 8. Briefly, 100 µL WIL2-S SF cells were pipetted in serum-free medium in 96-well plates (50.000 cells/well). Next, 25 µL purified C1q samples (2.5 µg/mL final concentration) and 25 µL antibody samples of a concentration dilution series (range 0.0003-20 µg/mL final concentrations in 5-folds dilutions) were added to the cells and incubated at 37° C. for 1 day. For the adherent cells BxPC-3, HPAF-II and HT-29, a 3-day viability assay was performed, essentially as described in Example 3. Briefly, 100 µL cells in culture medium (RPMI 1640 with 25 mM Hepes and L-Glutamine+10% heat inactivated DBSI+50 U/mL Pen/Strep) were pipetted in 96-well plates (5.000 cells/well) and allowed to adhere by overnight incubation at 37° C. Next, 25 µL purified C1q samples (2.5 µg/mL final concentration) and 25 µL antibody samples of a concentration dilution series (range 0.0003-20 µg/mL final concentrations in 5-folds dilutions) were added to the cells and incubated at 37° C. for 3 days. Cell viability was determined using the CellTiter-Glo assay as described in Example 2. Luminescence was measured on an EnVision Multilabel Reader (PerkinElmer). Data with log-transformed concentration axes were analyzed using non-linear regression (sigmoidal dose-response with variable slope) and plotted using GraphPad Prism software. FIG. 18 shows that introduction of the K326W/E333S/E430G substitutions in the IgG3 variant of the anti-DR5 antibody (IgG3-DR5-CONA-C49W-R435H-K326W/E333S/E430G) resulted in the induction of agonist activity in all tested cell lines: WIL2S-SF (FIG. 18A), BxPC-3 (FIG. 18B), HPAF-II (FIG. 18C) and HT29 (FIG. 18D). The IgG1 variant IgG1-DR5-CONA-C49W-K326W/E333S/E430G was more potent than the IgG3 variant IgG3-DR5-CONA-C49W-R435H-K326W/E333S/E430G in all tested cell lines.

Figure 19:
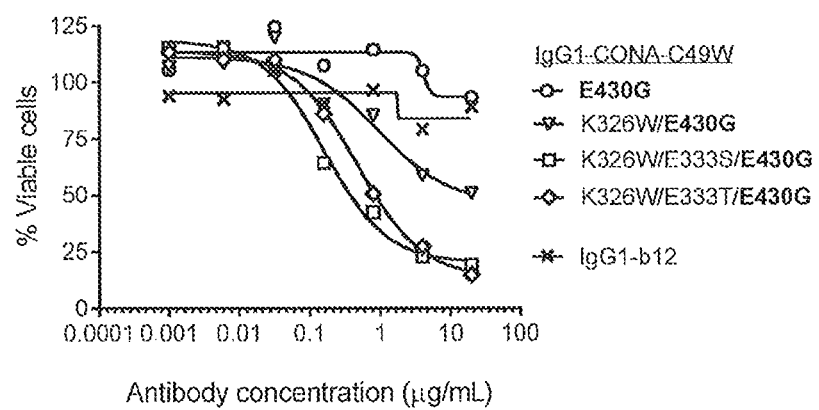
FIG. 19 shows the effect of introducing both the E430G hexamerization-enhancing mutation and the C1q binding-enhancing mutations K326W/E333T or K326W/E333S in anti-DR5 antibody IgG1-CONA-C49W on WIL2-S suspension cells as determined in a 24-hours viability assay (CellTiterGlo).

Example 20: Effect of Combining E430G with K326W/E333T on the Agonist Activity of Anti-DR5 Antibodies A viability assay was performed to evaluate the effect of the combination of Fc-Fc-enhancing substitution E430G and K326W/E333T compared to K326W/E333S on the agonistic activity of anti-DR5 antibody IgG1-CONA-C49W on DR5-positive WIL2-S cells. An in vitro viability assay was performed, essentially as described in Example 8. Briefly, 100 µL WIL2-S cells were pipetted in culture medium (RPMI 1640 with 25 mM Hepes and L-Glutamine (Lonza, Cat No BE12-115F)+10% heat inactivated DBSI+1 mM Sodium Pyruvate (Lonza, Cat No. 6E13-115E)+50 U/mL Pen/Strep) in 96-Wells plates (50.000 cells/well). Next, 50 µL antibody samples of a concentration dilution series (range 0.001-20 µg/mL final concentrations in 5-folds dilutions) and 10 µL purified C1q samples (2.5 µg/mL final concentration) were added to the cells and incubated at 37° C. for 1 day. Cell viability was determined using the cellTiterGlo assay as described in Example 2. Luminescence was measured on an EnVision Multilabel Reader (PerkinElmer). Data were analyzed and plotted using non-linear regression (sigmoidal dose-response with variable slope) using GraphPad Prism software. FIG. 19 shows that introduction of K326W/E333T/E430G in IgG1-CONA-C49W resulted in induction of DR5 agonist activity of the single agent with a similar killing efficacy in an in vitro viability assay on WIL2-S cells as by introduction of K326W/E333S/E430G.

Figure 20A:
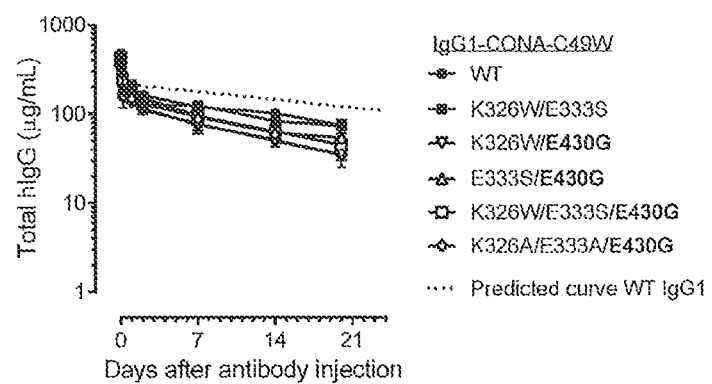
FIGS. 20A and 20B show the clearance rate of 450 μg i.v. administered antibody in SCID mice.
Figure 20B:
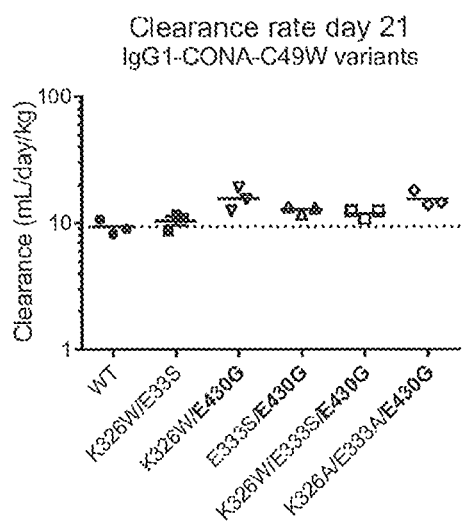

Example 21: Pharmacokinetic (PK) Analysis of IgG1-CONA-C49W Antibody Variants Containing Fc-Fc-Enhancing Mutation(s) and/or Fc Mutations that Affect C1q Binding The effect of E430G Fc-Fc-enhancing mutations and C1q binding-enhancing mutations on the clearance rate of IgG1-CONA-C49W was studied in a PK experiment in SCID mice. All tested antibody variants are listed in Table 6. The animal experiments were performed in compliance with the Dutch animal protection law (WoD) translated from the directives (2010/63/EU) and if applicable, the Code of Practice "animal experiments for cancer research" (Inspection V&W, Zutphen, The Netherlands, 1999) and were approved by the Ethical committee of Utrecht. The animals were housed and handled in accordance with good animal practice as defined by FELASA, in an AAALAC and ISO 9001:2000 accredited animal facility (GDL). 11-12 weeks old female SCID mice (C.B-17/IcrHan®Hsd-Prkdc$^{scid}$; Envigo SCID mice) were injected intravenously with 450 µg antibody (22.5 mg/kg) in a 200 µL injection volume (3 mice per group). 50 µL blood samples were collected from the saphenous vein at 10 minutes, 4 hours, 1 day, 2 days, 7 days, 14 days and 20 days after antibody administration. Blood was collected into heparin-containing vials and centrifuged for 10 minutes at 14,000 g. 20 µL plasma samples were diluted with 380 µL PBS (1:20) and stored at −20° C. until determination of antibody concentrations. Total human IgG concentrations were determined using a sandwich ELISA. Mouse anti-human IgG-kappa mAb clone MH16 (CLB Sanquin, Cat No. M1268) was used as capturing antibody and coated in 100 µL overnight at 4° C. to 96-well Microlon ELISA plates (Greiner, Germany) at a concentration of 2 µg/mL in PBS. Plates were blocked by incubating on a plate shaker for 1h at RT with PBS supplemented with 0.2% bovine serum albumin (BSA). After washing, 100 µL of the diluted plasma samples were added and incubated on a plate shaker for 1h at RT. Plates were washed three times with 300 µL PBST (PBS supplemented with 0.05% Tween 20) and subsequently incubated on a plate shaker for 1h at RT with 100 µL peroxidase-labeled goat anti-human IgG immunoglobulin (#109-035-098, Jackson, West Grace, PA; 1:10.000 in PBST supplemented with 0.2% BSA). Plates were washed again three times with 300 µL PBST before incubation for 15 minutes at RT with 100 µL substrate 2,2'-azino-bis (3-ethylbenzthiazoline-6-sulfonic acid) [ABTS; Roche, Cat No. 11112 422001; 1 tablet in 50 mL ABTS buffer (Roche, Cat No. 11112 597001)] protected from light. The reaction was stopped by adding 100 µL 2% oxalic acid and incubation for 10 minutes at RT. Absorbance was measured in a microplate reader (Biotek, Winooski, VT) at 405 nm. Concentration was calculated by using the injected material as a reference curve. As a plate control human myeloma protein containing IgG (The binding site, Cat No. BP078) was included. Human IgG concentrations (in µg/mL) were plotted (FIG. 20A) and Area Under the Curve (AUC) was calculated using Graphpad prism. Clearance rates until the last day of blood sampling (day 21) was determined by the formula D*1.000/AUC, in which D is the injection dose of 22.5 mg/kg (FIG. 20B). All tested IgG1-CONA-C-49W variants containing the E430G Fc-Fc-enhancing mutation and/or C1q binding-enhancing mutations showed a comparable clearance rate as WT IgG1 (FIGS. 20A,B). In conclusion, introduction of C1q binding-enhancing mutations such as K326W/E333S or K326A/E333A do not significantly affect the clearance rate of an IgG1 antibody containing an E430G Fc-Fc-enhancing mutation, such as in IgG1-CONA-C49W-K326W/E333S/E430G and IgG1-CONA-C49W-K326A/E333A/E430G.

TABLE 6

IqG1-CONA-C49W antibody variants tested in PK analysis in scid mice

| Antibody variant | Fc-Fc-enhancing mutation | C1q binding-enhancing mutation |
|---|---|---|
| IgG1-CONA-C49W | — | — |
| IgG1-CONA-C49W-K326W/E333S | — | K326W/E333S |
| IgG1-CONA-C49W-K326W/E430G | E430G | K326W |
| IgG1-CONA-C49W-E333S/E430G | E430G | E333S |
| IgG1-CONA-C49W-K326W/E333S/E430G | E430G | K326W/E333S |
| IgG1-CONA-C49W-K326A/E333A/E430G | E430G | K326A/E333A |

Example 22: Effect of Combining the E430G Fc-Fc-Enhancing Mutation and C1q Binding-Enhancing Mutations K326A/E333A or K326W/E333S on FcRn Binding of an IgG1 Antibody The neonatal Fc receptor (FcRn) is responsible for the long plasma half-life of IgG by protecting IgG from degradation. After internalization of the antibody, FcRn binds to antibody Fc regions in endosomes, where the interaction is stable in the mildly acidic environment (pH 6.0). Upon recycling to the plasma membrane, where the environment is neutral (pH 7.4), the interaction is lost and the antibody is released back into the circulation. This influences the plasma half-life of IgG.

Figure 21A:
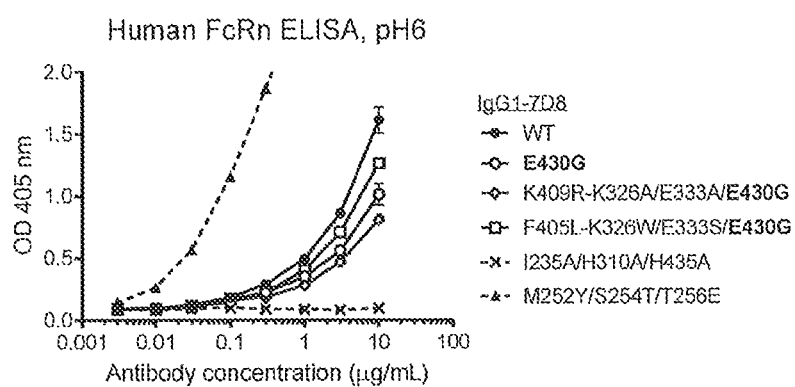
FIGS. 21A and 21B show the effect of the E430G Fc-Fc-enhancing mutation in combination with the C1q binding-enhancing mutations (K326A/E333A or K326W/E333S) on the binding of IgG1-7D8 antibody variants to human FcRn, as determined by an ELISA with coated FcRnECDHis-B2M-BIO at pH 6.0 and 7.4. IgG1-7D8-I235A/H310A/H435A was used as a negative control for FcRn binding at pH 6.0 (FcRn knockout); IgG1-7D8-M252Y/S254T/T256E was used as a control for enhanced FcRn binding at pH 7.4.
Figure 21B:
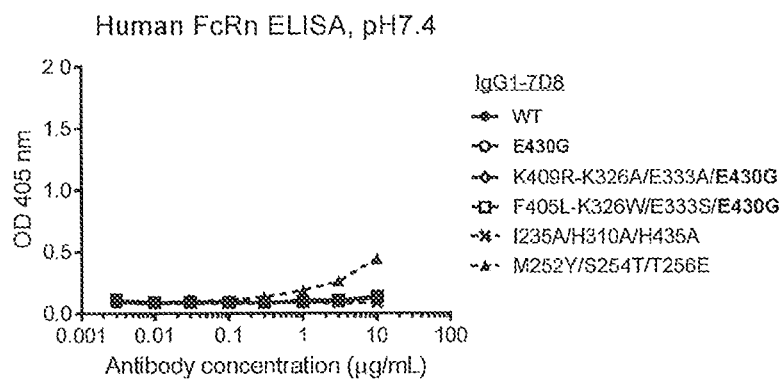

An FcRn binding ELISA was performed to evaluate the effect of introducing a combination of an Fc-Fc-enhancing mutation and C1q binding-enhancing mutations K326A/E333A or K326W/E333S on binding of human FcRn to the IgG1-7D8 antibody variants. IgG1-7D8-I235A/H310A/H435A was used as a negative control (FcRn knockout; Shields et al., J. Biol. Chem. 2001; 276:6591) for FcRn binding; IgG1-7D8-M252Y/S254T/T256E was used as a control for enhanced FcRn binding (Dall'Acqua et al., J Biol Chem. 2006 Aug. 18; 281(33):23514-24). All incubations were done at room temperature. 96 streptawell plates (Roche, Cat No. 1734776001) were coated for 1 hour with 5 µg/mL (100 µL/well) recombinantly produced biotinylated extracellular domain of human FcRn (FcRnECDHis-B2M-BIO, i.e. the extracellular domain of human FcRn with a C-terminal His and BAP tag as dimer with beta2microglobulin), diluted in PBST plus 0.2% BSA. Plates were washed three times with PBST. Serially diluted antibody samples (Range 0.003-10 µg/mL final concentrations in 3-fold dilutions in PBST/0.2% BSA, pH 6.0) were added and incubated for 1 hour. Plates were washed with PBST/0.2% BSA, pH 6.0. Horseradish Peroxidase (HRP)-conjugated polyclonal Goat-anti-Human IgG (1:10,000; Jackson ImmunoResearch, Cat No. 109-035-097) diluted in PBST/0.2% BSA, pH 6.0 or 7.4 was added, and plates were incubated for 1 hour. After washing, 100 µL ABTS (1 mg/mL) was added as substrate and plates were incubated for 30 minutes protected from light. The reaction was stopped using 100 µL 2% oxalic acid and absorbance was measured at 405 nm using an ELx808 Absorbance Microplate Reader (BioTek). Log-transformed data were analyzed by fitting sigmoidal dose-response curves with variable slope using GraphPad Prism software. The negative control (IgG1-7D8-I235A/H310A/H435A) showed complete loss of human FcRn binding at pH 6.0 (FIG. 21A), whereas the positive control (IgG1-7D8-M252Y/S254T/T256E) showed enhanced binding to human FcRn compared to WT IgG1-7D8 at pH 6.0 and loss of binding at pH 7.4 (FIG. 21B). All tested IgG1-7D8 variants with an Fc-Fc-enhancing mutation with or without C1q binding-enhancing mutations showed efficient binding to human FcRn at pH 6.0, and loss of binding at pH 7.4. However, compared to WT IgG1-7D8, introduction of the Fc-Fc-enhancing mutation E430G alone resulted in a slightly decreased binding to human FcRn at pH 6.0, which was a little bit further decreased when combined with the C1q binding-enhancing mutations K326A/E333A or K326W/E333S mutations.

Figure 22A:
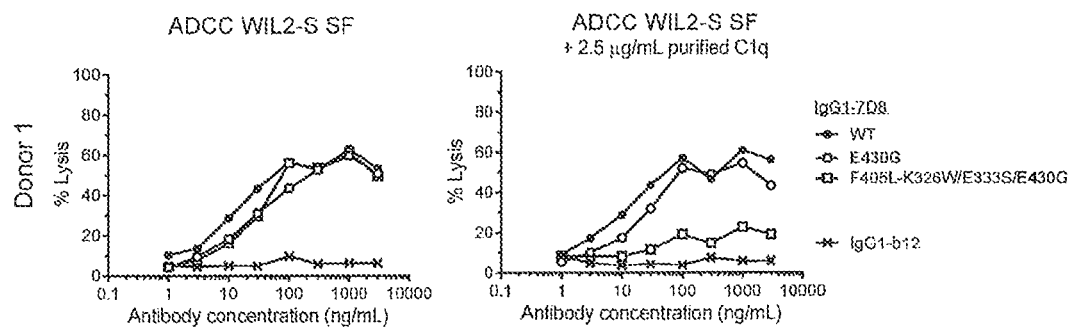
FIGS. 22A-22C show a chromium-release ADCC assay using WIL2-S SF as target cells and human PBMCs (3 donors) as effector cells (E:T ratio 100:1) in serum-free medium with and without the addition of purified human C1q. In the absence and presence of C1q, chromium-labeled WIL2-S SF cells were incubated with antibody concentration series to compare ADCC activity of IgG1-7D8-F405L-K326W/E333S/E430G with that of IgG1-7D8-E430G and WT IgG1-7D8. Non-specific antibody IgG1-b12 was used as negative control.
Figure 22B:
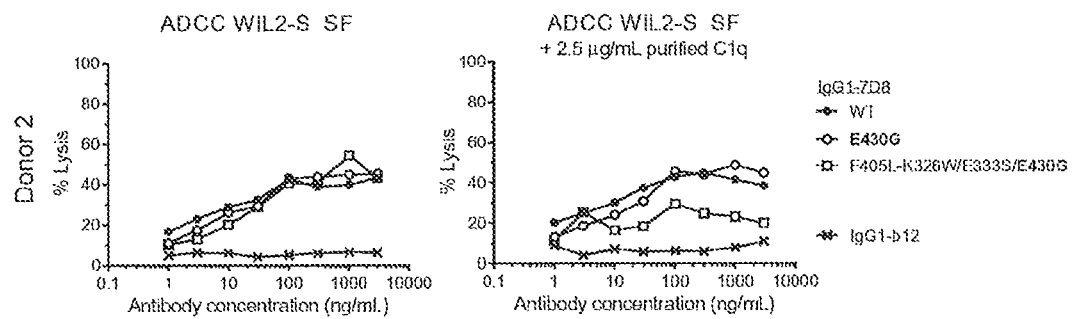
Figure 22C:
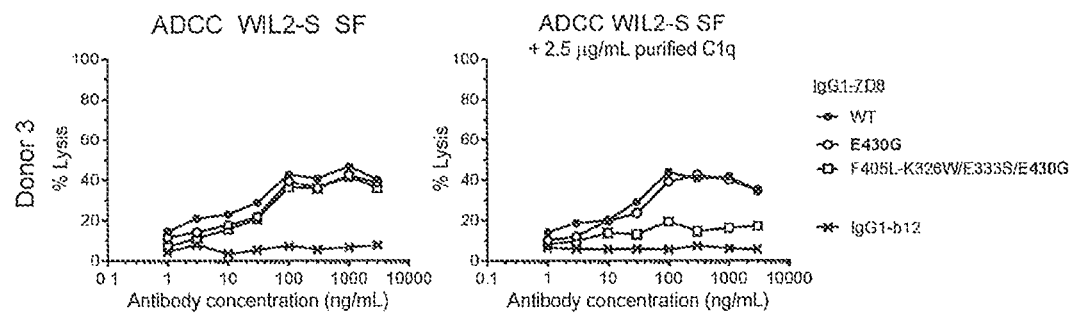

Example 23: Effect of C1q on ADCC Activity by Anti-CD20 IgG1-7D8 Antibody Variants Containing the K326W/E333S/E430G Substitutions The effect of C1q on the ADCC activity of anti-CD20 IgG1-7D8 antibody variants containing both the E430G Fc-Fc-enhancing mutation and the C1q binding-enhancing substitutions K326W/E333S was tested in a chromium-release assay using WIL2-S SF cells in serum-free medium. WIL2-S SF cells were harvested ($5\times10^6$ cells/mL), washed (twice in PBS, 1,200 rpm, 5 min) and collected in 1 mL serum-free medium (HyQ ADCF-Mab medium supplemented with 10% sodium pyruvate). 200 µCi $^{51}$Cr (Chromium-51; Amersham Biosciences Europe GmbH) was added and incubated in a shaking water bath for 1 hour at 37° C. After washing of the cells (twice in PBS, 1,200 rpm, 5 min), the cells were resuspended in serum-free medium. The chromium-labeled cells were counted by trypan blue exclusion and diluted to a concentration of $1\times10^5$ cells/mL. Human peripheral blood mononuclear cells (PBMCs) were isolated from fresh buffy coats from healthy donors (Sanquin) using standard Ficoll density centrifugation according to the manufacturer's instructions (lymphocyte separation medium; Lonza). After resuspension of the PBMCs in serum-free medium, the PBMCs were counted by trypan blue exclusion and concentrated to $1\times10^7$ cells/mL. For the ADCC experiment, 50 µL chromium-labeled WIL2-S SF cells were pipetted in 96-Well plates (5,000 cells/well). 25 µL antibody samples from dilutions series (range 0.003-10 µg/mL final concentrations in 3-fold dilutions) and 25 µL purified human C1q (2.5 µg/mL final concentration) or medium were added and pre-incubated for 10 minutes at RT. Next, 50 µL PBMCs (500.000 cells/well) were added, resulting in an effector to target ratio of 100:1, and incubated for 4 hours at 37° C. Maximal cell lysis was determined by incubating 50 µL chromium-labeled WIL2-S SF cells (5,000 cells/well) with 100 µL 5% Triton-X100 (Sigma-Aldrich). Spontaneous lysis was determined by incubating chromium-labeled WIL2-S SF cells (5,000 cells/well) in 150 µL medium without antibody and effector cells. Antibody-independent cell lysis was determined by incubating chromium-labeled WIL2-S SF cells (5,000 cells/well) with PBMCs (500.000 cells/well) in a total volume of 150 µL in absence of antibody. The amount of cell lysis was determined using a scintillation counter. The cells were centrifuged (1,200 rpm; 3 min) and 25 µL supernatant was transferred to 96-wells white optiplates filled with 100 µL microscint-40 solution. The released $^{51}$Cr in the supernatants was counted using a scintillation counter. The measured counts per minute (cpm) were used to calculate the percentage of antibody-mediated lysis according to the following formula: (cpm sample–cpm antibody-independent lysis)/(cpm maximal lysis–cpm spontaneous lysis)× 100%. As negative controls, a non-specific IgG1-b12 antibody and an IgG1-7D8 variant with the L234A/L235A/P329G substitutions, which are known to eliminate complement binding and activation as well as FcγR binding and induction of ADCC (Lo et al. JBC 2017) were tested. As expected, no ADCC activity was observed for the non-specific antibody IgG1-b12, neither in the absence or presence of C1q (FIG. 22). For the IgG1-7D8-F405L-K326W/E333S/E430G antibody, adding 2.5 µg/mL purified human C1q resulted in inhibition of ADCC activity on WIL2-S SF cells in serum-free medium. In contrast, C1q did not affect the ADCC activity of WT IgG1-7D8 and IgG1-7D8-E430G.

Example 24: Effect of K326W/E333S/E430G on the Agonist Activity of the Anti-DR5 Antibodies IgG1-hDR5-01-G56T and IgG1-hDR5-05

The effect of introducing the combination of the Fc-Fc-enhancing mutation E430G and the C1q binding-enhancing mutations K326W/E333S on the agonist activity of anti-DR5 antibodies IgG1-hDR5-01-G56T and IgG1-hDR5-05 was tested in an in vitro viability assay using WIL2-S SF cells. A 1-day viability assay was performed, essentially as described in Example 8. Briefly, 100 µL cells in serum-free medium were pipetted in 96-Wells plates (50.000 cells/well). 25 µL antibody samples of a concentration dilution series (range 0.0003-20 µg/mL final concentrations in 5-folds dilutions) and 25 µL purified C1q (2.5 µg/mL final concentration) were added and incubated at 37° C. for 1 day. Cell viability was determined using the CellTiterGlo assay as described in Example 2. Luminescence was measured on an EnVision Multilabel Reader (PerkinElmer). Data were analyzed and plotted using non-linear regression (sigmoidal dose-response with variable slope) using GraphPad Prism software.

Figure 23:
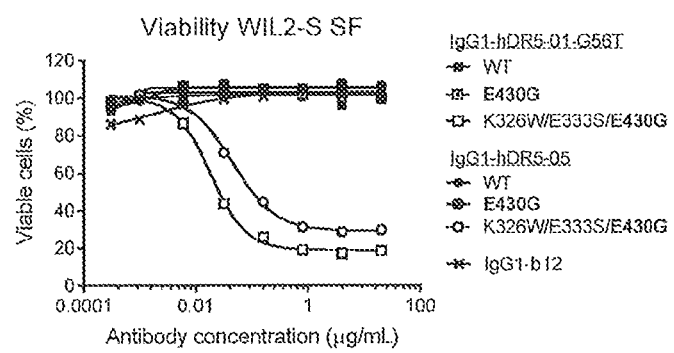
FIG. 23 shows the effect of K326W/E333S/E430G on the agonistic activity of the anti-DR5 antibodies IgG1-hDR5-01-G56T and IgG1-hDR5-05 on WIL2-S SF suspension cells as determined in a 24-hours viability assay (CellTiter-Glo).

Introduction of both the E430G Fc-Fc-enhancing and K326W/E333S C1q binding-enhancing mutations resulted in the induction of DR5 agonist activity for both tested antibodies IgG1-hDR5-01-G56T and IgG1-hDR5-05, whereas these antibodies did not induce cell kill when only the E430G Fc-Fc-enhancing mutation was introduced (FIG. 23).

Figure 24:
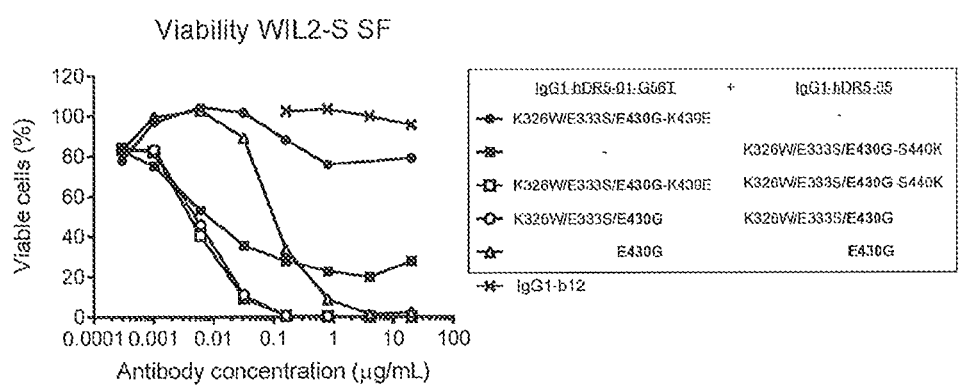
FIG. 24 shows the effect of the complementary Fc mutation pair K439E; S440K on the agonistic activity of the anti-DR5 dual epitope targeting antibody combination IgG1-hDR5-01-G56T-K326W/E333S/E430G+IgG1-hDR5-05-K326W/E333S/E430G on WIL2-S SF suspension cells as determined in a 24-hours viability assay (CellTiterGlo).

Example 25: Compatibility of the K326W/E333S/E430G with the Complementary Fc Mutation Pair K439E; S440K in Agonist an Anti-DR5 Antibody Combination Compatibility of the K326W/E333S/E430G mutations with other Fc-engineering mutations, such as the complementary Fc mutation pair K439E; S440K that can control intermolecular Fc-Fc interactions between different cell-surface-target-bound antibodies, was tested using the anti-DR5 agonist antibody combination IgG1-hDR5-01-K326W/E333S/E430G+IgG1-hDR5-05-K326W/E333S/E430G in an in vitro viability assay on WIL2-S SF cells. A 1-day viability assay was performed, essentially as described in Example 8. Briefly, 100 µL cells in serum-free medium were pipetted in 96-Wells plates (50.000 cells/well). 25 µL antibody samples of a concentration dilution series (range 0.0003-20 µg/mL final concentrations in 5-folds dilutions) and 25 µL purified C1q (2.5 µg/mL final concentration) were added and incubated at 37° C. for 1 day. Cell viability was determined using the CellTiterGlo assay as described in Example 2. Luminescence was measured on an EnVision Multilabel Reader (PerkinElmer). Data were analyzed and plotted using non-linear regression (sigmoidal dose-response with variable slope) using GraphPad Prism software. FIG. 24 shows that the single antibody IgG1-hDR5-01-K326W/E333S/E430G-K439E, containing the Fc-Fc-inhibiting mutation K439E, hardly induced any cell killing. IgG1-hDR5-05-K326W/E333S/E430G-S440K, containing the Fc-Fc-inhibiting mutation S440K, induced some cell kill, although maximal kill was not 100%. In contrast, the combination of both IgG1-hDR5-01-K326W/E333S/E430G-K439E+IgG1-hDR5-05-K326W/E333S/E430G-S440K, combining the two complementary Fc-Fc controlling mutations K439E and S440K showed efficient cell kill, that was similar as for the combination without the complementary Fc-Fc controlling mutations K439E and S440K. Cell kill by the antibody combinations containing the K326W/E333S/E430G mutations (with and without the complementary mutations K439E; S440K) was much more efficient than the combination of antibodies containing only the E430G Fc-Fc-enhancing mutation (IgG1-hDR5-01-K326W/E333S/E430G-K439E+IgG1-hDR5-05-K326W/E333S/E430G-S440K).

Figure 25:
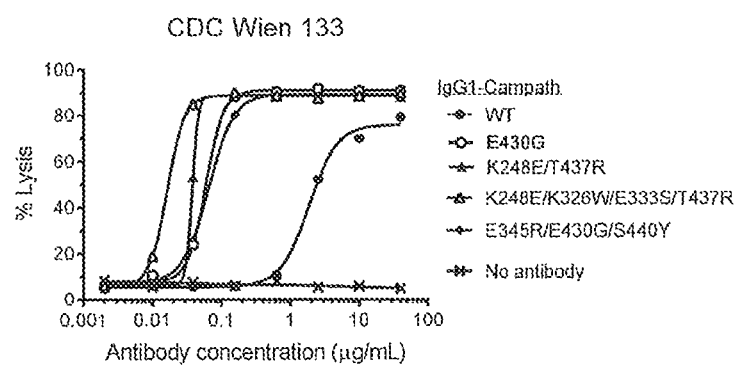
FIG. 25 shows the results of a CDC assay on Wien 133 cells testing IgG1-Campath antibody variants with the hexamerization-enhancing mutations E430G or K248E/T437R, and the hexamerization-enhancing mutations K248E/T437R combined with the C1q binding-enhancing mutations K326W/E333S. Wien 133 cells were incubated with concentration series of the antibody variants in the presence of 20% pooled normal human serum (NHS).

Example 26: Effect of Combining the C1q Binding-Enhancing Substitutions K326W/E333S with K248E/T437R on CDC Efficacy of an Anti-CD52 Antibody The effect of combining the K326W/E333S C1q binding-enhancing mutations with the K248E/T437R substitutions that facilitate antibody multimerization on the cell surface (Zhang et al., 2017 MAbs (9)7:1129-42) on CDC efficacy was tested using the anti-CD52 IgG1-Campath variants (based on alemtuzumab) on CD52-positive Wien 133 B cell lymphoma cells. Wien 133 cells (kindly provided by Dr. Geoff Hale, BioAnaLab Limited, Oxford, UK) were harvested and resuspended in medium [RPMI (Lonza, Cat No. BE12-115F) with 0.2% bovine serum albumin (BSA; Roche Cat No. 10735086001)]. 40 µL cells were pipetted in round-bottom 96-Well plates ($0.1 \times 10^6$ cells/well). 40 µL serial diluted antibody samples (range 0.002-40 µg/mL final concentrations in 4-fold dilutions) were added and incubated for 15 minutes at RT while shaking. Next, 20 µL NHS (20% final concentration) was added as a source of human complement and incubated for 45 minutes at 37° C. The reaction was stopped by placing the samples on ice. Cooled cells were pelleted and resuspended in 30 µL 2 µg/mL propidium iodide (PI; Sigma Aldrich). The samples were analyzed by flow cytometry on an Intellicyt iQue Screener PLUS and the percentage lysis was determined according to the following formula: % lysis=(number of PI-positive cells/total number of cells)×100%. FIG. 25 shows that introduction of the hexamerization-enhancing single mutation E430G or the multimerization-enhancing double mutation K248E/T437R in WT IgG1-Campath resulted in increased CDC efficacy on Wien 133 cells. CDC efficacy was further enhanced by combining the K248E/T437R mutations that facilitate multimerization on the cell surface and the K326W/E333S mutations that enhance C1q binding in IgG1-Campath-K248E/K326W/E333S/T437R.

Figure 26:
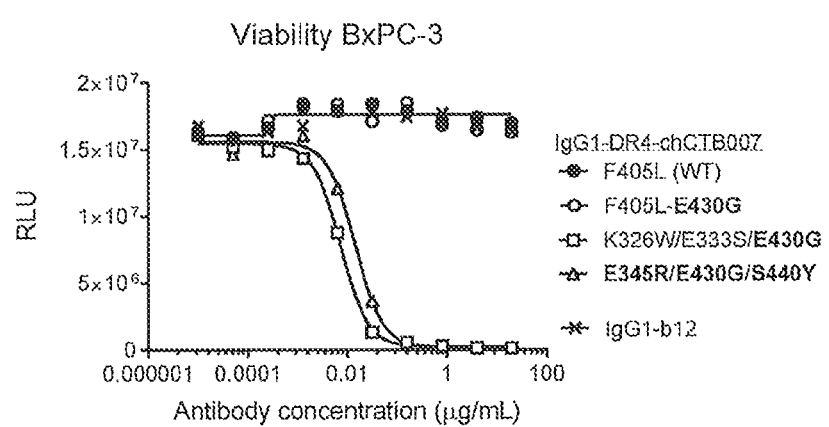
FIG. 26 shows the effect of combining the hexamerization-enhancing mutation E430G and the C1q binding-enhancing mutations K326W/E333S on the efficacy of anti-DR4 antibody IgG1-DR4-chCTB007 on adherent human BxPC-3 pancreatic cancer cells as determined in a 3-day viability assay (CellTiter-Glo).

Example 27: Effect of Combining E430G and K326W/E333S on the Efficacy of Agonistic Anti-DR4 Antibodies in the Presence of C1q A viability assay was performed to study the effect of the combination of the hexamerization-enhancing mutation E430G and K326W/E333S on the agonistic activity of anti-DR4 antibody chCTB007 on DR4-positive BxPC-3 cells. The viability was performed, essentially as described in Example 2. Briefly, 100 µL BxPC-3 single cell suspensions were seeded in culture medium (RPMI containing 10% heat-inactivated DBSI) in polystyrene 96-well flat-bottom plates (5,000 cells per well) and allowed to adhere overnight at 37° C. 25 µL purified C1q samples (2.5 µg/mL final concentration) and 25 µL antibody samples of a concentration dilution series (range 0.00001-20 µg/mL final concentrations in 5-folds dilutions) were added and incubated at 37° C. for 3 days. The viability of the cultured cells was determined in a CellTiter-Glo luminescent cell viability assay as described in Example 2. Luminescence was measured on an EnVision Multilabel Reader (PerkinElmer) and data were analyzed and plotted using non-linear regression (sigmoidal dose-response with variable slope) using GraphPad Prism software. FIG. 26 shows that combining the hexamerization-enhancing mutation E430G and the two mutations K326W/E333S resulted in induction of strong killing efficacy for the anti-DR4 antibody IgG1-DR4-chCTB007 similar as the triple mutant E345R/E430G/S440Y when tested as single agents in an in vitro viability assay on adherent human BxPC-3 pancreas cancer cells in the presence of heat inactivated fetal bovine serum supplemented with 2.5 µg/mL purified C1q. In contrast, these antibodies did not show efficient killing on these pre-adhered BxPC-3 cells when tested as wild type antibody IgG1-DR4-chCTB007 or when only mutation E430G was present. These data show that the K326W/E333S/E430G mutations induced strong agonistic activity for anti-DR4 antibodies on adherent BxPC-3 cells supplemented with C1q.

Figure 27A:
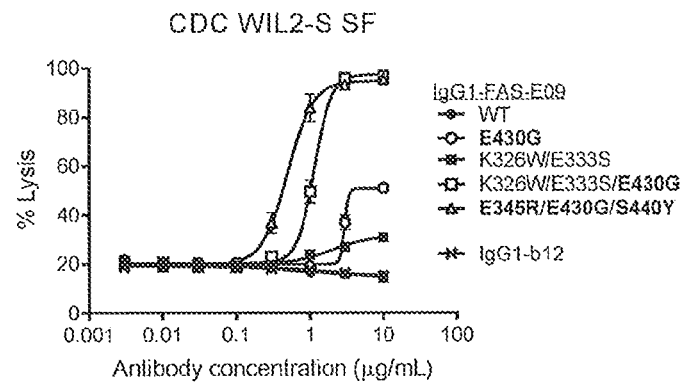
FIGS. 27A-27C show a CDC assay using WIL2S SF human B lymphocytes with variants of anti-FAS antibodies IgG1-FAS-E09 (FIG. 27A), IgG1-CD95-AP01 (FIG. 27B) and IgG1-CD95-HFE7A (FIG. 27C) in the presence of 20% normal human serum. WIL2-S SF cells were incubated for 45 minutes with concentration series of the antibody variants in the presence of 20% pooled normal human serum (NHS). IgG1-b12 was used as a non-binding control antibody.
Figure 27B:
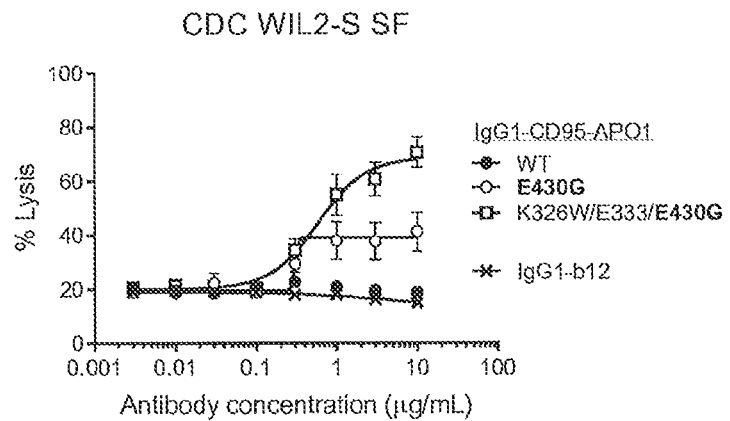
Figure 27C:
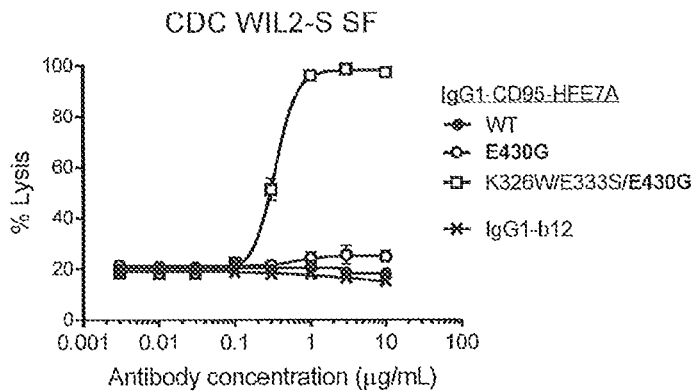

Example 28: Introduction of Hexamerization-Enhancing E430G Mutation Combined with C1q Binding-Enhancing Mutations K326W/E333S Improve the Efficacy of Complement Dependent Cytotoxicity (CDC) and Cell Death Induction by FAS Antibodies The FAS receptor is a death receptor on the surface of cells that leads to programmed cell death (apoptosis) by crosslinking of the receptor by Fas ligand (Wajant et al., 2002 Science 296 (5573): 1635-6). FAS is also known as apoptosis antigen 1 (APO-1 or APT), cluster of differentiation 95 (CD95) or tumor necrosis factor receptor superfamily member 6 (TNFRSF6). CDC by anti-FAS antibodies containing the K326W/E333S/E430G triple mutation was analyzed in an in vitro CDC assay on FAS-positive WIL2-S B-lymphocytes. The introducing hexamerization-enhancing mutation E430G in combination with C1q binding-enhancing mutations K326W E333S in different FAS antibodies IgG1-FAS-E09, IgG1-CD95-APO1 and IgG1-CD95-HFE7A was studied in a CDC assay using WIL2-S SF cells essentially as described in Example 26. Briefly, 30 µL WIL2-S SF cells in RPMI-1640 medium ($3.33 \times 10^6$ cells/mL) were pre-incubated in round-bottom 96-well plates ($0.1 \times 10^6$ cells/well) with 50 µL antibody concentration series (0.003-10.0 µg/mL final concentrations in 3-fold dilutions) for 15 min on a shaker at RT. Next, 20 µL normal human serum was added as a source of complement (20% final concentration) and incubated in a 37° C. incubator for 45 min. The reaction was stopped by putting the plates on ice. Cell lysis was determined by propidium iodide staining. The samples were analyzed by flow cytometry using an iQue Screener. Data with log-transformed concentration axes were analyzed and plotted using non-linear regression (sigmoidal dose-response with variable slope) using GraphPad Prism software. All three wild type anti-FAS antibodies IgG1-FAS-E09 (FIG. 27A), IgG1-CD95-APO1 (FIG. 27B) and IgG1-CD95-HFE7A (FIG. 27C) induced no CDC similar to the negative control antibody IgG1-b12. IgG1-FAS-E09 with Fc-Fc-enhancing mutation (E430G) or C1q binding-enhancing mutations (K326W/E333S) induce CDC. Combining E430G with K326W/E333S in IgG1-FAS-E09 resulted in maximal CDC, similar as IgG1-FAS-E09-E345R/E430G/S440Y. Similar pattern was seen with IgG1-CD95-APO1 in which IgG1-CD95-APO1-E430G induces CDC and IgG1-FAS-E09-K326W/E333S/E430G can further potentiate the CDC. For Antibody IgG1-CD95-HFE7A addition of mutation E430G had no effect on CDC, however IgG1-CD95-HFE7A with the triple mutations K326W/E333S/E430G completely rescued CDC to maximal lysis.

Figure 28A:
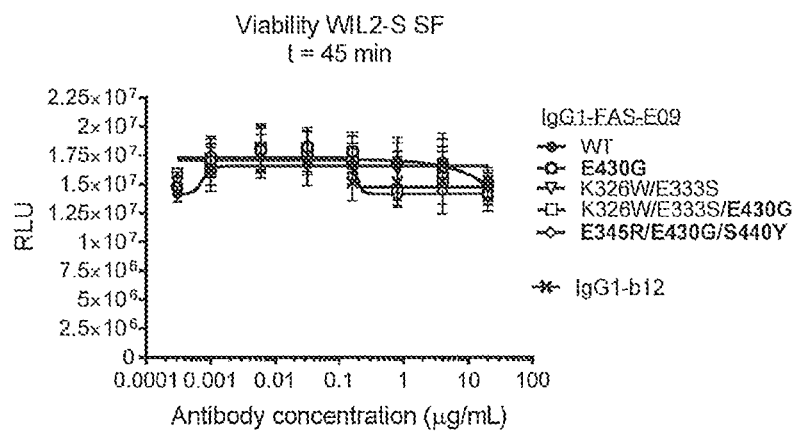
FIGS. 28A-28C show a 45-minute viability assay (Cell-Titer-Glo) using WIL2-S SF cells incubated with variants of anti-FAS antibodies IgG1-FAS-E09 (FIG. 28A), IgG1-CD95-AP01 (FIG. 28B) and IgG1-CD95-HFE7A (FIG. 28C) in serum-free medium without C1q.
Figure 28B:
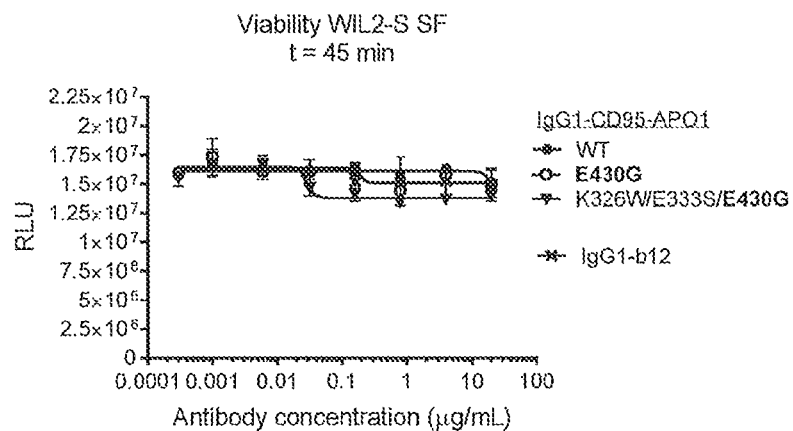
Figure 28C:
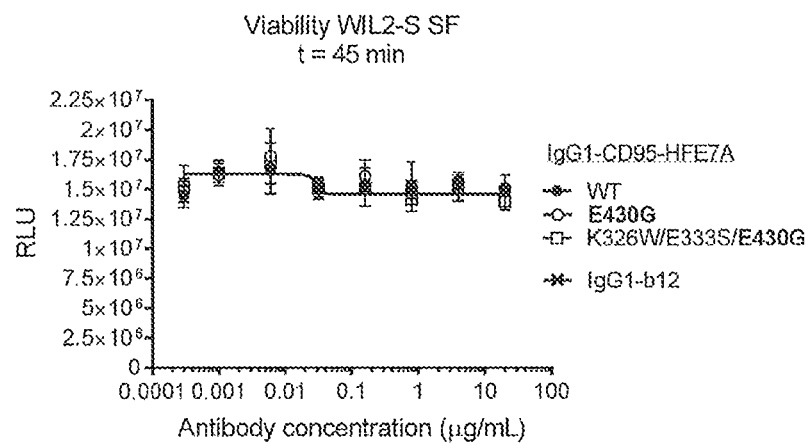

To confirm that the cell kill observed in the CDC assay described above was due to complement-mediated lysis, a viability assay was performed using WIL2-S SF in serum-free medium to which purified C1q (Quidel) was added as crosslinker. The viability assay was performed essentially as described in Example 8. Briefly, 100 µL WIL2-S SF cells were pipetted in serum-free medium in 96-well plates (50.000 cells/well). Next, 50 µL antibody samples of a concentration dilution series (range 0.0003-20 µg/mL final concentrations in 5-folds dilutions) and 10 µL purified C1q (2.5 µg/mL final concentration) were added to the cells and incubated at 37° C. for 45 minutes or 24 hours. The viability of the cultured cells was determined using the CellTiterGlo assay as described in Example 2. Luminescence was measured on an EnVision Multilabel Reader (PerkinElmer). Data with log-transformed concentration axes were analyzed and plotted using non-linear regression (sigmoidal dose-response with variable slope) using GraphPad Prism software. FIG. 28 shows the RLU (raw data) of the cells after 45 min incubation with the antibodies in presence of 2.5 µg/mL C1q. None of the antibodies affected the viability of the cells after this short incubation period.

Figure 29A:
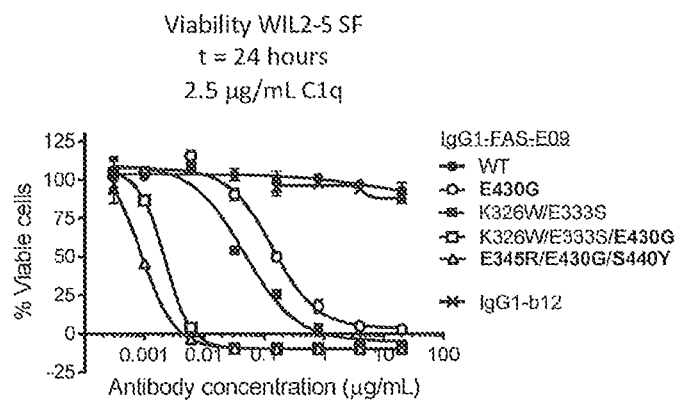
FIGS. 29A-29C show a 24-hour viability assay (CellTiter-Glo) using WIL2-S SF cells with variants of anti-FAS antibodies IgG1-FAS-E09 (FIG. 29A), IgG1-CD95-AP01 (FIG. 29B) and IgG1-CD95-HFE7A (FIG. 29C) in serum-free medium with C1q as crosslinker.
Figure 29B:
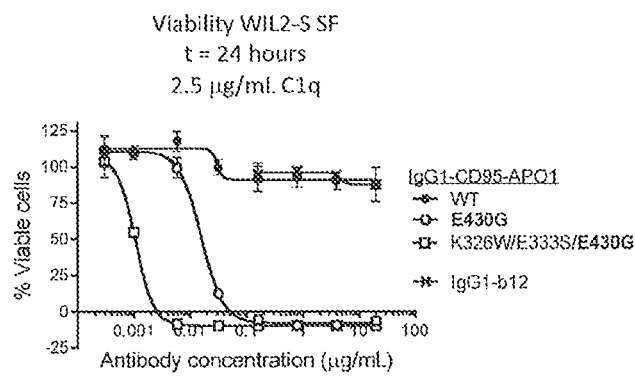
Figure 29C:
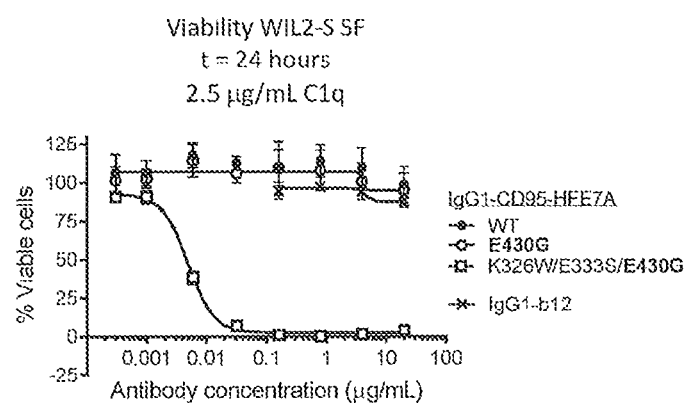

FIG. 29A shows that in the 24-hour viability assay, introduction of the single hexamerization-enhancing mutations E430G as well as the C1q binding-enhancing mutations K326W/E333S enabled the FAS antibody IgG1-FAS-E09 to induce dose-dependent killing of WIL2-S SF cells in presence of C1q, whereas the wild type antibody was unable to induce killing at the tested antibody concentrations. When the Fc-Fc-enhancing mutation E430G was combined with the C1q binding-enhancing mutations K326W/E333S in IgG1-FAS-E09, the antibody became as potent as with E345R/E430G/S440Y in the 24-hour viability assay in presence of C1q. FIG. 29B shows that also with the IgG1-CD95-APO1 antibody, introduction of E430G or K326W/E333S/E430G resulted in dose-dependent killing of WIL2-S SF in the presence of C1q, with the K326W/E333S/E430G triple mutant the most potent. FIG. 29C shows for IgG1-CD95-HFA7E that the combination of C1q binding enhancement and Fc-Fc enhancement were required (K326W/E333S/E430G) to induce proliferation inhibition in the presence of C1q.

Figure 30A:
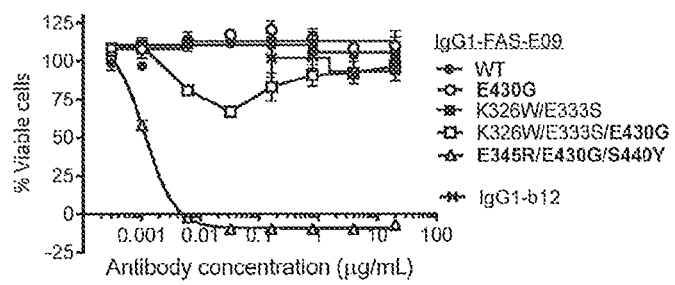
FIGS. 30A-30C show a 24-hour viability assay (CellTiter-Glo) using WIL2-S SF cells incubated with variants of anti-FAS antibodies IgG1-FAS-E09 (FIG. 30A), IgG1-CD95-AP01 (FIG. 30B) and IgG1-CD95-HFE7A (FIG. 30C) in serum-free medium without C1q.
Figure 30B:
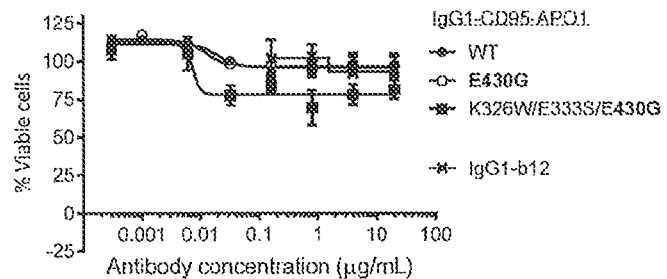
Figure 30C:
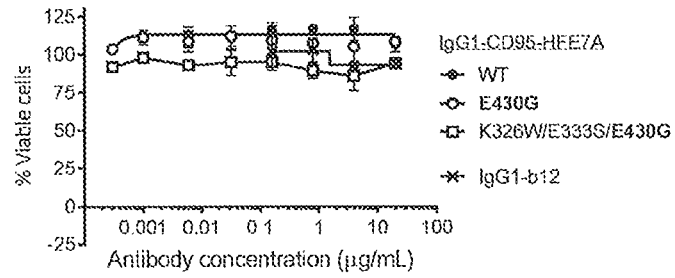

As a control experiment, also a 24-hour viability assay was performed using WIL2-S SF cells without C1q. FIG. 30A shows that introduction of the hexamerization-enhancing mutations E345R/E430G/S440Y enabled the FAS antibody IgG1-FAS-E09 to induce dose-dependent killing of WIL2-S SF cells independent of C1q, whereas the wild type antibody and the antibody variants with only the Fc-Fc-enhancing mutation E430G or the C1q binding-enhancing mutations K326W/E333S were unable to induce killing at the tested antibody concentrations in absence of C1q. However, introduction of both the Fc-Fc-enhancing and C1q binding-enhancing mutations (IgG1-FAS-E09-K326W/E333S/E430G) resulted in up to 25% loss of cell viability in absence of C1q. In absence of C1q, introduction of K326W/E333S/E430G had a similar effect for IgG1-CD95-APO1 (FIG. 30B), but no effect on IgG1-CD95-HFA7E (FIG. 30C).

In conclusion, combining Fc-Fc enhancing mutation E430G with C1q binding-enhancing mutations K326W/E333S in anti-FAS antibodies could induce CDC of WIL2-S SF cells after 45 minutes. This process was completely serum-dependent since C1q alone did not induce killing of the cells after 45 minutes. However, after 24 hrs incubation of anti-FAS antibodies with mutation K326W/E333S/E430G in the presence of C1q did induce killing and outperformed the killing potency of the E430G and K326W/E333S mutants.

Figure 31:
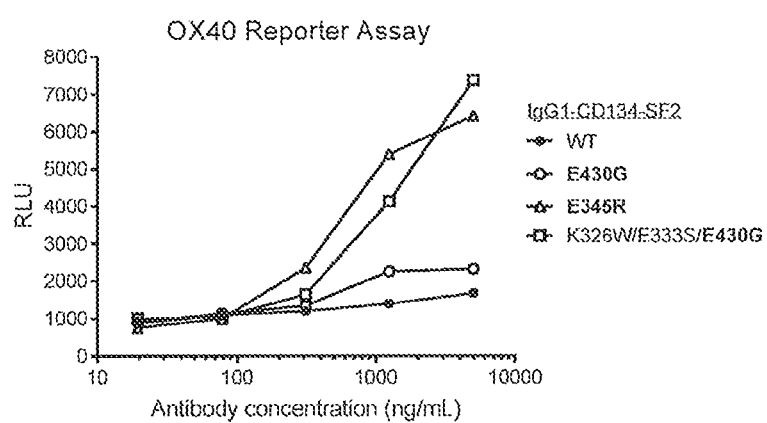
FIG. 31 shows the activity of IgG1-CD134-5F2 (WT), IgG1-CD134-5F2-E345R, IgG1-CD134-5F2-E430G and IgG1-CD134-5F2-K326W/E333S/E430G antibodies in an OX40 Jurkat reporter assay. Thaw-and-Use GloResponse NFκB-luc2/OX40 Jurkat cells were incubated for 5 hours with a concentration range of antibody in the presence of 8% fetal bovine serum. OX40 assay responses were recorded by luminescence detected after stimulation of OX40 by anti-OX40 antibodies which induce the expression of a luciferase reporter gene. RLU: Relative Luminescence Units.

Example 29: The Effect of Combining the E430G Fc-FC-Enhancing Mutation with the K326W/E333S Mutations on the Activation of OX40 on Jurkat Cells by Anti-OX40 Antibodies The crosslinking of OX40 ligand receptor (CD134) by OX40 ligand (OX40L) can induce the proliferation of T cells expressing OX40 (Gramaglia et al., 1998 J. Immunol. 161, 6510-6517). The effect of mutations K326W/E333S on OX40 signaling was tested using different variants of the anti-OX40 antibody IgG1-5F2 using the OX40 Bioassay Kit (Promega, Cat No. CS197704), essentially according to the instructions supplied by the manufacturer. Thaw-and-Use GloResponse NFκB-luc2/OX40 Jurkat cells (Promega, Cat No. CS197704), which stably express human OX40 and a luciferase reporter gene downstream of an NFAT response element, express luciferase upon OX40 activation. 25 µL freshly thawed cells were incubated overnight in 96-well white F-bottom Optiplates (Perkin Elmer, Cat No. 6005299) in 25 µL RPMI 1640 medium (Promega, Cat No. G708A) in the presence of 8% fetal bovine serum (FBS, Promega Ref. J121A). The following day, a serial dilution of antibodies (19.5-5,000 ng/mL final concentrations in 4-fold dilutions) was added to the cells in medium to an end volume of 80 µL. Cells were incubated for a further 5 hours prior to addition of the Bio-Glo Reagent (Promega, Cat No. CS197704). After 5-10 min incubation at ambient temperature, luminescence was recorded using an Envision MultiLabel Plate reader. FIG. 31 shows that wild type anti-OX40 antibody IgG1-CD134-5F2 did not induce an OX40 response. Introduction of an Fc-Fc-enhancing mutation resulted with E345R in a strong induction, and with E430G in a mild induction of OX40 response. Combining the E430G Fc-Fc-enhancing mutation with the C1q binding-enhancing mutations K326W/E333S resulted in strong agonist activity of IgG1-5F2.

Figure 32:
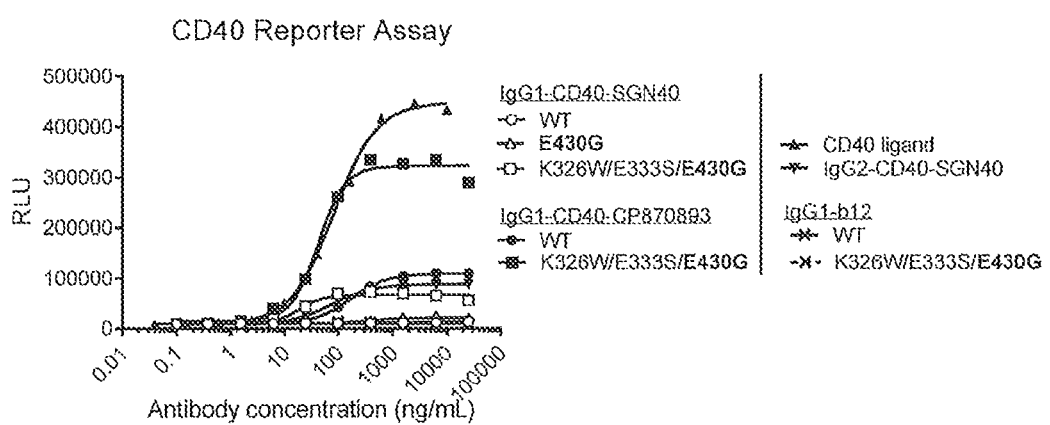
FIG. 32 shows the effect of Fc-Fc-enhancing mutation E430G combined with C1q binding-enhancing mutations K326W/E333S on the CD40 response of IgG1-CD40-SGN40 and IgG1-CD40-CP870893. Thaw-and-Use GloResponse NFκB-luc2/CD40 Jurkat cells were incubated for 5 hours with a concentration range of antibody in the presence of 8% fetal bovine serum. CD40 assay responses were recorded by luminescence detected after stimulation of CD40 by anti-CD40 antibodies or CD40 ligand, which induce the expression of a luciferase reporter gene. RLU: Relative Luminescence Units.

Example 30: The Effect of K326W/E333S/E430G Mutations on the Activation of CD40 on U20S Cells by Anti-CD40 Antibodies in the Presence of Fetal Calf Serum The crosslinking of CD40 receptors, found on antigen presenting cells, by CD40 ligand on TH cells can induce a variety of downstream effects (Chatzigeorgiou et al., 2009 BioFactors (Oxford, England) 35 (6): 474-83). The effect of mutations K326W/E333S/E430G on CD40 signaling was tested using different variants of the anti-CD40 antibodies, SGN40 and CP870893 using the CD40 Bioassay Kit (Promega, Cat No. CS1979A06) essentially according to the instructions supplied by the manufacturer. Thaw-and-Use GloResponse NFκB-luc2P/U20S cells which stably express human CD40 and a luciferase reporter gene downstream of an NFAT response element, express luciferase upon CD40 activation. 25 µL freshly thawed cells were incubated overnight in 96-well white F-bottom Optiplates (Perkin Elmer, Cat No. 6005299) in 25 µL RPMI 1640 medium (Promega, Cat No. G708A) in the presence of 8% fetal bovine serum (J1211). The following day, a serial dilution of antibodies or purified, recombinant CD40 ligand (R&D systems, Cat No. 6420-CL-025/CF) were added to the cells in medium to an end volume of 80 µL. Cells were incubated for a further 5 hours prior to addition of the Bio-Glo Reagent (Promega, Cat No. CS197704). After 5-10 min incubation at ambient temperature, luminescence was recorded using an Envision MultiLabel Plate reader. Fetal Bovine Serum (FBS, Promega Ref. J121A) was used as serum source. Antibodies were tested in a serial dilution ranging from 0.1 to 25,000 ng/mL. Recombinant CD40 ligand (serial dilution ranging from 0.04 to 10,000 ng/mL), which was used as a positive control in the CD40 response assay, induced clear response signals relative to the non-binding negative control antibody IgG1-b12 (FIG. 32). Wild type anti-CD40 antibody IgG1-SGN40 induced CD40 response levels essentially similar to the negative control antibody IgG1-b12. In contrast, IgG1-CD40-SGN40 variant that contained only the E430G mutation, which induces Fc-Fc interactions between antibodies after cell surface binding, induced a CD40 response (EC50 336.4±15.3 SD ng/mL). IgG1-CD40-SGN40 variant with the E430G Fc-Fc-enhancing mutation combined with C1q binding-enhancing mutations K326W/E333S further enhanced the potency of IgG1-SGN40 (EC50 18.0±1.1 SD ng/mL). Wild type antibody IgG1-CD40-CP870893 is already able to induce a CD40 response (EC50 187.4±9.2 SD ng/mL), which could be further potentiated by K326W/E333S/E430G (EC50 45.9±3.3 SD ng/mL) to a similar level as CD40 ligand.

In conclusion, K326W/E333S/E430G mutations potentiated the activation of CD40 on U20S cells by anti-CD40 antibodies in the presence of fetal calf serum.

TABLE 7

EC50 and SD of CD40 ligand and IgG1-CD40 antibodies and variants

|  | Average EC50 (ng/mL) | SD (ng/mL) |
| --- | --- | --- |
| CD40 ligand | 112.5 | 48.0 |
| IqG1-CD40-SGN40 | 3356.0 | 0.0 |
| IqG1-CD40-SGN40-E430G | 336.4 | 15.3 |
| IqG1-CD40-SGN40-WSG | 18.0 | 1.1 |
| IqG1-CD40-CP870893 | 187.4 | 9.2 |
| IqG1-CD40-CP870893-WSG | 45.9 | 3.3 |

Figure 33A:
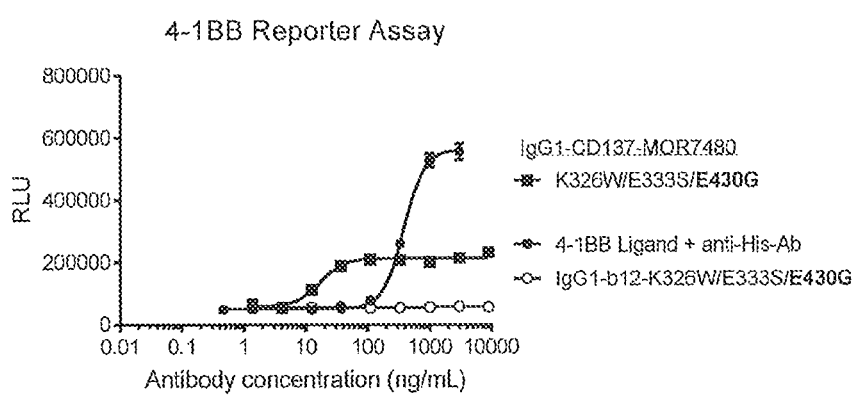
FIGS. 33A and 33B show the effect of Fc-Fc-enhancing mutation E430G combined with C1q binding-enhancing mutations K326W/E333S on the 4-1BB response of IgG1-CD137-MOR7480 and IgG1-BMS-663513. Thaw-and-Use GloResponse™ NFκB-luc2/4-1BB Jurkat cells were incubated for 5 hours with a concentration range of antibody in the presence of 1% fetal bovine serum. 4-1BB assay responses were recorded by luminescence detected after stimulation of 4-1BB by anti-4-1BB antibodies or 4-1BB ligand with anti-His antibody, which induce the expression of a luciferase reporter gene. IgG-b12-K326W/E333S/E430G was used as negative control. RLU: Relative Luminescence Units.
Figure 33B:
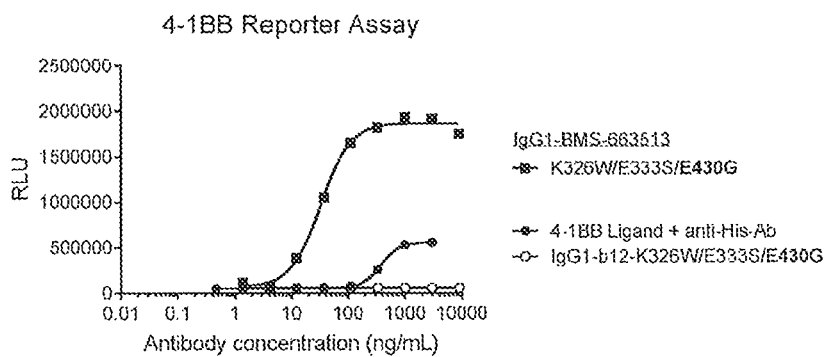

Example 31: The Effect of K326W/E333S/E430G Mutations on the Activation of 4-IBB (CD137) on Jurkat Cells by Anti-4-IBB Antibodies in the Presence of Fetal Calf Serum 4-1BB or CD137 or tumor necrosis factor receptor superfamily member 9 (TNFRSF9), is a member of the tumor necrosis factor receptor (TNFR) super family, and induced by lymphocyte activation (ILA) (Schwarz et al., 1993, Gene. 134 (2): 295-8). Crosslinking of 4-1BB enhances T cell proliferation, IL-2 secretion, survival and cytolytic activity (Sica et al., 2000 Arch. Immunol. Ther. Exp. (Warsz.). 47 (5): 275-9). The effect of mutations K326W/E333S/E430G on 4-1BB signaling was tested using different variants of the anti-4-1BB antibodies, MOR7480 and BMS-663513 using the 4-1BB Bioassay Kit (Promega, Cat No. CS196005) essentially according to the instructions supplied by the manufacturer. Thaw-and-Use GloResponse™ NFκB-luc2/4-1BB Jurkat cells which stably express human 4-1BB and a luciferase reporter gene downstream of an NFAT response element, express luciferase upon CD40 activation. 25 µL freshly thawed cells were incubated overnight in 96-well white F-bottom Optiplates (Perkin Elmer, Cat No. 6005299) in 25 µL RPMI 1640 medium (Promega, Cat No. G708A) in the presence of 1% fetal bovine serum (J121A). The following day, a serial dilution of antibodies or purified, recombinant 4-1BB ligand with His tag (R&D systems, 2295-4L-025/CF) anti-His-tag antibody (Clone 30991312) were added to the cells in medium to an end volume of 80 µL. Cells were incubated for a further 5 hours prior to addition of the Bio-Glo Reagent (Promega, Cat No. CS197704). After 5-10 min incubation at ambient temperature, luminescence was recorded using an Envision Multi-Label Plate reader. Fetal Bovine Serum (FBS, Promega Ref. J121A) was used as a serum source. Recombinant 4-1BB ligand and anti-His Ab mixture, which was used as a positive control in the 4-1BB response assay, induced clear response signals relative to the non-binding negative control antibody IgG1-b12-WSG (FIG. 33). The tested antibodies containing the Fc-Fc-enhancing mutation E430G combined with C1q binding-enhancing mutations K326W/E333S induced dose-dependent activation of 4-1BB signaling on Jurkat cells in the presence of fetal calf serum (EC50 16.9 ng/mL for IgG1-CD137-MOR7480-K326W/E333S/E430G and EC50 32.9 ng/mL for IgG1-BMS-663513-K326W/E333S/E430G).

Example 32: The Effect of K326W/E333S/E430G Mutations on the Activation of

GITR on Jurkat cells by anti-GITR antibodies in the presence of fetal calf serum. GITR (glucocorticoid-induced TNFR-related protein) or tumor necrosis factor receptor superfamily member 18 (TNFRSF18), is a member of the TNFR super family. GITR is activated by GITR ligand (GITRL), which is mainly expressed on APC. Engagement of GITR on T cells with agonist antibodies, recombinant GITRL or GITRL transfectants, following suboptimal TCR stimulation, enhances T cell activation by upregulating CD25, inducing IL-2 and IFNγ expression, and augmenting proliferation (reviewed by Knee et al. in Eur J Cancer. 2016 November; 67:1-10).

Figure 34:
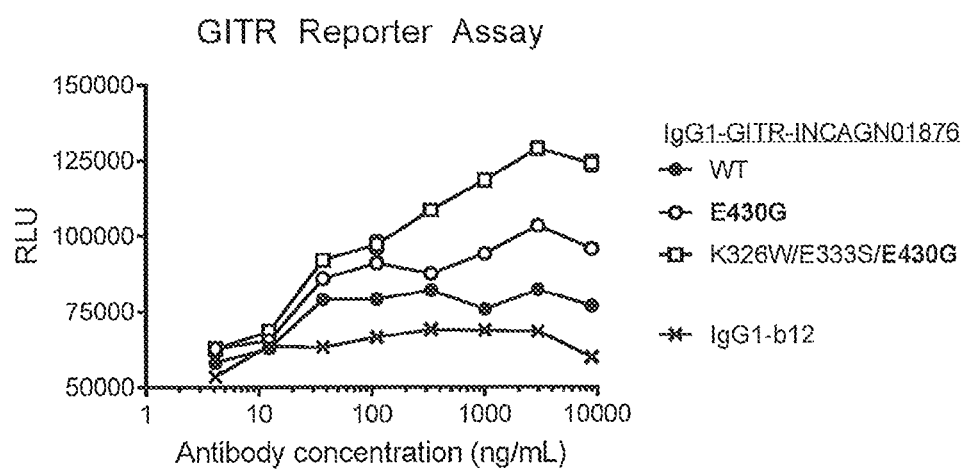
FIG. 34 shows the effect of Fc-Fc-enhancing mutation E430G combined with C1q binding-enhancing mutations K326W/E333S on the GITR response of IgG1-GITR-INCAGN01876. Thaw-and-Use GloResponse NFκB-luc2/GITR Jurkat cells were incubated for 6 hours with a concentration range antibodies in the presence of 1% fetal bovine serum. GITR assay responses were recorded by luminescence detected after stimulation of GITR by anti-GITR antibodies, which induce the expression of a luciferase reporter gene. RLU: Relative Luminescence Units.

The effect of mutations K326W/E333S/E430G on GITR signaling was tested using different variants of the anti-GITR antibody, INCAGN01876 using the GITR Bioassay Kit (Promega, Cat No. CS184006) essentially according to the instructions supplied by the manufacturer. Thaw-and-Use GloResponse NFκB-luc2P/GITR Jurkat cells which stably express human GITR and a luciferase reporter gene downstream of an NFAT response element, express luciferase upon GITR activation. 25 µL freshly thawed cells were incubated overnight in 96-well white F-bottom Optiplates (Perkin Elmer, Cat No. 6005299) in 25 μL RPMI 1640 medium (Promega, Cat No. G708A) in the presence of 8% fetal bovine serum (J1211). The following day, a serial dilution of antibodies were added to the cells in medium to an end volume of 80 μL. Cells were incubated for a further 5 hours prior to addition of the Bio-Glo Reagent (Promega, Cat No. CS197704). After 5-10 min incubation at ambient temperature, luminescence was recorded using an Envision MultiLabel Plate reader. Fetal Bovine Serum (FBS, Promega Ref. 3121A) was used as serum source. The non-binding negative control antibody IgG1-b12 defines the background signal. Wild type anti-GITR antibody IgG1-GITR-INCAGN01876 induced GITR response levels just above negative control antibody IgG1-b12 (FIG. 34). In contrast, IgG1-GITR-INCAGN01876 variant that contained only the E430G Fc-Fc-enhancing mutation induced a stronger GITR response. IgG1-GITR-INCAGN01876 with the E430G Fc-Fc-enhancing mutation combined with the C1q binding-enhancing mutations K326W/E333S further enhanced the potency of IgG1-GITR-INCAGN01876.

In conclusion, K326W/E333S/E430G mutations potentiate the activation of GITR on Jurkat cells by anti-GITR antibody in the presence of fetal calf serum.

Figure 35:
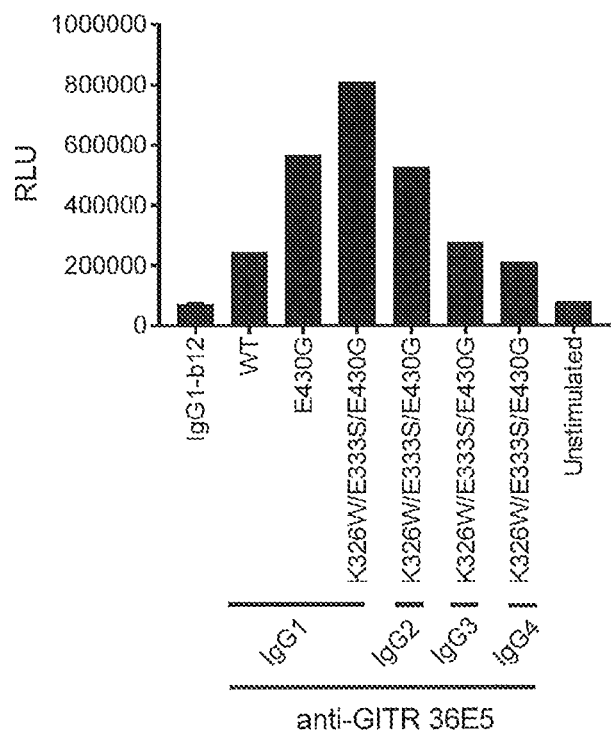
FIG. 35 shows the effect of Fc-Fc-enhancing mutation E430G combined with the C1q binding-enhancing mutations K326W/E333S on the GITR response of antibody GITR-36E5 in subclasses IgG1, IgG2, IgG3 and IgG4. Thaw-and-Use GloResponse NFκB-luc2/GITR Jurkat cells were incubated for 6 hours with a final concentration of 111 ng/mL antibody in the presence of 1% fetal bovine serum. GITR assay responses were recorded by luminescence detected after stimulation of GITR by anti-GITR antibodies, which induce the expression of a luciferase reporter gene. Antibody IgG1-b12 was used as a non-binding control. RLU: Relative Luminescence Units.

Example 33: The Effect of K326W/E333S/E430G Mutations on the Activation of GITR on Jurkat Cells by Anti-GITR Antibodies in Different IgG Subclasses in the Presence of Fetal Calf Serum The effect of mutations K326W/E333S/E430G on GITR signaling was tested using IgG1, IgG2, IgG3 and IgG4 subclass variants of the anti-GITR antibody 36E5 using the GITR Bioassay Kit as described in Example 32 in the presence of fetal bovine serum. The antibodies were tested at a final concentration of 111 ng/mL. Wild type IgG1 anti-GITR antibody IgG1-GITR-36E5 induced a low GITR agonist response in comparison to the non-binding control IgG1-b12 (FIG. 35). Introduction of the E430G Fc-Fc-enhancing mutation resulted in a modest increase of the GITR agonist response. The IgG1-GITR-36E5 variant with the E430G Fc-Fc-enhancing mutation combined with C1q binding-enhancing mutations K326W/E333S further enhanced the potency of the antibody to a maximal response. Introduction of K326W/E333S/E430G in IgG2 subclass IgG2-GITR-36E5 resulted in a modest GITR agonist response. In IgG3-GITR-36E5 and IgG4-GITR-36E5, introduction of the K326W/E333S/E430G mutations resulted in low GITR agonist responses, similar as to the levels of the WT IgG1 antibody.

The invention claimed is:

1. A polypeptide comprising an Fc region of a human IgG1 and an antigen binding region, wherein the Fc region comprises the following substitutions: E430G, K326W, and E333S,
wherein the numbering position is according to EU numbering.

2. The polypeptide according to claim 1, wherein the Fc region further comprises an F405L or a K409R substitution.

3. The polypeptide according to claim 1, wherein the polypeptide is an antibody, monospecific antibody, bispecific antibody or multispecific antibody.

4. The polypeptide according to claim 3, wherein the polypeptide is a bispecific antibody comprising a first heavy chain and a first antigen binding region, and a second heavy chain and a second antigen binding region, wherein
   a. said first heavy chain comprises an F405L substitution, and
   b. said second heavy chain comprises a K409R substitution.

5. The polypeptide according to claim 1, wherein the polypeptide is a human antibody, humanized antibody or chimeric antibody.

6. A composition comprising at least one polypeptide according to claim 1.

7. A kit of parts comprising the polypeptide of claim 1, wherein said polypeptide is in one or more containers.

8. A composition comprising at least one polypeptide according to claim 2.

9. A composition comprising at least one polypeptide according to claim 3.

10. A composition comprising at least one polypeptide according to claim 4.

11. A composition comprising at least one polypeptide according to claim 5.

12. A kit of parts comprising the polypeptide of claim 2, wherein said polypeptide is in one or more containers.

13. A kit of parts comprising the polypeptide of claim 3, wherein said polypeptide is in one or more containers.

14. A kit of parts comprising the polypeptide of claim 4, wherein said polypeptide is in one or more containers.

15. A kit of parts comprising the polypeptide of claim 5, wherein said polypeptide is in one or more containers.

* * * * *

SEQUENCE LISTING

```
<160> NUMBER OF SEQ ID NOS: 172

<210> SEQ ID NO 1
<211> LENGTH: 8
<212> TYPE: PRT
<213> ORGANISM: Artificial Sequence
<220> FEATURE:
<223> OTHER INFORMATION: Synthetic

<400> SEQUENCE: 1

Gly Phe Asn Ile Lys Asp Thr Phe
1               5

<210> SEQ ID NO 2
<211> LENGTH: 8
<212> TYPE: PRT
<213> ORGANISM: Artificial Sequence
<220> FEATURE:
<223> OTHER INFORMATION: Synthetic

<400> SEQUENCE: 2

Ile Asp Pro Ala Asn Thr Asn Thr
1               5

<210> SEQ ID NO 3
<211> LENGTH: 11
<212> TYPE: PRT
<213> ORGANISM: Artificial Sequence
<220> FEATURE:
<223> OTHER INFORMATION: Synthetic

<400> SEQUENCE: 3

Val Arg Gly Leu Tyr Thr Tyr Tyr Phe Asp Tyr
1               5                   10

<210> SEQ ID NO 4
<211> LENGTH: 118
<212> TYPE: PRT
```

<213> ORGANISM: Artificial Sequence
<220> FEATURE:
<223> OTHER INFORMATION: Synthetic

<400> SEQUENCE: 4

```
Glu Val Gln Leu Gln Gln Ser Gly Ala Glu Val Val Lys Pro Gly Ala
1               5                   10                  15

Ser Val Lys Leu Ser Cys Lys Ala Ser Gly Phe Asn Ile Lys Asp Thr
            20                  25                  30

Phe Ile His Trp Val Lys Gln Ala Pro Gly Gln Gly Leu Glu Trp Ile
        35                  40                  45

Gly Arg Ile Asp Pro Ala Asn Thr Asn Thr Lys Tyr Asp Pro Lys Phe
    50                  55                  60

Gln Gly Lys Ala Thr Ile Thr Thr Asp Thr Ser Ser Asn Thr Ala Tyr
65                  70                  75                  80

Met Glu Leu Ser Ser Leu Arg Ser Glu Asp Thr Ala Val Tyr Tyr Cys
                85                  90                  95

Val Arg Gly Leu Tyr Thr Tyr Tyr Phe Asp Tyr Trp Gly Gln Gly Thr
                100                 105                 110

Leu Val Thr Val Ser Ser
            115
```

<210> SEQ ID NO 5
<211> LENGTH: 448
<212> TYPE: PRT
<213> ORGANISM: Artificial Sequence
<220> FEATURE:
<223> OTHER INFORMATION: Synthetic

<400> SEQUENCE: 5

```
Glu Val Gln Leu Gln Gln Ser Gly Ala Glu Val Val Lys Pro Gly Ala
1               5                   10                  15

Ser Val Lys Leu Ser Cys Lys Ala Ser Gly Phe Asn Ile Lys Asp Thr
            20                  25                  30

Phe Ile His Trp Val Lys Gln Ala Pro Gly Gln Gly Leu Glu Trp Ile
        35                  40                  45

Gly Arg Ile Asp Pro Ala Asn Thr Asn Thr Lys Tyr Asp Pro Lys Phe
    50                  55                  60

Gln Gly Lys Ala Thr Ile Thr Thr Asp Thr Ser Ser Asn Thr Ala Tyr
65                  70                  75                  80

Met Glu Leu Ser Ser Leu Arg Ser Glu Asp Thr Ala Val Tyr Tyr Cys
                85                  90                  95

Val Arg Gly Leu Tyr Thr Tyr Tyr Phe Asp Tyr Trp Gly Gln Gly Thr
                100                 105                 110

Leu Val Thr Val Ser Ser Ala Ser Thr Lys Gly Pro Ser Val Phe Pro
            115                 120                 125

Leu Ala Pro Ser Ser Lys Ser Thr Ser Gly Gly Thr Ala Ala Leu Gly
        130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
        195                 200                 205
```

```
Asn Thr Lys Val Asp Lys Arg Val Glu Pro Lys Ser Cys Asp Lys Thr
    210                 215                 220

His Thr Cys Pro Pro Cys Pro Ala Pro Glu Leu Leu Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Asp Val Ser His Glu Asp Pro
            260                 265                 270

Glu Val Lys Phe Asn Trp Tyr Val Asp Gly Val Glu Val His Asn Ala
            275                 280                 285

Lys Thr Lys Pro Arg Glu Glu Gln Tyr Asn Ser Thr Tyr Arg Val Val
290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
                325                 330                 335

Ile Ser Lys Ala Lys Gly Gln Pro Arg Glu Pro Gln Val Tyr Thr Leu
            340                 345                 350

Pro Pro Ser Arg Glu Glu Met Thr Lys Asn Gln Val Ser Leu Thr Cys
            355                 360                 365

Leu Val Lys Gly Phe Tyr Pro Ser Asp Ile Ala Val Glu Trp Glu Ser
370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Lys Leu Thr Val Asp Lys Ser
                405                 410                 415

Arg Trp Gln Gln Gly Asn Val Phe Ser Cys Ser Val Met His Glu Ala
            420                 425                 430

Leu His Asn His Tyr Thr Gln Lys Ser Leu Ser Leu Ser Pro Gly Lys
            435                 440                 445

<210> SEQ ID NO 6
<211> LENGTH: 6
<212> TYPE: PRT
<213> ORGANISM: Artificial Sequence
<220> FEATURE:
<223> OTHER INFORMATION: Synthetic

<400> SEQUENCE: 6

Gln Ser Ile Ser Asn Asn
1               5

<210> SEQ ID NO 7
<211> LENGTH: 9
<212> TYPE: PRT
<213> ORGANISM: Artificial Sequence
<220> FEATURE:
<223> OTHER INFORMATION: Synthetic

<400> SEQUENCE: 7

Gln Gln Gly Asn Ser Trp Pro Tyr Thr
1               5

<210> SEQ ID NO 8
<211> LENGTH: 107
<212> TYPE: PRT
<213> ORGANISM: Artificial Sequence
<220> FEATURE:
<223> OTHER INFORMATION: Synthetic
```

<400> SEQUENCE: 8

Glu Ile Val Met Thr Gln Ser Pro Ala Thr Leu Ser Val Ser Pro Gly
1               5                   10                  15

Glu Arg Ala Thr Leu Ser Cys Arg Ala Ser Gln Ser Ile Ser Asn Asn
            20                  25                  30

Leu His Trp Tyr Gln Gln Lys Pro Gly Gln Ala Pro Arg Leu Leu Ile
        35                  40                  45

Lys Phe Ala Ser Gln Ser Ile Thr Gly Ile Pro Ala Arg Phe Ser Gly
    50                  55                  60

Ser Gly Ser Gly Thr Glu Phe Thr Leu Thr Ile Ser Ser Leu Gln Ser
65                  70                  75                  80

Glu Asp Phe Ala Val Tyr Tyr Cys Gln Gln Gly Asn Ser Trp Pro Tyr
                85                  90                  95

Thr Phe Gly Gln Gly Thr Lys Leu Glu Ile Lys
            100                 105

<210> SEQ ID NO 9
<211> LENGTH: 214
<212> TYPE: PRT
<213> ORGANISM: Artificial Sequence
<220> FEATURE:
<223> OTHER INFORMATION: Synthetic

<400> SEQUENCE: 9

Glu Ile Val Met Thr Gln Ser Pro Ala Thr Leu Ser Val Ser Pro Gly
1               5                   10                  15

Glu Arg Ala Thr Leu Ser Cys Arg Ala Ser Gln Ser Ile Ser Asn Asn
            20                  25                  30

Leu His Trp Tyr Gln Gln Lys Pro Gly Gln Ala Pro Arg Leu Leu Ile
        35                  40                  45

Lys Phe Ala Ser Gln Ser Ile Thr Gly Ile Pro Ala Arg Phe Ser Gly
    50                  55                  60

Ser Gly Ser Gly Thr Glu Phe Thr Leu Thr Ile Ser Ser Leu Gln Ser
65                  70                  75                  80

Glu Asp Phe Ala Val Tyr Tyr Cys Gln Gln Gly Asn Ser Trp Pro Tyr
                85                  90                  95

Thr Phe Gly Gln Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 10
<211> LENGTH: 8
<212> TYPE: PRT

```
<213> ORGANISM: Artificial Sequence
<220> FEATURE:
<223> OTHER INFORMATION: Synthetic

<400> SEQUENCE: 10

Gly Phe Asn Ile Lys Asp Thr His
1               5

<210> SEQ ID NO 11
<211> LENGTH: 8
<212> TYPE: PRT
<213> ORGANISM: Artificial Sequence
<220> FEATURE:
<223> OTHER INFORMATION: Synthetic

<400> SEQUENCE: 11

Ile Asp Pro Ala Asn Gly Asn Thr
1               5

<210> SEQ ID NO 12
<211> LENGTH: 11
<212> TYPE: PRT
<213> ORGANISM: Artificial Sequence
<220> FEATURE:
<223> OTHER INFORMATION: Synthetic

<400> SEQUENCE: 12

Ala Arg Trp Gly Thr Asn Val Tyr Phe Ala Tyr
1               5                   10

<210> SEQ ID NO 13
<211> LENGTH: 118
<212> TYPE: PRT
<213> ORGANISM: Artificial Sequence
<220> FEATURE:
<223> OTHER INFORMATION: Synthetic

<400> SEQUENCE: 13

Gln Val Gln Leu Val Gln Ser Gly Ala Glu Val Lys Lys Pro Gly Ala
1               5                   10                  15

Ser Val Lys Val Ser Cys Lys Ala Ser Gly Phe Asn Ile Lys Asp Thr
            20                  25                  30

His Met His Trp Val Arg Gln Ala Pro Gly Gln Arg Leu Glu Trp Ile
        35                  40                  45

Gly Arg Ile Asp Pro Ala Asn Gly Asn Thr Glu Tyr Asp Gln Lys Phe
    50                  55                  60

Gln Gly Arg Val Thr Ile Thr Val Asp Thr Ser Ala Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Trp Gly Thr Asn Val Tyr Phe Ala Tyr Trp Gly Gln Gly Thr
            100                 105                 110

Leu Val Thr Val Ser Ser
        115

<210> SEQ ID NO 14
<211> LENGTH: 448
<212> TYPE: PRT
<213> ORGANISM: Artificial Sequence
<220> FEATURE:
<223> OTHER INFORMATION: Synthetic

<400> SEQUENCE: 14
```

```
Gln Val Gln Leu Val Gln Ser Gly Ala Glu Val Lys Lys Pro Gly Ala
1               5                   10                  15

Ser Val Lys Val Ser Cys Lys Ala Ser Gly Phe Asn Ile Lys Asp Thr
            20                  25                  30

His Met His Trp Val Arg Gln Ala Pro Gly Gln Arg Leu Glu Trp Ile
        35                  40                  45

Gly Arg Ile Asp Pro Ala Asn Gly Asn Thr Glu Tyr Asp Gln Lys Phe
    50                  55                  60

Gln Gly Arg Val Thr Ile Thr Val Asp Thr Ser Ala Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Trp Gly Thr Asn Val Tyr Phe Ala Tyr Trp Gly Gln Gly Thr
            100                 105                 110

Leu Val Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Arg Val Glu Pro Lys Ser Cys Asp Lys Thr
    210                 215                 220

His Thr Cys Pro Pro Cys Pro Ala Pro Glu Leu Leu Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
            260                 265                 270

Glu Val Lys Phe Asn Trp Tyr Val Asp Gly Val Glu Val His Asn Ala
        275                 280                 285

Lys Thr Lys Pro Arg Glu Glu Gln Tyr Asn Ser Thr Tyr Arg Val Val
    290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
                325                 330                 335

Ile Ser Lys Ala Lys Gly Gln Pro Arg Glu Pro Gln Val Tyr Thr Leu
            340                 345                 350

Pro Pro Ser Arg Glu Glu Met Thr Lys Asn Gln Val Ser Leu Thr Cys
        355                 360                 365

Leu Val Lys Gly Phe Tyr Pro Ser Asp Ile Ala Val Glu Trp Glu Ser
    370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Lys Leu Thr Val Asp Lys Ser
                405                 410                 415

Arg Trp Gln Gln Gly Asn Val Phe Ser Cys Ser Val Met His Glu Ala
```

```
                       420                 425                 430
Leu His Asn His Tyr Thr Gln Lys Ser Leu Ser Leu Ser Pro Gly Lys
            435                 440                 445

<210> SEQ ID NO 15
<211> LENGTH: 8
<212> TYPE: PRT
<213> ORGANISM: Artificial Sequence
<220> FEATURE:
<223> OTHER INFORMATION: Synthetic

<400> SEQUENCE: 15

Ser Ser Val Ser Tyr Arg Thr Ser
1               5

<210> SEQ ID NO 16
<211> LENGTH: 9
<212> TYPE: PRT
<213> ORGANISM: Artificial Sequence
<220> FEATURE:
<223> OTHER INFORMATION: Synthetic

<400> SEQUENCE: 16

Gln Gln Tyr His Ser Tyr Pro Pro Thr
1               5

<210> SEQ ID NO 17
<211> LENGTH: 106
<212> TYPE: PRT
<213> ORGANISM: Artificial Sequence
<220> FEATURE:
<223> OTHER INFORMATION: Synthetic

<400> SEQUENCE: 17

Asp Ile Gln Leu Thr Gln Ser Pro Ser Ser Leu Ser Ala Ser Val Gly
1               5                   10                  15

Asp Arg Val Thr Ile Thr Cys Ser Ala Ser Ser Val Ser Tyr Met
            20                  25                  30

Tyr Trp Tyr Gln Gln Lys Pro Gly Lys Ala Pro Lys Pro Trp Ile Tyr
        35                  40                  45

Arg Thr Ser Asn Leu Ala Ser Gly Val Pro Ser Arg Phe Ser Gly Ser
    50                  55                  60

Gly Ser Gly Thr Asp Phe Thr Leu Thr Ile Ser Ser Leu Gln Pro Glu
65                  70                  75                  80

Asp Phe Ala Thr Tyr Tyr Cys Gln Gln Tyr His Ser Tyr Pro Pro Thr
                85                  90                  95

Phe Gly Gly Gly Thr Lys Val Glu Ile Lys
            100                 105

<210> SEQ ID NO 18
<211> LENGTH: 213
<212> TYPE: PRT
<213> ORGANISM: Artificial Sequence
<220> FEATURE:
<223> OTHER INFORMATION: Synthetic

<400> SEQUENCE: 18

Asp Ile Gln Leu Thr Gln Ser Pro Ser Ser Leu Ser Ala Ser Val Gly
1               5                   10                  15

Asp Arg Val Thr Ile Thr Cys Ser Ala Ser Ser Val Ser Tyr Met
            20                  25                  30

Tyr Trp Tyr Gln Gln Lys Pro Gly Lys Ala Pro Lys Pro Trp Ile Tyr
```

```
                35                  40                  45
Arg Thr Ser Asn Leu Ala Ser Gly Val Pro Ser Arg Phe Ser Gly Ser
 50                  55                  60
Gly Ser Gly Thr Asp Phe Thr Leu Thr Ile Ser Ser Leu Gln Pro Glu
 65                  70                  75                  80
Asp Phe Ala Thr Tyr Tyr Cys Gln Gln Tyr His Ser Tyr Pro Pro Thr
                 85                  90                  95
Phe Gly Gly Gly Thr Lys Val Glu Ile Lys Arg Thr Val Ala Ala Pro
            100                 105                 110
Ser Val Phe Ile Phe Pro Pro Ser Asp Glu Gln Leu Lys Ser Gly Thr
        115                 120                 125
Ala Ser Val Val Cys Leu Leu Asn Asn Phe Tyr Pro Arg Glu Ala Lys
    130                 135                 140
Val Gln Trp Lys Val Asp Asn Ala Leu Gln Ser Gly Asn Ser Gln Glu
145                 150                 155                 160
Ser Val Thr Glu Gln Asp Ser Lys Asp Ser Thr Tyr Ser Leu Ser Ser
                165                 170                 175
Thr Leu Thr Leu Ser Lys Ala Asp Tyr Glu Lys His Lys Val Tyr Ala
            180                 185                 190
Cys Glu Val Thr His Gln Gly Leu Ser Ser Pro Val Thr Lys Ser Phe
        195                 200                 205
Asn Arg Gly Glu Cys
    210

<210> SEQ ID NO 19
<211> LENGTH: 10
<212> TYPE: PRT
<213> ORGANISM: Homo Sapiens

<400> SEQUENCE: 19

Gly Gly Ser Ile Ser Ser Gly Asp Tyr Phe
1               5                   10

<210> SEQ ID NO 20
<211> LENGTH: 7
<212> TYPE: PRT
<213> ORGANISM: Homo Sapiens

<400> SEQUENCE: 20

Ile His Asn Ser Gly Thr Thr
1               5

<210> SEQ ID NO 21
<211> LENGTH: 14
<212> TYPE: PRT
<213> ORGANISM: Homo Sapiens

<400> SEQUENCE: 21

Ala Arg Asp Arg Gly Gly Asp Tyr Tyr Tyr Gly Met Asp Val
1               5                   10

<210> SEQ ID NO 22
<211> LENGTH: 122
<212> TYPE: PRT
<213> ORGANISM: Homo Sapiens

<400> SEQUENCE: 22

Gln Val Gln Leu Gln Glu Ser Gly Pro Gly Leu Val Lys Pro Ser Gln
1               5                   10                  15
```

```
Thr Leu Ser Leu Thr Cys Thr Val Ser Gly Gly Ser Ile Ser Ser Gly
            20                  25                  30

Asp Tyr Phe Trp Ser Trp Ile Arg Gln Leu Pro Gly Lys Gly Leu Glu
            35                  40                  45

Trp Ile Gly His Ile His Asn Ser Gly Thr Thr Tyr Tyr Asn Pro Ser
 50                  55                  60

Leu Lys Ser Arg Val Thr Ile Ser Val Asp Thr Ser Lys Lys Gln Phe
 65                  70                  75                  80

Ser Leu Arg Leu Ser Ser Val Thr Ala Ala Asp Thr Ala Val Tyr Tyr
            85                  90                  95

Cys Ala Arg Asp Arg Gly Gly Asp Tyr Tyr Tyr Gly Met Asp Val Trp
            100                 105                 110

Gly Gln Gly Thr Thr Val Thr Val Ser Ser
            115                 120
```

<210> SEQ ID NO 23
<211> LENGTH: 452
<212> TYPE: PRT
<213> ORGANISM: Homo Sapiens

<400> SEQUENCE: 23

```
Gln Val Gln Leu Gln Glu Ser Gly Pro Gly Leu Val Lys Pro Ser Gln
 1               5                   10                  15

Thr Leu Ser Leu Thr Cys Thr Val Ser Gly Gly Ser Ile Ser Ser Gly
            20                  25                  30

Asp Tyr Phe Trp Ser Trp Ile Arg Gln Leu Pro Gly Lys Gly Leu Glu
            35                  40                  45

Trp Ile Gly His Ile His Asn Ser Gly Thr Thr Tyr Tyr Asn Pro Ser
 50                  55                  60

Leu Lys Ser Arg Val Thr Ile Ser Val Asp Thr Ser Lys Lys Gln Phe
 65                  70                  75                  80

Ser Leu Arg Leu Ser Ser Val Thr Ala Ala Asp Thr Ala Val Tyr Tyr
            85                  90                  95

Cys Ala Arg Asp Arg Gly Gly Asp Tyr Tyr Tyr Gly Met Asp Val Trp
            100                 105                 110

Gly Gln Gly Thr Thr Val Thr Val Ser Ser Ala Ser Thr Lys Gly Pro
            115                 120                 125

Ser Val Phe Pro Leu Ala Pro Ser Ser Lys Ser Thr Ser Gly Gly Thr
130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
                165                 170                 175

Ala Val Leu Gln Ser Ser Gly Leu Tyr Ser Leu Ser Ser Val Val Thr
            180                 185                 190

Val Pro Ser Ser Ser Leu Gly Thr Gln Thr Tyr Ile Cys Asn Val Asn
            195                 200                 205

His Lys Pro Ser Asn Thr Lys Val Asp Lys Arg Val Glu Pro Lys Ser
    210                 215                 220

Cys Asp Lys Thr His Thr Cys Pro Pro Cys Pro Ala Pro Glu Leu Leu
225                 230                 235                 240

Gly Gly Pro Ser Val Phe Leu Phe Pro Pro Lys Pro Lys Asp Thr Leu
                245                 250                 255

Met Ile Ser Arg Thr Pro Glu Val Thr Cys Val Val Val Asp Val Ser
            260                 265                 270
```

```
His Glu Asp Pro Glu Val Lys Phe Asn Trp Tyr Val Asp Gly Val Glu
        275                 280                 285

Val His Asn Ala Lys Thr Lys Pro Arg Glu Glu Gln Tyr Asn Ser Thr
    290                 295                 300

Tyr Arg Val Val Ser Val Leu Thr Val Leu His Gln Asp Trp Leu Asn
305                 310                 315                 320

Gly Lys Glu Tyr Lys Cys Lys Val Ser Asn Lys Ala Leu Pro Ala Pro
                325                 330                 335

Ile Glu Lys Thr Ile Ser Lys Ala Lys Gly Gln Pro Arg Glu Pro Gln
            340                 345                 350

Val Tyr Thr Leu Pro Pro Ser Arg Glu Glu Met Thr Lys Asn Gln Val
        355                 360                 365

Ser Leu Thr Cys Leu Val Lys Gly Phe Tyr Pro Ser Asp Ile Ala Val
    370                 375                 380

Glu Trp Glu Ser Asn Gly Gln Pro Glu Asn Asn Tyr Lys Thr Thr Pro
385                 390                 395                 400

Pro Val Leu Asp Ser Asp Gly Ser Phe Phe Leu Tyr Ser Lys Leu Thr
                405                 410                 415

Val Asp Lys Ser Arg Trp Gln Gln Gly Asn Val Phe Ser Cys Ser Val
            420                 425                 430

Met His Glu Ala Leu His Asn His Tyr Thr Gln Lys Ser Leu Ser Leu
        435                 440                 445

Ser Pro Gly Lys
        450

<210> SEQ ID NO 24
<211> LENGTH: 7
<212> TYPE: PRT
<213> ORGANISM: Homo Sapiens

<400> SEQUENCE: 24

Gln Gly Ile Ser Arg Ser Tyr
1               5

<210> SEQ ID NO 25
<211> LENGTH: 9
<212> TYPE: PRT
<213> ORGANISM: Homo Sapiens

<400> SEQUENCE: 25

Gln Gln Phe Gly Ser Ser Pro Trp Thr
1               5

<210> SEQ ID NO 26
<211> LENGTH: 108
<212> TYPE: PRT
<213> ORGANISM: Homo Sapiens

<400> SEQUENCE: 26

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Gly Ile Ser Arg Ser
            20                  25                  30

Tyr Leu Ala Trp Tyr Gln Gln Lys Pro Gly Gln Ala Pro Ser Leu Leu
        35                  40                  45

Ile Tyr Gly Ala Ser Ser Arg Ala Thr Gly Ile Pro Asp Arg Phe Ser
    50                  55                  60
```

```
Gly Ser Gly Ser Gly Thr Asp Phe Thr Leu Thr Ile Ser Arg Leu Glu
 65                  70                  75                  80

Pro Glu Asp Phe Ala Val Tyr Tyr Cys Gln Gln Phe Gly Ser Ser Pro
                 85                  90                  95

Trp Thr Phe Gly Gln Gly Thr Lys Val Glu Ile Lys
            100                 105
```

<210> SEQ ID NO 27
<211> LENGTH: 323
<212> TYPE: PRT
<213> ORGANISM: Homo Sapiens

<400> SEQUENCE: 27

```
Glu Ile Val Leu Thr Gln Ser Pro Gly Thr Leu Ser Leu Ser Pro Gly
  1               5                  10                  15

Glu Arg Ala Thr Leu Ser Cys Arg Ala Ser Gln Gly Ile Ser Arg Ser
                 20                  25                  30

Tyr Leu Ala Trp Tyr Gln Gln Lys Pro Gly Gln Ala Pro Ser Leu Leu
             35                  40                  45

Ile Tyr Gly Ala Ser Ser Arg Ala Thr Gly Ile Pro Asp Arg Phe Ser
 50                  55                  60

Gly Ser Gly Ser Gly Thr Asp Phe Thr Leu Thr Ile Ser Arg Leu Glu
 65                  70                  75                  80

Pro Glu Asp Phe Ala Val Tyr Tyr Cys Gln Gln Phe Gly Ser Ser Pro
                 85                  90                  95

Trp Thr Phe Gly Gln Gly Thr Lys Val Glu Ile Lys Glu Ile Val Leu
            100                 105                 110

Thr Gln Ser Pro Gly Thr Leu Ser Leu Ser Pro Gly Glu Arg Ala Thr
            115                 120                 125

Leu Ser Cys Arg Ala Ser Gln Gly Ile Ser Arg Ser Tyr Leu Ala Trp
        130                 135                 140

Tyr Gln Gln Lys Pro Gly Gln Ala Pro Ser Leu Leu Ile Tyr Gly Ala
145                 150                 155                 160

Ser Ser Arg Ala Thr Gly Ile Pro Asp Arg Phe Ser Gly Ser Gly Ser
                165                 170                 175

Gly Thr Asp Phe Thr Leu Thr Ile Ser Arg Leu Glu Pro Glu Asp Phe
            180                 185                 190

Ala Val Tyr Tyr Cys Gln Gln Phe Gly Ser Ser Pro Trp Thr Phe Gly
        195                 200                 205

Gln Gly Thr Lys Val Glu Ile Lys Arg Thr Val Ala Ala Pro Ser Val
210                 215                 220

Phe Ile Phe Pro Pro Ser Asp Glu Gln Leu Lys Ser Gly Thr Ala Ser
225                 230                 235                 240

Val Val Cys Leu Leu Asn Asn Phe Tyr Pro Arg Glu Ala Lys Val Gln
                245                 250                 255

Trp Lys Val Asp Asn Ala Leu Gln Ser Gly Asn Ser Gln Glu Ser Val
            260                 265                 270

Thr Glu Gln Asp Ser Lys Asp Ser Thr Tyr Ser Leu Ser Ser Thr Leu
        275                 280                 285

Thr Leu Ser Lys Ala Asp Tyr Glu Lys His Lys Val Tyr Ala Cys Glu
    290                 295                 300

Val Thr His Gln Gly Leu Ser Ser Pro Val Thr Lys Ser Phe Asn Arg
305                 310                 315                 320

Gly Glu Cys
```

```
<210> SEQ ID NO 28
<211> LENGTH: 8
<212> TYPE: PRT
<213> ORGANISM: Homo Sapiens

<400> SEQUENCE: 28

Gly Phe Thr Phe His Asp Tyr Ala
1               5

<210> SEQ ID NO 29
<211> LENGTH: 8
<212> TYPE: PRT
<213> ORGANISM: Homo Sapiens

<400> SEQUENCE: 29

Ile Ser Trp Asn Ser Gly Thr Ile
1               5

<210> SEQ ID NO 30
<211> LENGTH: 15
<212> TYPE: PRT
<213> ORGANISM: Homo Sapiens

<400> SEQUENCE: 30

Ala Lys Asp Ile Gln Tyr Gly Asn Tyr Tyr Tyr Gly Met Asp Val
1               5                   10                  15

<210> SEQ ID NO 31
<211> LENGTH: 122
<212> TYPE: PRT
<213> ORGANISM: Homo Sapiens

<400> SEQUENCE: 31

Glu Val Gln Leu Val Glu Ser Gly Gly Gly Leu Val Gln Pro Asp Arg
1               5                   10                  15

Ser Leu Arg Leu Ser Cys Ala Ala Ser Gly Phe Thr Phe His Asp Tyr
            20                  25                  30

Ala Met His Trp Val Arg Gln Ala Pro Gly Lys Gly Leu Glu Trp Val
        35                  40                  45

Ser Thr Ile Ser Trp Asn Ser Gly Thr Ile Gly Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Leu Tyr Tyr Cys
                85                  90                  95

Ala Lys Asp Ile Gln Tyr Gly Asn Tyr Tyr Tyr Gly Met Asp Val Trp
            100                 105                 110

Gly Gln Gly Thr Thr Val Thr Val Ser Ser
        115                 120

<210> SEQ ID NO 32
<211> LENGTH: 452
<212> TYPE: PRT
<213> ORGANISM: Homo Sapiens

<400> SEQUENCE: 32

Glu Val Gln Leu Val Glu Ser Gly Gly Gly Leu Val Gln Pro Asp Arg
1               5                   10                  15

Ser Leu Arg Leu Ser Cys Ala Ala Ser Gly Phe Thr Phe His Asp Tyr
            20                  25                  30
```

Ala Met His Trp Val Arg Gln Ala Pro Gly Lys Gly Leu Glu Trp Val
 35                  40                  45

Ser Thr Ile Ser Trp Asn Ser Gly Thr Ile Gly Tyr Ala Asp Ser Val
 50                  55                  60

Lys Gly Arg Phe Thr Ile Ser Arg Asp Asn Ala Lys Asn Ser Leu Tyr
 65                  70                  75                  80

Leu Gln Met Asn Ser Leu Arg Ala Glu Asp Thr Ala Leu Tyr Tyr Cys
                 85                  90                  95

Ala Lys Asp Ile Gln Tyr Gly Asn Tyr Tyr Gly Met Asp Val Trp
             100                 105                 110

Gly Gln Gly Thr Thr Val Thr Val Ser Ser Ala Ser Thr Lys Gly Pro
             115                 120                 125

Ser Val Phe Pro Leu Ala Pro Ser Ser Lys Ser Thr Ser Gly Gly Thr
 130                 135                 140

Ala Ala Leu Gly Cys Leu Val Lys Asp Tyr Phe Pro Glu Pro Val Thr
 145                 150                 155                 160

Val Ser Trp Asn Ser Gly Ala Leu Thr Ser Gly Val His Thr Phe Pro
                 165                 170                 175

Ala Val Leu Gln Ser Ser Gly Leu Tyr Ser Leu Ser Ser Val Val Thr
             180                 185                 190

Val Pro Ser Ser Ser Leu Gly Thr Gln Thr Tyr Ile Cys Asn Val Asn
             195                 200                 205

His Lys Pro Ser Asn Thr Lys Val Asp Lys Arg Val Glu Pro Lys Ser
 210                 215                 220

Cys Asp Lys Thr His Thr Cys Pro Pro Cys Pro Ala Pro Glu Leu Leu
225                  230                 235                 240

Gly Gly Pro Ser Val Phe Leu Phe Pro Pro Lys Pro Lys Asp Thr Leu
                 245                 250                 255

Met Ile Ser Arg Thr Pro Glu Val Thr Cys Val Val Val Asp Val Ser
             260                 265                 270

His Glu Asp Pro Glu Val Lys Phe Asn Trp Tyr Val Asp Gly Val Glu
             275                 280                 285

Val His Asn Ala Lys Thr Lys Pro Arg Glu Glu Gln Tyr Asn Ser Thr
 290                 295                 300

Tyr Arg Val Val Ser Val Leu Thr Val Leu His Gln Asp Trp Leu Asn
305                  310                 315                 320

Gly Lys Glu Tyr Lys Cys Lys Val Ser Asn Lys Ala Leu Pro Ala Pro
                 325                 330                 335

Ile Glu Lys Thr Ile Ser Lys Ala Lys Gly Gln Pro Arg Glu Pro Gln
             340                 345                 350

Val Tyr Thr Leu Pro Pro Ser Arg Glu Glu Met Thr Lys Asn Gln Val
             355                 360                 365

Ser Leu Thr Cys Leu Val Lys Gly Phe Tyr Pro Ser Asp Ile Ala Val
 370                 375                 380

Glu Trp Glu Ser Asn Gly Gln Pro Glu Asn Asn Tyr Lys Thr Thr Pro
385                  390                 395                 400

Pro Val Leu Asp Ser Asp Gly Ser Phe Phe Leu Tyr Ser Lys Leu Thr
                 405                 410                 415

Val Asp Lys Ser Arg Trp Gln Gln Gly Asn Val Phe Ser Cys Ser Val
             420                 425                 430

Met His Glu Ala Leu His Asn His Tyr Thr Gln Lys Ser Leu Ser Leu
 435                 440                 445

Ser Pro Gly Lys

450

<210> SEQ ID NO 33
<211> LENGTH: 6
<212> TYPE: PRT
<213> ORGANISM: Homo Sapiens

<400> SEQUENCE: 33

Gln Ser Val Ser Ser Tyr
1               5

<210> SEQ ID NO 34
<211> LENGTH: 9
<212> TYPE: PRT
<213> ORGANISM: Homo Sapiens

<400> SEQUENCE: 34

Gln Gln Arg Ser Asn Trp Pro Ile Thr
1               5

<210> SEQ ID NO 35
<211> LENGTH: 107
<212> TYPE: PRT
<213> ORGANISM: Homo Sapiens

<400> SEQUENCE: 35

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
                20                  25                  30

Leu Ala Trp Tyr Gln Gln Lys Pro Gly Gln Ala Pro Arg Leu Leu Ile
            35                  40                  45

Tyr Asp Ala Ser Asn Arg Ala Thr Gly Ile Pro Ala Arg Phe Ser Gly
        50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Ser Asn Trp Pro Ile
                85                  90                  95

Thr Phe Gly Gln Gly Thr Arg Leu Glu Ile Lys
            100                 105

<210> SEQ ID NO 36
<211> LENGTH: 214
<212> TYPE: PRT
<213> ORGANISM: Homo Sapiens

<400> SEQUENCE: 36

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
                20                  25                  30

Leu Ala Trp Tyr Gln Gln Lys Pro Gly Gln Ala Pro Arg Leu Leu Ile
            35                  40                  45

Tyr Asp Ala Ser Asn Arg Ala Thr Gly Ile Pro Ala Arg Phe Ser Gly
        50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Ser Asn Trp Pro Ile
                85                  90                  95

```
Thr Phe Gly Gln Gly Thr Arg Leu Glu Ile Lys Arg Thr Val Ala Ala
                100                 105                 110
Pro Ser Val Phe Ile Phe Pro Pro Ser Asp Glu Gln Leu Lys Ser Gly
            115                 120                 125
Thr Ala Ser Val Val Cys Leu Leu Asn Asn Phe Tyr Pro Arg Glu Ala
        130                 135                 140
Lys Val Gln Trp Lys Val Asp Asn Ala Leu Gln Ser Gly Asn Ser Gln
145                 150                 155                 160
Glu Ser Val Thr Glu Gln Asp Ser Lys Asp Ser Thr Tyr Ser Leu Ser
                165                 170                 175
Ser Thr Leu Thr Leu Ser Lys Ala Asp Tyr Glu Lys His Lys Val Tyr
            180                 185                 190
Ala Cys Glu Val Thr His Gln Gly Leu Ser Ser Pro Val Thr Lys Ser
        195                 200                 205
Phe Asn Arg Gly Glu Cys
    210
```

<210> SEQ ID NO 37
<211> LENGTH: 8
<212> TYPE: PRT
<213> ORGANISM: Homo Sapiens

<400> SEQUENCE: 37

```
Gly Phe Thr Phe Ser Tyr His Ala
1               5
```

<210> SEQ ID NO 38
<211> LENGTH: 7
<212> TYPE: PRT
<213> ORGANISM: Homo Sapiens

<400> SEQUENCE: 38

```
Ile Gly Thr Gly Gly Val Thr
1               5
```

<210> SEQ ID NO 39
<211> LENGTH: 19
<212> TYPE: PRT
<213> ORGANISM: Homo Sapiens

<400> SEQUENCE: 39

```
Ala Arg Asp Tyr Tyr Gly Ala Gly Ser Phe Tyr Asp Gly Leu Tyr Gly
1               5                   10                  15
Met Asp Val
```

<210> SEQ ID NO 40
<211> LENGTH: 125
<212> TYPE: PRT
<213> ORGANISM: Homo Sapiens

<400> SEQUENCE: 40

```
Glu Val Gln Leu Val Gln Ser Gly Gly Gly Leu Val His Pro Gly Gly
1               5                   10                  15
Ser Leu Arg Leu Ser Cys Thr Gly Ser Gly Phe Thr Phe Ser Tyr His
            20                  25                  30
Ala Met His Trp Val Arg Gln Ala Pro Gly Lys Gly Leu Glu Trp Val
        35                  40                  45
Ser Ile Ile Gly Thr Gly Gly Val Thr Tyr Tyr Ala Asp Ser Val Lys
    50                  55                  60
```

```
Gly Arg Phe Thr Ile Ser Arg Asp Asn Val Lys Asn Ser Leu Tyr Leu
65                  70                  75                  80

Gln Met Asn Ser Leu Arg Ala Glu Asp Met Ala Val Tyr Tyr Cys Ala
                85                  90                  95

Arg Asp Tyr Tyr Gly Ala Gly Ser Phe Tyr Asp Gly Leu Tyr Gly Met
            100                 105                 110

Asp Val Trp Gly Gln Gly Thr Thr Val Thr Val Ser Ser
            115                 120                 125

<210> SEQ ID NO 41
<211> LENGTH: 455
<212> TYPE: PRT
<213> ORGANISM: Homo Sapiens

<400> SEQUENCE: 41

Glu Val Gln Leu Val Gln Ser Gly Gly Gly Leu Val His Pro Gly Gly
1               5                   10                  15

Ser Leu Arg Leu Ser Cys Thr Gly Ser Gly Phe Thr Phe Ser Tyr His
            20                  25                  30

Ala Met His Trp Val Arg Gln Ala Pro Gly Lys Gly Leu Glu Trp Val
        35                  40                  45

Ser Ile Ile Gly Thr Gly Gly Val Thr Tyr Tyr Ala Asp Ser Val Lys
    50                  55                  60

Gly Arg Phe Thr Ile Ser Arg Asp Asn Val Lys Asn Ser Leu Tyr Leu
65                  70                  75                  80

Gln Met Asn Ser Leu Arg Ala Glu Asp Met Ala Val Tyr Tyr Cys Ala
                85                  90                  95

Arg Asp Tyr Tyr Gly Ala Gly Ser Phe Tyr Asp Gly Leu Tyr Gly Met
            100                 105                 110

Asp Val Trp Gly Gln Gly Thr Thr Val Thr Val Ser Ser Ala Ser Thr
            115                 120                 125

Lys Gly Pro Ser Val Phe Pro Leu Ala Pro Ser Ser Lys Ser Thr Ser
130                 135                 140

Gly Gly Thr Ala Ala Leu Gly Cys Leu Val Lys Asp Tyr Phe Pro Glu
145                 150                 155                 160

Pro Val Thr Val Ser Trp Asn Ser Gly Ala Leu Thr Ser Gly Val His
                165                 170                 175

Thr Phe Pro Ala Val Leu Gln Ser Ser Gly Leu Tyr Ser Leu Ser Ser
            180                 185                 190

Val Val Thr Val Pro Ser Ser Ser Leu Gly Thr Gln Thr Tyr Ile Cys
        195                 200                 205

Asn Val Asn His Lys Pro Ser Asn Thr Lys Val Asp Lys Arg Val Glu
210                 215                 220

Pro Lys Ser Cys Asp Lys Thr His Thr Cys Pro Cys Pro Ala Pro
225                 230                 235                 240

Glu Leu Leu Gly Gly Pro Ser Val Phe Leu Phe Pro Lys Pro Lys
                245                 250                 255

Asp Thr Leu Met Ile Ser Arg Thr Pro Glu Val Thr Cys Val Val Val
            260                 265                 270

Asp Val Ser His Glu Asp Pro Glu Val Lys Phe Asn Trp Tyr Val Asp
        275                 280                 285

Gly Val Glu Val His Asn Ala Lys Thr Lys Pro Arg Glu Glu Gln Tyr
    290                 295                 300

Asn Ser Thr Tyr Arg Val Val Ser Val Leu Thr Val Leu His Gln Asp
305                 310                 315                 320
```

-continued

```
Trp Leu Asn Gly Lys Glu Tyr Lys Cys Lys Val Ser Asn Lys Ala Leu
                325                 330                 335
Pro Ala Pro Ile Glu Lys Thr Ile Ser Lys Ala Lys Gly Gln Pro Arg
            340                 345                 350
Glu Pro Gln Val Tyr Thr Leu Pro Pro Ser Arg Glu Met Thr Lys
        355                 360                 365
Asn Gln Val Ser Leu Thr Cys Leu Val Lys Gly Phe Tyr Pro Ser Asp
    370                 375                 380
Ile Ala Val Glu Trp Glu Ser Asn Gly Gln Pro Glu Asn Asn Tyr Lys
385                 390                 395                 400
Thr Thr Pro Pro Val Leu Asp Ser Asp Gly Ser Phe Phe Leu Tyr Ser
                405                 410                 415
Lys Leu Thr Val Asp Lys Ser Arg Trp Gln Gln Gly Asn Val Phe Ser
            420                 425                 430
Cys Ser Val Met His Glu Ala Leu His Asn His Tyr Thr Gln Lys Ser
        435                 440                 445
Leu Ser Leu Ser Pro Gly Lys
    450                 455

<210> SEQ ID NO 42
<211> LENGTH: 6
<212> TYPE: PRT
<213> ORGANISM: Homo Sapiens

<400> SEQUENCE: 42

Gln Ser Val Ser Ser Tyr
1               5

<210> SEQ ID NO 43
<211> LENGTH: 9
<212> TYPE: PRT
<213> ORGANISM: Homo Sapiens

<400> SEQUENCE: 43

Gln Gln Arg Ser Asp Trp Pro Leu Thr
1               5

<210> SEQ ID NO 44
<211> LENGTH: 107
<212> TYPE: PRT
<213> ORGANISM: Homo Sapiens

<400> SEQUENCE: 44

Glu Ile Val Leu Thr Gln Ser Pro Ala Thr Leu Ser Leu Ser Pro Gly
1               5                   10                  15
Glu Arg Ala Thr Leu Ser Cys Arg Ala Ser Gln Ser Val Ser Ser Tyr
            20                  25                  30
Leu Ala Trp Tyr Gln Gln Lys Pro Gly Gln Ala Pro Arg Leu Leu Ile
        35                  40                  45
Tyr Asp Ala Ser Asn Arg Ala Thr Gly Ile Pro Ala Arg Phe Ser Gly
    50                  55                  60
Ser Gly Ser Gly Thr Asp Phe Thr Leu Thr Ile Ser Ser Leu Glu Pro
65                  70                  75                  80
Glu Asp Phe Ala Val Tyr Tyr Cys Gln Gln Arg Ser Asp Trp Pro Leu
                85                  90                  95
Thr Phe Gly Gly Gly Thr Lys Val Glu Ile Lys
            100                 105
```

```
<210> SEQ ID NO 45
<211> LENGTH: 214
<212> TYPE: PRT
<213> ORGANISM: Homo Sapiens

<400> SEQUENCE: 45

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Ser Asp Trp Pro Leu
                85                  90                  95

Thr Phe Gly Gly Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 46
<211> LENGTH: 8
<212> TYPE: PRT
<213> ORGANISM: Artificial Sequence
<220> FEATURE:
<223> OTHER INFORMATION: Synthetic

<400> SEQUENCE: 46

Gly Phe Thr Phe Thr Asp Phe Tyr
1               5

<210> SEQ ID NO 47
<211> LENGTH: 10
<212> TYPE: PRT
<213> ORGANISM: Artificial Sequence
<220> FEATURE:
<223> OTHER INFORMATION: Synthetic

<400> SEQUENCE: 47

Ile Arg Asp Lys Ala Lys Gly Tyr Thr Thr
1               5                   10

<210> SEQ ID NO 48
<211> LENGTH: 12
```

```
<212> TYPE: PRT
<213> ORGANISM: Artificial Sequence
<220> FEATURE:
<223> OTHER INFORMATION: Synthetic

<400> SEQUENCE: 48

Ala Arg Glu Gly His Thr Ala Ala Pro Phe Asp Tyr
1               5                   10

<210> SEQ ID NO 49
<211> LENGTH: 121
<212> TYPE: PRT
<213> ORGANISM: Artificial Sequence
<220> FEATURE:
<223> OTHER INFORMATION: Synthetic

<400> SEQUENCE: 49

Gln Val Gln Leu Gln Glu Ser Gly Pro Gly Leu Val Arg Pro Ser Gln
1               5                   10                  15

Thr Leu Ser Leu Thr Cys Thr Val Ser Gly Phe Thr Phe Thr Asp Phe
            20                  25                  30

Tyr Met Asn Trp Val Arg Gln Pro Pro Gly Arg Gly Leu Glu Trp Ile
        35                  40                  45

Gly Phe Ile Arg Asp Lys Ala Lys Gly Tyr Thr Thr Glu Tyr Asn Pro
    50                  55                  60

Ser Val Lys Gly Arg Val Thr Met Leu Val Asp Thr Ser Lys Asn Gln
65                  70                  75                  80

Phe Ser Leu Arg Leu Ser Ser Val Thr Ala Ala Asp Thr Ala Val Tyr
                85                  90                  95

Tyr Cys Ala Arg Glu Gly His Thr Ala Ala Pro Phe Asp Tyr Trp Gly
            100                 105                 110

Gln Gly Ser Leu Val Thr Val Ser Ser
            115                 120

<210> SEQ ID NO 50
<211> LENGTH: 451
<212> TYPE: PRT
<213> ORGANISM: Artificial Sequence
<220> FEATURE:
<223> OTHER INFORMATION: Synthetic

<400> SEQUENCE: 50

Gln Val Gln Leu Gln Glu Ser Gly Pro Gly Leu Val Arg Pro Ser Gln
1               5                   10                  15

Thr Leu Ser Leu Thr Cys Thr Val Ser Gly Phe Thr Phe Thr Asp Phe
            20                  25                  30

Tyr Met Asn Trp Val Arg Gln Pro Pro Gly Arg Gly Leu Glu Trp Ile
        35                  40                  45

Gly Phe Ile Arg Asp Lys Ala Lys Gly Tyr Thr Thr Glu Tyr Asn Pro
    50                  55                  60

Ser Val Lys Gly Arg Val Thr Met Leu Val Asp Thr Ser Lys Asn Gln
65                  70                  75                  80

Phe Ser Leu Arg Leu Ser Ser Val Thr Ala Ala Asp Thr Ala Val Tyr
                85                  90                  95

Tyr Cys Ala Arg Glu Gly His Thr Ala Ala Pro Phe Asp Tyr Trp Gly
            100                 105                 110

Gln Gly Ser Leu Val Thr Val Ser Ser Ala Ser Thr Lys Gly Pro Ser
            115                 120                 125

Val Phe Pro Leu Ala Pro Ser Ser Lys Ser Thr Ser Gly Gly Thr Ala
```

-continued

```
            130                 135                 140
Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
                195                 200                 205

Lys Pro Ser Asn Thr Lys Val Asp Lys Arg Val Glu Pro Lys Ser Cys
            210                 215                 220

Asp Lys Thr His Thr Cys Pro Pro Cys Pro Ala Pro Glu Leu Leu Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
                260                 265                 270

Glu Asp Pro Glu Val Lys Phe Asn Trp Tyr Val Asp Gly Val Glu Val
            275                 280                 285

His Asn Ala Lys Thr Lys Pro Arg Glu Glu Gln Tyr Asn Ser Thr Tyr
            290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
                325                 330                 335

Glu Lys Thr Ile Ser Lys Ala Lys Gly Gln Pro Arg Glu Pro Gln Val
            340                 345                 350

Tyr Thr Leu Pro Pro Ser Arg Glu Glu Met Thr Lys Asn Gln Val Ser
            355                 360                 365

Leu Thr Cys Leu Val Lys Gly Phe Tyr Pro Ser Asp Ile Ala Val Glu
            370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
                405                 410                 415

Asp Lys Ser Arg Trp Gln Gln Gly Asn Val Phe Ser Cys Ser Val Met
            420                 425                 430

His Glu Ala Leu His Asn His Tyr Thr Gln Lys Ser Leu Ser Leu Ser
            435                 440                 445

Pro Gly Lys
450

<210> SEQ ID NO 51
<211> LENGTH: 6
<212> TYPE: PRT
<213> ORGANISM: Artificial Sequence
<220> FEATURE:
<223> OTHER INFORMATION: Synthetic

<400> SEQUENCE: 51

Gln Asn Ile Asp Lys Tyr
1               5

<210> SEQ ID NO 52
<211> LENGTH: 9
<212> TYPE: PRT
```

```
<213> ORGANISM: Artificial Sequence
<220> FEATURE:
<223> OTHER INFORMATION: Synthetic

<400> SEQUENCE: 52

Leu Gln His Ile Ser Arg Pro Arg Thr
1               5

<210> SEQ ID NO 53
<211> LENGTH: 107
<212> TYPE: PRT
<213> ORGANISM: Artificial Sequence
<220> FEATURE:
<223> OTHER INFORMATION: Synthetic

<400> SEQUENCE: 53

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asn Ile Asp Lys Tyr
            20                  25                  30

Leu Asn Trp Tyr Gln Gln Lys Pro Gly Lys Ala Pro Lys Leu Leu Ile
        35                  40                  45

Tyr Asn Thr Asn Asn Leu Gln Thr Gly Val Pro Ser Arg Phe Ser Gly
    50                  55                  60

Ser Gly Ser Gly Thr Asp Phe Thr Phe Thr Ile Ser Ser Leu Gln Pro
65                  70                  75                  80

Glu Asp Ile Ala Thr Tyr Tyr Cys Leu Gln His Ile Ser Arg Pro Arg
                85                  90                  95

Thr Phe Gly Gln Gly Thr Lys Val Glu Ile Lys
            100                 105

<210> SEQ ID NO 54
<211> LENGTH: 214
<212> TYPE: PRT
<213> ORGANISM: Artificial Sequence
<220> FEATURE:
<223> OTHER INFORMATION: Synthetic

<400> SEQUENCE: 54

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asn Ile Asp Lys Tyr
            20                  25                  30

Leu Asn Trp Tyr Gln Gln Lys Pro Gly Lys Ala Pro Lys Leu Leu Ile
        35                  40                  45

Tyr Asn Thr Asn Asn Leu Gln Thr Gly Val Pro Ser Arg Phe Ser Gly
    50                  55                  60

Ser Gly Ser Gly Thr Asp Phe Thr Phe Thr Ile Ser Ser Leu Gln Pro
65                  70                  75                  80

Glu Asp Ile Ala Thr Tyr Tyr Cys Leu Gln His Ile Ser Arg Pro Arg
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160
```

```
Glu Ser Val Thr Glu Gln Asp Ser Lys Asp Ser Thr Tyr Ser Leu Ser
            165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
            195                 200                 205

Phe Asn Arg Gly Glu Cys
    210

<210> SEQ ID NO 55
<211> LENGTH: 8
<212> TYPE: PRT
<213> ORGANISM: Homo Sapiens

<400> SEQUENCE: 55

Gly Phe Thr Phe Ser Thr Tyr Gly
1               5

<210> SEQ ID NO 56
<211> LENGTH: 8
<212> TYPE: PRT
<213> ORGANISM: Homo Sapiens

<400> SEQUENCE: 56

Ile Trp Asp Asp Gly Ser Tyr Lys
1               5

<210> SEQ ID NO 57
<211> LENGTH: 18
<212> TYPE: PRT
<213> ORGANISM: Homo Sapiens

<400> SEQUENCE: 57

Ala Arg Asp Gly Ile Thr Met Val Arg Gly Val Met Lys Asp Tyr Phe
1               5                   10                  15

Asp Tyr

<210> SEQ ID NO 58
<211> LENGTH: 125
<212> TYPE: PRT
<213> ORGANISM: Homo Sapiens

<400> SEQUENCE: 58

Gln Val Gln Leu Val Glu Ser Gly Gly Val Val Gln Pro Gly Arg
1               5                   10                  15

Ser Leu Arg Leu Ser Cys Ala Ala Ser Gly Phe Thr Phe Ser Thr Tyr
            20                  25                  30

Gly Met His Trp Val Arg Gln Ala Pro Gly Lys Gly Leu Glu Trp Val
            35                  40                  45

Ala Val Ile Trp Asp Asp Gly Ser Tyr Lys Tyr Gly Asp Ser Val
        50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Gly Ile Thr Met Val Arg Gly Val Met Lys Asp Tyr Phe
            100                 105                 110

Asp Tyr Trp Gly Gln Gly Thr Leu Val Thr Val Ser Ser
            115                 120                 125
```

<210> SEQ ID NO 59
<211> LENGTH: 455
<212> TYPE: PRT
<213> ORGANISM: Homo Sapiens

<400> SEQUENCE: 59

```
Gln Val Gln Leu Val Glu Ser Gly Gly Val Val Gln Pro Gly Arg
1               5                   10                  15

Ser Leu Arg Leu Ser Cys Ala Ala Ser Gly Phe Thr Phe Ser Thr Tyr
                20                  25                  30

Gly Met His Trp Val Arg Gln Ala Pro Gly Lys Gly Leu Glu Trp Val
            35                  40                  45

Ala Val Ile Trp Asp Asp Gly Ser Tyr Lys Tyr Tyr Gly Asp Ser Val
        50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Gly Ile Thr Met Val Arg Gly Val Met Lys Asp Tyr Phe
            100                 105                 110

Asp Tyr Trp Gly Gln Gly Thr Leu Val Thr Val Ser Ser Ala Ser Thr
        115                 120                 125

Lys Gly Pro Ser Val Phe Pro Leu Ala Pro Ser Ser Lys Ser Thr Ser
    130                 135                 140

Gly Gly Thr Ala Ala Leu Gly Cys Leu Val Lys Asp Tyr Phe Pro Glu
145                 150                 155                 160

Pro Val Thr Val Ser Trp Asn Ser Gly Ala Leu Thr Ser Gly Val His
                165                 170                 175

Thr Phe Pro Ala Val Leu Gln Ser Ser Gly Leu Tyr Ser Leu Ser Ser
            180                 185                 190

Val Val Thr Val Pro Ser Ser Leu Gly Thr Gln Thr Tyr Ile Cys
        195                 200                 205

Asn Val Asn His Lys Pro Ser Asn Thr Lys Val Asp Lys Arg Val Glu
210                 215                 220

Pro Lys Ser Cys Asp Lys Thr His Thr Cys Pro Pro Cys Pro Ala Pro
225                 230                 235                 240

Glu Leu Leu Gly Gly Pro Ser Val Phe Leu Phe Pro Pro Lys Pro Lys
                245                 250                 255

Asp Thr Leu Met Ile Ser Arg Thr Pro Glu Val Thr Cys Val Val Val
            260                 265                 270

Asp Val Ser His Glu Asp Pro Glu Val Lys Phe Asn Trp Tyr Val Asp
        275                 280                 285

Gly Val Glu Val His Asn Ala Lys Thr Lys Pro Arg Glu Glu Gln Tyr
    290                 295                 300

Asn Ser Thr Tyr Arg Val Val Ser Val Leu Thr Val Leu His Gln Asp
305                 310                 315                 320

Trp Leu Asn Gly Lys Glu Tyr Lys Cys Lys Val Ser Asn Lys Ala Leu
                325                 330                 335

Pro Ala Pro Ile Glu Lys Thr Ile Ser Lys Ala Lys Gly Gln Pro Arg
            340                 345                 350

Glu Pro Gln Val Tyr Thr Leu Pro Pro Ser Arg Glu Glu Met Thr Lys
        355                 360                 365

Asn Gln Val Ser Leu Thr Cys Leu Val Lys Gly Phe Tyr Pro Ser Asp
```

```
                370                 375                 380
Ile Ala Val Glu Trp Glu Ser Asn Gly Gln Pro Glu Asn Asn Tyr Lys
385                 390                 395                 400

Thr Thr Pro Pro Val Leu Asp Ser Asp Gly Ser Phe Phe Leu Tyr Ser
                405                 410                 415

Lys Leu Thr Val Asp Lys Ser Arg Trp Gln Gln Gly Asn Val Phe Ser
            420                 425                 430

Cys Ser Val Met His Glu Ala Leu His Asn His Tyr Thr Gln Lys Ser
        435                 440                 445

Leu Ser Leu Ser Pro Gly Lys
    450                 455

<210> SEQ ID NO 60
<211> LENGTH: 6
<212> TYPE: PRT
<213> ORGANISM: Homo Sapiens

<400> SEQUENCE: 60

Gln Asp Ile Ser Ser Ala
1               5

<210> SEQ ID NO 61
<211> LENGTH: 9
<212> TYPE: PRT
<213> ORGANISM: Homo Sapiens

<400> SEQUENCE: 61

Gln Gln Phe Asn Ser Tyr Pro Leu Thr
1               5

<210> SEQ ID NO 62
<211> LENGTH: 107
<212> TYPE: PRT
<213> ORGANISM: Homo Sapiens

<400> SEQUENCE: 62

Ala Ile Gln Leu Thr Gln Ser Pro Ser Ser Leu Ser Ala Ser Val Gly
1               5                   10                  15

Asp Arg Val Thr Ile Thr Cys Arg Ala Ser Gln Asp Ile Ser Ser Ala
            20                  25                  30

Leu Val Trp Tyr Gln Gln Lys Pro Gly Lys Ala Pro Lys Leu Leu Ile
        35                  40                  45

Tyr Asp Ala Ser Ser Leu Glu Ser Gly Val Pro Ser Arg Phe Ser Gly
    50                  55                  60

Ser Glu Ser Gly Thr Asp Phe Thr Leu Thr Ile Ser Ser Leu Gln Pro
65                  70                  75                  80

Glu Asp Phe Ala Thr Tyr Tyr Cys Gln Gln Phe Asn Ser Tyr Pro Leu
                85                  90                  95

Thr Phe Gly Gly Gly Thr Lys Val Glu Ile Lys
            100                 105

<210> SEQ ID NO 63
<211> LENGTH: 214
<212> TYPE: PRT
<213> ORGANISM: Homo Sapiens

<400> SEQUENCE: 63

Ala Ile Gln Leu Thr Gln Ser Pro Ser Ser Leu Ser Ala Ser Val Gly
1               5                   10                  15
```

```
Asp Arg Val Thr Ile Thr Cys Arg Ala Ser Gln Asp Ile Ser Ser Ala
            20                  25                  30

Leu Val Trp Tyr Gln Gln Lys Pro Gly Lys Ala Pro Lys Leu Leu Ile
        35                  40                  45

Tyr Asp Ala Ser Ser Leu Glu Ser Gly Val Pro Ser Arg Phe Ser Gly
    50                  55                  60

Ser Glu Ser Gly Thr Asp Phe Thr Leu Thr Ile Ser Ser Leu Gln Pro
65                  70                  75                  80

Glu Asp Phe Ala Thr Tyr Tyr Cys Gln Gln Phe Asn Ser Tyr Pro Leu
                85                  90                  95

Thr Phe Gly Gly Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 64
<211> LENGTH: 8
<212> TYPE: PRT
<213> ORGANISM: Homo Sapiens

<400> SEQUENCE: 64

Gly Tyr Arg Phe Ser Asn Phe Val
1               5

<210> SEQ ID NO 65
<211> LENGTH: 8
<212> TYPE: PRT
<213> ORGANISM: Homo Sapiens

<400> SEQUENCE: 65

Ile Asn Pro Tyr Asn Gly Asn Lys
1               5

<210> SEQ ID NO 66
<211> LENGTH: 20
<212> TYPE: PRT
<213> ORGANISM: Homo Sapiens

<400> SEQUENCE: 66

Ala Arg Val Gly Pro Tyr Ser Trp Asp Asp Ser Pro Gln Asp Asn Tyr
1               5                   10                  15

Tyr Met Asp Val
            20

<210> SEQ ID NO 67
<211> LENGTH: 127
<212> TYPE: PRT
```

<213> ORGANISM: Homo Sapiens

<400> SEQUENCE: 67

```
Gln Val Gln Leu Val Gln Ser Gly Ala Glu Val Lys Lys Pro Gly Ala
1               5                   10                  15

Ser Val Lys Val Ser Cys Gln Ala Ser Gly Tyr Arg Phe Ser Asn Phe
            20                  25                  30

Val Ile His Trp Val Arg Gln Ala Pro Gly Gln Arg Phe Glu Trp Met
        35                  40                  45

Gly Trp Ile Asn Pro Tyr Asn Gly Asn Lys Glu Phe Ser Ala Lys Phe
    50                  55                  60

Gln Asp Arg Val Thr Phe Thr Ala Asp Thr Ser Ala Asn Thr Ala Tyr
65                  70                  75                  80

Met Glu Leu Arg Ser Leu Arg Ser Ala Asp Thr Ala Val Tyr Tyr Cys
                85                  90                  95

Ala Arg Val Gly Pro Tyr Ser Trp Asp Asp Ser Pro Gln Asp Asn Tyr
            100                 105                 110

Tyr Met Asp Val Trp Gly Lys Gly Thr Thr Val Ile Val Ser Ser
        115                 120                 125
```

<210> SEQ ID NO 68
<211> LENGTH: 457
<212> TYPE: PRT
<213> ORGANISM: Homo Sapiens

<400> SEQUENCE: 68

```
Gln Val Gln Leu Val Gln Ser Gly Ala Glu Val Lys Lys Pro Gly Ala
1               5                   10                  15

Ser Val Lys Val Ser Cys Gln Ala Ser Gly Tyr Arg Phe Ser Asn Phe
            20                  25                  30

Val Ile His Trp Val Arg Gln Ala Pro Gly Gln Arg Phe Glu Trp Met
        35                  40                  45

Gly Trp Ile Asn Pro Tyr Asn Gly Asn Lys Glu Phe Ser Ala Lys Phe
    50                  55                  60

Gln Asp Arg Val Thr Phe Thr Ala Asp Thr Ser Ala Asn Thr Ala Tyr
65                  70                  75                  80

Met Glu Leu Arg Ser Leu Arg Ser Ala Asp Thr Ala Val Tyr Tyr Cys
                85                  90                  95

Ala Arg Val Gly Pro Tyr Ser Trp Asp Asp Ser Pro Gln Asp Asn Tyr
            100                 105                 110

Tyr Met Asp Val Trp Gly Lys Gly Thr Thr Val Ile Val Ser Ser Ala
        115                 120                 125

Ser Thr Lys Gly Pro Ser Val Phe Pro Leu Ala Pro Ser Ser Lys Ser
    130                 135                 140

Thr Ser Gly Gly Thr Ala Ala Leu Gly Cys Leu Val Lys Asp Tyr Phe
145                 150                 155                 160

Pro Glu Pro Val Thr Val Ser Trp Asn Ser Gly Ala Leu Thr Ser Gly
                165                 170                 175

Val His Thr Phe Pro Ala Val Leu Gln Ser Ser Gly Leu Tyr Ser Leu
            180                 185                 190

Ser Ser Val Val Thr Val Pro Ser Ser Leu Gly Thr Gln Thr Tyr
        195                 200                 205

Ile Cys Asn Val Asn His Lys Pro Ser Asn Thr Lys Val Asp Lys Arg
    210                 215                 220

Val Glu Pro Lys Ser Cys Asp Lys Thr His Thr Cys Pro Pro Cys Pro
```

```
          225                 230                 235                 240
Ala Pro Glu Leu Leu Gly Gly Pro Ser Val Phe Leu Phe Pro Pro Lys
                    245                 250                 255

Pro Lys Asp Thr Leu Met Ile Ser Arg Thr Pro Glu Val Thr Cys Val
                260                 265                 270

Val Val Asp Val Ser His Glu Asp Pro Glu Val Lys Phe Asn Trp Tyr
            275                 280                 285

Val Asp Gly Val Glu Val His Asn Ala Lys Thr Lys Pro Arg Glu Glu
        290                 295                 300

Gln Tyr Asn Ser Thr Tyr Arg Val Val Ser Val Leu Thr Val Leu His
305                 310                 315                 320

Gln Asp Trp Leu Asn Gly Lys Glu Tyr Lys Cys Lys Val Ser Asn Lys
                325                 330                 335

Ala Leu Pro Ala Pro Ile Glu Lys Thr Ile Ser Lys Ala Lys Gly Gln
            340                 345                 350

Pro Arg Glu Pro Gln Val Tyr Thr Leu Pro Pro Ser Arg Glu Glu Met
        355                 360                 365

Thr Lys Asn Gln Val Ser Leu Thr Cys Leu Val Lys Gly Phe Tyr Pro
370                 375                 380

Ser Asp Ile Ala Val Glu Trp Glu Ser Asn Gly Gln Pro Glu Asn Asn
                385                 390                 395                 400

Tyr Lys Thr Thr Pro Pro Val Leu Asp Ser Asp Gly Ser Phe Phe Leu
                405                 410                 415

Tyr Ser Lys Leu Thr Val Asp Lys Ser Arg Trp Gln Gln Gly Asn Val
            420                 425                 430

Phe Ser Cys Ser Val Met His Glu Ala Leu His Asn His Tyr Thr Gln
        435                 440                 445

Lys Ser Leu Ser Leu Ser Pro Gly Lys
    450                 455

<210> SEQ ID NO 69
<211> LENGTH: 7
<212> TYPE: PRT
<213> ORGANISM: Homo Sapiens

<400> SEQUENCE: 69

His Ser Ile Arg Ser Arg Arg
1               5

<210> SEQ ID NO 70
<211> LENGTH: 9
<212> TYPE: PRT
<213> ORGANISM: Homo Sapiens

<400> SEQUENCE: 70

Gln Val Tyr Gly Ala Ser Ser Tyr Thr
1               5

<210> SEQ ID NO 71
<211> LENGTH: 108
<212> TYPE: PRT
<213> ORGANISM: Homo Sapiens

<400> SEQUENCE: 71

Glu Ile Val Leu Thr Gln Ser Pro Gly Thr Leu Ser Leu Ser Pro Gly
1               5                   10                  15

Glu Arg Ala Thr Phe Ser Cys Arg Ser Ser His Ser Ile Arg Ser Arg
            20                  25                  30
```

Arg Val Ala Trp Tyr Gln His Lys Pro Gly Gln Ala Pro Arg Leu Val
            35                  40                  45

Ile His Gly Val Ser Asn Arg Ala Ser Gly Ile Ser Asp Arg Phe Ser
        50                  55                  60

Gly Ser Gly Ser Gly Thr Asp Phe Thr Leu Thr Ile Thr Arg Val Glu
65                  70                  75                  80

Pro Glu Asp Phe Ala Leu Tyr Tyr Cys Gln Val Tyr Gly Ala Ser Ser
                85                  90                  95

Tyr Thr Phe Gly Gln Gly Thr Lys Leu Glu Arg Lys
                100                 105

<210> SEQ ID NO 72
<211> LENGTH: 215
<212> TYPE: PRT
<213> ORGANISM: Homo Sapiens

<400> SEQUENCE: 72

Glu Ile Val Leu Thr Gln Ser Pro Gly Thr Leu Ser Leu Ser Pro Gly
1               5                   10                  15

Glu Arg Ala Thr Phe Ser Cys Arg Ser Ser His Ser Ile Arg Ser Arg
            20                  25                  30

Arg Val Ala Trp Tyr Gln His Lys Pro Gly Gln Ala Pro Arg Leu Val
            35                  40                  45

Ile His Gly Val Ser Asn Arg Ala Ser Gly Ile Ser Asp Arg Phe Ser
        50                  55                  60

Gly Ser Gly Ser Gly Thr Asp Phe Thr Leu Thr Ile Thr Arg Val Glu
65                  70                  75                  80

Pro Glu Asp Phe Ala Leu Tyr Tyr Cys Gln Val Tyr Gly Ala Ser Ser
                85                  90                  95

Tyr Thr Phe Gly Gln Gly Thr Lys Leu Glu Arg Lys Arg Thr Val Ala
                100                 105                 110

Ala Pro Ser Val Phe Ile Phe Pro Pro Ser Asp Glu Gln Leu Lys Ser
            115                 120                 125

Gly Thr Ala Ser Val Val Cys Leu Leu Asn Asn Phe Tyr Pro Arg Glu
        130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
                180                 185                 190

Tyr Ala Cys Glu Val Thr His Gln Gly Leu Ser Ser Pro Val Thr Lys
                195                 200                 205

Ser Phe Asn Arg Gly Glu Cys
            210                 215

<210> SEQ ID NO 73
<211> LENGTH: 330
<212> TYPE: PRT
<213> ORGANISM: Homo Sapiens

<400> SEQUENCE: 73

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

```
Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
 50                  55                  60

Leu Ser Ser Val Val Thr Val Pro Ser Ser Ser Leu Gly Thr Gln Thr
 65                  70                  75                  80

Tyr Ile Cys Asn Val Asn His Lys Pro Ser Asn Thr Lys Val Asp Lys
                 85                  90                  95

Arg Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
            115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
            195                 200                 205

Lys Ala Leu Pro Ala Pro Ile Glu Lys Thr Ile Ser Lys Ala Lys Gly
            210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
            275                 280                 285

Leu Tyr Ser Lys Leu Thr Val Asp Lys Ser Arg Trp Gln Gln Gly Asn
            290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 74
<211> LENGTH: 330
<212> TYPE: PRT
<213> ORGANISM: Homo Sapiens

<400> SEQUENCE: 74

Ala Ser Thr Lys Gly Pro Ser Val Phe Pro Leu Ala Pro Ser Ser Lys
 1               5                  10                  15

Ser Thr Ser Gly Gly Thr Ala Ala Leu Gly Cys Leu Val Lys Asp Tyr
             20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
 50                  55                  60

Leu Ser Ser Val Val Thr Val Pro Ser Ser Ser Leu Gly Thr Gln Thr
```

```
            65                  70                  75                  80
Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Pro Ser Val Phe Leu Phe Pro Pro
        115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 75
<211> LENGTH: 330
<212> TYPE: PRT
<213> ORGANISM: Homo Sapiens

<400> SEQUENCE: 75

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Pro Val Glu Pro Lys Ser Cys Asp Lys Thr His Thr Cys Pro Pro Cys
            100                 105                 110
```

```
Pro Ala Pro Glu Leu Leu Gly Gly Pro Ser Val Phe Leu Phe Pro Pro
            115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 76
<211> LENGTH: 330
<212> TYPE: PRT
<213> ORGANISM: Homo Sapiens

<400> SEQUENCE: 76

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Pro Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160
```

```
Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Gly Leu His Asn His Tyr Thr
305                 310                 315                 320

Gln Lys Ser Leu Ser Leu Ser Pro Gly Lys
                325                 330

<210> SEQ ID NO 77
<211> LENGTH: 330
<212> TYPE: PRT
<213> ORGANISM: Artificial Sequence
<220> FEATURE:
<223> OTHER INFORMATION: Synthetic

<400> SEQUENCE: 77

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Arg Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190
```

His Gln Asp Trp Leu Asn Gly Lys Glu Tyr Lys Cys Lys Val Ser Asn
            195                 200                 205

Lys Ala Leu Pro Ala Pro Ile Glu Lys Thr Ile Ser Lys Ala Lys Gly
        210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Gly Ala Leu His Asn His Tyr Thr
305                 310                 315                 320

Gln Lys Ser Leu Ser Leu Ser Pro Gly Lys
                325                 330

<210> SEQ ID NO 78
<211> LENGTH: 330
<212> TYPE: PRT
<213> ORGANISM: Artificial Sequence
<220> FEATURE:
<223> OTHER INFORMATION: Synthetic

<400> SEQUENCE: 78

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Arg Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

```
Gln Pro Arg Lys Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
            245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
            325                 330

<210> SEQ ID NO 79
<211> LENGTH: 330
<212> TYPE: PRT
<213> ORGANISM: Artificial Sequence
<220> FEATURE:
<223> OTHER INFORMATION: Synthetic

<400> SEQUENCE: 79

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Arg Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Ala Ala Leu Pro Ala Pro Ile Ala Lys Thr Ile Ser Lys Ala Lys Gly
    210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
            245                 250                 255
```

```
Pro Ser Asp Ile Ala Val Glu Trp Glu Ser Asn Gly Gln Pro Glu Asn
            260                 265                 270

Asn Tyr Lys Thr Thr Pro Leu Val Leu Asp Ser Asp Gly Ser Phe Phe
            275                 280                 285

Leu Tyr Ser Lys Leu Thr Val Asp Lys Ser Arg Trp Gln Gln Gly Asn
            290                 295                 300

Val Phe Ser Cys Ser Val Met His Glu Ala Leu His Asn His Tyr Thr
305             310                 315                 320

Gln Lys Ser Leu Ser Leu Ser Pro Gly Lys
            325                 330

<210> SEQ ID NO 80
<211> LENGTH: 330
<212> TYPE: PRT
<213> ORGANISM: Artificial Sequence
<220> FEATURE:
<223> OTHER INFORMATION: Synthetic

<400> SEQUENCE: 80

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Arg Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Ala Ala Leu Pro Ala Pro Ile Ala Lys Thr Ile Ser Lys Ala Lys Gly
    210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Leu Val Leu Asp Ser Asp Gly Ser Phe Phe
            275                 280                 285
```

```
Leu Tyr Ser Lys Leu Thr Val Asp Lys Ser Arg Trp Gln Gln Gly Asn
            290                 295                 300

Val Phe Ser Cys Ser Val Met His Gly Ala Leu His Asn His Tyr Thr
305                 310                 315                 320

Gln Lys Ser Leu Ser Leu Ser Pro Gly Lys
            325                 330

<210> SEQ ID NO 81
<211> LENGTH: 330
<212> TYPE: PRT
<213> ORGANISM: Artificial Sequence
<220> FEATURE:
<223> OTHER INFORMATION: Synthetic

<400> SEQUENCE: 81

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Arg Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Ala Ala Leu Pro Ala Pro Ile Ala Lys Thr Ile Ser Lys Ala Lys Gly
    210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320
```

Gln Lys Ser Leu Ser Leu Ser Pro Gly Lys
            325                 330

<210> SEQ ID NO 82
<211> LENGTH: 330
<212> TYPE: PRT
<213> ORGANISM: Artificial Sequence
<220> FEATURE:
<223> OTHER INFORMATION: Synthetic

<400> SEQUENCE: 82

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Arg Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Ala Ala Leu Pro Ala Pro Ile Ala Lys Thr Ile Ser Lys Ala Lys Gly
    210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Gly Ala Leu His Asn His Tyr Thr
305                 310                 315                 320

Gln Lys Ser Leu Ser Leu Ser Pro Gly Lys
            325                 330

<210> SEQ ID NO 83

<211> LENGTH: 330
<212> TYPE: PRT
<213> ORGANISM: Artificial Sequence
<220> FEATURE:
<223> OTHER INFORMATION: Synthetic

<400> SEQUENCE: 83

```
Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Arg Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Ala Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Leu Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Gly Ala Leu His Asn His Tyr Thr
305                 310                 315                 320

Gln Lys Ser Leu Ser Leu Ser Pro Gly Lys
                325                 330
```

<210> SEQ ID NO 84
<211> LENGTH: 330
<212> TYPE: PRT
<213> ORGANISM: Artificial Sequence
<220> FEATURE:
<223> OTHER INFORMATION: Synthetic

<400> SEQUENCE: 84

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Leu Gly Thr Gln Thr
65                  70                  75                  80

Tyr Ile Cys Asn Val Asn His Lys Pro Ser Asn Thr Lys Val Asp Lys
                85                  90                  95

Arg Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Ala Lys Thr Ile Ser Lys Ala Lys Gly
    210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Leu Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Gly Ala Leu His Asn His Tyr Thr
305                 310                 315                 320

Gln Lys Ser Leu Ser Leu Ser Pro Gly Lys
                325                 330

<210> SEQ ID NO 85
<211> LENGTH: 330
<212> TYPE: PRT
<213> ORGANISM: Artificial Sequence
<220> FEATURE:
<223> OTHER INFORMATION: Synthetic

<400> SEQUENCE: 85

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr

```
            20                  25                  30
Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Arg Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Asp Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Ala Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 86
<211> LENGTH: 330
<212> TYPE: PRT
<213> ORGANISM: Artificial Sequence
<220> FEATURE:
<223> OTHER INFORMATION: Synthetic

<400> SEQUENCE: 86

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
```

```
                    50                  55                  60
Leu Ser Ser Val Val Thr Val Pro Ser Ser Leu Gly Thr Gln Thr
 65                  70                  75                  80

Tyr Ile Cys Asn Val Asn His Lys Pro Ser Asn Thr Lys Val Asp Lys
                     85                  90                  95

Arg Val Glu Pro Lys Ser Cys Asp Lys Thr His Thr Cys Pro Pro Cys
                100                 105                 110

Pro Ala Pro Glu Leu Leu Gly Gly Pro Ser Val Phe Leu Phe Pro Pro
            115                 120                 125

Lys Pro Lys Asp Thr Leu Met Ile Ser Arg Thr Pro Glu Val Thr Cys
        130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Trp Ala Leu Pro Ala Pro Ile Ser Lys Thr Ile Ser Lys Ala Lys Gly
    210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 87
<211> LENGTH: 330
<212> TYPE: PRT
<213> ORGANISM: Artificial Sequence
<220> FEATURE:
<223> OTHER INFORMATION: Synthetic

<400> SEQUENCE: 87

Ala Ser Thr Lys Gly Pro Ser Val Phe Pro Leu Ala Pro Ser Ser Lys
 1               5                  10                  15

Ser Thr Ser Gly Gly Thr Ala Ala Leu Gly Cys Leu Val Lys Asp Tyr
                 20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Leu Gly Thr Gln Thr
 65                  70                  75                  80

Tyr Ile Cys Asn Val Asn His Lys Pro Ser Asn Thr Lys Val Asp Lys
```

```
                     85                  90                  95
Arg Val Glu Pro Lys Ser Cys Asp Lys Thr His Thr Cys Pro Pro Cys
                100                 105                 110

Pro Ala Pro Glu Leu Leu Gly Gly Pro Ser Val Phe Leu Phe Pro Pro
            115                 120                 125

Lys Pro Lys Asp Thr Leu Met Ile Ser Arg Thr Pro Glu Val Thr Cys
        130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Trp Ala Leu Pro Ala Pro Ile Ser Lys Thr Ile Ser Lys Ala Lys Gly
    210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Gly Ala Leu His Asn His Tyr Thr
305                 310                 315                 320

Gln Lys Ser Leu Ser Leu Ser Pro Gly Lys
                325                 330

<210> SEQ ID NO 88
<211> LENGTH: 330
<212> TYPE: PRT
<213> ORGANISM: Artificial Sequence
<220> FEATURE:
<223> OTHER INFORMATION: Synthetic

<400> SEQUENCE: 88

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Arg Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
```

```
            115                 120                 125
Lys Pro Lys Asp Thr Leu Met Ile Ser Arg Thr Pro Glu Val Thr Cys
    130                 135                 140
Val Val Val Asp Val Glu Phe Glu Asp Pro Glu Val Lys Phe Asn Trp
145                 150                 155                 160
Tyr Val Asp Gly Val Glu Val His Asn Ala Lys Thr Lys Pro Arg Glu
                165                 170                 175
Glu Gln Tyr Asn Ser Thr Tyr Arg Val Val Ser Val Leu Thr Val Leu
            180                 185                 190
His Gln Asp Trp Leu Asn Gly Lys Glu Tyr Lys Cys Lys Val Thr Asn
        195                 200                 205
Lys Ala Leu Pro Ala Pro Ile Glu Lys Thr Ile Ser Lys Ala Lys Gly
    210                 215                 220
Gln Pro Arg Glu Pro Gln Val Tyr Thr Leu Pro Pro Ser Arg Glu Glu
225                 230                 235                 240
Met Thr Lys Asn Gln Val Ser Leu Thr Cys Leu Val Lys Gly Phe Tyr
                245                 250                 255
Pro Ser Asp Ile Ala Val Glu Trp Glu Ser Asn Gly Gln Pro Glu Asn
            260                 265                 270
Asn Tyr Lys Thr Thr Pro Pro Val Leu Asp Ser Asp Gly Ser Phe Phe
        275                 280                 285
Leu Tyr Ser Lys Leu Thr Val Asp Lys Ser Arg Trp Gln Gln Gly Asn
    290                 295                 300
Val Phe Ser Cys Ser Val Met His Glu Ala Leu His Asn His Tyr Thr
305                 310                 315                 320
Gln Lys Ser Leu Ser Leu Ser Pro Gly Lys
                325                 330

<210> SEQ ID NO 89
<211> LENGTH: 330
<212> TYPE: PRT
<213> ORGANISM: Artificial Sequence
<220> FEATURE:
<223> OTHER INFORMATION: Synthetic

<400> SEQUENCE: 89

Ala Ser Thr Lys Gly Pro Ser Val Phe Pro Leu Ala Pro Ser Ser Lys
1               5                   10                  15
Ser Thr Ser Gly Gly Thr Ala Ala Leu Gly Cys Leu Val Lys Asp Tyr
            20                  25                  30
Phe Pro Glu Pro Val Thr Val Ser Trp Asn Ser Gly Ala Leu Thr Ser
        35                  40                  45
Gly Val His Thr Phe Pro Ala Val Leu Gln Ser Ser Gly Leu Tyr Ser
    50                  55                  60
Leu Ser Ser Val Val Thr Val Pro Ser Ser Leu Gly Thr Gln Thr
65                  70                  75                  80
Tyr Ile Cys Asn Val Asn His Lys Pro Ser Asn Thr Lys Val Asp Lys
                85                  90                  95
Arg Val Glu Pro Lys Ser Cys Asp Lys Thr His Thr Cys Pro Pro Cys
            100                 105                 110
Pro Ala Pro Glu Leu Leu Gly Gly Pro Ser Val Phe Leu Phe Pro Pro
        115                 120                 125
Lys Pro Lys Asp Thr Leu Met Ile Ser Arg Thr Pro Glu Val Thr Cys
    130                 135                 140
Val Val Val Asp Val Ser His Glu Asp Pro Glu Val Gln Phe Lys Trp
```

```
                145                 150                 155                 160
Tyr Val Asp Gly Val Glu Val His Asn Ala Lys Thr Lys Pro Arg Glu
                165                 170                 175

Glu Gln Tyr Asn Ser Thr Phe Arg Val Val Ser Val Leu Thr Val Leu
                180                 185                 190

His Gln Asp Trp Leu Asn Gly Lys Glu Tyr Lys Cys Lys Val Ser Asn
                195                 200                 205

Lys Ala Leu Pro Ala Pro Ile Glu Lys Thr Ile Ser Lys Thr Lys Gly
210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Ser Ser Gly Gln Pro Glu Asn
                260                 265                 270

Asn Tyr Asn Thr Thr Pro Pro Met Leu Asp Ser Asp Gly Ser Phe Phe
                275                 280                 285

Leu Tyr Ser Lys Leu Thr Val Asp Lys Ser Arg Trp Gln Gln Gly Asn
                290                 295                 300

Ile Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 90
<211> LENGTH: 330
<212> TYPE: PRT
<213> ORGANISM: Artificial Sequence
<220> FEATURE:
<223> OTHER INFORMATION: Synthetic

<400> SEQUENCE: 90

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
                35                  40                  45

Gly Val His Thr Phe Pro Ala Val Leu Gln Ser Ser Gly Leu Tyr Ser
                50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Arg Val Glu Pro Lys Ser Cys Asp Lys Thr His Thr Cys Pro Pro Cys
                100                 105                 110

Pro Ala Pro Glu Leu Leu Gly Gly Pro Ser Val Phe Leu Phe Pro Pro
                115                 120                 125

Lys Pro Lys Asp Thr Leu Met Ile Ser Arg Thr Pro Glu Val Thr Cys
                130                 135                 140

Val Val Val Asp Val Ser His Glu Asp Pro Glu Val Gln Phe Lys Trp
145                 150                 155                 160

Tyr Val Asp Gly Val Glu Val His Asn Ala Lys Thr Lys Pro Arg Glu
                165                 170                 175

Glu Gln Tyr Asn Ser Thr Phe Arg Val Val Ser Val Leu Thr Val Leu
```

```
                180                 185                 190
His Gln Asp Trp Leu Asn Gly Lys Glu Tyr Lys Cys Lys Val Ser Asn
            195                 200                 205

Lys Ala Leu Pro Ala Pro Ile Glu Lys Thr Ile Ser Lys Thr Lys Gly
        210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Ser Gly Gln Pro Glu Asn
            260                 265                 270

Asn Tyr Asn Thr Thr Pro Pro Met Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Ile Phe Ser Cys Ser Val Met His Gly Ala Leu His Asn His Tyr Thr
305                 310                 315                 320

Gln Lys Ser Leu Ser Leu Ser Pro Gly Lys
                325                 330

<210> SEQ ID NO 91
<211> LENGTH: 8
<212> TYPE: PRT
<213> ORGANISM: Homo Sapiens

<400> SEQUENCE: 91

Gly Gly Ser Phe Ser Gly Tyr Tyr
1               5

<210> SEQ ID NO 92
<211> LENGTH: 7
<212> TYPE: PRT
<213> ORGANISM: Homo Sapiens

<400> SEQUENCE: 92

Ile Asn His Gly Gly Tyr Val
1               5

<210> SEQ ID NO 93
<211> LENGTH: 15
<212> TYPE: PRT
<213> ORGANISM: Homo Sapiens

<400> SEQUENCE: 93

Ala Arg Asp Tyr Gly Pro Gly Asn Tyr Asp Trp Tyr Phe Asp Leu
1               5                   10                  15

<210> SEQ ID NO 94
<211> LENGTH: 121
<212> TYPE: PRT
<213> ORGANISM: Homo Sapiens

<400> SEQUENCE: 94

Gln Val Gln Leu Gln Gln Trp Gly Ala Gly Leu Leu Lys Pro Ser Glu
1               5                   10                  15

Thr Leu Ser Leu Thr Cys Ala Val Tyr Gly Gly Ser Phe Ser Gly Tyr
            20                  25                  30

Tyr Trp Ser Trp Ile Arg Gln Ser Pro Glu Lys Gly Leu Glu Trp Ile
        35                  40                  45
```

```
Gly Glu Ile Asn His Gly Gly Tyr Val Thr Tyr Asn Pro Ser Leu Glu
 50                  55                  60

Ser Arg Val Thr Ile Ser Val Asp Thr Ser Lys Asn Gln Phe Ser Leu
 65                  70                  75                  80

Lys Leu Ser Ser Val Thr Ala Ala Asp Thr Ala Val Tyr Tyr Cys Ala
                 85                  90                  95

Arg Asp Tyr Gly Pro Gly Asn Tyr Asp Trp Tyr Phe Asp Leu Trp Gly
            100                 105                 110

Arg Gly Thr Leu Val Thr Val Ser Ser
            115                 120
```

```
<210> SEQ ID NO 95
<211> LENGTH: 6
<212> TYPE: PRT
<213> ORGANISM: Homo Sapiens

<400> SEQUENCE: 95

Gln Ser Val Ser Ser Tyr
1               5
```

```
<210> SEQ ID NO 96
<211> LENGTH: 11
<212> TYPE: PRT
<213> ORGANISM: Homo Sapiens

<400> SEQUENCE: 96

Gln Gln Arg Ser Asn Trp Pro Pro Ala Leu Thr
1               5                   10
```

```
<210> SEQ ID NO 97
<211> LENGTH: 109
<212> TYPE: PRT
<213> ORGANISM: Homo Sapiens

<400> SEQUENCE: 97

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
                20                  25                  30

Leu Ala Trp Tyr Gln Gln Lys Pro Gly Gln Ala Pro Arg Leu Leu Ile
            35                  40                  45

Tyr Asp Ala Ser Asn Arg Ala Thr Gly Ile Pro Ala Arg Phe Ser Gly
 50                  55                  60

Ser Gly Ser Gly Thr Asp Phe Thr Leu Thr Ile Ser Ser Leu Glu Pro
 65                  70                  75                  80

Glu Asp Phe Ala Val Tyr Tyr Cys Gln Gln Arg Ser Asn Trp Pro Pro
                 85                  90                  95

Ala Leu Thr Phe Gly Gly Gly Thr Lys Val Glu Ile Lys
            100                 105
```

```
<210> SEQ ID NO 98
<211> LENGTH: 8
<212> TYPE: PRT
<213> ORGANISM: Artificial Sequence
<220> FEATURE:
<223> OTHER INFORMATION: Synthetic

<400> SEQUENCE: 98

Gly Tyr Thr Phe Lys Asp Tyr Thr
1               5
```

<210> SEQ ID NO 99
<211> LENGTH: 8
<212> TYPE: PRT
<213> ORGANISM: Artificial Sequence
<220> FEATURE:
<223> OTHER INFORMATION: Synthetic

<400> SEQUENCE: 99

Ile Tyr Pro Asn Asn Gly Gly Ser
1               5

<210> SEQ ID NO 100
<211> LENGTH: 14
<212> TYPE: PRT
<213> ORGANISM: Artificial Sequence
<220> FEATURE:
<223> OTHER INFORMATION: Synthetic

<400> SEQUENCE: 100

Ala Arg Met Gly Tyr His Gly Pro His Leu Asp Phe Asp Val
1               5                   10

<210> SEQ ID NO 101
<211> LENGTH: 121
<212> TYPE: PRT
<213> ORGANISM: Artificial Sequence
<220> FEATURE:
<223> OTHER INFORMATION: Synthetic

<400> SEQUENCE: 101

Gln Val Gln Leu Val Gln Ser Gly Ala Glu Val Lys Lys Pro Gly Ser
1               5                   10                  15

Ser Val Lys Val Ser Cys Lys Ala Ser Gly Tyr Thr Phe Lys Asp Tyr
            20                  25                  30

Thr Met His Trp Val Arg Gln Ala Pro Gly Gln Gly Leu Glu Trp Ile
        35                  40                  45

Gly Gly Ile Tyr Pro Asn Asn Gly Gly Ser Thr Tyr Asn Gln Asn Phe
    50                  55                  60

Lys Asp Arg Val Thr Leu Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Met Gly Tyr His Gly Pro His Leu Asp Phe Asp Val Trp Gly
            100                 105                 110

Gln Gly Thr Thr Val Thr Val Ser Ser
        115                 120

<210> SEQ ID NO 102
<211> LENGTH: 6
<212> TYPE: PRT
<213> ORGANISM: Artificial Sequence
<220> FEATURE:
<223> OTHER INFORMATION: Synthetic

<400> SEQUENCE: 102

Gln Asp Val Gly Ala Ala
1               5

<210> SEQ ID NO 103
<211> LENGTH: 9
<212> TYPE: PRT
<213> ORGANISM: Artificial Sequence
<220> FEATURE:

```
<223> OTHER INFORMATION: Synthetic

<400> SEQUENCE: 103

Gln Gln Tyr Ile Asn Tyr Pro Leu Thr
1               5

<210> SEQ ID NO 104
<211> LENGTH: 107
<212> TYPE: PRT
<213> ORGANISM: Artificial Sequence
<220> FEATURE:
<223> OTHER INFORMATION: Synthetic

<400> SEQUENCE: 104

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asp Val Gly Ala Ala
            20                  25                  30

Val Ala Trp Tyr Gln Gln Lys Pro Gly Lys Ala Pro Lys Leu Leu Ile
        35                  40                  45

Tyr Trp Ala Ser Thr Arg His Thr Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Ile Asn Tyr Pro Leu
                85                  90                  95

Thr Phe Gly Gly Gly Thr Lys Val Glu Ile Lys
            100                 105

<210> SEQ ID NO 105
<211> LENGTH: 8
<212> TYPE: PRT
<213> ORGANISM: Artificial Sequence
<220> FEATURE:
<223> OTHER INFORMATION: Synthetic

<400> SEQUENCE: 105

Gly Tyr Ser Phe Ser Thr Tyr Trp
1               5

<210> SEQ ID NO 106
<211> LENGTH: 8
<212> TYPE: PRT
<213> ORGANISM: Artificial Sequence
<220> FEATURE:
<223> OTHER INFORMATION: Synthetic

<400> SEQUENCE: 106

Ile Tyr Pro Gly Asp Ser Tyr Thr
1               5

<210> SEQ ID NO 107
<211> LENGTH: 9
<212> TYPE: PRT
<213> ORGANISM: Artificial Sequence
<220> FEATURE:
<223> OTHER INFORMATION: Synthetic

<400> SEQUENCE: 107

Ala Arg Gly Tyr Gly Ile Phe Asp Tyr
1               5

<210> SEQ ID NO 108
```

```
<211> LENGTH: 116
<212> TYPE: PRT
<213> ORGANISM: Artificial Sequence
<220> FEATURE:
<223> OTHER INFORMATION: Synthetic

<400> SEQUENCE: 108

Glu Val Gln Leu Val Gln Ser Gly Ala Glu Val Lys Lys Pro Gly Glu
1               5                   10                  15

Ser Leu Arg Ile Ser Cys Lys Gly Ser Gly Tyr Ser Phe Ser Thr Tyr
            20                  25                  30

Trp Ile Ser Trp Val Arg Gln Met Pro Gly Lys Gly Leu Glu Trp Met
        35                  40                  45

Gly Lys Ile Tyr Pro Gly Asp Ser Tyr Thr Asn Tyr Ser Pro Ser Phe
    50                  55                  60

Gln Gly Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg Gly Tyr Gly Ile Phe Asp Tyr Trp Gly Gln Gly Thr Leu Val
            100                 105                 110

Thr Val Ser Ser
        115

<210> SEQ ID NO 109
<211> LENGTH: 6
<212> TYPE: PRT
<213> ORGANISM: Artificial Sequence
<220> FEATURE:
<223> OTHER INFORMATION: Synthetic

<400> SEQUENCE: 109

Asn Ile Gly Asp Gln Tyr
1               5

<210> SEQ ID NO 110
<211> LENGTH: 6
<212> TYPE: PRT
<213> ORGANISM: Artificial Sequence
<220> FEATURE:
<223> OTHER INFORMATION: Synthetic

<400> SEQUENCE: 110

Asn Ile Gly Asp Gln Tyr
1               5

<210> SEQ ID NO 111
<211> LENGTH: 108
<212> TYPE: PRT
<213> ORGANISM: Artificial Sequence
<220> FEATURE:
<223> OTHER INFORMATION: Synthetic

<400> SEQUENCE: 111

Ser Tyr Glu Leu Thr Gln Pro Pro Ser Val Ser Val Ser Pro Gly Gln
1               5                   10                  15

Thr Ala Ser Ile Thr Cys Ser Gly Asp Asn Ile Gly Asp Gln Tyr Ala
            20                  25                  30

His Trp Tyr Gln Gln Lys Pro Gly Gln Ser Pro Val Leu Val Ile Tyr
        35                  40                  45

Gln Asp Lys Asn Arg Pro Ser Gly Ile Pro Glu Arg Phe Ser Gly Ser
    50                  55                  60
```

Asn Ser Gly Asn Thr Ala Thr Leu Thr Ile Ser Gly Thr Gln Ala Met
65                  70                  75                  80

Asp Glu Ala Asp Tyr Tyr Cys Ala Thr Tyr Thr Gly Phe Gly Ser Leu
                85                  90                  95

Ala Val Phe Gly Gly Gly Thr Lys Leu Thr Val Leu
            100                 105

<210> SEQ ID NO 112
<211> LENGTH: 8
<212> TYPE: PRT
<213> ORGANISM: Artificial Sequence
<220> FEATURE:
<223> OTHER INFORMATION: Synthetic

<400> SEQUENCE: 112

Gly Tyr Thr Phe Thr Gly Tyr Tyr
1               5

<210> SEQ ID NO 113
<211> LENGTH: 8
<212> TYPE: PRT
<213> ORGANISM: Artificial Sequence
<220> FEATURE:
<223> OTHER INFORMATION: Synthetic

<400> SEQUENCE: 113

Ile Asn Pro Asp Ser Gly Gly Thr
1               5

<210> SEQ ID NO 114
<211> LENGTH: 19
<212> TYPE: PRT
<213> ORGANISM: Artificial Sequence
<220> FEATURE:
<223> OTHER INFORMATION: Synthetic

<400> SEQUENCE: 114

Ala Arg Asp Gln Pro Leu Gly Tyr Cys Thr Asn Gly Val Cys Ser Tyr
1               5                   10                  15

Phe Asp Tyr

<210> SEQ ID NO 115
<211> LENGTH: 126
<212> TYPE: PRT
<213> ORGANISM: Artificial Sequence
<220> FEATURE:
<223> OTHER INFORMATION: Synthetic

<400> SEQUENCE: 115

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
                20                  25                  30

Tyr Met His Trp Val Arg Gln Ala Pro Gly Gln Gly Leu Glu Trp Met
            35                  40                  45

Gly Trp Ile Asn Pro Asp Ser Gly Gly Thr Asn Tyr Ala Gln Lys Phe
        50                  55                  60

Gln Gly Arg Val Thr Met Thr Arg Asp Thr Ser Ile Ser Thr Ala Tyr
65                  70                  75                  80

Met Glu Leu Asn Arg Leu Arg Ser Asp Asp Thr Ala Val Tyr Tyr Cys
                85                  90                  95

Ala Arg Asp Gln Pro Leu Gly Tyr Cys Thr Asn Gly Val Cys Ser Tyr
            100                 105                 110

Phe Asp Tyr Trp Gly Gln Gly Thr Leu Val Thr Val Ser Ser
        115                 120                 125

<210> SEQ ID NO 116
<211> LENGTH: 6
<212> TYPE: PRT
<213> ORGANISM: Artificial Sequence
<220> FEATURE:
<223> OTHER INFORMATION: Synthetic

<400> SEQUENCE: 116

Gln Gly Ile Tyr Ser Trp
1               5

<210> SEQ ID NO 117
<211> LENGTH: 9
<212> TYPE: PRT
<213> ORGANISM: Artificial Sequence
<220> FEATURE:
<223> OTHER INFORMATION: Synthetic

<400> SEQUENCE: 117

Gln Gln Ala Asn Ile Phe Pro Leu Thr
1               5

<210> SEQ ID NO 118
<211> LENGTH: 107
<212> TYPE: PRT
<213> ORGANISM: Artificial Sequence
<220> FEATURE:
<223> OTHER INFORMATION: Synthetic

<400> SEQUENCE: 118

Asp Ile Gln Met Thr Gln Ser Pro Ser Ser Val Ser Ala Ser Val Gly
1               5                   10                  15

Asp Arg Val Thr Ile Thr Cys Arg Ala Ser Gln Gly Ile Tyr Ser Trp
            20                  25                  30

Leu Ala Trp Tyr Gln Gln Lys Pro Gly Lys Ala Pro Asn Leu Leu Ile
        35                  40                  45

Tyr Thr Ala Ser Thr Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ala Asn Ile Phe Pro Leu
                85                  90                  95

Thr Phe Gly Gly Gly Thr Lys Val Glu Ile Lys
            100                 105

<210> SEQ ID NO 119
<211> LENGTH: 8
<212> TYPE: PRT
<213> ORGANISM: Artificial Sequence
<220> FEATURE:
<223> OTHER INFORMATION: Synthetic

<400> SEQUENCE: 119

Gly Tyr Ser Phe Thr Gly Tyr Tyr
1               5

<210> SEQ ID NO 120
<211> LENGTH: 8

```
<212> TYPE: PRT
<213> ORGANISM: Artificial Sequence
<220> FEATURE:
<223> OTHER INFORMATION: Synthetic

<400> SEQUENCE: 120

Val Ile Pro Asn Ala Gly Gly Thr
1               5

<210> SEQ ID NO 121
<211> LENGTH: 7
<212> TYPE: PRT
<213> ORGANISM: Artificial Sequence
<220> FEATURE:
<223> OTHER INFORMATION: Synthetic

<400> SEQUENCE: 121

Ala Arg Glu Gly Ile Tyr Trp
1               5

<210> SEQ ID NO 122
<211> LENGTH: 114
<212> TYPE: PRT
<213> ORGANISM: Artificial Sequence
<220> FEATURE:
<223> OTHER INFORMATION: Synthetic

<400> SEQUENCE: 122

Glu Val Gln Leu Val Glu Ser Gly Gly Gly Leu Val Gln Pro Gly Gly
1               5                   10                  15

Ser Leu Arg Leu Ser Cys Ala Ala Ser Gly Tyr Ser Phe Thr Gly Tyr
            20                  25                  30

Tyr Ile His Trp Val Arg Gln Ala Pro Gly Lys Gly Leu Glu Trp Val
        35                  40                  45

Ala Arg Val Ile Pro Asn Ala Gly Gly Thr Ser Tyr Asn Gln Lys Phe
    50                  55                  60

Lys Gly Arg Phe Thr Leu Ser Val Asp Asn Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Arg Glu Gly Ile Tyr Trp Trp Gly Gln Gly Thr Leu Val Thr Val
            100                 105                 110

Ser Ser

<210> SEQ ID NO 123
<211> LENGTH: 11
<212> TYPE: PRT
<213> ORGANISM: Artificial Sequence
<220> FEATURE:
<223> OTHER INFORMATION: Synthetic

<400> SEQUENCE: 123

Gln Ser Leu Val His Ser Asn Gly Asn Thr Phe
1               5                   10

<210> SEQ ID NO 124
<211> LENGTH: 9
<212> TYPE: PRT
<213> ORGANISM: Artificial Sequence
<220> FEATURE:
<223> OTHER INFORMATION: Synthetic

<400> SEQUENCE: 124
```

Ser Gln Thr Thr His Val Pro Trp Thr
1               5

<210> SEQ ID NO 125
<211> LENGTH: 112
<212> TYPE: PRT
<213> ORGANISM: Artificial Sequence
<220> FEATURE:
<223> OTHER INFORMATION: Synthetic

<400> SEQUENCE: 125

Asp Ile Gln Met Thr Gln Ser Pro Ser Ser Leu Ser Ala Ser Val Gly
1               5                   10                  15

Asp Arg Val Thr Ile Thr Cys Arg Ser Ser Gln Ser Leu Val His Ser
            20                  25                  30

Asn Gly Asn Thr Phe Leu His Trp Tyr Gln Gln Lys Pro Gly Lys Ala
        35                  40                  45

Pro Lys Leu Leu Ile Tyr Thr Val Ser Asn Arg Phe Ser Gly Val Pro
    50                  55                  60

Ser Arg Phe Ser Gly Ser Gly Ser Gly Thr Asp Phe Thr Leu Thr Ile
65                  70                  75                  80

Ser Ser Leu Gln Pro Glu Asp Phe Ala Thr Tyr Phe Cys Ser Gln Thr
                85                  90                  95

Thr His Val Pro Trp Thr Phe Gly Gln Gly Thr Lys Val Glu Ile Lys
            100                 105                 110

<210> SEQ ID NO 126
<211> LENGTH: 8
<212> TYPE: PRT
<213> ORGANISM: Artificial Sequence
<220> FEATURE:
<223> OTHER INFORMATION: Synthetic

<400> SEQUENCE: 126

Gly Phe Thr Phe Asn Thr Asn Ala
1               5

<210> SEQ ID NO 127
<211> LENGTH: 10
<212> TYPE: PRT
<213> ORGANISM: Artificial Sequence
<220> FEATURE:
<223> OTHER INFORMATION: Synthetic

<400> SEQUENCE: 127

Ile Arg Ser Lys Ser Asn Asn Tyr Ala Thr
1               5                   10

<210> SEQ ID NO 128
<211> LENGTH: 6
<212> TYPE: PRT
<213> ORGANISM: Artificial Sequence
<220> FEATURE:
<223> OTHER INFORMATION: Synthetic

<400> SEQUENCE: 128

Val Thr Asp Gly Tyr Tyr
1               5

<210> SEQ ID NO 129
<211> LENGTH: 115
<212> TYPE: PRT
<213> ORGANISM: Artificial Sequence
<220> FEATURE:

<223> OTHER INFORMATION: Synthetic

<400> SEQUENCE: 129

Glu Val Gln Leu Val Glu Thr Gly Gly Gly Leu Val Gln Pro Lys Gly
1               5                   10                  15

Ser Leu Lys Leu Ser Cys Ala Ala Ser Gly Phe Thr Phe Asn Thr Asn
            20                  25                  30

Ala Met Asn Trp Val Arg Gln Ala Pro Gly Lys Gly Leu Glu Trp Val
        35                  40                  45

Ala Arg Ile Arg Ser Lys Ser Asn Asn Tyr Ala Thr Tyr Tyr Ala Glu
    50                  55                  60

Ser Val Lys Asp Arg Phe Thr Ile Ser Arg Asp Asp Ser Gln Ser Met
65                  70                  75                  80

Leu Tyr Leu Gln Met Asn Asn Leu Lys Ala Glu Asp Thr Ala Met Tyr
                85                  90                  95

Tyr Cys Val Thr Asp Gly Tyr Tyr Trp Gly Gln Gly Thr Thr Leu Thr
            100                 105                 110

Val Ser Ser
        115

<210> SEQ ID NO 130
<211> LENGTH: 10
<212> TYPE: PRT
<213> ORGANISM: Artificial Sequence
<220> FEATURE:
<223> OTHER INFORMATION: Synthetic

<400> SEQUENCE: 130

Glu Ser Val Glu Tyr Tyr Gly Thr Ser Leu
1               5                   10

<210> SEQ ID NO 131
<211> LENGTH: 9
<212> TYPE: PRT
<213> ORGANISM: Artificial Sequence
<220> FEATURE:
<223> OTHER INFORMATION: Synthetic

<400> SEQUENCE: 131

Gln Gln Ser Thr Lys Val Pro Trp Thr
1               5

<210> SEQ ID NO 132
<211> LENGTH: 111
<212> TYPE: PRT
<213> ORGANISM: Artificial Sequence
<220> FEATURE:
<223> OTHER INFORMATION: Synthetic

<400> SEQUENCE: 132

Asp Ile Val Leu Thr Gln Ser Pro Ala Ser Leu Ala Val Ser Leu Gly
1               5                   10                  15

Gln Arg Ala Thr Ile Ser Cys Arg Ala Ser Glu Ser Val Glu Tyr Tyr
            20                  25                  30

Gly Thr Ser Leu Met Gln Trp Tyr Gln Gln Lys Pro Gly Gln Pro Pro
        35                  40                  45

Lys Leu Leu Ile Tyr Val Ala Ser Asn Val Glu Ser Gly Val Pro Ala
    50                  55                  60

Arg Phe Ser Gly Ser Gly Ser Gly Thr Asp Phe Ser Leu Asn Ile His
65                  70                  75                  80

```
Pro Val Glu Glu Asp Asp Ile Ala Met Tyr Phe Cys Gln Gln Ser Thr
                85                  90                  95

Lys Val Pro Trp Thr Phe Gly Gly Gly Thr Lys Leu Glu Ile Lys
            100                 105                 110

<210> SEQ ID NO 133
<211> LENGTH: 8
<212> TYPE: PRT
<213> ORGANISM: Mus Musculus

<400> SEQUENCE: 133

Gly Tyr Thr Phe Thr Ser Tyr Trp
1               5

<210> SEQ ID NO 134
<211> LENGTH: 8
<212> TYPE: PRT
<213> ORGANISM: Mus Musculus

<400> SEQUENCE: 134

Ile Asp Pro Ser Asp Ser Tyr Thr
1               5

<210> SEQ ID NO 135
<211> LENGTH: 14
<212> TYPE: PRT
<213> ORGANISM: Mus Musculus

<400> SEQUENCE: 135

Ala Arg Asn Arg Asp Tyr Ser Asn Asn Trp Tyr Phe Asp Val
1               5                   10

<210> SEQ ID NO 136
<211> LENGTH: 121
<212> TYPE: PRT
<213> ORGANISM: Mus Musculus

<400> SEQUENCE: 136

Gln Val Gln Leu Gln Gln Pro Gly Ala Glu Leu Val Lys Pro Gly Ala
1               5                   10                  15

Ser Val Lys Leu Ser Cys Lys Ala Ser Gly Tyr Thr Phe Thr Ser Tyr
            20                  25                  30

Trp Met Gln Trp Val Lys Gln Arg Pro Gly Gln Gly Leu Glu Trp Ile
        35                  40                  45

Gly Glu Ile Asp Pro Ser Asp Ser Tyr Thr Asn Tyr Asn Gln Lys Phe
    50                  55                  60

Lys Gly Lys Ala Thr Leu Thr Val Asp Thr Ser Ser Ser Thr Ala Tyr
65                  70                  75                  80

Met Gln Leu Ser Ser Leu Thr Ser Glu Asp Ser Ala Val Tyr Tyr Cys
                85                  90                  95

Ala Arg Asn Arg Asp Tyr Ser Asn Asn Trp Tyr Phe Asp Val Trp Gly
            100                 105                 110

Thr Gly Thr Thr Val Thr Val Ser Ser
        115                 120

<210> SEQ ID NO 137
<211> LENGTH: 10
<212> TYPE: PRT
<213> ORGANISM: Mus Musculus

<400> SEQUENCE: 137
```

```
Gln Ser Val Asp Tyr Asp Gly Asp Ser Tyr
1               5                   10
```

<210> SEQ ID NO 138
<211> LENGTH: 9
<212> TYPE: PRT
<213> ORGANISM: Mus Musculus

<400> SEQUENCE: 138

```
Gln Gln Ser Asn Glu Asp Pro Arg Thr
1               5
```

<210> SEQ ID NO 139
<211> LENGTH: 111
<212> TYPE: PRT
<213> ORGANISM: Mus Musculus

<400> SEQUENCE: 139

```
Asp Ile Val Leu Thr Gln Ser Pro Ala Ser Leu Ala Val Ser Leu Gly
1               5                   10                  15

Gln Arg Ala Thr Ile Ser Cys Lys Ala Ser Gln Ser Val Asp Tyr Asp
                20                  25                  30

Gly Asp Ser Tyr Met Asn Trp Tyr Gln Gln Lys Pro Gly Gln Pro Pro
            35                  40                  45

Lys Leu Leu Ile Tyr Ala Ala Ser Asn Leu Glu Ser Gly Ile Pro Ala
        50                  55                  60

Arg Phe Ser Gly Ser Gly Ser Gly Thr Asp Phe Thr Leu Asn Ile His
65                  70                  75                  80

Pro Val Glu Glu Glu Asp Ala Ala Thr Tyr Tyr Cys Gln Gln Ser Asn
                85                  90                  95

Glu Asp Pro Arg Thr Phe Gly Gly Gly Thr Lys Leu Glu Ile Lys
            100                 105                 110
```

<210> SEQ ID NO 140
<211> LENGTH: 8
<212> TYPE: PRT
<213> ORGANISM: Mus Musculus

<400> SEQUENCE: 140

```
Gly Phe Asn Ile Lys Asp Thr Tyr
1               5
```

<210> SEQ ID NO 141
<211> LENGTH: 8
<212> TYPE: PRT
<213> ORGANISM: Mus Musculus

<400> SEQUENCE: 141

```
Ile Asp Pro Ala Asn Gly Asn Thr
1               5
```

<210> SEQ ID NO 142
<211> LENGTH: 12
<212> TYPE: PRT
<213> ORGANISM: Mus Musculus

<400> SEQUENCE: 142

```
Ala Tyr Tyr Tyr Val Ser Asn Ala Trp Phe Thr Tyr
1               5                   10
```

<210> SEQ ID NO 143
<211> LENGTH: 119

```
<212> TYPE: PRT
<213> ORGANISM: Mus Musculus

<400> SEQUENCE: 143

Glu Val Gln Leu Gln Gln Ser Gly Ala Glu Leu Val Lys Pro Gly Ala
1               5                   10                  15

Ser Val Lys Leu Ser Cys Thr Ala Ser Gly Phe Asn Ile Lys Asp Thr
            20                  25                  30

Tyr Met His Trp Val Lys Gln Arg Pro Glu Gln Gly Leu Glu Trp Ile
        35                  40                  45

Gly Arg Ile Asp Pro Ala Asn Gly Asn Thr Lys Tyr Asp Pro Lys Phe
    50                  55                  60

Gln Gly Lys Ala Thr Ile Thr Ala Asp Thr Ser Ser Asn Thr Ala Tyr
65                  70                  75                  80

Leu Gln Leu Ser Ser Leu Thr Ser Glu Asp Thr Ala Val Tyr Tyr Cys
                85                  90                  95

Ala Tyr Tyr Tyr Val Ser Asn Ala Trp Phe Thr Tyr Trp Gly Gln Gly
            100                 105                 110

Thr Leu Val Thr Val Ser Ala
        115

<210> SEQ ID NO 144
<211> LENGTH: 6
<212> TYPE: PRT
<213> ORGANISM: Mus Musculus

<400> SEQUENCE: 144

Glu Asn Ile Tyr Ser Asn
1               5

<210> SEQ ID NO 145
<211> LENGTH: 8
<212> TYPE: PRT
<213> ORGANISM: Mus Musculus

<400> SEQUENCE: 145

Gln His Phe Trp Gly Thr Trp Thr
1               5

<210> SEQ ID NO 146
<211> LENGTH: 106
<212> TYPE: PRT
<213> ORGANISM: Mus Musculus

<400> SEQUENCE: 146

Asp Ile Gln Met Thr Gln Ser Pro Ala Ser Leu Ser Val Ser Val Gly
1               5                   10                  15

Glu Thr Val Thr Ile Thr Cys Arg Ala Ser Glu Asn Ile Tyr Ser Asn
            20                  25                  30

Leu Glu Trp Tyr Gln Gln Lys Gln Gly Lys Ser Pro Gln Leu Leu Val
        35                  40                  45

Tyr Ala Ala Thr Asn Leu Ala Asp Gly Val Pro Ser Arg Phe Ser Gly
    50                  55                  60

Ser Gly Ser Gly Thr Gln Tyr Ser Leu Lys Ile Asn Ser Leu Gln Ser
65                  70                  75                  80

Glu Asp Phe Gly Ser Tyr Tyr Cys Gln His Phe Trp Gly Thr Trp Thr
                85                  90                  95

Phe Gly Gly Gly Thr Lys Leu Glu Ile Lys
            100                 105
```

<210> SEQ ID NO 147
<211> LENGTH: 10
<212> TYPE: PRT
<213> ORGANISM: Artificial Sequence
<220> FEATURE:
<223> OTHER INFORMATION: Synthetic

<400> SEQUENCE: 147

Gly Ala Ser Ile Ser Ala Asn Ser Tyr Tyr
1               5                   10

<210> SEQ ID NO 148
<211> LENGTH: 12
<212> TYPE: PRT
<213> ORGANISM: Artificial Sequence
<220> FEATURE:
<223> OTHER INFORMATION: Synthetic

<400> SEQUENCE: 148

Ile Ala Tyr Arg Gly Asn Ser Asn Ser Gly Ser Thr
1               5                   10

<210> SEQ ID NO 149
<211> LENGTH: 19
<212> TYPE: PRT
<213> ORGANISM: Artificial Sequence
<220> FEATURE:
<223> OTHER INFORMATION: Synthetic

<400> SEQUENCE: 149

Ala Arg Arg Gln Leu Leu Asp Asp Gly Thr Gly Tyr Gln Trp Ala Ala
1               5                   10                  15

Phe Asp Val

<210> SEQ ID NO 150
<211> LENGTH: 132
<212> TYPE: PRT
<213> ORGANISM: Artificial Sequence
<220> FEATURE:
<223> OTHER INFORMATION: Synthetic

<400> SEQUENCE: 150

Gln Leu Gln Leu Gln Glu Ser Gly Pro Gly Leu Val Lys Pro Ser Glu
1               5                   10                  15

Thr Leu Ser Leu Thr Cys Thr Val Ser Gly Ala Ser Ile Ser Ala Asn
                20                  25                  30

Ser Tyr Tyr Gly Val Trp Val Arg Gln Ser Pro Gly Lys Gly Leu Glu
            35                  40                  45

Trp Val Gly Ser Ile Ala Tyr Arg Gly Asn Ser Asn Ser Gly Ser Thr
    50                  55                  60

Tyr Tyr Asn Pro Ser Leu Lys Ser Arg Ala Thr Val Ser Val Asp Thr
65                  70                  75                  80

Ser Lys Asn Gln Val Ser Leu Arg Leu Thr Ser Val Thr Ala Ala Asp
                85                  90                  95

Thr Ala Leu Tyr Tyr Cys Ala Arg Arg Gln Leu Leu Asp Asp Gly Thr
            100                 105                 110

Gly Tyr Gln Trp Ala Ala Phe Asp Val Trp Gly Gln Gly Thr Met Val
        115                 120                 125

Thr Val Ser Ser
        130

<210> SEQ ID NO 151
<211> LENGTH: 8
<212> TYPE: PRT
<213> ORGANISM: Artificial Sequence
<220> FEATURE:
<223> OTHER INFORMATION: Synthetic

<400> SEQUENCE: 151

Ser Phe Asn Ile Gly Arg Tyr Pro
1               5

<210> SEQ ID NO 152
<211> LENGTH: 11
<212> TYPE: PRT
<213> ORGANISM: Artificial Sequence
<220> FEATURE:
<223> OTHER INFORMATION: Synthetic

<400> SEQUENCE: 152

Ser Thr Trp Asp Asp Thr Leu Lys Gly Trp Val
1               5                   10

<210> SEQ ID NO 153
<211> LENGTH: 110
<212> TYPE: PRT
<213> ORGANISM: Artificial Sequence
<220> FEATURE:
<223> OTHER INFORMATION: Synthetic

<400> SEQUENCE: 153

Gln Ser Val Leu Thr Gln Pro Pro Ser Val Ser Glu Ala Pro Arg Gln
1               5                   10                  15

Thr Val Thr Ile Ser Cys Ser Gly Asn Ser Phe Asn Ile Gly Arg Tyr
            20                  25                  30

Pro Val Asn Trp Tyr Gln Gln Leu Pro Gly Lys Ala Pro Lys Leu Leu
        35                  40                  45

Ile Tyr Tyr Asn Asn Leu Arg Phe Ser Gly Val Ser Asp Arg Phe Ser
    50                  55                  60

Gly Ser Lys Ser Gly Thr Ser Ala Ser Leu Ala Ile Arg Asp Leu Leu
65                  70                  75                  80

Ser Glu Asp Glu Ala Asp Tyr Tyr Cys Ser Thr Trp Asp Asp Thr Leu
                85                  90                  95

Lys Gly Trp Val Phe Gly Gly Gly Thr Lys Val Thr Val Leu
            100                 105                 110

<210> SEQ ID NO 154
<211> LENGTH: 8
<212> TYPE: PRT
<213> ORGANISM: Artificial Sequence
<220> FEATURE:
<223> OTHER INFORMATION: Synthetic

<400> SEQUENCE: 154

Gly Phe Thr Phe Ser Ser Tyr Ala
1               5

<210> SEQ ID NO 155
<211> LENGTH: 7
<212> TYPE: PRT
<213> ORGANISM: Artificial Sequence
<220> FEATURE:
<223> OTHER INFORMATION: Synthetic

<400> SEQUENCE: 155

```
Ile Ser Ser Gly Gly Thr Thr
1               5

<210> SEQ ID NO 156
<211> LENGTH: 12
<212> TYPE: PRT
<213> ORGANISM: Artificial Sequence
<220> FEATURE:
<223> OTHER INFORMATION: Synthetic

<400> SEQUENCE: 156

Ala Arg Val Gly Gly Tyr Tyr Asp Ser Met Asp Tyr
1               5                   10

<210> SEQ ID NO 157
<211> LENGTH: 118
<212> TYPE: PRT
<213> ORGANISM: Artificial Sequence
<220> FEATURE:
<223> OTHER INFORMATION: Synthetic

<400> SEQUENCE: 157

Glu Val Asn Leu Val Glu Ser Gly Gly Leu Val Lys Pro Gly Gly
1               5                   10                  15

Ser Leu Lys Val Ser Cys Ala Ala Ser Gly Phe Thr Phe Ser Ser Tyr
                20                  25                  30

Ala Met Ser Trp Val Arg Gln Thr Pro Glu Lys Arg Leu Glu Trp Val
            35                  40                  45

Ala Ser Ile Ser Ser Gly Gly Thr Thr Tyr Tyr Pro Asp Ser Val Lys
        50                  55                  60

Gly Arg Phe Thr Ile Ser Arg Asp Asn Ala Arg Asn Ile Leu Tyr Leu
65                  70                  75                  80

Gln Met Ser Ser Leu Arg Ser Glu Asp Thr Ala Met Tyr Tyr Cys Ala
                85                  90                  95

Arg Val Gly Gly Tyr Tyr Asp Ser Met Asp Tyr Trp Gly Gln Gly Ile
            100                 105                 110

Ser Val Thr Asp Ser Ser
        115

<210> SEQ ID NO 158
<211> LENGTH: 10
<212> TYPE: PRT
<213> ORGANISM: Artificial Sequence
<220> FEATURE:
<223> OTHER INFORMATION: Synthetic

<400> SEQUENCE: 158

Glu Ser Val Asp Asn Tyr Gly Val Ser Phe
1               5                   10

<210> SEQ ID NO 159
<211> LENGTH: 9
<212> TYPE: PRT
<213> ORGANISM: Artificial Sequence
<220> FEATURE:
<223> OTHER INFORMATION: Synthetic

<400> SEQUENCE: 159

Gln Gln Thr Lys Glu Val Thr Trp Thr
1               5

<210> SEQ ID NO 160
```

<211> LENGTH: 111
<212> TYPE: PRT
<213> ORGANISM: Artificial Sequence
<220> FEATURE:
<223> OTHER INFORMATION: Synthetic

<400> SEQUENCE: 160

```
Asp Ile Val Leu Thr Gln Ser Pro Ala Ser Leu Ala Val Ser Leu Gly
1               5                   10                  15
Gln Arg Ala Thr Ile Ser Cys Arg Ala Ser Glu Ser Val Asp Asn Tyr
            20                  25                  30
Gly Val Ser Phe Met Asn Trp Phe Gln Gln Lys Pro Gly Gln Pro Pro
        35                  40                  45
Lys Leu Leu Ile Tyr Ala Ala Ser Asn Gln Gly Ser Gly Val Pro Ala
    50                  55                  60
Arg Phe Ser Gly Ser Gly Ser Gly Thr Asp Phe Ser Leu Asn Ile His
65                  70                  75                  80
Pro Met Glu Glu Asp Asp Thr Ala Met Tyr Phe Cys Gln Gln Thr Lys
                85                  90                  95
Glu Val Thr Trp Thr Phe Gly Gly Gly Thr Lys Leu Glu Ile Lys
            100                 105                 110
```

<210> SEQ ID NO 161
<211> LENGTH: 8
<212> TYPE: PRT
<213> ORGANISM: Artificial Sequence
<220> FEATURE:
<223> OTHER INFORMATION: Synthetic

<400> SEQUENCE: 161

```
Gly Tyr Thr Phe Thr Asp Tyr Ala
1               5
```

<210> SEQ ID NO 162
<211> LENGTH: 8
<212> TYPE: PRT
<213> ORGANISM: Artificial Sequence
<220> FEATURE:
<223> OTHER INFORMATION: Synthetic

<400> SEQUENCE: 162

```
Ile Arg Thr Tyr Ser Gly Asp Val
1               5
```

<210> SEQ ID NO 163
<211> LENGTH: 11
<212> TYPE: PRT
<213> ORGANISM: Artificial Sequence
<220> FEATURE:
<223> OTHER INFORMATION: Synthetic

<400> SEQUENCE: 163

```
Ala Lys Ser Gly Thr Val Arg Gly Phe Ala Tyr
1               5                   10
```

<210> SEQ ID NO 164
<211> LENGTH: 118
<212> TYPE: PRT
<213> ORGANISM: Artificial Sequence
<220> FEATURE:
<223> OTHER INFORMATION: Synthetic

<400> SEQUENCE: 164

```
Gln Val Gln Leu Leu Gln Ser Gly Thr Glu Leu Val Arg Pro Gly Val
```

```
                1               5                  10                  15
Ser Val Lys Ile Ser Cys Lys Gly Ser Gly Tyr Thr Phe Thr Asp Tyr
                20                  25                  30

Ala Met Tyr Trp Val Lys Gln Ser His Ala Lys Ser Leu Glu Trp Ile
            35                  40                  45

Gly Val Ile Arg Thr Tyr Ser Gly Asp Val Thr Tyr Asn Gln Lys Phe
        50                  55                  60

Lys Asp Lys Ala Thr Met Thr Val Asp Lys Ser Ser Ile Ala Tyr
65                  70                  75                  80

Met Glu Leu Ala Arg Leu Ser Ser Glu Asp Ser Ala Ile Tyr Tyr Cys
                85                  90                  95

Ala Lys Ser Gly Thr Val Arg Gly Phe Ala Tyr Trp Gly Gln Gly Thr
            100                 105                 110

Leu Val Thr Val Ser Ser
        115

<210> SEQ ID NO 165
<211> LENGTH: 12
<212> TYPE: PRT
<213> ORGANISM: Artificial Sequence
<220> FEATURE:
<223> OTHER INFORMATION: Synthetic

<400> SEQUENCE: 165

Gln Ser Leu Leu Asn Ser Gly Asn Gln Lys Asn Tyr
1               5                   10

<210> SEQ ID NO 166
<211> LENGTH: 9
<212> TYPE: PRT
<213> ORGANISM: Artificial Sequence
<220> FEATURE:
<223> OTHER INFORMATION: Synthetic

<400> SEQUENCE: 166

Gln Asn Asp Tyr Ser Tyr Pro Tyr Thr
1               5

<210> SEQ ID NO 167
<211> LENGTH: 113
<212> TYPE: PRT
<213> ORGANISM: Artificial Sequence
<220> FEATURE:
<223> OTHER INFORMATION: Synthetic

<400> SEQUENCE: 167

Asp Ile Val Met Thr Gln Ser Pro Ser Ser Leu Thr Val Thr Ala Gly
1               5                   10                  15

Glu Lys Val Ile Met Ser Cys Lys Ser Ser Gln Ser Leu Leu Asn Ser
            20                  25                  30

Gly Asn Gln Lys Asn Tyr Leu Thr Trp Tyr Gln Gln Lys Pro Gly Gln
        35                  40                  45

Pro Pro Lys Leu Leu Ile Tyr Trp Ala Ser Thr Arg Glu Ser Gly Val
    50                  55                  60

Pro Asp Arg Phe Thr Gly Ser Gly Ser Gly Thr Asp Phe Thr Leu Thr
65                  70                  75                  80

Ile Ser Ser Val Gln Ala Glu Asp Leu Ala Val Tyr His Cys Gln Asn
                85                  90                  95

Asp Tyr Ser Tyr Pro Tyr Thr Phe Gly Gly Gly Thr Lys Leu Glu Ile
            100                 105                 110
```

Lys

<210> SEQ ID NO 168
<211> LENGTH: 326
<212> TYPE: PRT
<213> ORGANISM: Homo Sapiens

<400> SEQUENCE: 168

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Asn Phe Gly Thr Gln Thr
65                  70                  75                  80

Tyr Thr Cys Asn Val Asp His Lys Pro Ser Asn Thr Lys Val Asp Lys
                85                  90                  95

Thr Val Glu Arg Lys Cys Cys Val Glu Cys Pro Pro Cys Pro Ala Pro
                100                 105                 110

Pro Val Ala Gly Pro Ser Val Phe Leu Phe Pro Pro Lys Pro Lys Asp
            115                 120                 125

Thr Leu Met Ile Ser Arg Thr Pro Glu Val Thr Cys Val Val Val Asp
        130                 135                 140

Val Ser His Glu Asp Pro Glu Val Gln Phe Asn Trp Tyr Val Asp Gly
145                 150                 155                 160

Val Glu Val His Asn Ala Lys Thr Lys Pro Arg Glu Glu Gln Phe Asn
                165                 170                 175

Ser Thr Phe Arg Val Val Ser Val Leu Thr Val Val His Gln Asp Trp
                180                 185                 190

Leu Asn Gly Lys Glu Tyr Lys Cys Lys Val Ser Asn Lys Gly Leu Pro
            195                 200                 205

Ala Pro Ile Glu Lys Thr Ile Ser Lys Thr Lys Gly Gln Pro Arg Glu
        210                 215                 220

Pro Gln Val Tyr Thr Leu Pro Pro Ser Arg Glu Glu Met Thr Lys Asn
225                 230                 235                 240

Gln Val Ser Leu Thr Cys Leu Val Lys Gly Phe Tyr Pro Ser Asp Ile
                245                 250                 255

Ala Val Glu Trp Glu Ser Asn Gly Gln Pro Glu Asn Asn Tyr Lys Thr
                260                 265                 270

Thr Pro Pro Met Leu Asp Ser Asp Gly Ser Phe Phe Leu Tyr Ser Lys
            275                 280                 285

Leu Thr Val Asp Lys Ser Arg Trp Gln Gln Gly Asn Val Phe Ser Cys
        290                 295                 300

Ser Val Met His Glu Ala Leu His Asn His Tyr Thr Gln Lys Ser Leu
305                 310                 315                 320

Ser Leu Ser Pro Gly Lys
                325

<210> SEQ ID NO 169
<211> LENGTH: 377
<212> TYPE: PRT
<213> ORGANISM: Homo Sapiens

<400> SEQUENCE: 169

Ala Ser Thr Lys Gly Pro Ser Val Phe Pro Leu Ala Pro Cys Ser Arg
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Leu Gly Thr Gln Thr
65                  70                  75                  80

Tyr Thr Cys Asn Val Asn His Lys Pro Ser Asn Thr Lys Val Asp Lys
                85                  90                  95

Arg Val Glu Leu Lys Thr Pro Leu Gly Asp Thr Thr His Thr Cys Pro
            100                 105                 110

Arg Cys Pro Glu Pro Lys Ser Cys Asp Thr Pro Pro Cys Pro Arg
            115                 120                 125

Cys Pro Glu Pro Lys Ser Cys Asp Thr Pro Pro Cys Pro Arg Cys
130                 135                 140

Pro Glu Pro Lys Ser Cys Asp Thr Pro Pro Cys Pro Arg Cys Pro
145                 150                 155                 160

Ala Pro Glu Leu Leu Gly Gly Pro Ser Val Phe Leu Phe Pro Pro Lys
            165                 170                 175

Pro Lys Asp Thr Leu Met Ile Ser Arg Thr Pro Glu Val Thr Cys Val
            180                 185                 190

Val Val Asp Val Ser His Glu Asp Pro Glu Val Gln Phe Lys Trp Tyr
            195                 200                 205

Val Asp Gly Val Glu Val His Asn Ala Lys Thr Lys Pro Arg Glu Glu
210                 215                 220

Gln Tyr Asn Ser Thr Phe Arg Val Val Ser Val Leu Thr Val Leu His
225                 230                 235                 240

Gln Asp Trp Leu Asn Gly Lys Glu Tyr Lys Cys Lys Val Ser Asn Lys
            245                 250                 255

Ala Leu Pro Ala Pro Ile Glu Lys Thr Ile Ser Lys Thr Lys Gly Gln
            260                 265                 270

Pro Arg Glu Pro Gln Val Tyr Thr Leu Pro Pro Ser Arg Glu Glu Met
            275                 280                 285

Thr Lys Asn Gln Val Ser Leu Thr Cys Leu Val Lys Gly Phe Tyr Pro
            290                 295                 300

Ser Asp Ile Ala Val Glu Trp Glu Ser Ser Gly Gln Pro Glu Asn Asn
305                 310                 315                 320

Tyr Asn Thr Thr Pro Pro Met Leu Asp Ser Asp Gly Ser Phe Phe Leu
                325                 330                 335

Tyr Ser Lys Leu Thr Val Asp Lys Ser Arg Trp Gln Gln Gly Asn Ile
            340                 345                 350

Phe Ser Cys Ser Val Met His Glu Ala Leu His Asn Arg Phe Thr Gln
            355                 360                 365

Lys Ser Leu Ser Leu Ser Pro Gly Lys
            370                 375

<210> SEQ ID NO 170
<211> LENGTH: 327
<212> TYPE: PRT

<213> ORGANISM: Homo Sapiens

<400> SEQUENCE: 170

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Glu Ser Lys Tyr Gly Pro Pro Cys Pro Ser Cys Pro Ala Pro
            100                 105                 110

Glu Phe Leu Gly Gly Pro Ser Val Phe Leu Phe Pro Pro Lys Pro Lys
        115                 120                 125

Asp Thr Leu Met Ile Ser Arg Thr Pro Glu Val Thr Cys Val Val Val
    130                 135                 140

Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
                165                 170                 175

Asn Ser Thr Tyr Arg Val Val Ser Val Leu Thr Val Leu His Gln Asp
            180                 185                 190

Trp Leu Asn Gly Lys Glu Tyr Lys Cys Lys Val Ser Asn Lys Gly Leu
        195                 200                 205

Pro Ser Ser Ile Glu Lys Thr Ile Ser Lys Ala Lys Gly Gln Pro Arg
    210                 215                 220

Glu Pro Gln Val Tyr Thr Leu Pro Pro Ser Gln Glu Glu Met Thr Lys
225                 230                 235                 240

Asn Gln Val Ser Leu Thr Cys Leu Val Lys Gly Phe Tyr Pro Ser Asp
                245                 250                 255

Ile Ala Val Glu Trp Glu Ser Asn Gly Gln Pro Glu Asn Asn Tyr Lys
            260                 265                 270

Thr Thr Pro Pro Val Leu Asp Ser Asp Gly Ser Phe Phe Leu Tyr Ser
        275                 280                 285

Arg Leu Thr Val Asp Lys Ser Arg Trp Gln Glu Gly Asn Val Phe Ser
    290                 295                 300

Cys Ser Val Met His Glu Ala Leu His Asn His Tyr Thr Gln Lys Ser
305                 310                 315                 320

Leu Ser Leu Ser Leu Gly Lys
                325

<210> SEQ ID NO 171
<211> LENGTH: 303
<212> TYPE: PRT
<213> ORGANISM: Artificial Sequence
<220> FEATURE:
<223> OTHER INFORMATION: Synthetic

<400> SEQUENCE: 171

Ala Glu Ser His Leu Ser Leu Leu Tyr His Leu Thr Ala Val Ser Ser
1               5                   10                  15

```
Pro Ala Pro Gly Thr Pro Ala Phe Trp Val Ser Gly Trp Leu Gly Pro
            20                  25                  30

Gln Gln Tyr Leu Ser Tyr Asn Ser Leu Arg Gly Glu Ala Glu Pro Cys
        35                  40                  45

Gly Ala Trp Val Trp Glu Asn Gln Val Ser Trp Tyr Trp Lys Glu
    50                  55                  60

Thr Thr Asp Leu Arg Ile Lys Glu Lys Leu Phe Leu Glu Ala Phe Lys
65                  70                  75                  80

Ala Leu Gly Gly Lys Gly Pro Tyr Thr Leu Gln Gly Leu Leu Gly Cys
                85                  90                  95

Glu Leu Gly Pro Asp Asn Thr Ser Val Pro Thr Ala Lys Phe Ala Leu
            100                 105                 110

Asn Gly Glu Glu Phe Met Asn Phe Asp Leu Lys Gln Gly Thr Trp Gly
        115                 120                 125

Gly Asp Trp Pro Glu Ala Leu Ala Ile Ser Gln Arg Trp Gln Gln Gln
    130                 135                 140

Asp Lys Ala Ala Asn Lys Glu Leu Thr Phe Leu Leu Phe Ser Cys Pro
145                 150                 155                 160

His Arg Leu Arg Glu His Leu Glu Arg Gly Arg Gly Asn Leu Glu Trp
                165                 170                 175

Lys Glu Pro Pro Ser Met Arg Leu Lys Ala Arg Pro Ser Ser Pro Gly
            180                 185                 190

Phe Ser Val Leu Thr Cys Ser Ala Phe Ser Phe Tyr Pro Pro Glu Leu
        195                 200                 205

Gln Leu Arg Phe Leu Arg Asn Gly Leu Ala Ala Gly Thr Gly Gln Gly
    210                 215                 220

Asp Phe Gly Pro Asn Ser Asp Gly Ser Phe His Ala Ser Ser Ser Leu
225                 230                 235                 240

Thr Val Lys Ser Gly Asp Glu His His Tyr Cys Cys Ile Val Gln His
                245                 250                 255

Ala Gly Leu Ala Gln Pro Leu Arg Val Glu Leu Glu Ser Pro Ala Lys
            260                 265                 270

Ser Ser Pro Gly Ser Ser Ser His His His His His His Pro Gly Gly
        275                 280                 285

Gly Leu Asn Asp Ile Phe Glu Ala Gln Lys Ile Glu Trp His Glu
    290                 295                 300

<210> SEQ ID NO 172
<211> LENGTH: 99
<212> TYPE: PRT
<213> ORGANISM: Homo Sapiens

<400> SEQUENCE: 172

Ile Gln Arg Thr Pro Lys Ile Gln Val Tyr Ser Arg His Pro Ala Glu
1               5                   10                  15

Asn Gly Lys Ser Asn Phe Leu Asn Cys Tyr Val Ser Gly Phe His Pro
            20                  25                  30

Ser Asp Ile Glu Val Asp Leu Leu Lys Asn Gly Glu Arg Ile Glu Lys
        35                  40                  45

Val Glu His Ser Asp Leu Ser Phe Ser Lys Asp Trp Ser Phe Tyr Leu
    50                  55                  60
```

-continued

```
Leu Tyr Tyr Thr Glu Phe Thr Pro Thr Glu Lys Asp Glu Tyr Ala Cys
 65              70                  75                  80

Arg Val Asn His Val Thr Leu Ser Gln Pro Lys Ile Val Lys Trp Asp
             85                  90                  95

Arg Asp Met
```